United States Patent
Davidson et al.

(10) Patent No.: US 10,689,364 B2
(45) Date of Patent: Jun. 23, 2020

(54) ISOINDOLINE OR ISOQUINOLINE COMPOUNDS, A PROCESS FOR THEIR PREPARATION AND PHARMACEUTICAL COMPOSITIONS CONTAINING THEM

(71) Applicants: LES LABORATOIRES SERVIER, Suresnes (FR); VERNALIS (R&D) LTD, Winnersh (GB)

(72) Inventors: James Edward Paul Davidson, Great Shelford (GB); James Brooke Murray, Linton (GB); I-Jen Chen, Cambridge (GB); Claire Walmsley, Ely (GB); Mark Dodsworth, Fulbourn (GB); Johannes W. G. Meissner, Linton (GB); Paul Brough, Haverhill Suffolk (GB); Imre Fejes, Budapest (HU); János Tatai, Budapest (HU); Miklós Nyerges, Leányfalu (HU); András Kotschy, Törökbálint (HU); Zoltán Szlávik, Budapest (HU); Olivier Geneste, Rueil-Malmaison (FR); Arnaud Le Tiran, Croissy sur Seine (FR); Thierry Le Diguarher, Saint Denis de l'Hôtel (FR); Jean-Michel Henlin, Suresnes (FR); Jérôme-Benoît Starck, Rueil Malmaison (FR); Anne-Françoise Guillouzic, Nanterre (FR); Guillaume De Nanteuil, Suresnes (FR)

(73) Assignees: LES LABORATOIRES SERVIER, Suresnes (FR); VERNALIS (R&D) LTD, Winnersh Berkshire (GB)

( * ) Notice: Subject to any disclaimer, the term of this patent is extended or adjusted under 35 U.S.C. 154(b) by 0 days.

(21) Appl. No.: 15/704,330

(22) Filed: Sep. 14, 2017

(65) Prior Publication Data
US 2018/0002313 A1  Jan. 4, 2018

Related U.S. Application Data

(63) Continuation of application No. 14/905,985, filed as application No. PCT/EP2014/065764 on Jul. 22, 2014, now Pat. No. 9,809,574.

(30) Foreign Application Priority Data

Jul. 23, 2013 (FR) ...................... 13 57276

(51) Int. Cl.
C07D 401/14    (2006.01)
C07D 405/14    (2006.01)
(Continued)

(52) U.S. Cl.
CPC ........ *C07D 401/14* (2013.01); *A61K 31/4725* (2013.01); *A61K 31/496* (2013.01); *A61K 31/497* (2013.01); *A61K 31/5377* (2013.01); *A61K 31/675* (2013.01); *A61K 45/06* (2013.01); *A61N 5/10* (2013.01); *C07D 405/14* (2013.01); *C07D 409/14* (2013.01); *C07D 417/14* (2013.01); *C07D 471/04* (2013.01); *C07F 9/65616* (2013.01)

(58) Field of Classification Search
CPC . A61K 31/4725; A61K 31/496; A61K 31/497
See application file for complete search history.

(56) References Cited

U.S. PATENT DOCUMENTS 9,120,791 B2   9/2015  Le Diguarher
2005/0070570 A1  3/2005  Garcia et al.

FOREIGN PATENT DOCUMENTS

WO    WO 03/093297    11/2003
WO    WO 2006/023778   3/2006
(Continued)

OTHER PUBLICATIONS

Porter; Biorganic and Medicinal Chemistry Letters, 19 (2009) 230-233.*

(Continued)

*Primary Examiner* — Pancham Bakshi
(74) *Attorney, Agent, or Firm* — Hueschen and Sage

(57) ABSTRACT

Compounds of formula (I):

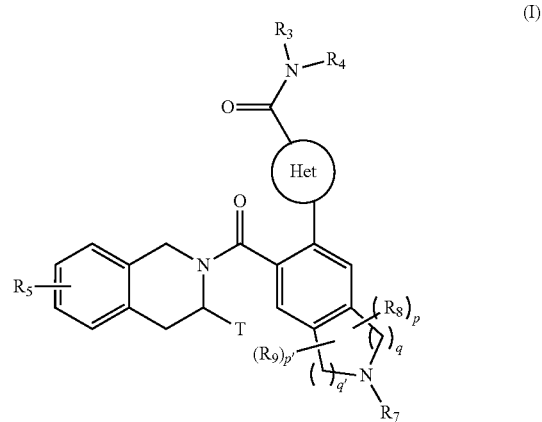

wherein Het, $R_3$, $R_4$, $R_5$, $R_7$, $R_8$, $R_9$, T, p, p', q, and q' are as defined in the description.
Medicinal products containing the same which are useful in treating conditions requiring a pro-apoptotic agent.

22 Claims, No Drawings

(51) Int. Cl.
| | |
|---|---|
| A61K 31/4725 | (2006.01) |
| C07D 409/14 | (2006.01) |
| C07D 471/04 | (2006.01) |
| A61K 31/496 | (2006.01) |
| A61K 31/497 | (2006.01) |
| A61K 31/5377 | (2006.01) |
| A61K 31/675 | (2006.01) |
| A61K 45/06 | (2006.01) |
| A61N 5/10 | (2006.01) |
| C07D 417/14 | (2006.01) |
| C07F 9/6561 | (2006.01) |

(56) References Cited

FOREIGN PATENT DOCUMENTS

| | | |
|---|---|---|
| WO | WO 2008/131000 | 10/2008 |
| WO | WO 2009/073545 | 6/2009 |
| WO | WO 2009/102468 | 8/2009 |
| WO | WO 2012/162365 | 11/2012 |
| WO | WO 2013/110890 | 8/2013 |

OTHER PUBLICATIONS

Bardwell, et al., Journal of Immunology, 2009, 182, 7482-7489.
Collison, Nature Reviews Immunology, 2016, doi: 10.1038/nrrheum.2016.90.
Deng, et al., Cancer Cell, 2007, 12, 171-185.
Hanada, et al., Blood, 1993, 82, 1820-1828.
Hockenbery, et al., Proc. Natl. Acad. Sci. USA, 1991, 88, 6961-6965.
International Preliminary Report on Patentability for PCT/FR2013/050136 dated Jul. 29, 2014.
International Search Report for PCT/EP2014/065764 dated Sep. 25, 2014.
International Search Report for PCT/FR2013/050136 dated Mar. 5, 2013.
Juin, et al., Nature Reviews Cancer, 2013, 13, 455-465.
Kelly, et al., Cell Death and Differentiation, 2011, 18, 1414-1424.
Kirkin, et al., Biochimica et Biophysica Acta, 2004, 1644, 229-249.
Letai, et al., Blood, 2005, 106, 5008.
Monni, et al., Blood, 1997, 90, 1168-1174.
Perez, H.L., et al., Bioorganic & Medicinal Chemistry Letters, 2012, 22, 3946-3950.
Porter, J. et al., Bioorganic and Medicinal Chemistry Letters, vol. 19, No. 1, p. 230-233, Jan. 1, 2009.
Porter, J. et al., Bioorganic and Medicinal Chemistry Letters, vol. 19, No. 6, p. 1767-1772, Mar. 15, 2009.
Schroeder, G.M., et al., Bioorganic & Medicinal Chemistry Letters, 2012, 22, 3951-3956.
Slavov, et al., Proc. Natl. Acad. Sci. USA, 2009, 106, 4079-4084.
Strasser, et al., Proc. Natl. Acad. Sci. USA, 1991, 88, 8661-8665.
Strasser, Nature Reviews, 2005, 189-200.
Tsujimoto, et al., Science, 1985, 228, 1440-1443.
Vaux, et al., Nature, 1988, 335, 440-442.
Yip, et al., Oncogene, 2008, 27, 6398-6406.

Azmi, Sameena, et al. "Bcl-2 expression is correlated with low apoptotic index and associated with histopathological grading in esophageal squamous cell carcinomas", Tumor Biol 21, 2000, pp. 3-10.
Barrasa, Juan, I., et al., "Resistance to butyrate impairs bile acid-induced apoptosis in human colon adenocarcinoma cells via up-regulation of Bcl-2 and inactivation of Bax", Biochimica et Biophysica Acta, 1823, 2012, pp. 2201-2209.
Bray, Kevin, et al., "Bcl-2 modulation to activate apoptosis in prostate cancer", Mol Cancer Res, 7(9), Sep. 2009, pp. 1487-1496.
Catz, S.D., et al., "Bcl-2 in prostate cancer: a minireview". Apoptosis, 8, 2003, pp. 29-37.
Chen, Kuen-Feng, et al., "Inhibition of Bcl-2 improves effect of LCL161, a SMAC mimetic, in hepatocellular carcinoma cells", Biochemical Pharmacology, 84, 2012, pp. 268-277.
Cooke, P.W., et al., "Bcl-2 expression identifies patients with advanced bladder cancer treated by radiotherapy who benefit from neoadjuvant chemotherapy", BJU International, 85, 2000, pp. 829-835.
Fassl, A., et al., "Notch 1 signaling promotes survival of gioblastoma cells via EGFR-mediated induction of anti-apoptotic Mcl-1", Oncogene, 31, 2012, pp. 4698-4708.
Goldsmith, Kelly, C., et al., "Mitochondrial Bcl-2 family dynamics define therapy response and resistance in neuroblastoma", Cancer Res, 72(10), 2012, pp. 2565-2577.
Hanahan, Douglas, et al., "Hallmarks of cancer: the next generation", Cell, 144, Mar. 4, 2011, pp. 646-674.
Jiang, Shi-Xu, et al., "Expression of Bcl-2 oncogene protein is prevalent in small cell lung carcinomas", Journal of Pathology, vol. 177, 1995, pp. 135-138.
Lestini, Brian, J., et al., "Mcl1 downregulation sensitizes neuroblastoma to cytotoxic chemotherapy and small molecule Bcl2-family antagonists", Cancer Biol Ther. 8(16), Aug. 2009, pp. 1587-1595.
Liu, Qun, et al., "Potentiation of dexamethasone-, paclitaxel-, and Ad-p53-induced apoptosis by Bcl-2 antisense oligodeoxynucleotides in drug-resistant multiple myeloma cells", Blood, vol. 101, No. 10, May 15, 2003, pp. 4106-4114.
Maamer-Azzabi, A., et al., "Metastatic SW620 colon cancer cells are primed for death when detached and can be sensitized to anoikis by the BH3-mimetic ABT-737", Cell Death and Disease, 4, e801, 2013, pp. 1-9.
Mano, Y., et al., "Bcl-2 as a predictor of chemosensitivity and prognosis in primary epithelial ovarian cancer", European Journal of Cancer, vol. 35, No. 8, 1999, pp. 1214-1219.
Miyake, H., et al., "Overexpression of Bcl-2 enhances metastatic potential of human bladder cancer cells", British Journal of Cancer, 79(11/12), 1999, pp. 1651-1656.
Sarbia, Mario, et al., "Expression of Bcl-2 and amplification of c-myc are frequent in basaloid squamous cell carcinomas of the esophagus", American Journal of Pathology, vol. 155, No. 4, Oct. 1999, pp. 1027-1032.
Vaillant, Francois, et al., "Targeting Bcl-2 with the BH3 mimetic ABT-199 in estrogen receptor-positive breast cancer", Cancer Cell, 24, Jul. 8, 2013, pp. 120-129.
Witham, James, et al., "The Bcl-2/Bcl-XL family inhibitor ABT-737 sensitizes ovarian cancer cells to carboplatin", Clin Cancer Res, 13(23), Dec. 1, 2007, pp. 7191-7198.
Zhao, Xiangxuan, et al., "Survivin inhibition is critical for Bcl-2 inhibitor-induced apoptosis in hepatocellular carcinoma cells", PLOS One, vol. 6, Issue 8, e21980, Aug. 2011, pp. 1-9.

\* cited by examiner

ISOINDOLINE OR ISOQUINOLINE COMPOUNDS, A PROCESS FOR THEIR PREPARATION AND PHARMACEUTICAL COMPOSITIONS CONTAINING THEM

The present invention relates to new isoindoline or isoquinoline compounds, to a process for their preparation and to pharmaceutical compositions containing them.

The compounds of the present invention are new and have very valuable pharmacological characteristics in the field of apoptosis and cancerology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory S. et al., Nature Review Cancer, 2002, 2, 647-656).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in autoimmune diseases, inflammatory diseases and viral infections. Accordingly, absence of apoptosis is one of the phenotypic signatures of cancer (Hanahan D. et al., Cell 2000, 100, 57-70).

The anti-apoptotic proteins of the Bcl-2 family are associated with numerous pathologies. The involvement of proteins of the Bcl-2 family is described in numerous types of cancer, such as colon cancer, breast cancer, small-cell lung cancer, non-small-cell lung cancer, bladder cancer, ovarian cancer, prostate cancer, chronic lymphoid leukaemia, follicular lymphoma, myeloma, etc. Overexpression of the anti-apoptotic proteins of the Bcl-2 family is involved in tumorigenesis, in resistance to chemotherapy and in the clinical prognosis of patients affected by cancer. There is, therefore, a therapeutic need for compounds that inhibit the anti-apoptotic activity of the proteins of the Bcl-2 family.

In addition to being new, the compounds of the present invention have pro-apoptotic properties making it possible to use them in pathologies involving a defect in apoptosis, such as, for example, in the treatment of cancer and of auto-immune and immune system diseases.

The present invention relates more especially to compounds of formula (I):

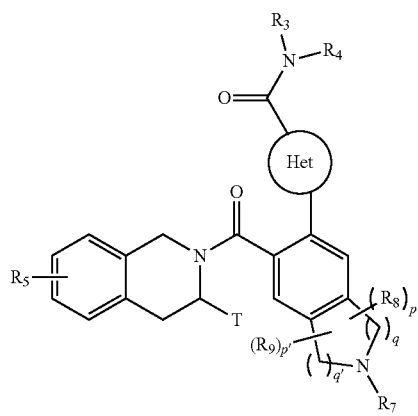

wherein:
Het represents a heteroaryl group,
T represents a hydrogen atom, a linear or branched $(C_1-C_6)$alkyl group optionally substituted by one to three halogen atoms, an alkyl$(C_1-C_4)$—$NR_1R_2$ group or an alkyl$(C_1-C_4)$—$OR_6$ group,
$R_1$ and $R_2$ independently of one another represent a hydrogen atom or a linear or branched $(C_1-C_6)$alkyl group,
or $R_1$ and $R_2$ form with the nitrogen atom carrying them a heterocycloalkyl group,
$R_3$ represents a linear or branched $(C_1-C_6)$alkyl group, a linear or branched $(C_2-C_6)$alkenyl group, a linear or branched $(C_2-C_6)$alkynyl group, a cycloalkyl group, a $(C_3-C_{10})$cycloalkyl-$(C_1-C_6)$alkyl group wherein the alkyl group may be linear or branched, a heterocycloalkyl group, an aryl group or a heteroaryl group, it being understood that one or more carbon atoms of the groups defined hereinbefore, or carbon atoms of their possible substituents, may be deuterated,
$R_4$ represents an aryl, heteroaryl, cycloalkyl or linear or branched $(C_1-C_6)$alkyl group, it being understood that one or more carbon atoms of the groups defined hereinbefore, or carbon atoms of their possible substituents, may be deuterated,
$R_5$ represents a hydrogen atom or a halogen atom, a linear or branched $(C_1-C_6)$alkyl group, or a linear or branched $(C_1-C_6)$alkoxy group,
$R_6$ represents a hydrogen atom or a linear or branched $(C_1-C_6)$alkyl group,
$R_7$ represents a group selected from $R'_7$, $R'_7$—CO—, $R'_7$—O—CO—, $NR'_7R''_7$—CO—, $R'_7$—$SO_2$—, $R'_7$—$NR''_7$—$SO_2$— wherein $R'_7$ and $R''_7$ independently of one another represent a hydrogen atom, a linear or branched $(C_1-C_6)$alkyl group, a linear or branched $(C_2-C_6)$alkenyl group, a linear or branched $(C_2-C_6)$alkynyl group, a cycloalkyl, a heterocycloalkyl, an aryl group, or a heteroaryl,
$R_8$ and $R_9$ represent, independently of one another, an oxo group or a halogen atom,
p and p' are, independently of one another, integers equal to 0, 1, 2, 3 or 4,
q and q' are, independently of one another, integers equal to 1, 2 or 3,
it being understood that when compound of formula (I) contains a hydroxy group, this latter group may be optionally substituted by one of the following groups: —PO(OM)(OM'), —PO(OM)($O^-M_1^+$), —PO($O^-M_1^+$)($O^-M_2^+$), —PO($O^-$)($O^-$)$M_3^{2+}$, —PO(OM)(O[$CH_2CH_2O$]$_n$$CH_3$), or —PO($O^-M_1^+$)(O[$CH_2CH_2O$]$_n$$CH_3$), wherein M and M' independently of one another represent a hydrogen atom, a linear or branched $(C_1-C_6)$alkyl group, a linear or branched $(C_2-C_6)$alkenyl group, a linear or branched $(C_2-C_6)$alkynyl group, a cycloalkyl or a heterocycloalkyl, both of them being composed of from 5 to 6 ring members, while $M_1^+$ and $M_2^+$ independently of one another represent a pharmaceutically acceptable monovalent cation, $M_3^{2+}$ represents a pharmaceutically acceptable divalent cation and n is an integer comprised between 1 to 5,
it also being understood that:
"aryl" means a phenyl, naphthyl, biphenyl or indenyl group,
"heteroaryl" means any mono- or bi-cyclic group composed of from 5 to 10 ring members, having at least one aromatic moiety and containing from 1 to 4 hetero atoms selected from oxygen, sulphur and nitrogen (including quaternary nitrogens), "cycloalkyl" means any mono- or bi-cyclic non-aromatic carbocyclic group containing from 3 to 10 ring members, which may include fused, bridged or spiro ring systems, "heterocycloalkyl" means any mono- or bi-cyclic non-aromatic carbocyclic group, composed of from 3 to 10 ring members, and containing from one to 3 hetero atoms selected from oxygen, sulphur, $SO$, $SO_2$ and nitrogen, it being understood that bicyclic group may be fused or spiro type, it being possible for the aryl, heteroaryl, cycloalkyl and heterocycloalkyl groups so defined and the alkyl, alkenyl, alkynyl, alkoxy, to be substituted by from 1 to 3 groups selected from: optionally substituted linear or branched $(C_1-C_6)$alkyl; optionally substituted linear or branched $(C_2-C_6)$alkenyl group; optionally substituted linear or branched $(C_2-C_6)$alkynyl group; $(C_3-C_6)$spiro; optionally substituted linear or branched $(C_1-C_6)$alkoxy; $(C_1-C_6)$alkyl-S—; hydroxyl; oxo (or N-oxide where appropriate); nitro; cyano; —COOR'; —OCOR'; —NR'R''; R'CONR''—; NR'R''CO—; linear or branched $(C_1-C_6)$polyhaloalkyl; trifluoromethoxy; $(C_1-C_6)$alkylsulphonyl; halogen; optionally substituted aryl; optionally substituted heteroaryl; optionally substituted aryloxy; optionally substituted arylthio; optionally substituted cycloalkyl or optionally substituted heterocycloalkyl, it being understood that R' and R" independently of one another represent a hydrogen atom, an optionally substituted linear or branched $(C_1-C_6)$alkyl group or an aryl group, their enantiomers and diastereoisomers, and addition salts thereof with a pharmaceutically acceptable acid or base.

More preferably, the present invention relates to compounds of formula (IA):

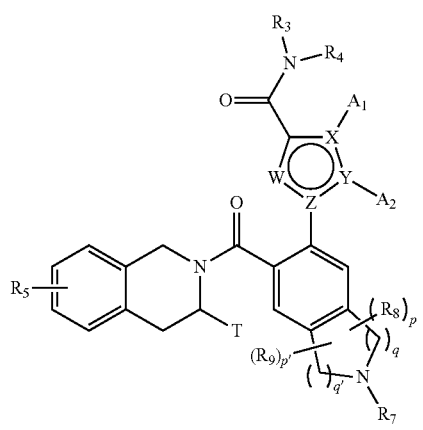

(IA)

wherein:
W represents a $C-A_3$ group or a nitrogen atom,
X, Y and Z represent a carbon atom or a nitrogen atom, it being understood that only one of them represent a nitrogen atom, while the two others represent carbon atoms,
$A_1$, $A_2$ and $A_3$ independently of one another represent a hydrogen atom or a halogen atom, a linear or branched $(C_1-C_6)$polyhaloalkyl group, a linear or branched $(C_1-C_6)$alkyl group or a cycloalkyl group,
or $A_3$ represents a hydrogen atom (when W represents a $C-A_3$ group) while $A_1$ and $A_2$ form together with the atoms carrying them an optionally substituted aromatic or non-aromatic ring Cy, composed of 5, 6 or 7 ring members, which may contain from one to 4 hetero atoms selected independently from oxygen, sulphur and nitrogen, it being understood that the nitrogen in question may be substituted by a group representing a hydrogen atom, a linear or branched $(C_1-C_6)$alkyl group or a group —C(O)—O-Alk wherein Alk is a linear or branched $(C_1-C_6)$alkyl group, or W represents a nitrogen atom while $A_1$ and $A_2$ form together with the atoms carrying them an optionally substituted aromatic or non-aromatic ring Cy, composed of 5, 6 or 7 ring members, which may contain from one to 4 hetero atoms selected independently from oxygen, sulphur and nitrogen, it being understood that the nitrogen in question may be substituted by a group representing a hydrogen atom, a linear or branched $(C_1-C_6)$alkyl group or a group —C(O)—O-Alk wherein Alk is a linear or branched $(C_1-C_6)$alkyl group, T represents a hydrogen atom, a linear or branched $(C_1-C_6)$alkyl group optionally substituted by one to three halogen atoms, an alkyl$(C_1-C_4)$—$NR_1R_2$, group or an alkyl$(C_1-C_4)$—$OR_6$ group, $R_1$ and $R_2$ independently of one another represent a hydrogen atom or a linear or branched $(C_1-C_6)$alkyl group, or $R_1$ and $R_2$ form with the nitrogen atom carrying them a heterocycloalkyl, $R_3$ represents a linear or branched $(C_1-C_6)$alkyl group, a linear or branched $(C_2-C_6)$alkenyl group, a linear or branched $(C_2-C_6)$alkynyl group, a cycloalkyl group, a $(C_3-C_{10})$cycloalkyl-$(C_1-C_6)$alkyl group wherein the alkyl group may be linear or branched, a heterocycloalkyl group, an aryl group or a heteroaryl group, it being understood that one or more carbon atoms of the groups defined hereinbefore, or carbon atoms of their possible substituents, may be deuterated, $R_4$ represents an aryl, heteroaryl, cycloalkyl or linear or branched $(C_1-C_6)$alkyl group, it being understood that one or more carbon atoms of the groups defined hereinbefore, or carbon atoms of their possible substituents, may be deuterated, $R_5$ represents a hydrogen atom or a halogen atom, a linear or branched $(C_1-C_6)$alkyl group, or a linear or branched $(C_1-C_6)$alkoxy group, $R_6$ represents a hydrogen atom or a linear or branched $(C_1-C_6)$alkyl group, $R_7$ represents a group selected from $R'_7$, $R'_7$—CO—, $R'_7$—O—CO—, $NR'_7R''_7$—CO—, $R'_7$—$SO_2$—, $R'_7$—$NR''_7$—$SO_2$— wherein $R'_7$ and $R''_7$ independently of one another represent a hydrogen atom, a linear or branched $(C_1-C_6)$alkyl group, a linear or branched $(C_2-C_6)$alkenyl group, a linear or branched $(C_2-C_6)$alkynyl group, a cycloalkyl, a heterocycloalkyl, an aryl group, or a heteroaryl, $R_8$ and $R_9$ represent, independently of one another, an oxo group or a halogen atom, p and p' are, independently of one another, integers equal to 0, 1, 2, 3 or 4, q and q' are, independently of one another, integers equal to 1, 2 or 3, it being understood that when compound of formula (I) contains a hydroxy group, this latter group may be optionally substituted by one of the following groups: —PO(OM)(OM'), —PO(OM)($O^-M_1^+$), —PO($O^-M_1^+$)($O^-M_2^+$), —PO($O^-$)($O^-$)$M_3^{2+}$, —PO(OM)(O[$CH_2CH_2O]_nCH_3$), or —PO($O^-M_1^+$)(O[$CH_2CH_2O]_nCH_3$), wherein M and M' independently of one another represent a hydrogen atom, a linear or branched $(C_1-C_6)$alkyl group, a linear or branched $(C_2-C_6)$alkenyl group, a linear or branched $(C_2-C_6)$alkynyl group, a cycloalkyl or a heterocycloalkyl, both of them being composed of from 5 to 6 ring members, while $M_1^+$ and $M_2^+$ independently of one another represent a pharmaceutically acceptable monovalent cation, $M_3^{2+}$ represents a pharmaceutically acceptable divalent cation and n is an integer comprised between 1 to 5, it also being understood that:
"aryl" means a phenyl, naphthyl, biphenyl or indenyl group,
"heteroaryl" means any mono- or bi-cyclic group composed of from 5 to 10 ring members, having at least one aromatic moiety and containing from 1 to 4 hetero atoms selected from oxygen, sulphur and nitrogen (including quaternary nitrogens),
"cycloalkyl" means any mono- or bi-cyclic non-aromatic carbocyclic group containing from 3 to 10 ring members, which may include fused, bridged or spiro ring systems,
"heterocycloalkyl" means any mono- or bi-cyclic non-aromatic carbocyclic group, composed of from 3 to 10 ring members, and containing from one to 3 hetero atoms selected from oxygen, sulphur, SO, $SO_2$ and nitrogen, it being understood that bicyclic group may be fused or spiro type,
it being possible for the aryl, heteroaryl, cycloalkyl and heterocycloalkyl groups so defined and the alkyl, alkenyl, alkynyl, alkoxy, to be substituted by from 1 to 3 groups selected from: optionally substituted linear or branched ($C_1$-$C_6$)alkyl; optionally substituted linear or branched ($C_2$-$C_6$)alkenyl group; optionally substituted linear or branched ($C_2$-$C_6$)alkynyl group; ($C_3$-$C_6$)spiro; optionally substituted linear or branched ($C_1$-$C_6$)alkoxy; ($C_1$-$C_6$)alkyl-S—; hydroxyl; oxo (or N-oxide where appropriate); nitro; cyano; —COOR'; —OCOR'; —NR'R''; R'CONR''—; NR'R''CO—; linear or branched ($C_1$-$C_6$)polyhaloalkyl; trifluoromethoxy; ($C_1$-$C_6$)alkylsulphonyl; halogen; optionally substituted aryl; optionally substituted heteroaryl; optionally substituted aryloxy; optionally substituted arylthio; optionally substituted cycloalkyl or optionally substituted heterocycloalkyl, it being understood that R' and R'' independently of one another represent a hydrogen atom, an optionally substituted linear or branched ($C_1$-$C_6$)alkyl group or an aryl group,
it being possible for the Cy moiety defined in formula (IA) to be substituted by from 1 to 3 groups selected from linear or branched ($C_1$-$C_6$)alkyl, linear or branched ($C_1$-$C_6$)polyhaloalkyl, hydroxy, linear or branched ($C_1$-$C_6$)alkoxy, COOH, $NR_1'R_1''$ and halogen, it being understood that $R_1'$ and $R_1''$ have the same definitions than the groups R' and R'' mentioned hereinbefore,
their enantiomers and diastereoisomers, and addition salts thereof with a pharmaceutically acceptable acid or base.

Compounds of formula (IA-1), their enantiomers and diastereoisomers, and addition salts thereof with a pharmaceutically acceptable acid or base, are more preferred:

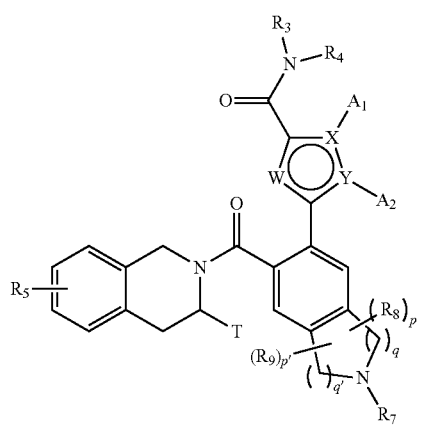

(IA-1)

wherein X, Y, W, $A_1$, $A_2$, $R_3$, $R_4$, $R_5$, $R_7$, $R_8$, $R_9$, T, p, p', q and q' are as defined for formula (IA).

Compounds of formula (IA-2), their enantiomers and diastereoisomers, and addition salts thereof with a pharmaceutically acceptable acid or base, are even more preferred:

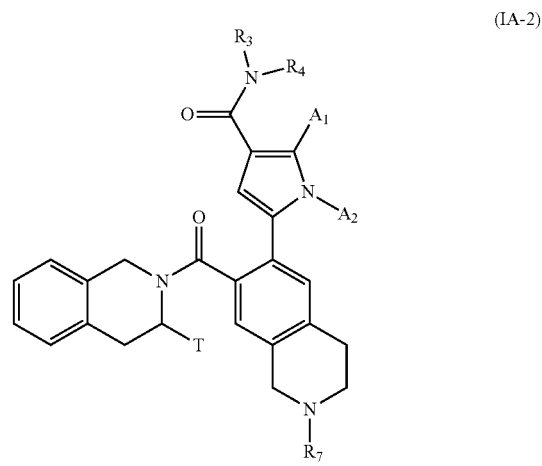

(IA-2)

wherein $A_1$, $A_2$, $R_3$, $R_4$, $R_7$ and T are as defined for formula (IA).

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

In a preferred embodiment of the invention, $R_4$ represents a phenyl substituted at the para position by a group of formula —OPO(OM)(OM'), —OPO(OM)($O^-M_1^+$), —OPO($O^-M_1^+$)($O^-M_2^+$), —OPO($O^-$)($O^-$)$M_3^{2+}$, —OPO(OM)(O[$CH_2CH_2O$]$_n$$CH_3$), or —OPO($O^-M_1^+$)(O[$CH_2CH_2O$]$_n$ $CH_3$), wherein M and M' independently of one another represent a hydrogen atom, a linear or branched ($C_1$-$C_6$) alkyl group, a linear or branched ($C_2$-$C_6$)alkenyl group, a linear or branched ($C_2$-$C_6$)alkynyl group, a cycloalkyl or a heterocycloalkyl, both of them being composed of from 5 to 6 ring members, while $M_1^+$ and $M_2^+$ independently of one another represent a pharmaceutically acceptable monovalent cation, $M_3^{2+}$ represents a pharmaceutically acceptable divalent cation and n is an integer comprised between 1 to 5, it being understood that the phenyl group may be optionally substituted by one or more halogen atoms.

The group Het advantageously represents one of the following groups: tetrahydroindolizine, indolizine or 1,2-dimethyl-1H-pyrrole. The group 1,2-dimethyl-1H-pyrrole is more especially preferred. Alternatively, the group 5,6,7,8-tetrahydroindolizine is more preferred.

In the preferred compounds of the invention, q=1 and q'=1. Alternatively, q=2 and q'=1.

Preferably, T represents a hydrogen atom, a methyl group, a (morpholin-4-yl)alkyl group, a dimethylaminomethyl group, or an (alkylpiperazin-1-yl)alkyl group. More preferably, T represents a methyl group, a (morpholin-4-yl)methyl group, a 3-(morpholin-4-yl)propyl group or a (4-methylpiperazin-1-yl)methyl group. Even more preferably, T represents a methyl group. Alternatively, T represents more preferably a (morpholin-4-yl)methyl group.

In preferred compounds of the invention, $R_3$ represents a linear or branched $(C_1-C_6)$alkyl group, an aryl group or a heteroaryl group. More specifically, $R_3$ is a group selected from phenyl, methyl, ethyl, propyl, butyl, 1-methyl-1H-pyrrolo[2,3-b]pyridine or 5-cyano-1,2-dimethyl-1H-pyrrole. More preferably, $R_3$ represents a methyl, propyl or butyl group. Even more preferably, $R_3$ represents a methyl group.

Preferably, $R_4$ represents a linear or branched $(C_1-C_6)$ alkyl group (more especially a butyl) or an aryl group. $R_4$ represents advantageously a phenyl group optionally substituted.

Preference is given to the $R_4$ group being a 4-hydroxyphenyl.

Advantageously, $R_7$ represents a group $R'_7$—CO— or $R'_7$—O—CO—.

In preferred compounds of the invention, $R'_7$ represents an aryl optionally substituted, a cycloalkyl optionally substituted or an alkyl optionally substituted. More preferably, $R'_7$ represents an optionally substituted naphthalene, phenyl or indole group. The most preferred substitutions for the phenyl group are alkyl optionally substituted, cyano, alkynyl, halogen, alkoxy optionally substituted, or —NR'R''. Even more preferably preferred substitutions for the phenyl group are methyl, ethyl, methoxy, chloro, bromo, cyano, 2-dimethylaminoethylamino, ethynyl, 2-dimethylaminoethoxy, 2-(dimethylamino)ethyl(methyl)amino, dimethylcarbamoylethyl.

In a preferred embodiment, p=p'=0.

More particularly, the invention relates to the following compounds:

N-(4-Hydroxyphenyl)-N-methyl-3-{7-[(3R)-3-methyl-1,2,3,4-tetrahydro isoquinoline-2-carbonyl]-2-(2-phenylacetyl)-1,2,3,4-tetrahydroisoquinolin-6-yl}-5,6,7,8-tetrahydroindolizine-1-carboxamide;

Phenyl 6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydro isoquinoline-2-carboxylate;

Phenyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydro isoquinoline-2-carboxylate;

Phenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate hydrochloride;

Phenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate hydrochloride;

4-Methylphenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate hydrochloride;

2-Methylphenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Methoxyphenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Chlorophenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Ethylphenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Cyanophenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

2-Methoxyphenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Methylphenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Chlorophenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Cyanophenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Cyanophenyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate;

4-{[2-(Dimethylamino)ethyl]amino}phenyl 6-{1-[(4-hydroxyphenyl)(methyl) carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate;

Phenyl 6-{4-[(4-hydroxyphenyl)(propyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

Phenyl 6-{4-[butyl(4-hydroxyphenyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

Phenyl 6-{4-[(4-hydroxyphenyl)(methyl)carbamoyl]-1,5-dimethyl-1H-pyrrol-2-yl}-7-[(3S)-3-[(4-methylpiperazin-1-yl)methyl]-1,2,3,4-tetrahydroisoquinoline-2-carbonyl]-1,2,3,4-tetrahydroisoquinoline-2-carboxylate;

N-Butyl-N-(4-hydroxyphenyl)-1,2-dimethyl-5-{7-[(3S)-3-(morpholin-4-ylmethyl)-1,2,3,4-tetrahydroisoquinoline-2-carbonyl]-2-(2-phenylacetyl)-1,2,3,4-tetrahydroisoquinolin-6-yl}-1H-pyrrole-3-carboxamide;

3-[2-(Dimethylamino)ethoxy]phenyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate;

4-{[2-(Dimethylamino)ethyl](methyl)amino}phenyl 6-{4-[(4-hydroxyphenyl) (methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate;

4-Ethynylphenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

Naphthalen-2-yl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

1H-Indol-5-yl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

3-[2-(Dimethylcarbamoyl)ethyl]phenyl 6-{4-[(4-hydroxyphenyl)(methyl) carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate;

4-Bromophenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

(1r,4r)-4-{[(tert-Butoxy)carbonyl]amino}cyclohexyl 6-{4-[(4-hydroxyphenyl) (methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate;

4-[2-(Dimethylcarbamoyl)ethyl]phenyl 6-{4-[(4-hydroxyphenyl)(methyl) carbamoyl]-1,5-dimethyl-1H-pyrrol-2-yl}-7-[(3R)-3-methyl-1,2,3,4-tetrahydro isoquinoline-2-carbonyl]-1,2,3,4-tetrahydroisoquinoline-2-carboxylate;

Cyclohexyl 6-{4-[(4-hydroxyphenyl)(methyl)carbamoyl]-1,5-dimethyl-1H-pyrrol-2-yl}-7-[(3R)-3-[3-(morpholin-4-yl)propyl]-1,2,3,4-tetrahydroisoquinoline-2-carbonyl]-1,2,3,4-tetrahydroisoquinoline-2-carboxylate.

The invention relates also to a process for the preparation of compounds of formula (I) characterised in that there is used as starting material the compound of formula (II):

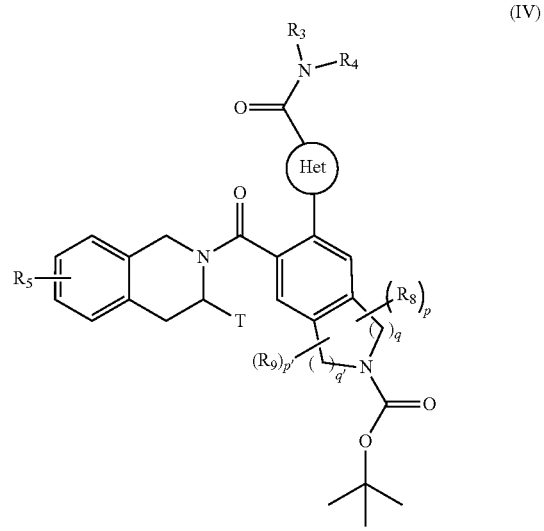

wherein Het, $R_3$, $R_4$, $R_8$, $R_9$, p, p', q and q' are as defined for formula (I) and Alk represents a linear or branched ($C_1$-$C_6$) alkyl group, the ester function of which compound of formula (II) is hydrolysed to yield the corresponding carboxylic acid which is then subjected to peptide coupling with a compound of formula (III):

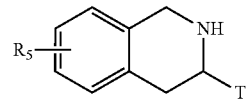

wherein $R_5$ and T are as defined for formula (I),
to yield the compound of formula (IV):

(IV)

wherein Het, $R_3$, $R_4$, $R_5$, $R_8$, $R_9$, T, p, p', q and q' are as defined for formula (I), compound of formula (IV) which is deprotected and subjected to an acylation or a sulfonylation reaction, and which can optionally be subjected to the action of a pyrophosphate or a phosphonate derivative in basic conditions, to yield the compound of formula (I), which compound of formula (I) may be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected and subsequently deprotected, as required by the synthesis.

More specifically, the invention relates also to a process for the preparation of compounds of formula (IA-1) characterised in that there is used as starting material the compound of formula (V):

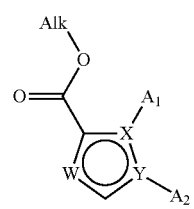

wherein X, Y, W, $A_1$ and $A_2$ are as defined for formula (IA) and Alk represents a linear or branched ($C_1$-$C_6$) alkyl group, the ester function of which compound of formula (V) is hydrolysed to yield the carboxylic acid or the corresponding carboxylate, which may be converted into an acid derivative such as acyl chloride or the corresponding anhydride before being coupled with an amine $NHR_3R_4$ wherein $R_3$ and $R_4$ have the same meanings as for formula (IA), to yield the compound of formula (VI):

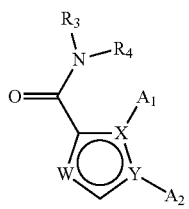

(VI)

wherein X, Y, W, $A_1$, $A_2$, $R_3$ and $R_4$ are as defined for formula (IA),
compound of formula (VI) which is then halogenated and further converted into the corresponding borohydride derivative of formula (VII):

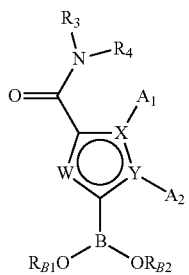

(VII)

wherein X, Y, W, $A_1$, $A_2$, $R_3$ and $R_4$ are as defined for formula (IA), and
$R_{B1}$ and $R_{B2}$ represent a hydrogen, a linear or branched ($C_1$-$C_6$) alkyl group, or $R_{B1}$ and $R_{B2}$ form with the oxygen atoms carrying them an optionally methylated ring,
which compound of formula (VII) is further subjected to coupling with a compound of formula (VIII):

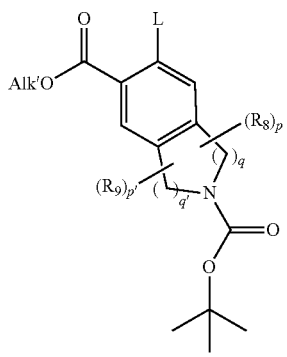

(VIII)

wherein $R_8$, $R_9$, p, p', q and q' are as defined for formula (IA), and

Alk' represents a linear or branched ($C_1$-$C_6$) alkyl group, and L represents a leaving group selected from halogen or sulfonate,
to yield the compound of formula (IIA-1):

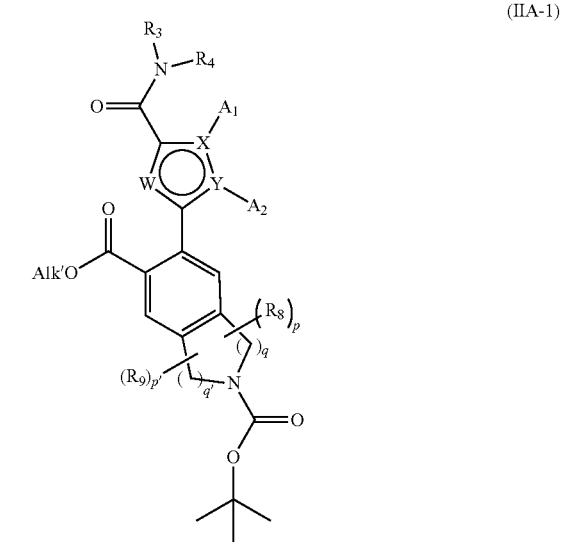

(IIA-1)

wherein X, Y, W, $A_1$, $A_2$, $R_3$, $R_4$, $R_8$, $R_9$, p, p', q, and q' are as defined for formula (IA) and Alk' is as defined previously, the ester function of which compound of formula (IIA-1) is hydrolysed to yield the corresponding carboxylic acid which is then subjected to peptide coupling with a compound of formula (III):

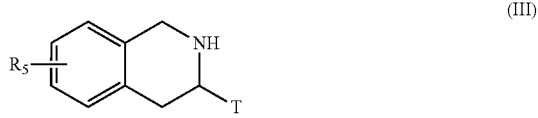

(III)

wherein $R_5$ and T are as defined for formula (IA),
to yield the compound of formula (IVA-1):

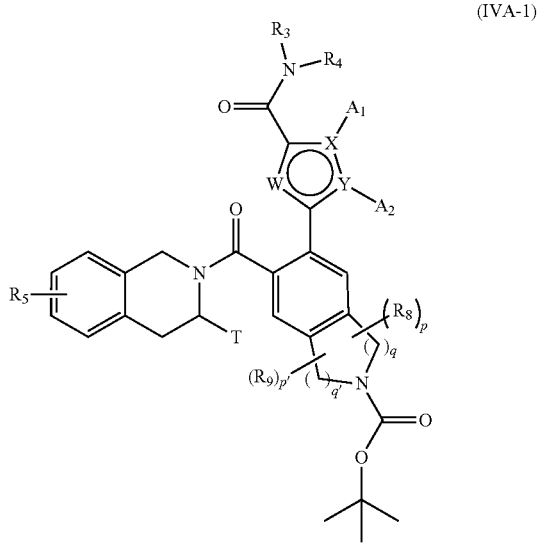

(IVA-1)

wherein X, Y, W, A$_1$, A$_2$, R$_3$, R$_4$, R$_5$, R$_8$, R$_9$, T, p, p', q, q' are as defined for formula (IA),
compound of formula (IVA-1) which is deprotected and subjected to an acylation or a sulfonylation reaction, and which can optionally be subjected to the action of a pyrophosphate or a phosphonate derivative in basic conditions, to yield the compound of formula (IA-1):

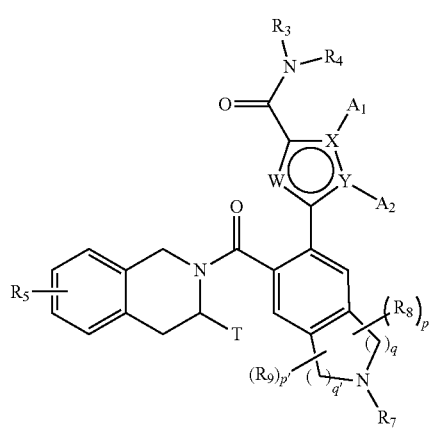

(IA-1)

wherein X, Y, W, A$_1$, A$_2$, R$_3$, R$_4$, R$_5$, R$_7$, R$_8$, R$_9$, T, p, p', q and q' are as defined for formula (IA),
which compound of formula (IA-1) may be purified according to a conventional separation technique, which is converted, if desired, into its addition salts with a pharmaceutically acceptable acid or base and which is optionally separated into its isomers according to a conventional separation technique,
it being understood that at any moment considered appropriate during the course of the process described above, some groups (hydroxy, amino . . . ) of the starting reagents or of the synthesis intermediates can be protected and subsequently deprotected, as required by the synthesis.

More particularly, when one of the groups R$_3$ or R$_4$ of the amine NHR$_3$R$_4$ is substituted by a hydroxy function, the latter may be subjected beforehand to a protection reaction prior to coupling with the carboxylic acid formed from the compound of formula (V), or with a corresponding acid derivative thereof, the resulting protected function subsequently undergoes a deprotection reaction in the last stage of the process.

The compounds of formulae (III), (V), (VIII) and the amine NHR$_3$R$_4$ are either commercially available or can be obtained by the person skilled in the art using conventional chemical reactions described in the literature.

Pharmacological study of the compounds of the invention has shown that they have pro-apoptotic properties. The ability to reactivate the apoptotic process in cancerous cells is of major therapeutic interest in the treatment of cancers and of auto-immune and immune system diseases.

More especially, the compounds according to the invention will be useful in the treatment of chemo- or radio-resistant cancers, and in malignant haemopathies and small-cell lung cancer.

Among the cancer treatments envisaged there may be mentioned, without implying any limitation, treatment of cancers of the bladder, brain, breast and uterus, chronic lymphoid leukaemias, cancer of the colon, oesophagus and liver, lymphoblastic leukaemias, non-Hodgkin lymphomas, melanomas, malignant haemopathies, myelomas, ovarian cancer, non-small-cell lung cancer, prostate cancer and small-cell lung cancer. Among non-Hodgkin lymphomas, there may be mentioned preferably follicular lymphomas, mantle cell lymphomas, diffuse large B-cell lymphomas, small lymphocytic lymphomas and marginal zone B-cell lymphomas.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the association of a compound of formula (I) with an anticancer agent selected from genotoxic agents, mitotic poisons, anti-metabolites, proteasome inhibitors, kinase inhibitors and antibodies, and also to pharmaceutical compositions comprising that type of association and their use in the manufacture of medicaments for use in the treatment of cancer.

The compounds of the invention may also be used in association with radiotherapy in the treatment of cancer.

Finally, the compounds of the invention may be linked to monoclonal antibodies or fragments thereof or linked to scaffold proteins that can be related or not to monoclonal antibodies.

Antibody fragments must be understood as fragments of Fv, scFv, Fab, F(ab')2, F(ab'), scFv-Fc type or diabodies, which generally have the same specificity of binding as the antibody from which they are descended. According to the present invention, antibody fragments of the invention can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows how to select the protein scaffold. More particularly, it is known that, to be selected, such a scaffold should display several features as follow (Skerra A., J. Mol. Recogn., 13, 2000, 167-187): phylogenetically good conservation, robust architecture with a well-known three-dimensional molecular organization (such as, for example, crystallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FNfn10), lipocalin, anticalin (Skerra A., J. Biotechnol., 2001, 74(4):257-75), the protein Z derivative from the domain B of staphylococcal protein A, thioredoxin A or any protein with a repeated domain such as an "ankyrin repeat" (Kohl et al., PNAS, 2003, vol. 100, No. 4, 1700-1705), "armadillo repeat", "leucine-rich repeat" or "tetratricopeptide repeat". There could also be mentioned a scaffold derivative from toxins (such as, for example, scorpion, insect, plant or mollusc toxins) or protein inhibitors of neuronal nitric oxide synthase (PIN).

The following Preparations and Examples illustrate the invention but do not limit it in any way.

General Procedures

All reagents obtained from commercial sources were used without further purification. Anhydrous solvents were obtained from commercial sources and used without further drying. Flash chromatography was performed on ISCO CombiFlash Rf 200i with pre-packed silica-gel cartridges (SiliaSep™ F60 (40-63 µm, 60 Å). Thin layer chromatography was conducted with 5×10 cm plates coated with Merck Type 60 $F_{254}$ silica-gel. Microwave heating was performed with a CEM Discover® SP instrument.

Analytical LC-MS

The compounds of the present invention were characterized by high performance liquid chromatography-mass spectroscopy (HPLC-MS) on either an Agilent HP1200 Rapid Resolution Mass detector 6140 multi mode source m/z range 150 to 1000 amu or an Agilent HP1100 Mass detector 1946D ESI source m/z range 150 to 1000 amu. The conditions and methods listed below are identical for both machines.

Detection: UV detection at 230, 254 and 270 nm.
Injection Volume: 2 µL
Mobile Phases: A—Water+10 mMol/ammonium formate+ 0.08% (v/v) formic acid at pH ca 3.5.
B—95% Acetonitrile+5% A+0.08% (v/v) formic acid Method a (3.75 Min; Either Positive (Pos) or Positive and Negative (Pos/Neg) Ionisation)
Column: Gemini 5 µm, C18, 30 mm×4.6 mm (Phenomenex).
Temperature: 35° C.
Gradient:

| Time (min) | Solvent A (%) | Solvent B (%) | Flow (mL/min) |
|---|---|---|---|
| 0 | 95 | 5 | 2 |
| 0.25 | 95 | 5 | 2 |
| 2.50 | 95 | 5 | 2 |
| 2.55 | 5 | 95 | 3 |
| 3.60 | 5 | 95 | 3 |
| 3.65 | 5 | 95 | 2 |
| 3.70 | 95 | 5 | 2 |
| 3.75 | 95 | 5 | 2 |

Method B (1.9 Min; Either Positive (Pos) or Positive and Negative (Pos/Neg) Ionisation)
Column: Gemini 5 µm, C18, 30 mm×4.6 mm (Phenomenex).
Temperature: 35° C.
Gradient:

| Time (min) | Solvent A (%) | Solvent B (%) | Flow (mL/min) |
|---|---|---|---|
| 0 | 95 | 5 | 1.1 |
| 0.12 | 95 | 5 | 1.1 |
| 1.30 | 5 | 95 | 1.1 |
| 1.35 | 5 | 95 | 1.7 |
| 1.85 | 5 | 95 | 1.7 |
| 1.90 | 5 | 95 | 1.1 |
| 1.95 | 95 | 5 | 1.1 |

Preparative HPLC

Some compounds of the invention were purified by preparative HPLC. These were performed on a Waters FractionLynx MS autopurification system, with a Gemini® 5 µm C18(2), 100 mm×20 mm i.d. column from Phenomenex, running at a flow rate of 20 cm³ min⁻¹ with UV diode array detection (210-400 nm) and mass-directed collection. Gradients used for each compound are shown in Table 1.

At pH 4: solvent A=10 mM ammonium acetate in HPLC grade water+0.08% v/v formic acid. Solvent B=95% v/v HPLC grade acetonitrile+5% v/v solvent A+0.08% v/v formic acid.

At pH 9: solvent A=10 mM ammonium acetate in HPLC grade water+0.08% v/v ammonia solution. Solvent B=95% v/v HPLC grade acetonitrile+5% v/v solvent A+0.08% v/v ammonia solution.

The mass spectrometer was a Waters Micromass ZQ2000 spectrometer, operating in positive or negative ion electrospray ionisation modes, with a molecular weight scan range of 150 to 1000.

Preparation 1a: 2-tert-Butyl 7-methyl 6-[(nonafluorobutanesulfonyl)oxy]-1,2,3,4-tetrahydroisoquinoline-2,7-dicarboxylate Step A: tert-Butyl 7-formyl-6-hydroxy-1,2,3,4-tetrahydroisoquinoline-2-carboxylate tert-Butyl 6-hydroxy-3,4-dihydro-1H-isoquinoline-2-carboxylate (15.0 g, 0.06 mol) is dissolved in 96 mL of 7% dimethoxymagnesium in methanol (0.06 mol) solution and stirred for 30 minutes at room temperature. The reaction mixture is then concentrated and co-evaporated with toluene to afford a powder, which is then suspended in toluene (300 ml). Paraformaldehyde (6.32 g, 0.21 mol) is added and the suspension heated to reflux. A further 6.32 g of paraformaldehyde (0.21 mol) is added and allowed to stir for 48 h. The reaction mixture is cooled to room temperature, diluted with ethyl acetate and washed with 1 N HCl. The organic phase is separated and the aqueous washed with ethyl acetate. The organics are combined, filtered through a celite pad and the filtrate washed with brine, dried over magnesium sulphate, filtered and concentrated in vacuo. The crude material is taken up in dichloromethane, loaded onto isolute and purified on CombiFlash (220 g silica, dichloromethane to 3% methanol/dichloromethane) to afford the undesired regioisomer cleanly as an oil. The remaining fractions are combined, concentrated to a solid, and re-purified on CombiFlash (220 g silica, iso-hexane to 30% ethyl acetate/iso-hexane). The product is obtained as a 2:1 ratio in favour of desired regioisomer.

LC/MS ($C_{15}H_{19}NO_4$) 177 [M–Boc+H]⁺; RT 1.29 (Method B)

Step B: 2-tert-Butyl 7-methyl 6-hydroxy-1,2,3,4-tetrahydroisoquinoline-2,7-dicarboxylate To a stirred solution of 6.4 g of a mixture of regioisomers of the aldehyde obtained in Step A (approx. 4.22 g, 15.23 mmol) in methanol (250 mL) is added sodium cyanide (0.75 g, 0.02 mol). After 1 minute, activated manganese dioxide (10.03 g, 115.4 mmol) is added and the reaction is stirred at ambient temperature overnight. The reaction mixture is filtered through a celite pad and concentrated. The crude material is purified on CombiFlash (220 g silica, iso-hexane to 20% ethyl acetate/iso-hexane) and dried in vacuo to afford a solid.

LC/MS ($C_{16}H_{21}NO_5$) 208 [M−Boc+H]$^+$; RT 1.40 (Method B)

Step C: 2-tert-Butyl 7-methyl 6-[(nonafluorobutane-sulfonyl)oxy]-1,2,3,4-tetrahydroisoquinoline-2,7-dicarboxylate To a solution of the phenol obtained in Step B (5.97 g, 19.41 mmol) in dichloromethane (10 mL) cooled to 0° C. is added triethylamine (8.1 mL, 58.23 mmol), followed by nonafluorobutane sulphonyl fluoride (10.46 mL, 58.23 mmol). After complete addition, the mixture is left to warm to room temperature and stirred for 1 day, after which time a further 10.46 mL of the sulphonylating reagent is added and stirring is maintained for a further day. 20.92 ml is subsequently added and the reaction stirred for a further 4-5 days. The reaction mixture is cooled to 0° C. and water (100 mL) is added. The mixture is extracted with dichloromethane and the organic layers dried over magnesium sulphate, filtered and concentrated in vacuo. The crude material is taken up in dichloromethane, loaded onto isolute and purified on CombiFlash (120 g silica, iso-hexane to 10% ethyl acetate/iso-hexane), and dried in vacuo to afford an oil which slowly crystallises to a solid.

LC/MS ($C_{20}H_{20}NO_7F_9S$) no ionisation; RT 1.62 (Method B)

Preparation 1b: 2-tert-Butyl 7-methyl 6-(trifluoromethanesulfonyloxy)-1,2,3,4-tetrahydroisoquinoline-2,7-dicarboxylate To a solution of the phenol from Step B of Preparation 1a (2.06 g, 6.70 mmol) and pyridine (1.27 mL, 20.1 mmol) in dichloromethane (75 mL) is added triflic anhydride (1.69 mL, 10.05 mmol) at −10-0° C. over 30 min. The mixture is stirred at 0° C. for 2 h, then ice-water (50 mL) is added and the mixture is acidified with dilute aqueous hydrochloric acid to give pH 2-3. The mixture is extracted with ethyl acetate and the organic extracts are washed sequentially with brine and saturated aqueous copper sulfate, dried over magnesium sulphate, and concentrated in vacuo to afford the product.

Preparation 1c: tert-Butyl 7-formyl-6-(trifluoromethanesulfonyloxy)-1,2,3,4-tetrahydroisoquinoline-2-carboxylate To a solution of the product from Step A of Preparation 1a (3.1 g, 11.2 mmol) in anhydrous dichloromethane (50 mL), cooled in an ice-bath, is added pyridine (4.52 mL, 56 mmol) followed by slow addition of triflic anhydride (2.75 mL, 16.8 mmol). The mixture is allowed to warm to ambient temperature and left stirring for ca 16 h.

The reaction is diluted with ice-cold water, acidified with dilute HCl to ~pH 3, and then extracted into ethyl acetate, and washed with saturated aqueous copper sulphate solution. The organic phase is dried over magnesium sulphate, filtered and evaporated. The crude material is purified by column chromatography on silica, eluting with a gradient of iso-hexane to 25% ethyl acetate/iso-hexane to afford the desired product as a mixture with the corresponding regioisomer (tert-butyl 5-formyl-6-(trifluoromethanesulfonyloxy)-1,2,3,4-tetrahydroisoquinoline-2-carboxylate).

Preparation 1d: 2-tert-Butyl 5-methyl 6-bromo-2,3-dihydro-1H-isoindole-2,5-dicarboxylate

Step A: 5-Bromobenzene-1,2,4-tricarboxylic acid

Bromotrimethyl benzene (40.7 g, 205 mmol) was added to a mixture of water (3.25 L), potassium permanganate (232 g, 1.468 mol) and sodium carbonate (28.5 g, 206 mmol). The mixture was stirred at reflux for 60 h. Ethanol (820 mL) was added dropwise, and the resultant mixture was filtered hot through celite, then allowed to cool to ambient temperature. The filtrate was acidified with concentrated aqueous HCl, and the organic solvent was removed in vacuo. The solid product was isolated by filtration.

Step B: 6-Bromo-1,3-dioxo-2,3-dihydro-1H-isoindole-5-carboxylic acid

The product from Step A (42.8 g, 148 mmol) and ammonium bromide (43.5 g, 444 mmol) were finely powdered, and homogenised. The resulting solid mixture was heated at 230-240° C. for 2 h while carefully mixing every 15 min. The mixture was allowed to cool to ambient temperature, then added to water (230 mL), acidified to pH 1-2 with concentrated aqueous HCl, and extracted with multiple portions of ethyl acetate. The combined organic extracts were evaporated, and the resultant solid was triturated with a minimal amount of ethyl acetate, and then subsequently with ethanol to afford the desired product as a solid.

Step C: (4-Methoxyphenyl)methyl 6-bromo-2-[(4-methoxyphenyl)methyl]-1,3-dioxo-2,3-dihydro-1H-isoindole-5-carboxylate The product from Step B (40 g, 148 mmol), 1-(chloromethyl)-4-methoxybenzene (48.7 g, 311 mmol), and potassium carbonate (61.3 g, 444 mmol) were added to DMF (760 mL) and the mixture was heated at 45° C. for ca 16 h. Water (1140 mL) was added, and the resultant precipitate was isolated by filtration, dissolved in chloroform (1100 mL), and dried (sodium sulphate). Evaporation afforded the desired product as a solid.

Step D: {6-Bromo-2-[(4-methoxyphenyl)methyl]-2,3-dihydro-1H-isoindol-5-yl}methanol The product from Step C (55.4 g, 108.5 mmol) was suspended in dry THF (165 mL) and borane-THF (1M in THF; 542 mL, 542 mmol) was added dropwise under argon. After 30 min the mixture was heated to 60° C. for 6 h. Methanol (244.5 mL) was added dropwise (liberating gas) and the resultant solution was evaporated under reduced pressure to a volume of 300 mL. Methanol (170 mL) and 10% aqueous HCl (220 mL) were added and the resultant mixture was heated at 70° C. for 3.5 h. The solution was evaporated under reduced pressure, and the residue was partitioned between saturated aqueous potassium carbonate and dichloromethane. The aqueous phase was extracted with dichloromethane, and the combined organic extracts were concentrated in vacuo and purified by flash column chromatography, eluting with a gradient of 5-60% ethyl acetate/hexane to afford the desired product.

Step E: tert-Butyl 5-bromo-6-(hydroxymethyl)-2,3-dihydro-1H-isoindole-2-carboxylate A solution of the compound from Step D (11.3 g, 32.5 mmol) in trifluoroacetic acid (145 mL) was heated as rapidly as possible at 200° C. under microwave irradiation for 7 min. The trifluoroacetic acid was removed under vacuum, 10% aqueous sodium hydroxide (185 mL) was added, and the resultant mixture was carefully triturated/homogenised, then extracted with several portions of dichloromethane. The combined organic extracts were evaporated, then dissolved in a 1:1 mixture of methanol/dichloromethane (210 mL) and di-tert-butyl dicarbonate (1.2 eq) was added. After 40 min, the solvent was removed in vacuo and the crude material was purified by flash column chromatography on silica, eluting with 1:1 hexane/ethyl acetate to afford the product.

Step F: tert-Butyl 5-bromo-6-formyl-2,3-dihydro-1H-isoindole-2-carboxylate

The product from Step E (5 g, 15.2 mmol) was dissolved in dichloromethane (63.5), and Dess-Martin periodinane (8.4 g, 19.8 mmol) was added portion-wise. After 1 h, the mixture was concentrated in vacuo and the crude material was purified by flash column chromatography on silica, eluting with a gradient of 2%-15% ethyl acetate/hexane to afford the desired product.

Step G: 2-tert-Butyl 5-methyl 6-bromo-2,3-dihydro-1H-isoindole-2,5-dicarboxylate The compound from Step F (1.63 g, 5.0 mmol), manganese dioxide (8.69 g, 100 mmol), sodium cyanide (1.47 g, 30 mmol) and acetic acid (601 mg, 10.0 mmol) were suspended in methanol (50 mL) and the mixture was stirred for ca 16 h. The reaction was filtered through celite, concentrated in vacuo, and the residue partitioned between ethyl acetate and water. The organic phase was concentrated in vacuo and purified by flash column chromatography on silica, eluting with a gradient of 0%-10% ethyl acetate/hexane to afford the desired product.

Preparation 1e: tert-Butyl 5-bromo-6-[(3S)-3-(morpholin-4-ylmethyl)-1,2,3,4-tetrahydroisoquinoline-2-carbonyl]-2,3-dihydro-1H-isoindole-2-carboxylate

Step A: 6-Bromo-2-[(tert-butoxy)carbonyl]-2,3-dihydro-1H-isoindole-5-carboxylic acid To a solution of the product of Preparation 1d (1 g, 2.81 mmol) in dioxane (5 mL) is added a solution of lithium hydroxide monohydrate (236 mg, 5.62 mmol) in water (5 mL), and the reaction is heated to 90° C. After 40 min, the reaction is allowed to cool, and is diluted with water and acidified to ~pH 2 with 2N aqueous HCl. The mixture is extracted with ethyl acetate, and the organic extracts are dried and evaporated under reduced to pressure to afford the product as a solid.
LC/MS ($C_{14}H_{16}BrNO_4$) 342 [M+H]$^+$; RT 2.30 (Method A)

Step B: tert-Butyl 5-bromo-6-[(3S)-3-(morpholin-4-ylmethyl)-1,2,3,4-tetrahydroisoquinoline-2-carbonyl]-2,3-dihydro-1H-isoindole-2-carboxylate To a solution of the product from Step A (933 mg, 2.73 mmol) in DMF (10 mL) is added triethylamine (1.33 mL, 9.55 mmol), HBTU (1.04 g, 2.73 mmol) followed by the product of Preparation 2a (832 mg, 2.73 mmol) and the mixture is stirred at ambient temperature for ca 16 h. The reaction is diluted with water and the resulting precipitate is filtered and washed with water. The solid is taken-up in ethyl acetate, dried over magnesium sulphate, filtered and evaporated. The crude material is purified by column chromatography over silica gel, eluting with a gradient of iso-hexane to 1:1 ethyl acetate/iso-hexane to afford the product as a foam.
LC/MS ($C_{28}H_{34}BrN_3O_4$) 556 [M+H]$^+$; RT 2.35 (Method A)

Preparation 1f: tert-Butyl 5-bromo-6-[(3R)-3-methyl-1,2,3,4-tetrahydroisoquinoline-2-carbonyl]-2,3-dihydro-1H-isoindole-2-carboxylate The procedure is as in Preparation 1e, replacing the product of Preparation 2a used in Step C with (3R)-3-methyl-1,2,3,4-tetrahydroisoquinoline hydrochloride obtained from Preparation 2b.
LC/MS ($C_{24}H_{27}BrN_2O_3$) 471 [M+H]$^+$; RT 2.76 (Method A)

Preparation 1 g: 6-Bromo-2-(trifluoroacetyl)-1,2,3,4-tetrahydroisoquinoline-7-carboxylic acid

Step A: 2-(3-Bromo-4-methoxyphenyl)ethanamine

To a solution of 2-(4-methoxyphenyl)ethanamine (25.0 g, 0.165 mol) in glacial acetic acid (300 mL) was added a solution of bromine (31.7 g, 0.198 mol) in glacial acetic acid (200 mL) dropwise. A white precipitate formed immediately, and the reaction was stirred at rt for 48 h. The white solid was filtered off and washed with hexane to obtain the hydrobromide salt. The mother liquor was evaporated and it was washed with a small amount of acetic acid and hexane. These salts were dissolved in water and the pH was adjusted to 8. The suspension was extracted with DCM and dried, and concentrated under reduced pressure. The crude product was used in the next step without further purification.

Step B: N-[2-(3-Bromo-4-methoxyphenyl)ethyl]-2,2,2-trifluoroacetamide 2-(3-bromo-4-methoxyphenyl)ethanamine (600 mg) was dissolved in 6 mL TFAA and 6 mL DCM and the mixture was stirred for 1 h. It was cooled in ice bath and 24 mL water was added to the mixture. The organic phase was washed with water several times, dried and concentrated under reduced pressure. The crude product was used in the next step without further purification.

Step C: 1-(6-Bromo-7-methoxy-3,4-dihydroisoquinolin-2(1H)-yl)-2,2,2-trifluoroethanone To a solution of 40% sulphuric acid in acetic acid (150 mL) was added N-[2-(3-bromo-4-methoxyphenyl)ethyl]-2,2,2-trifluoroacetamide (15.5 g, 52.4 mmol) and paraformaldehyde (2.4 g, 80 mmol). The reaction mixture was stirred at room temperature for 18 h, poured into cold water and extracted with ethyl acetate. The combined organic layer was washed with sodium hydrogen carbonate solution, dried and concentrated under reduced pressure. The crude product was purified with flash chromatography (eluent: n-hexane: EtOAc gradient).

Step D: 1-(6-Bromo-7-hydroxy-3,4-dihydroisoquinolin-2(1H)-yl)-2,2,2-trifluoroethanone Under argon atmosphere a solution of 1-(6-bromo-7-methoxy-3,4-dihydroisoquinolin-2(1H)-yl)-2,2,2-trifluoroethanone (1 mmol) in 20 mL DCM was slowly added to a precooled solution of boron tribromide (1 mmol) in 30 mL DCM at −30° C. The resulting solution was slowly warmed to −12° C. and stirred for 16 h. The reaction was quenched by adding ice and the product was extracted with EtOAc. The organic phase was washed with water and saturated aqueous NaCl and dried, The crude product was purified with flash chromatography (eluent: n-hexane:DCM gradient).

Step E: 6-Bromo-2-(trifluoroacetyl)-1,2,3,4-tetrahydroisoquinolin-7-yl trifluoromethanesulfonate 1-(6-bromo-7-hydroxy-3,4-dihydroisoquinolin-2(1H)-yl)-2,2,2-trifluoroethanone (5.72 g, 17.7 mmol) and 2.2 mL pyridine (2.12 g, 26.5 mmol) was dissolved in DCM (130 mL). At 0° C. 21.2 mL (21.2 mmol) trifluoromethanesulfonic anhydride (1M in DCM) was added dropwise and the temperature was left to be warmed to rt. When the reaction reached an appropriate conversion it was diluted with brine. The layers were separated and the organics were dried with $Na_2SO_4$, filtered and concentrated under reduced pressure. The crude product was purified via flash chromatography using heptane and ethyl acetate as eluents to obtain 6-bromo-2-(trifluoroacetyl)-1,2,3,4-tetrahydroisoquinolin-7-yl trifluoromethanesulfonate.

Step F: 6-Bromo-2-(trifluoroacetyl)-1,2,3,4-tetrahydroisoquinoline-7-carboxylic acid 6-bromo-2-(trifluoroacetyl)-1,2,3,4-tetrahydroisoquinolin-7-yl trifluoromethanesulfonate (912 mg, 2.0 mmol) and 146 mg (dppf)PdCl$_2$ (0.2 mmol) were dissolved in 15 mL DMF and 5 mL H$_2$O. 560 µL TEA (404 mg, 4.0 mmol) was added and the mixture was stirred at 75° C. under CO atmosphere (1 bar). When the reaction reached an appropriate conversion it was diluted with DCM, extracted with 0.2 M HCl$_{aq}$. The layers were separated, the organics were dried with Na$_2$SO$_4$ filtered and concentrated under reduced pressure. The crude product was purified with flash chromatography using DCM and methanol as eluents to obtain 6-bromo-2-(trifluoroacetyl)-1,2,3,4-tetrahydroisoquinoline-7-carboxylic acid.

Preparation 1ha: 1-{6-Bromo-7-[(3S)-3-(morpholin-4-ylmethyl)-1,2,3,4-tetrahydroisoquinoline-2-carbonyl]-1,2,3,4-tetrahydroisoquinolin-2-yl}-2,2,2-trifluoroethan-1-one To a solution of the acid from Preparation 1g (2 g, 0.01 mol) in N,N-dimethylformamide (15 mL) was added N,N-diisopropylethylamine (1.98 mL, 11.36 mmol), the amine from Preparation 2a (1.39 g, 5.96 mmol) and HBTU (2.15 g, 5.68 mmol), and the mixture was stirred at ambient temperature for ca 16 h. The reaction was concentrated in vacuo then redissolved in ethylacetate, and washed with water and brine. The organic extract was dried over magnesium sulphate, concentrated in vacuo, and purified by flash column chromatography (40 g silica, dichloromethane to 3% methanol in dichloromethane).

LC/MS (C$_{26}$H$_{27}$BrF$_3$N$_3$O$_3$) 566 [M+H]$^+$; RT 1.26 (Method B)

Preparation 1hb: 1-{6-Bromo-7-[(3R)-3-methyl-1,2,3,4-tetrahydroisoquinoline-2-carbonyl]-1,2,3,4-tetrahydroisoquinolin-2-yl}-2,2,2-trifluoroethan-1-one The procedure is as in Preparation 1ha, replacing the amine from Preparation 2a with the amine from Preparation 2b.

LC/MS (C$_{22}$H$_{20}$BrF$_3$N$_2$O$_2$) 481 [M+H]$^+$; RT 1.46 (Method B)

Preparation 2a: (3S)-3-(Morpholin-4-ylmethyl)-1,2,3,4-tetrahydroisoquinoline dihydrochloride

Step A: Benzyl (3S)-3-(4-morpholinykarbonyl)-3,4-dihydro-2(1H)-isoquinoline carboxylate To a solution of 5 g of (3S)-2-[(benzyloxy)carbonyl]-1,2,3,4-tetrahydro-3-isoquinoline-carboxylic acid (16 mmol) in 160 mL of dichloromethane there are added 1.5 mL of morpholine (17.6 mmol) and then 9 mL of N,N,N-triethylamine (64 mmol), 3.3 g of 1-ethyl-3-(3'-dimethylaminopropyl)-carbodiimide (EDC) (19.2 mmol) and 2.6 g of hydroxybenzotriazole (HOBT) (19.2 mmol). The reaction mixture is stirred at ambient temperature overnight and is then poured onto a solution of ammonium chloride and extracted with ethyl acetate. The organic phase is subsequently dried over magnesium sulphate and then filtered and evaporated to dryness. The crude product so obtained is then purified by chromatography over silica gel (dichloromethane/methanol gradient). The product is obtained in the form of a foam.

$^1$H-NMR: δ (400 MHz; dmso-d6; 353° K): 7.30 (m, 5H benzyl); 7.15 (m, 4H aromatic); 5.2-5.0 (m, 3H, 2H benzyl, 1H dihydroisoquinoline); 4.75-4.5 (2d, 2H dihydroisoquinoline); 3.55-3.3 (m, 8H morpholine); 3.15-2.9 (2dd, 2H dihydroisoquinoline)

IR: ν: >C=O: 1694; 1650 cm$^{-1}$

Step B: Benzyl (3S)-3-(4-morpholinylmethyl)-3,4-dihydro-2(1H)-isoquinoline carboxylate To a solution of 5.3 g of the product obtained in Step A (13.9 mmol) in 278 mL of tetrahydrofuran there are added 14 mL of BH$_3$Me$_2$S (27.8 mmol) at ambient temperature. The whole is heated for 4 hours at 80° C. It is allowed to return to ambient temperature, and then there are added 7 mL (14 mmol) of BH$_3$Me$_2$S. The reaction mixture is again heated at 80° C. for 2 hours. The tetrahydrofuran is subsequently evaporated off, and there are then added slowly methanol and then 5.6 mL of 5N hydrochloric acid (27.8 mmol). The mixture is stirred at ambient temperature overnight and then at 80° C. for one hour. There is subsequently added a saturated NaHCO$_3$ solution to the reaction mixture at 0° C. until a pH of 8 is reached, and then extraction with ethyl acetate is carried out. The organic phase is subsequently dried over magnesium sulphate and then filtered and evaporated to dryness. The title product is obtained in the form of an oil.

$^1$H-NMR: δ (400 MHz; dmso-d6; 353° K): 7.43-7.30 (unresolved peak, 5H benzyl); 7.19 (m, 4H aromatic); 5.16 (m, 2H, 2H benzyl); 4.79-4.29 (d, 2H dihydroisoquinoline); 4.58 (m, 1H dihydroisoquinoline); 3.50 (m, 4H morpholine); 3.02-2.80 (dd, 2H dihydroisoquinoline); 2.42-2.28 (unresolved peak, 5H, 4H morpholine, 1H morpholine); 2.15 (dd, 1H morpholine)

IR: ν: >CH: 2810 cm$^{-1}$; ν: >C=O: 1694 cm$^{-1}$; ν: >C—O—C<: 1114 cm$^{-1}$; ν: >CH—Ar: 751; 697 cm$^{-1}$

Step C: (3S)-3-(4-Morpholinylmethyl)-1,2,3,4-tetrahydroisoquinoline

To a solution of 4.9 g of the compound of Step B (13.4 mmol) in 67 mL of ethanol there is added 0.980 g of palladium dihydroxide (20% by mass) at ambient temperature. The reaction mixture is placed under 1.2 bar of hydrogen at ambient temperature for 4 hours. It is subsequently passed over a Whatman filter, and then the palladium is rinsed several times with ethanol. The filtrate is evaporated to dryness. The title product is obtained in the form of an oil.

$^1$H-NMR: δ (400 MHz; dmso-d6; 300° K): 7.12-7.0 (unresolved peak, 4H aromatic); 3.92 (s, 2H tetrahydroisoquinoline); 3.60 (t, 4H morpholine); 2.98 (m, 1H tetrahydroisoquinoline); 2.68 (dd, 1H tetrahydroisoquinoline); 2.5-2.3 (unresolved peak, 8H, 1H tetrahydroisoquinoline, 6H morpholine, 1H NH)

IR: ν: >NH: 3322 cm$^{-1}$ ν: >C—O—C<: 1115 cm$^{-1}$; ν: >CH—Ar: 742 cm$^{-1}$

Step D: (3S)-3-(4-Morpholinylmethyl)-1,2,3,4-tetrahydroisoquinoline dihydrochloride The free base obtained in Step C is dissolved in a minimum volume of dichloromethane. To the stirred solution at room temperature is added 1M HCl solution in diethyl ether (3 equiv). The reaction is stirred for 15 minutes, after which time diethyl ether is added. The resulting precipitate is filtered, washed with diethyl ether, then dried under vacuum to afford the product.

Preparation 2b:
(3R)-3-Methyl-1,2,3,4-tetrahydroisoquinoline

Step A: 3-Methyl-1,2,3,4-tetrahydroisoquinoline

To a solution of 3-methylisoquinoline and NiCl2*6H2O (1.2 eq) in methanol (3 mL/mmol), cooled to 0° C., is added sodium borohydride (12 eq) portion-wise over 1 h. The reaction mixture is stirred at ambient temperature for 1 h, then quenched by addition of water. The solvent is removed under reduced pressure, and the residue is partitioned between ethyl acetate and water. The organic phase is dried over sodium sulphate and evaporated to afford the crude product.

Step B:
(3R)-3-Methyl-1,2,3,4-tetrahydroisoquinoline

The product from Step A (4.5 g) is dissolved in a 1:9 isopropanol/heptane mixture (55 mL), and the resultant solution is repeat-injected onto an IC Column (50×500 mm, 20 um particle size), eluting with 5:95 mixture of 2-propanol/heptane containing 0.05% diethylamine, with a flow rate of 50 ml/min at ambient temperature. Under these conditions the (R)-isomer eluted as the second fraction.

Preparation 2c: tert-Butyl [(3S)-1,2,3,4-tetrahydroisoquinolin-3-ylmethyl]carbamate Step A: Benzyl (3S)-3-(hydroxymethyl)-3,4-dihydro-1H-isoquinoline-2-carboxylate This compound is obtained using a protocol from the literature (R. B. Kawthekar et al *South Africa Journal of Chemistry* 63, 195, 2009) starting from 15 g of (3S)-1,2,3,4-tetrahydroisoquinolin-3-ylmethanol (91.9 mmol) in the presence of benzyl chloroformate and triethylamine dissolved in dichloromethane. After purification on silica gel (gradient petroleum ether/AcOEt), the title product is obtained in the form of an oil.

$^1$H NMR: δ (300 MHz; DMSO-d6; 300K): 7.33 (m, 5H, aromatic Hs, O-benzyl); 7.15 (s, 4H, aromatic Hs, H tetrahydroisoquinoline); 5.13 (s, 2H, CH$_2$-Ph); 4.73 (d, 1H, H tetrahydroisoquinoline); 4.47 (m, H, CH$_2$OH); 4.36 (m, 1H, H tetrahydroisoquinoline); 4.28 (d, 1H, H tetrahydroisoquinoline); 3.39 (dd, 1H, CH$_2$OH); 3.23 (dd, 1H, CH$_2$OH); 2.93 (dd, 1H, H tetrahydroisoquinoline); 2.86 (dd, 1H, H tetrahydroisoquinoline).

IR: ν OH: 3416 cm$^{-1}$; ν<C=O 1694 cm$^{-1}$; ν aromatic>C—H: 754 cm$^{-1}$

Step B: Benzyl (3S)-3-(azidomethyl)-3,4-dihydroisoquinoline-2(1H)-carboxylate

This compound is obtained using a protocol from the literature (D. Pagé et al *J. Med. Chem,* 44, 2387, 2001) starting from 23 g of the compound obtained in Step A (77.3 mmol) in the presence of diphenylphosphoryl azide and triphenylphosphine dissolved in THF. After purification on silica gel (gradient petroleum ether/AcOEt), the title product is obtained in the form of an oil.

$^1$H NMR: δ (400 MHz; DMSO-d6; 300K): 7.36 (m, 5H, aromatic Hs, O-benzyl); 7.19 (m, 4H, aromatic Hs, H tetrahydroisoquinoline); 5.16 (s, 2H, CH$_2$-Ph); 4.76 (d, 1H, H tetrahydroisoquinoline); 4.53 (m, 1H, H tetrahydroisoquinoline); 4.30 (m, 1H, H tetrahydroisoquinoline); 3.28 (m, 2H, CH$_2$N$_3$); 3.06 (dd, 1H, H tetrahydroisoquinoline); 2.78 (dd, 1H, H tetrahydroisoquinoline)

IR: ν N$_3$: 2095 cm$^{-1}$; ν<C=O: 1694 cm$^{-1}$; ν aromatic>C—H: 754 cm$^{-1}$ Step C: Benzyl (3S)-3-(aminomethyl)-3,4-dihydroisoquinoline-2(1H)-carboxylate To a solution of 20.9 g (64.5 mmol) of the azido compound obtained in Step B in 650 mL of THF there are successively added 25.5 g (97.2 mmol) of triphenylphosphine and 157 mL of water. The complete batch is heated at reflux for 2 hours 30 minutes. The reaction mixture is then concentrated to dryness and the residual oil is then taken up in isopropyl ether. A white precipitate appears, which is filtered off and washed with isopropyl ether. The filtrate is then concentrated to dryness and is then purified by chromatography on silica gel (gradient CH$_2$Cl$_2$/MeOH). The title product is obtained in the form of an oil.

$^1$H NMR: δ (400 MHz; DMSO-d6; 300K): 7.40 (m, 5H, aromatic Hs, O-benzyl); 7.20 (m, 4H, aromatic Hs, H tetrahydroisoquinoline); 5.15 (s, 2H, CH$_2$-Ph); 4.75-4.3 (m, 2H, H tetrahydroisoquinoline); 4.30 (d, 1H, H tetrahydroisoquinoline); 2.90 (m, 2H, CH$_2$NH$_2$); 2.45 (m, 2H, H tetrahydroisoquinoline); 1.40 (m, 2H, NH$_2$)

IR: ν NH$_2$: 3400-3300 cm$^{-1}$; ν<C=O: 1688 cm$^{-1}$

Step D: Benzyl (3S)-3-{[(tert-butoxycarbonyl) amino]methyl}-3,4-dihydroisoquinoline-2(1H)-carboxylate To a solution of 18.4 g (62.1 mmol) of the compound obtained in Step C in 630 mL of dichloromethane there are successively added 17.5 mL (124 mmol) of triethylamine and, in portions, 14.9 g (68.3 mmol) of di-tert-butyl dicarbonate. The complete batch is stirred at ambient temperature for 2 hours. The reaction mixture is then concentrated, and then ethyl acetate is added. The organic phase is successively washed with 1M HCl solution, saturated NaCl solution, saturated NaHCO$_3$ solution and then saturated NaCl solution. After drying, concentrating to dryness and purification by chromatography on silica gel (gradient petroleum ether/AcOEt), the title product is obtained in the form of an oil.

$^1$H NMR: δ (400 MHz; DMSO-d6; 300K): 7.35 (m, 5H, aromatic Hs, O-benzyl); 7.15 (m, 4H, aromatic Hs, H tetrahydroisoquinoline); 6.51 (m, 1H, NHBoc); 5.12 (s, 2H, CH$_2$-Ph); 4.76 (d, 1H, H tetrahydroisoquinoline); 4.51 (m, 1H, H tetrahydroisoquinoline); 4.36 (d, 1H, H tetrahydroisoquinoline); 2.95 (m, 3H, H tetrahydroisoquinoline+ CH$_2$NHBoc); 2.71 (d, 1H, H tetrahydroisoquinoline); 1.34 (s, 9H, NHBoc)

IR: ν NH: 3351 cm$^{-1}$; ν<C=O: 1686 cm$^{-1}$

Step E: tert-Butyl [(3S)-1,2,3,4-tetrahydroisoquinolin-3-ylmethyl]carbamate

To a solution of 21 g (53 mmol) of the compound obtained in Step D in 600 mL of ethyl acetate there are added 2.1 g of palladium-on-carbon 10%. The complete batch is stirred at ambient temperature under 1.3 bar of dihydrogen pressure for 5 hours. The reaction mixture is then filtered, and then concentrated to dryness. The title product is obtained in the form of a solid.

$^1$H NMR: δ (400 MHz; DMSO-d6; 300K): 7.15 (m, 4H, aromatic Hs, H tetrahydroisoquinoline); 6.85 (t, 1H, NHBoc); 3.90 (m, 2H, H tetrahydroisoquinoline); 3.00 (m, 2H, CH$_2$NHBoc); 2.80 (m, 1H, H tetrahydroisoquinoline); 2.65 (dd, 1H, H tetrahydroisoquinoline); 2.40 (dd, 1H, H tetrahydroisoquinoline); 1.40 (s, 9H, NHBoc)

IR: ν NH: 3386-3205 cm$^{-1}$ (NH amide); ν<C=O: 1688 cm$^{-1}$; ν NH: 1526 cm$^{-1}$ (NH amine)

Preparation 2d: (3S)-3-[2-(Morpholin-4-yl)ethyl]-1,2,3,4-tetrahydroisoquinoline hydrochloride

Step A: tert-Butyl (3S)-3-(2-morpholino-2-oxoethyl)-3,4-dihydro-1H-isoquinoline-2-carboxylate To a solution of 3 g (10.30 mmol) of [(3S)-2-(tert-butoxycarbonyl)-1,2,3,4-tetrahydroisoquinolin-3-yl]acetic acid in 100 mL of dichloromethane there are added, dropwise, 1.10 mL (11.32 mmol) of morpholine and, dropwise throughout, 4.3 mL (30.9 mmol) of triethylamine, 2.20 g (12.40 mmol) of 1,2-dichloromethane and 1.70 g (1.68 mmol) of hydroxybenzotriazole. The complete batch is stirred at ambient temperature for 15 hours. The reaction mixture is then diluted with dichloromethane and washed successively with 1M HCl solution, saturated NaHCO$_3$ solution and then saturated NaCl solution until neutral. The organic phase is then dried over MgSO$_4$, filtered and concentrated to dryness. After purification by column chromatography on silica gel (dichloromethane/MeOH), the title product is obtained in the form of an oil.

$^1$H NMR: δ (400 MHz; dmso-d6; 300K): 7.20-7.10 (m, 4H, aromatic Hs, tetrahydroisoquinoline); 4.70 (m, 1H, aliphatic Hs, CH tetrahydroisoquinoline); 4.75-4.20 (2m, 2H, aliphatic Hs, CH$_2$ alpha to tetrahydroisoquinoline N); 3.60 (m, 8H, aliphatic Hs, morpholine); 3.00 and 2.70 (2 dd, 2H, aliphatic H, tetrahydroisoquinoline); 2.50-2.20 (2d, 2H, aliphatic Hs, CH$_2$CO); 1.40 (s, 9H, $^t$Bu)

IR: ν C=O: 1687; 1625 cm$^{-1}$

Step B: 1-(Morpholin-4-yl)-2-[(3S)-1,2,3,4-tetrahydroisoquinolin-3-yl]ethanone hydrochloride To a solution of 2.88 g (7.18 mmol) of the compound obtained in Step A in 16 mL of dichloromethane there are added, dropwise, 80 mL (80 mmol) of 1M ethereal HCl solution. The complete batch is stirred at ambient temperature for 15 hours, the suspension is then filtered and the precipitate is washed with ether. After drying, the title product is obtained in the form of a solid.

$^1$H NMR: δ (400 MHz; dmso-d6; 300K): 9.80-9.50 (m, 2H, NH$_2^+$); 7.30-7.10 (m, 4H, aromatic Hs, tetrahydroisoquinoline); 4.30 (m, 2H, aliphatic Hs, CH$_2$ alpha to tetrahydroisoquinoline N); 3.80 (m, 1H, aliphatic Hs, CH tetrahydroisoquinoline); 3.70-3.40 (2m, 8H, aliphatic Hs, morpholine); 3.15 and 2.8 (m, 4H, aliphatic H, CH$_2$ tetrahydroisoquinoline and CH$_2$CO)

IR: ν —NH$_2^+$: 2800-1900 cm$^{-1}$; ν C=O: 1620 cm$^{-1}$

Step C: (3S)-3-[2-(Morpholin-4-yl)ethyl]-1,2,3,4-tetrahydroisoquinoline hydrochloride A solution of 2.2 g (7.44 mmol) of the compound obtained in Step B in 22 mL of MTBE and 5 mL of dichloromethane is prepared. After cooling in an ice bath at 0° C., there are then added, dropwise, 15 mL (15 mmol) of a 1M solution of LiAlH$_4$ in tetrahydrofuran. The complete batch is then stirred at ambient temperature for 6 hours. It is placed at 0° C., and there is then added, dropwise, 1 mL of 5M NaOH solution. The complete batch is stirred at ambient temperature for 45 minutes. The solid is then filtered off and washed with MTBE and then with dichloromethane, and the filtrate is concentrated to dryness. The oil thereby obtained is diluted with dichloromethane and there are added, dropwise, 6.3 mL of 1M ethereal HCl solution. The complete batch is stirred at ambient temperature for 1 hour and then filtered. The crystals thereby obtained are washed with ethyl ether. After drying, the title product is obtained in the form of a solid.

$^1$H NMR: δ (400 MHz; dmso-d6; 300K): 11.35+9.80 (2m, 2H, NH$_2^+$); 10.00 (m, H, NH$^+$); 7.20 (m, 4H, aromatic Hs, tetrahydroisoquinoline); 4.30 (s, 2H, aliphatic Hs, CH$_2$ alpha to tetrahydroisoquinoline N); 4.00+3.85 (2m, 4H, aliphatic Hs, CH$_2$ alpha to morpholine N); 3.70 (m, 1H, aliphatic Hs, CH tetrahydroisoquinoline); 3.55-3.30 (m, 4H, aliphatic Hs, CH alpha to morpholine O and CH$_2$-Morpholine); 3.15 (dd, 1H, aliphatic H, CH$_2$ tetrahydroisoquinoline); 3.10 (m, 2H, aliphatic H, CH alpha to morpholine O); 2.90 (dd, 1H, aliphatic H, CH$_2$ tetrahydroisoquinoline); 2.30+2.15 (2m, 2H, aliphatic H, CH$_2$-tetrahydroisoquinoline)

IR: ν NH$^+$/—NH$_2^+$: between 3500 and 2250 cm$^{-1}$; ν C=C: weak 1593 cm$^{-1}$; ν aromatic C—H: 765 cm$^{-1}$

Preparation 2e: tert-Butyl {2-[(3S)-1,2,3,4-tetrahydroisoquinolin-3-yl]ethyl}carbamate

Step A: Benzyl (3S)-3-(2-hydroxyethyl)-3,4-dihydroisoquinoline-2(1H)-carboxylate The title compound is obtained starting from (3S)-2-[(benzyloxy)carbonyl]-1,2,3,4-tetrahydroisoquinoline-3-carboxylic acid, based on a protocol from the literature (Jinlong Jiang et al Bioorganic & Medicinal Chemistry Letters, 14, 1795, 2004).

Step B: Benzyl (3S)-3-{2-[(methylsulphonyl)oxy]ethyl}-3,4-dihydroisoquinoline-2(1H)-carboxylate To a solution of 10.6 g of the compound of Step A (35.6 mmol) in 350 mL of anhydrous $CH_2Cl_2$, placed at 0° C., there are successively added triethylamine 10.1 mL (71.2 mmol) and then, dropwise, methanesulphonyl chloride 3.1 mL (39 mmol). The reaction mixture is then stirred at ambient temperature for 2 hours. Hydrolysis is then carried out by slowly adding water. The product is extracted several times with $CH_2Cl_2$. The organic phases are then combined and successively washed with 1N HCl solution, saturated NaCl solution, saturated $NaHCO_3$ solution and saturated NaCl solution until neutral. They are then dried over $MgSO_4$ and concentrated to dryness. After purification by chromatography on silica gel (gradient petroleum ether/AcOEt), the expected product is obtained in the form of a foam.
LC/MS: m/z=$(M+H)^+$=375

Step C: Benzyl (3S)-3-(cyanomethyl)-3,4-dihydroisoquinoline-2(1H)-carboxylate To a solution of 15.4 g of the compound obtained in Step B (41.02 mmol) in 250 mL of anhydrous DMSO there are added 22 g (449 mmol) of sodium cyanide. The complete batch is then heated at 60° C. for 12 hours. It is allowed to cool and then the reaction mixture is diluted by adding ethyl acetate. Hydrolysis is then carried out using saturated $NaHCO_3$ solution. After again extracting twice with ethyl acetate, the organic phases are combined, washed with $H_2O$, dried over $MgSO_4$ and concentrated to dryness. After purification by chromatography on silica gel (hexane/AcOEt 7/3), the expected product is obtained in the form of an oil.
LC/MS: m/z=$[M+H]^+$=307.1

Step D: Benzyl (3S)-3-(2-aminoethyl)-3,4-dihydroisoquinoline-2(1H)-carboxylate To a solution of 15.4 g of the compound obtained in Step C (50.3 mmol) in 300 mL of anhydrous THF, placed at 0° C., there is added, dropwise, a 1N solution of $BH_3$-THF. The reaction mixture is allowed to gradually come back to ambient temperature and then the complete batch is stirred for 14 hours. The reaction mixture is then hydrolysed by slowly adding saturated $NH_4Cl$ solution. After extracting twice with ethyl acetate, the organic phases are combined and dried over $MgSO_4$. After concentrating to dryness, the expected product is obtained in the form of a foam which is used directly, without purification, in the next, protection step.

Step E: Benzyl (3S)-3-{2-[(tert-butoxycarbonyl)amino]ethyl}-3,4-dihydroisoquinoline-2(1H)-carboxylate To a solution of 15.6 g of the compound obtained in Step D (50.3 mmol) in 670 mL of $CH_2Cl_2$, there are successively added 13.2 g (60.36 mmol) of $Boc_2O$ in portions, 14 mL (100.6 mmol) of triethylamine, and DMAP in a catalytic amount. The complete batch is stirred at ambient temperature for 5 hours. The reaction mixture is then hydrolysed with water and extracted twice with $CH_2Cl_2$. The organic phases are combined, washed with water and dried over $MgSO_4$. After concentrating to dryness and purification by chromatography on silica gel (gradient heptane/AcOEt), the expected product is obtained in the form of an oil.
LC/MS: m/z=$(M+H)^+$=411

Step F: tert-Butyl {2-[(3S)-1,2,3,4-tetrahydroisoquinolin-3-yl]ethyl}carbamate To a solution of 10.4 g of the compound obtained in Step E (25.5 mmol) in 210 mL of anhydrous MeOH there are added 2.71 g (2.55 mmol) of Pd/C 10%. The complete batch is degassed for 30 minutes and then stirred under a hydrogen atmosphere for 16 hours. The reaction mixture is then filtered and concentrated to dryness. The expected product is obtained in the form of a solid which is taken up in a mixture of pentane/$Et_2O$ (90/10), triturated and filtered. After drying, the product is obtained in the form of a solid.
$^1H$ NMR: δ (400 MHz; dmso-d6; 300K): 7.1-6.98 (m, 4H, aromatic Hs, tetrahydroisoquinoline); 6.83 (m, 1H, $CH_2NHBoc$); 3.85 (s, 2H, aliphatic Hs, tetrahydroisoquinoline); 3.09 (q, 2H, $CH_2NHBoc$); 2.73 (m, 1H, aliphatic Hs, tetrahydroisoquinoline); 2.70 and 2.39 (2m, 2H, aliphatic Hs, tetrahydroisoquinoline); 1.63 (m, 2H, aliphatic Hs); 1.38 (s, 9H, NHCOOtBu)
IR: v: >NH: 3378, –3201 $cm^{-1}$ (amine, amide); v: >C=O: 1683 $cm^{-1}$ (amide); v: >NH: 1524 $cm^{-1}$ (amide); v: >C=O: 1168 $cm^{-1}$
LC/MS: m/z=$[M+H]^+$=277

Preparation 2f: (3R)-3-[3-(Morpholin-4-yl)propyl]-1,2,3,4-tetrahydroisoquinoline dihydrochloride

Step A: {(3S)-2-[(4-Methylphenyl)sulphonyl]-1,2,3,4-tetrahydroisoquinolin-3-yl}methyl 4-methylbenzenesulphonate The procedure is the same as that of Step A of Preparation 1'.

Step B: tert-Butyl 24{(3R)-2-[(4-methylphenyl)sulphonyl]-1,2,3,4-tetrahydroisoquinolin-3-yl}methyl)-3-(morpholin-4-yl)-3-oxopropanoate To a suspension of 1 g of NaH (60%) (25.08 mmol) in 30 mL of MTBE there are added, dropwise, a solution of 5 g of tert-butyl 3-morpholino-3-oxopropanoate (21.81 mmol) in 20 mL of anhydrous MTBE. This suspension stirred at ambient temperature for 1 hour and then the compound obtained in Step A is added in the form of a powder. The batch is stirred at 60° C. for 30 hours. 100 mL of saturated ammonium chloride solution are added. The resulting solution is extracted with dichloromethane. The organic phase is then dried over $MgSO_4$, filtered and concentrated to dryness. After purification by column chromatography over silica gel (dichloromethane/MeOH), the expected product is obtained in the form of an oil.
NMR $^1H$ (500 MHz, dmso-d6) δ ppm: 7.63/7.59 (2d, 2H), 7.3/7.26 (2d, 2H), 7.13 (m, 2H), 7.09/6.97 (2t, 2H), 4.64/4.55/4.36/4.28 (2AB, 2H), 4.25/4.11 (2m, 1H), 3.81 (m, 1H), 3.73-3.48 (m, 4H), 3.57-3.32 (m, 4H), 2.51 (m, 2H), 2.32/2.31 (2s, 3H), 1.88/1.79 (2m, 2H), 1.39/1.38 (2s, 9H)
IR (ATR) $cm^{-1}$: v: >C=O: 1731 (ester); v: >C=O: 1644 (amide); v: —SO2: 1334-1156; v: >C—O—C<: 1115; γ: >CH—Ar: 815-746-709

Step C: 2-({(3R)-2-[(4-Methylphenyl)sulphonyl]-1,2,3,4-tetrahydroisoquinolin-3-yl}methyl)-3-(morpholin-4-yl)-3-oxopropanoic acid To a solution of 9.5 g (17.97 mmol) of the compound obtained in Step B in 40 mL of dioxane there are added, dropwise, 20 mL of a 4M solution of HCl in dioxane. The batch is stirred at ambient temperature for 48 hours and then the solution is concentrated to dryness. After drying, the expected product is obtained in the form of an oil.

NMR $^1$H (400 MHz, dmso-d6) δ ppm: 12.75 (m, 1H), 7.6 (2*d, 2H), 7.3 (2*d, 2H), 7.1/6.95 (2*m, 4H), 4.7-4.2 (d, 2H), 4.25/4.12 (2*m, 1H), 3.9-3.3 (m, 9H), 2.55 (d, 2H), 2.3 (2*s, 3H), 1.8 (t, 2H)

IR (ATR) cm$^{-1}$: ν: —OH: 3500 à 2000; ν: >C═O: 1727 (acid); ν: >C═O: 1634 (amide); ν: —SO2: 1330-1155

Step D: 3-{(3R)-2-[(4-Methylphenyl)sulphonyl]-1,2,3,4-tetrahydroisoquinolin-3-yl}-1-(morpholin-4-yl)propan-1-one To a solution of 7.80 g (16.51 mmol) of the compound obtained in Step C in 100 mL of DMSO there are added 1.16 g (19.83 mmol) of solid sodium chloride and then, dropwise, 5 mL of water. The batch is stirred at 130° C. for 1 hour and then the solution is concentrated to 3/4. The reaction mixture is then diluted with dichloromethane and washed successively with saturated lithium chloride solution and then with saturated NaCl solution. The organic phase is then dried over MgSO$_4$, filtered and concentrated to dryness. After purification by column chromatography over silica gel (cyclohexane/ethyl acetate), the expected product is obtained in the form of an oil.

NMR $^1$H (400 MHz, dmso-d6) δ ppm: 7.65 (d, 2H), 7.3 (d, 2H), 7.15/7 (2 m, 4H), 4.6 (d, 1H), 4.25 (d, 1H), 4.2 (m, 1H), 3.5 (m, 4H), 3.4 (2 m, 4H), 2.6 (2 dd, 2H), 2.35 (s, 3H), 2.3 (m, 2H), 1.5 (quad., 2H)

IR (ATR) cm$^{-1}$: ν: >C═O: 1639; ν: —SO2: 1331-1156; γ: >CH—Ar: 815-675

Step E: (3R)-2-[(4-Methylphenyl)sulphonyl]-3-[3-(morpholin-4-yl)propyl]-1,2,3,4-tetrahydroisoquinoline To a solution of 6.0 g (14.0 mmol) of the compound obtained in Step D in 60 mL of MTBE and 14 mL of dichloromethane there are added 1.06 g (28 mmol) of LAH in portions over 5 minutes. The batch is stirred at ambient temperature for 15 hours. There are added, dropwise, 1.5 mL of water and stirring is carried out for 15 minutes. There are then added, dropwise, 1.5 mL of 5M sodium hydroxide solution and stirring is carried out for 15 minutes. The reaction mixture is then diluted with MTBE and dichloromethane. The suspension is then filtered and the precipitate is washed with MTBE and dichloromethane. The organic phase is then dried over MgSO$_4$, filtered and concentrated to dryness. After purification by column chromatography over silica gel (dichloromethane/EtOH/NH$_4$OH), the expected product is obtained in the form of an oil.

NMR $^1$H (400 MHz, dmso-d6) δ ppm: 7.68 (d, 2H), 7.32 (d, 2H), 7.1 (massif, 4H), 4.65/4.23 (AB, 2H), 4.2 (m, 1H), 3.55 (t, 4H), 2.7/2.6 (ABx, 2H), 2.35 (s, 3H), 2.25 (t, 4H), 2.2 (t, 2H), 1.4/1.3 (2m, 4H)

IR (ATR) cm$^{-1}$: ν: —SO2: 1333-1158

Step F: (3R)-3-[3-(Morpholin-4-yl)propyl]-1,2,3,4-tetrahydroisoquinoline

To a solution of 1.50 g (3.62 mmol) of the compound obtained in Step E in 20 mL of anhydrous methanol there are added 2.0 g (82.3 mmol), in portions, of magnesium turnings. The batch is stirred in the presence of ultrasound for 96 hours. The reaction mixture is then filtered, the solid is washed several times with methanol, and the filtrate is concentrated to dryness. After purification by column chromatography over silica gel (dichloromethane/EtOH/NH$_4$OH), the expected product is obtained in the form of an oil.

NMR $^1$H (400 MHz, dmso-d6) δ ppm: 7.3 (d, 2H), 7.1 (t, 2H), 7.1 (d+t, 3H), 7 (d, 2H), 3.9 (s, 2H), 3.55 (t, 4H), 2.75 (m, 1H), 2.72/2.45 (dd, 2H), 2.35 (t, 4H), 2.25 (t, 2H), 1.6 (m, 2H), 1.45 (m, 2H)

IR (ATR) cm$^{-1}$: ν: >NH2+/NH+: 3500-2300; ν: >C—O—C<: 1115

High-Resolution Mass Spectroscopy (ESI-+-/FIA/HR):
Formule brute: $C_{16}H_{24}N_2O$
[M+H]$^+$ calculated: 261.1961
[M+H]$^+$ measured: 261.1959

Step G: (3R)-3-[3-(Morpholin-4-yl)propyl]-1,2,3,4-tetrahydroisoquinoline dihydrochloride The free base obtained in Step F is dissolved in a minimum volume of dichloromethane. To the stirred solution at room temperature is added 1M HCl solution in diethyl ether (3 equiv). The reaction is stirred for 15 minutes, after which time diethyl ether is added. The resulting precipitate is filtered, washed with diethyl ether, then dried under vacuum to afford the product.

Preparation 22: N,N-Dimethyl[(3S)-1,2,3,4-tetrahydroisoquinolin-3-ylmethyl]amine dihydrochloride The procedure is as in the process of Preparation 2a, replacing the morpholine used in Step A by N,N-dimethylamine.

Preparation 2h: (3S)-3-[(4-Methylpiperazin-1-yl)methyl]-1,2,3,4-tetrahydroisoquinoline trihydrochloride The procedure is as in the process of Preparation 2a, replacing the morpholine used in Step A by 1-methylpiperazine and using 4.5 equivalents of 1M HCl solution in diethyl ether in Step D (salification step).

Preparation 3a: 4-[(tert-Butyldimethylsilyl)oxy]-N-methylaniline

To a solution of 3.69 g 4-methylamino-phenol (30 mmol) and 3.20 g imidazole (47 mmol) in 65 mL of dichloromethane containing 1% ethanol, 5.88 g tert-butyl-dimethylsilyl chloride (39 mmol) is added with rapid stirring at ambient temperature. After 30 minutes the mixture is poured onto 160 mL water. The organic phase is separated and the aqueous phase is extracted with 50 mL dichloromethane. The combined organic phases are subsequently dried over magnesium sulphate and then filtered and evaporated to dryness. The crude product so obtained is then purified by chromatography over silica gel (hexane/ethyl acetate 100:1) to give the product (6.2 g, 87%) as an oil.

Preparation 3b: 4-(Benzyloxy)-N-phenylaniline

Benzyl bromide (1.79 mL, 15.08 mmol) was added to a mixture of 4-hydroxydiphenylamine (2.54 g, 13.71 mmol), cesium carbonate (5.58 g, 1.25 equiv) and potassium iodide (283 mg, 0.1 equiv) in acetone (20 mL).

The mixture was stirred and heated at 50° C. for 1.25 h. After this time, a further portion of benzyl bromide (0.2 eq)

and cesium carbonate (0.2 eq) were added and the mixture was heated for 45 min. The reaction mixture was allowed to cool to ambient temperature, then diluted with ethyl acetate, filtered, and the solvent removed in vacuo. The residue was purified by flash chromatography (Combiflash; 120 g SilaSep Silica column) eluting with 0-20% ethyl acetate in hexane gradient to afford the desired product as a solid.

LC/MS ($C_{19}H_{17}NO$) 276 [M+H]$^+$; RT 1.48 (Method B)

Preparation 3c: 4-(Benzyloxy)-N-ethylaniline

Step A: tert-Butyl-N-[4-(benzyloxy)phenyl]carbamate

To a mixture of tert-butyl-N-(4-hydroxyphenyl)carbamate (25 g, 0.12 mol) and potassium carbonate (24.77 g, 0.18 mol) in DMF (400 mL) was added benzyl bromide (22.48 g, 0.13 mmol) and the reaction was heated at 50° C. for 16 h. The reaction was allowed to cool to ambient temperature, and water (100 mL) was added, causing the precipitation of a white solid. Further water (500 mL) was added and the resultant suspension was stirred for 30 min. The solid material was isolated by filtration, washed with water and dried under vacuum. This solid material was then dissolved in dichloromethane (250 mL), dried over magnesium sulfate and concentrated in vacuo to afford the desired material (32.05 g, 0.11 mmol) as a white crystalline solid.

LC/MS ($C_{18}H_{21}NO_3$) 200 [M-Boc+H]$^+$; RT 1.45 (Method B)

Step B: tert-Butyl-N-[4-(benzyloxy)phenyl]-N-ethylcarbamate

To a cooled solution of the compound obtained in Step A (5 g, 16.7 mmol) in THF (50 mL) was added sodium hydride (1.34 g, 33.4 mmol) portion-wise, and the resultant mixture was allowed to stir for 40 min. Iodoethane (2.69 mL, 33.4 mmol) was added and the reaction was allowed to stir at ambient temperature for 1 h and then at 40° C. for ca 16 h. The reaction was cooled, quenched with water and then extracted with ethyl acetate. The organic phase was washed successively with aqueous sodium thiosulfate solution, aqueous sodium bicarbonate solution, and brine. The organic extract was dried over magnesium sulphate, filtered and concentrated in vacuo, and then adsorbed onto isolute and purified by chromatography (CombiFlash R$_f$, 80 g RediSep™ silica cartridge) eluting in a gradient of iso-hexane to 15% ethyl acetate in iso-hexane to afford the desired product (5.37 g, 16.4 mmol).

LC/MS ($C_{20}H_{25}NO_3$) 228 [M-Boc+H]$^+$; RT 1.52 (Method B)

Step C: 4-(Benzyloxy)-N-ethylaniline

To a solution of compound obtained in Step B (5.37 g, 16.4 mmol, 1 eq) in dichloromethane (50 mL) was added trifluroacetic acid (5 mL) and the mixture was stirred at ambient temperature for 2 hours. The reaction mixture was diluted with water and basified with aqueous 1M sodium hydroxide. The organic extract was dried over magnesium sulphate, concentrated in vacuo and then adsorbed onto isolute and purified by chromatography (CombiFlash R$_f$, 40 g RediSep™ silica cartridge) eluting in a gradient of iso-hexane to 25% ethyl acetate in iso-hexane to afford the product as a yellow oil (3.24 g, 14.25 mmol).

LC/MS ($C_{15}H_{17}NO$) 228 [M+H]$^+$; RT 1.03 (Method B)

Preparation 3d: 4-(Benzyloxy)-N-propylaniline

The procedure is as in Preparation 3c, replacing iodoethane used in Step B with 1-iodopropane.

LC/MS ($C_{16}H_{19}NO$) 242 [M+H]$^+$; RT 1.21 (Method B)

Preparation 3e: 4-(Benzyloxy)-N-butylaniline

The procedure is as in Preparation 3c, replacing iodoethane used in Step B with 1-iodobutane.

LC/MS ($C_{17}H_{21}NO$) 256 [M+H]$^+$; RT 1.56 (Method B)

Preparation 3f: 4-({4-[(tert-Butyldimethylsilyl)oxy]phenyl}amino)-1,5-dimethyl-1H-pyrrole-2-carbonitrile Step A: 4-Bromo-1,5-dimethyl-1H-pyrrole-2-carbonitrile A solution of bromine (6.58 mL, 0.13 mol) in acetic acid (60 mL) is added dropwise with the aid of a dropping funnel to a solution of 1,5-dimethyl-1H-pyrrole-2-carbonitrile (15.0 g, 0.12 mol) in acetic acid (300 mL). The whole is stirred at ambient temperature for 24 hours. The reaction mixture is then poured into a beaker containing 300 mL of water. The solid formed is filtered off and rinsed with water. It is then dissolved in dichloromethane (300 mL) and the organic phase is washed with brine, dried over sodium sulphate, filtered and concentrated in vacuo to give the expected product in the form of a solid.

$^1$H NMR (CDCl$_3$) δ ppm: 2.25 (s, 3H), 3.67 (s, 3H), 6.74 (s, 1H)

Step B: 4-({4-[(tert-Butyldimethylsilyl)oxy]phenyl}amino)-1,5-dimethyl-1H-pyrrole-2-carbonitrile A solution of the compound of the preceding step (1.5 g, 7.53 mmol), 4-[(tert-butyldimethylsilyl)oxy]aniline (2.02 g, 9.04 mmol), sodium tert-butoxide (1.45 g, 15.06 mmol) and 2-di-tert-butylphosphino-2',4',6'-triisopropylbiphenyl (0.13 g, 0.30 mmol) in toluene (20 mL) is purged with nitrogen. Tris(dibenzylideneacetone)dipalladium(0) (0.28 g, 0.30 mmol) is added, and then the reaction mixture is heated at 90° C. until the reaction is complete (monitored by TLC). Heating is stopped and the mixture is allowed to return to ambient temperature. Water (75 mL) is added and the mixture is extracted with ethyl acetate (3×75 mL). The combined organic phases are washed with brine and then concentrated. The crude product is absorbed on silica gel and purified by flash chromatography over silica gel with a mixture of ethyl acetate and heptane (0 to 30%). The product so obtained is dissolved while hot in heptane and is allowed to precipitate with stirring at ambient temperature and then at 0° C. The solid is filtered off and the operation is repeated on the filtrate to give the expected compound in the form of a solid.

$^1$H NMR (400 MHz, CDCl$_3$) δ ppm: 0.15 (s, 6H), 0.97 (s, 9H), 2.13 (s, 3H), 3.66 (s, 3H), 4.68 (br. s, 1H), 6.49 (d, J=8.5 Hz, 2H), 6.64 (s, 1H), 6.66 (d, J=8.7 Hz, 2H)

$^{13}$C NMR (100 MHz, CDCl$_3$) δ ppm: 4.34, 9.72, 18.30, 25.88, 32.94, 101.27, 114.37, 114.70, 116.41, 120.73, 124.52, 131.23, 141.54, 148.27

MS (ESI+): [M+H]$^+$ measured: 342.3

Preparation 4a: N-[4-(Benzyloxy)phenyl]-N-methyl-3-(tetramethyl-1,3,2-dioxaborolan-2-yl)-5,6,7,8-tetrahydroindolizine-1-carboxamide

Step A: 1-Formylpiperidine-2-carboxylic acid

To a mixture of DL-pipecolinic acid (33.45 g, 259 mmol) in formic acid (250 mL) cooled to 0° C., is added acetic anhydride (171 mL, 1.81 mol) drop-wise over ca 60 minutes. The reaction mixture is allowed to warm to room temperature, stirred for ca 16 hours and then cooled in an ice-water bath. Water (250 mL) is added, the mixture is stirred for 10 minutes and then concentrated in vacuo. Toluene is added and evaporated in vacuo (3×50 mL) to azeotropically remove water and acetic acid, and then the residue is dissolved in dichloromethane (60 mL), filtered through a hydrophobic frit and the filtrate evaporated in vacuo to afford the product as an oil.

Step B: Methyl 5,6,7,8-tetrahydroindolizine-1-carboxylate

To a stirring solution of formylated pipecolinic acid obtained in Step A (13.26 g 84.48 mmol) in dichloroethane (100 mL) is added tosyl chloride (17.69 g, 92.8 mmol) followed by methyl-alpha-chloroacrylate (15.4 mL, 151.86 mmol). Triethylamine (23.52 mL, 168.74 mmol) is then added dropwise. The reaction mixture is stirred for 10 minutes, before heating to reflux. After 3 hours the reaction is cooled to room temperature and a further portion of methyl-alpha-chloroacrylate (6.0 mL, 59.1 mmol) is added followed by dropwise addition of triethylamine (11 mL, 78.9 mmol) and the reaction is heated at reflux for ca. 16 h. The reaction mixture is allowed to cool to room temperature, partitioned between dichloromethane and 1M HCl, filtered through a pad of celite and the phases separated. The organic phase is washed sequentially with 1N HCl, saturated $NaHCO_3$ solution and then brine. The organic extract is dried over magnesium sulphate, filtered and concentrated in vacuo and then adsorbed onto silica gel and purified by chromatography (CombiFlash $R_f$, 220 g RediSep™ silica cartridge) eluting in a gradient of iso-hexane to 30% ethyl acetate in iso-hexane to obtain an oil.

LC/MS ($C_{10}H_{13}NO_2$) 180 [M+H]$^+$; RT 1.13 (Method B)

Step C: 5,6,7,8-Tetrahydroindolizine-1-carboxylic acid

To a solution of the ester obtained in Step B (2 g, 11.2 mmol) in dioxane (15 mL) is added a solution of LiOH (936 mg, 22.3 mmol) in water (15 mL) and the reaction stirred at 100° C. for 5 hours. The reaction is cooled, diluted with water, acidified to ~pH 2 with 2M HCl and the resulting precipitate is filtered and washed with water and then dried under vacuum to afford the product as a powder.

LC/MS ($C_9H_{11}NO_2$) 166 [M+H]$^+$; RT 1.72 (Method A)

Step D: N-[4-(Benzyloxy)phenyl]-N-methyl-5,6,7,8-tetrahydroindolizine-1-carboxamide The acid obtained in Step C (1 g, 6.05 mmol) is azeotroped with a minimal volume of toluene and then dissolved in anhydrous dichloromethane (50 mL). This is cooled to −10° C. under nitrogen and oxalyl chloride (2M in dichloromethane, 3 mL, 6.05 mmol) is added dropwise and then stirred for an hour maintaining the temperature at −10° C. A solution of pyridine (0.73 mL, 9.08 mmol) and 4-(benzyloxy)-N-methylaniline (1.42 g, 6.7 mmol) in dichloromethane (3 mL) is added drop-wise to the reaction mixture at −10° C. and then allowed to warm to ambient temperature. Further pyridine (0.24 mL, 3 mmol) is added after 4 hours and stirring is maintained at ambient temperature for ca. 16 h. The reaction mixture is loaded onto a pre-packed silica column and purified in a gradient of iso-hexane to 40% ethyl acetate/iso-hexane to afford the desired product as a powder.

LC/MS ($C_{23}H_{24}N_2O_2$) 361 [M+H]$^+$; RT 2.68 (Method A)

Step E: N-[4-(Benzyloxy)phenyl]-3-bromo-N-methyl-5,6,7,8-tetrahydroindolizine-1-carboxamide To a solution of the compound obtained in Step D (3.49 g, 9.68 mmol) in tetrahydrofuran (35 mL), cooled to −78° C. under nitrogen, is added N-bromosuccinimide (1 eq) portion-wise and then the resultant mixture is stirred for 1 hour. The reaction is allowed to warm to ambient temperature, then diluted with ethyl acetate and washed with 10% sodium thiosulphate solution, saturated sodium bicarbonate solution and brine. The organic phase is subsequently dried over magnesium sulphate, filtered and concentrated in vacuo. The crude product is purified by chromatography over silica gel in a gradient of iso-hexane to 1:1 ethyl acetate/iso-hexane, then triturated with ether and filtered to afford a powder.

LC/MS ($C_{23}H_{23}N_2O_2Br$) 439 [M+H]$^+$; RT 2.74 (Method A)

Step F: N-[4-(Benzyloxy)phenyl]-N-methyl-3-(tetramethyl-1,3,2-dioxaborolan-2-yl)-5,6,7,8-tetrahydroindolizine-1-carboxamide To a solution of the bromide obtained in Step E (6.47 g, 14.73 mmol) in anhydrous tetrahydrofuran (83 mL), cooled to −78° C., is added n-butyl lithium solution in hexanes (2.17 M, 7.47 mL, 16.20 mmol) drop-wise over ca 20 mins. After a further 15 minutes, 2-isopropyl-4,4,5,5-tetramethyl-1,3,2-dioxaborolane (3.61 mL, 17.67 mmol) is added drop-wise and stirring is continued for 15 min. The reaction mixture is quenched at −78° C. by the addition of 20 mL saturated ammonium chloride solution, and then allowed to warm to ambient temperature. The reaction mixture is partitioned between water and ethyl acetate and the phases separated. The organic phase is washed with water, saturated NaCl solution, then dried over magnesium sulphate, filtered and the filtrate concentrated in vacuo to a solid. The solid is then triturated with diethyl ether, filtered, washed with cold ether and dried in vacuo to afford the product as a powder.

LC/MS ($C_{29}H_{35}BN_2O_4$) 487 [M+H]$^+$; RT 1.59 (Method B)

Preparation 4b: N-[4-(Benzyloxy)phenyl]-N,1,2-trimethyl-5-(tetramethyl-1,3,2-dioxaborolan-2-yl)-1H-pyrrole-3-carboxamide

Step A: Ethyl 1,2-dimethyl-1H-pyrrole-3-carboxylate

To a cooled solution of 2-methyl-1H-pyrrole-3-carboxylate (5 g, 32.64 mmol) in THF (50 ml) is added 60% NaH in mineral oil (2.61 g, 65.28 mmol) and the resultant mixture is stirred at 0° C. for 40 minutes. Methyl iodide (4.07 ml, 65.28 mmol) is then added and allowed to stir for 1 hour. The reaction is quenched by the dropwise addition of water (20 mL) and then extracted with ethyl acetate (20 mL×2). The organic extracts are washed sequentially with 10% aqueous thiosulphate solution and brine, then dried over magnesium sulphate, filtered and concentrated. The crude product is taken-up in dichloromethane and loaded onto isolute for purification on CombiFlash (120 g silica, Hex to 20% EtOAc/Hex) to yield the desired product as an oil.

LC/MS ($C_9H_{13}NO_2$) 168 [M+H]$^+$; RT 1.11 (Method B)

Step B: 1,2-Dimethyl-1H-pyrrole-3-carboxylic acid

To a solution of the product from Step A (5.3 g, 31.7 mmol) in 1,4-dioxane (60 mL) is added 1M LiOH (2.66 g, 63.4 mmol) in water (60 ml) and the reaction stirred at 100° C. for ca 16 h. The reaction is allowed to cool to ambient temperature, diluted with water and acidified with 2M HCl. The resulting precipitate is collected by vacuum filtration to afford the desired product. The filtrate is extracted with ethyl acetate and the organic extracts dried over magnesium sulphate, filtered and concentrated to obtain an additional crop of desired product.

LC/MS ($C_7H_9NO_2$) no ionisation; RT 0.71 (Method B)

Step C: N-[4-(Benzyloxy)phenyl]-N,1,2-trimethyl-1H-pyrrole-3-carboxamide

The acid obtained from Step B (1 g, 7.19 mmol) is dissolved in dichloromethane (20 ml) and to this is added 1-chloro-N,N,2-trimethyl-1-propenylamine (1.15 g, 8.62 mmol) and stirred at ambient temperature for 2 hours. The mixture is concentrated to an oil which is re-dissolved in toluene (50 mL). A solution of 4-(benzyloxy)-N-methylaniline (1.84 g, 8.62 mmol) in toluene (10 ml) is added and the resultant mixture is stirred at reflux for 2 hours. The reaction is allowed to cool to ambient temperature and left to stand for ca 16 h. The reaction is partitioned between ethyl acetate and water, separated, and the organics are washed with water, dried over magnesium sulphate, filtered and concentrated. The crude product is purified on CombiFlash (80 g silica, Hex to 60% EtOAc) to obtain the desired product as a solid.

LC/MS ($C_{21}H_{22}N_2O_2$) 335 [M+H]$^+$; RT 1.33 (Method B)

Step D: N-[4-(Benzyloxy)phenyl]-5-bromo-N,1,2-trimethyl-1H-pyrrole-3-carboxamide The product from Step C (1.74 g, 5.19 mmol) is dissolved in THF (20 ml) and cooled to −78° C. N-Bromosuccinimide (924 mg, 5.19 mmol) is then added portion-wise until complete addition and then stirred for 15 minutes. The reaction mixture is allowed to warm to ambient temperature, diluted with ethyl acetate and washed sequentially with 10% sodium thiosulfate solution, saturated sodium bicarbonate solution and brine. The organics are then dried over magnesium sulphate, filtered and concentrated. The crude material is taken-up in dichloromethane, loaded onto isolute and purified on CombiFlash (80 g silica, Hex to 70% EtOAc/Hex) to afford the product as a solid.

LC/MS ($C_{21}H_{21}N_2O_2Br$) 413 [M+H]$^+$; RT 1.42 (Method B)

Step E: N-[4-(Benzyloxy)phenyl]-N,1,2-trimethyl-5-(tetramethyl-1,3,2-dioxaborolan-2-yl)-1H-pyrrole-3-carboxamide The bromide from Step D (1.74 g, 4.21 mmol) and 2-isopropoxy-4,4,5,5-tetramethyl-1,3,2-dioxaborolane (0.94 g, 5.05 mmol) are combined and dissolved in anhydrous THF (20 ml). The reaction mixture is cooled to −78° C. under nitrogen, followed by the dropwise addition of 2M n-BuLi (2.13 ml, 4.25 mmol) over 50 minutes. The reaction is then quenched by the addition of saturated aqueous ammonium chloride solution, and allowed to warm to ambient temperature, diluted in ethyl acetate and then washed with water followed by brine. The organics are dried over magnesium sulphate, filtered and concentrated to an oil, which solidifies on addition of ether. Re-evaporation and drying in vacuo affords the desired product.

LC/MS ($C_{27}H_{33}BN_2O_4$) 461 [M+H]$^+$; RT 1.51 (Method B)

Preparation 4c: N,1,2-Trimethyl-N-phenyl-5-(tetramethyl-1,3,2-dioxaborolan-2-yl)-1H-pyrrole-3-carboxamide The procedure is as in Preparation 4b, replacing 4-(benzyloxy)-N-methylaniline used in Step C with N-methylaniline.

LC/MS ($C_{20}H_{27}BN_2O_3$) 355 [M+H]$^+$; RT 1.39 (Method B)

Preparation 4d: N,N-Dibutyl-1,2-dimethyl-5-(tetramethyl-1,3,2-dioxaborolan-2-yl)-1H-pyrrole-3-carboxamide The procedure is as in Preparation 4b, replacing 4-(benzyloxy)-N-methylaniline used in Step C with dibutylamine LC/MS ($C_{21}H_{37}BN_2O_3$) 377 [M+H]$^+$; RT 1.55 (Method B)

Preparation 4e: N-{4-[(tert-Butyldimethylsilyl)oxy]phenyl}-N-methyl-3-(tetramethyl-1,3,2-dioxaborolan-2-yl)-5,6,7,8-tetrahydroindolizine-1-carboxamide The procedure is as in Preparation 4a, replacing 4-(benzyloxy)-N-methylaniline in Step D with 4-[(tert-butyldimethylsilyl)oxy]-N-methylaniline from Preparation 3a.

Preparation 4f: N-[4-(Benzyloxy)phenyl]-N-phenyl-3-(tetramethyl-1,3,2-dioxaborolan-2-yl)-5,6,7,8-tetrahydroindolizine-1-carboxamide The procedure is as in Preparation 4a, replacing 4-(benzyloxy)-N-methylaniline in Step D with 4-(benzyloxy)-N-phenylaniline from Preparation 3b.

Preparation 4g: N-[4-(Benzyloxy)phenyl]-N-ethyl-1,2-dimethyl-5-(tetramethyl-1,3,2-dioxaborolan-2-yl)-1H-pyrrole-3-carboxamide The procedure is as in Preparation 4b, replacing 4-(benzyloxy)-N-methylaniline used in Step C with 4-(benzyloxy)-N-ethylaniline from Preparation 3c.

LC/MS ($C_{28}H_{35}BN_2O_4$) 475 [M+H]$^+$; RT 1.49 (Method B)

Preparation 4h: N-[4-(Benzyloxy)phenyl]-1,2-dimethyl-N-propyl-5-(tetramethyl-1,3,2-dioxaborolan-2-yl)-1H-pyrrole-3-carboxamide The procedure is as in Preparation 4b, replacing 4-(benzyloxy)-N-methylaniline used in Step C with 4-(benzyloxy)-N-propylaniline from Preparation 3d.

LC/MS ($C_{29}H_{37}BN_2O_4$) 489 [M+H]$^+$; RT 1.57 (Method B)

Preparation 4i: N-[4-(Benzyloxy)phenyl]-N-butyl-1,2-dimethyl-5-(tetramethyl-1,3,2-dioxaborolan-2-yl)-1H-pyrrole-3-carboxamide The procedure is as in Preparation 4b, replacing 4-(benzyloxy)-N-methylaniline used in Step C with 4-(benzyloxy)-N-butylaniline from Preparation 3e.

LC/MS ($C_{30}H_{39}BN_2O_4$) 503 [M+H]$^+$; RT 1.55 (Method B)

Preparation 5a: 6-(1-{[4-(Benzyloxy)phenyl](methyl)carbamoyl}-5,6,7,8-tetrahydroindolizin-3-yl)-2-[(tert-butoxy)carbonyl]-1,2,3,4-tetrahydroisoquinoline-7-carboxylic acid

Step A: 2-tert-Butyl 7-methyl 6-(1-[{4-(benzyloxy)phenyl](methyl)carbamoyl}-5,6,7,8-tetrahydroindolizin-3-yl)-1,2,3,4-tetrahydroisoquinoline-2,7-dicarboxylate The boronic ester obtained in Preparation 4a (1.22 g, 2.50 mmol) and the triflate obtained in Preparation 1b (1.1 g, 2.50 mmol) are suspended in 15 mL of anhydrous N,N-dimethylformamide and the mixture is degassed (bubbling with $N_2$) for 45 minutes. $Cs_2CO_3$ (1.63 g, 5 mmol) and bis(di-tert-butyl(4-dimethylaminophenyl)-phosphine) dichloropalladium(II) (88.5 mg, 0.13 mmol) are added and the resultant mixture is sealed and immediately heated in the microwave at 130° C. for 30 minutes. The reaction mixture is concentrated and re-dissolved in ethyl acetate, washed with brine, dried over magnesium sulphate, filtered and concentrated. The crude product is purified by flash chromatography on CombiFlash (120 g silica, dichloromethane to 20% methanol/dichloromethane) to afford the desired product.

LC/MS ($C_{39}H_{43}N_3O_6$) 650 [M+H]$^+$; RT 1.54 (Method B)

Step B: 6-(1-[{4-(Benzyloxy)phenyl](methyl)carbamoyl}-5,6,7,8-tetrahydroindolizin-3-yl)-2-[(tert-butoxy)carbonyl]-1,2,3,4-tetrahydroisoquinoline-7-carboxylic acid To a solution of the ester obtained in Step A (730 mg, 1.12 mmol) in dioxane (10 mL) is added a solution of LiOH (94 mg, 2.24 mmol) in water (5 mL). The reaction is then heated at 90° C. for ca 16 h. A further 94 mg of LiOH (2.24 mmol) in water (5 mL) is added and stirred for 1 hour to complete the reaction. The mixture is cooled, diluted with water and acidified to ~pH 4 with dilute aqueous HCl. The precipitate which forms is stirred for 30 minutes and then filtered off, washed with cold water and dried under vacuum to afford the desired product.

LC/MS ($C_{38}H_{41}N_3O_6$) 636 [M+H]$^+$; RT 1.46 (Method B)

Preparation 5b: 2-tert-Butyl 7-lithio 6-(4-{[4-(benzyloxy)phenyl](methyl)carbamoyl}-1,5-dimethyl-1H-pyrrol-2-yl)-1,2,3,4-tetrahydroisoquinoline-2,7-dicarboxylate

Step A: 2-tert-Butyl 7-methyl 6-(4-{[4-(benzyloxy)phenyl](methyl)carbamoyl}-1,5-dimethyl-1H-pyrrol-2-yl)-1,2,3,4-tetrahydroisoquinoline-2,7-dicarboxylate The boronic ester from Preparation 4b (1 g, 1.7 mmol) and the nonaflate from Preparation 1a (0.94 g, 2.04 mmol) are dissolved in DMF (20 mL) and degassed (bubbling nitrogen) for 20 minutes. Cesium carbonate (1.3 g, 4.04 mmol) and bis(di-tert-butyl(4-dimethylaminophenyl)phosphine)dichloropalladium(II) (60 mg, 0.085 mmol) are added and the resultant mixture is immediately heated in the microwave at 130° C. for 30 minutes. The DMF is evaporated, and the residue dissolved in ethyl acetate, washed with brine, then dried over magnesium sulphate, filtered and concentrated. The crude material is taken up in dichloromethane, loaded onto isolute and purified on CombiFlash (120 g silica, Hex to 70% EtOAc/Hex to obtain the product as a foam.

LC/MS ($C_{37}H_{41}N_3O_6$) 624 [M+H]$^+$; RT 1.55 (Method B)

Step B: 2-tert-Butyl 7-lithio 6-(4-{[4-(benzyloxy)phenyl](methyl)carbamoyl}-1,5-dimethyl-1H-pyrrol-2-yl)-1,2,3,4-tetrahydroisoquinoline-2,7-dicarboxylate To a solution of the ester obtained in Step A (2.17 g, 3.48 mmol) in dioxane (20 ml) is added an aqueous solution of LiOH (2 M; 3.48 mL, 6.96 mmol), and the resultant mixture is heated at reflux for ca 16 h. The reaction mixture is allowed to cool to ambient temperature and the solids removed by filtration. The solution is concentrated to obtain the desired product as a solid.

LC/MS ($C_{36}H_{39}N_3O_6$) 610 [M+H]$^+$; RT 1.47 (Method B)

Preparation 5c: 2-[(tert-Butoxy)carbonyl]-6-{1,5-dimethyl-4-[methyl(phenyl)carbamoyl]-1H-pyrrol-2-yl}-1,2,3,4-tetrahydroisoquinoline-7-carboxylic acid

Step A: 2-tert-Butyl 7-methyl 6-{1,5-dimethyl-4-[methyl(phenyl)carbamoyl]-1H-pyrrol-2-yl}-1,2,3,4-tetrahydroisoquinoline-2,7-dicarboxylate The procedure is as in Step A of Procedure 5b, replacing N-[4-(benzyloxy)phenyl]-N,1,2-trimethyl-5-(tetramethyl-1,3,2-dioxaborolan-2-yl)-1H-pyrrole-3-carboxamide with product from Procedure 4c.

Step B: 2-[(tert-Butoxy)carbonyl]-6-{1,5-dimethyl-4-[methyl(phenyl)carbamoyl]-1H-pyrrol-2-yl}-1,2,3,4-tetrahydroisoquinoline-7-carboxylic acid The procedure is as in Step B from Procedure 5a, replacing 2-tert-butyl 7-methyl 6-(1-{[4-(benzyloxy)phenyl](methyl)carbamoyl}-5,6,7,8-tetrahydroindolizin-3-yl)-1,2,3,4-tetrahydroisoquinoline-2,7-dicarboxylate with the product from Step A.

Preparation 5d: 2-tert-Butyl 7-lithio 6-[4-(dibutylcarbamoyl)-1,5-dimethyl-1H-pyrrol-2-yl]-1,2,3,4-tetrahydroisoquinoline-2,7-dicarboxylate The procedure is as in Preparation 5b, replacing N-[4-(benzyloxy)phenyl]-N,1,2-trimethyl-5-(tetramethyl-1,3,2-dioxaborolan-2-yl)-1H-pyrrole-3-carboxamide with the product from Procedure 4d.

Preparation 5e: 2-[(tert-Butoxy)carbonyl]-6-{1-[(4-hydroxyphenyl)(methyl)carbamoyl]-5,6,7,8-tetrahydroindolizin-3-yl}-1,2,3,4-tetrahydroisoquinoline-7-carboxylic acid

Step A: tert-Butyl 6-[1-({4-[(tert-butyldimethylsilyl)oxy]phenyl}(methyl)carbamoyl)-5,6,7,8-tetrahydroindolizin-3-yl]-7-formyl-1,2,3,4-tetrahydroisoquinoline-2-carboxylate The triflate from Preparation 1c (610 mg, 1.49 mmol), the boronic ester from Preparation 4e (910 mg, 1.79 mmol) and potassium carbonate (412 mg, 2.98 mmol) are dissolved in THF/Water and degassed (nitrogen bubbling) for 15 mins. To this is added tetrakis(triphenylphosphine)palladium(0) (5 mol %) and the resultant mixture is stirred at room temperature for 45 min. The reaction is diluted with ethyl acetate, washed with water followed by brine, and the organics dried over magnesium sulphate and evaporated under reduced pressure. The crude product thus obtained is purified on CombiFlash (40 g silica; isohexane to ethyl acetate), affording the desired product.

LC/MS ($C_{37}H_{49}N_3O_5Si$) 644 [M+H]$^+$; RT 1.71 (Method B)

Step B: 2-tert-Butyl 7-methyl 6-{1-[(4-hydroxyphenyl)(methyl)carbamoyl]-5,6,7,8-tetrahydroindolizin-3-yl}-1,2,3,4-tetrahydroisoquinoline-2,7-dicarboxylate The procedure is as in Step B of Preparation 1a, replacing the 2:1 isomer mixture of tert-butyl 7-formyl-6-hydroxy-1,2,3,4-tetrahydroisoquinoline-2-carboxylate and tert-butyl 5-formyl-6-hydroxy-1,2,3,4-tetrahydroisoquinoline-2-carboxylate with tert-butyl 6-[1-({4-[(tert-butyldimethylsilyl)oxy]phenyl}(methyl)carbamoyl)-5,6,7,8-tetrahydroindolizin-3-yl]-7-formyl-1,2,3,4-tetrahydroisoquinoline-2-carboxylate. The reaction was heated at 45° C. external temperature for 24 h to facilitate completion of the observed partial de-silylation.

Step C: 2-[(tert-Butoxy)carbonyl]-6-{1-[(4-hydroxyphenyl)(methyl)carbamoyl]-5,6,7,8-tetrahydroindolizin-3-yl}-1,2,3,4-tetrahydroisoquinoline-7-carboxylic acid The procedure is as in Step B of Preparation 5a, replacing 2-tert-butyl 7-methyl 6-(1-{[(4-(benzyloxy)phenyl](methyl)carbamoyl}-5,6,7,8-tetrahydroindolizin-3-yl)-1,2,3,4-tetrahydroisoquinoline-2,7-dicarboxylate with 2-tert-butyl 7-methyl 6-{1-[(4-hydroxyphenyl)(methyl)carbamoyl]-5,6,7,8-tetrahydroindolizin-3-yl}-1,2,3,4-tetrahydroisoquinoline-2,7-dicarboxylate.

Preparation 5f: 2-tert-butyl 7-lithio 6-(4-{[4-(benzyloxy)phenyl](ethyl)carbamoyl}-1,5-dimethyl-1H-pyrrol-2-yl)-1,2,3,4-tetrahydroisoquinoline-2,7-dicarboxylate The procedure is as in Preparation 5b, replacing N-[4-(benzyloxy)phenyl]-N,1,2-trimethyl-5-(tetramethyl-1,3,2-dioxaborolan-2-yl)-1H-pyrrole-3-carboxamide with the product from Procedure 4g.

LC/MS ($C_{37}H_{41}N_3O_6$) 624 [M+H]$^+$; RT 1.50 (Method B)

Preparation 5g: 2-tert-butyl 7-lithio 6-(4-{[4-(benzyloxy)phenyl](propyl)carbamoyl}-1,5-dimethyl-1H-pyrrol-2-yl)-1,2,3,4-tetrahydroisoquinoline-2,7-dicarboxylate The procedure is as in Preparation 5b, replacing N-[4-(benzyloxy)phenyl]-N,1,2-trimethyl-5-(tetramethyl-1,3,2-dioxaborolan-2-yl)-1H-pyrrole-3-carboxamide with the product from Procedure 4h.

LC/MS ($C_{38}H_{43}N_3O_6$) 638 [M+H]$^+$; RT 1.54 (Method B)

Preparation 6aa: N-[4-(Benzyloxy)phenyl]-N-methyl-3-{7-[(3S)-3-(morpholin-4-ylmethyl)-1,2,3,4-tetrahydroisoquinoline-2-carbonyl]-1,2,3,4-tetrahydroisoquinolin-6-yl}-5,6,7,8-tetrahydroindolizine-1-carboxamide, bis-trifluoroacetic acid salt Step A: tert-Butyl 6-(1-{[4-(benzyloxy)phenyl](methyl)carbamoyl}-5,6,7,8-tetrahydroindolizin-3-yl)-7-[(3S)-3-(morpholin-4-ylmethyl)-1,2,3,4-tetrahydroisoquinoline-2-carbonyl]-1,2,3,4-tetrahydroisoquinoline-2-carboxylate To a solution of the acid obtained in Preparation 5a (150 mg, 0.24 mmol) in N,N-dimethylformamide (2 mL) is added triethylamine (0.13 mL, 0.96 mmol), HBTU (91 mg, 0.24 mmol) and the (3S)-3-(morpholin-4-ylmethyl)-1,2,3,4-tetrahydroisoquinoline dihydrochloride obtained in Preparation 2a (72 mg, 0.24 mmol). The reaction is stirred at room temperature for 15 minutes and then diluted with water, and the resulting suspension stirred. The product is then extracted with ethyl acetate and the organic extract dried over magnesium sulphate, filtered and concentrated. The crude material is purified on CombiFlash (12 g silica, dichloromethane to 4% methanol/dichloromethane) and then dried in vacuo to obtain the product as a glassy solid.

LC/MS ($C_{52}H_{59}N_5O_6$) 850 [M+H]$^+$; RT 1.49 (Method B)

Step B: N-[4-(Benzyloxy)phenyl]-N-methyl-3-{7-[(3S)-3-(morpholin-4-ylmethyl)-1,2,3,4-tetrahydroisoquinoline-2-carbonyl]-1,2,3,4-tetrahydroisoquinolin-6-yl}-5,6,7,8-tetrahydroindolizine-1-carboxamide, bis-trifluoroacetic acid salt The Boc-protected material obtained in Step A (173 mg, 0.2 mmol) is dissolved in dichloromethane (10 mL) and to this is added trifluoroacetic acid (1 mL). The reaction is allowed to stir for 1 hour at ambient temperature and then concentrated in vacuo. The residue is triturated in diethyl ether to afford a precipitate which is filtered off and dried under vacuum.

LC/MS ($C_{47}H_{51}N_5O_4$) 750 [M+H]$^+$; RT 1.10 (Method B)

Preparation 6ab: N-[4-(Benzyloxy)phenyl]-N-methyl-3-{7-[(3R)-3-methyl-1,2,3,4-tetrahydroisoquinoline-2-carbonyl]-1,2,3,4-tetrahydroisoquinolin-6-yl}-5,6,7,8-tetrahydroindolizine-1-carboxamide; trifluoroacetic acid salt Step A: tert-Butyl 6-(1-{[4-(benzyloxy)phenyl](methyl)carbamoyl}-5,6,7,8-tetrahydroindolizin-3-yl)-7-[(3R)-3-methyl-1,2,3,4-tetrahydroisoquinoline-2-carbonyl]-1,2,3,4-tetrahydroisoquinoline-2-carboxylate To a stirring solution of the acid obtained from Preparation 5a (0.87 g, 1.36 mmol) in DMF (10 mL) was added diisopropylethylamine (0.47 mL, 2.72 mmol) and (3R)-3-methyl-1,2,3,4-tetrahydroisoquinoline from Preparation 2b (210 mg, 1.43 mmol) followed by HBTU (516 mg, 1.36 mmol). The reaction was stirred for 1 h, then diluted with water and extracted with ethyl acetate. The organic extracts were sequentially washed with aqueous sodium bicarbonate and brine, then dried over magnesium sulphate and evaporated in vacuo. The crude product was taken-up in dichloromethane, loaded onto isolute and purified on CombiFlash (40 g silica, isohexane to ethyl acetate gradient) to afford the desired product as a foam.

LC/MS ($C_{48}H_{52}N_4O_5$) 765 [M+H]$^+$; RT 1.62 (Method B)

Step B: N-[4-(Benzyloxy)phenyl]-N-methyl-3-{7-[(3R)-3-methyl-1,2,3,4-tetrahydroisoquinoline-2-carbonyl]-1,2,3,4-tetrahydroisoquinolin-6-yl}-5,6,7,8-tetrahydroindolizine-1-carboxamide; trifluoroacetic acid salt The Boc-protected product from Step A (0.90 g, 1.18 mmol) was dissolved in dichloromethane (10 mL) and to this was added TFA (1 mL). The reaction was stirred for 1 h, then solvent was removed under reduced pressure, and residual solvent was removed under high vacuum. Addition of ether to the resultant oil induced the oil to solidify. The mixture was stirred for 45 min, then cooled, filtered, and washed with cold ether to afford the desired product. Concentration of the filtrate afforded further solid product. The combined solids were dried under vacuum to afford the product.

LC/MS ($C_{43}H_{44}N_4O_3$) 665 [M+H]$^+$; RT 1.24 (Method B)

Preparation 6ba: N-[4-(Benzyloxy)phenyl]-N,1,2-trimethyl-5-{7-[(3S)-3-(morpholin-4-ylmethyl)-1,2,3,4-tetrahydroisoquinoline-2-carbonyl]-1,2,3,4-tetrahydroisoquinolin-6-yl}-1H-pyrrole-3-carboxamide; bis trifluoroacetic acid salt Step A: tert-Butyl 6-(4-{[4-(benzyloxy)phenyl](methyl)carbamoyl}-1,5-dimethyl-1H-pyrrol-2-yl)-7-[(3S)-3-(morpholin-4-ylmethyl)-1,2,3,4-tetrahydroisoquinoline-2-carbonyl]-1,2,3,4-tetrahydroisoquinoline-2-carboxylate The lithium salt from Preparation 5b (1.07 g, 1.74 mmol) is taken-up in DMF (10 mL) and to this is added triethylamine (0.97 ml, 6.96 mmol), HBTU (660 mg, 1.74 mmol), and the (3S)-3-(morpholin-4-ylmethyl)-1,2,3,4-tetrahydroisoquinoline dihydrochloride obtained in Preparation 2a (0.58 g, 1.91 mmol) and the resultant mixture is then stirred for 15 minutes at ambient temperature. The reaction is diluted with water and extracted with ethyl acetate. The organic extract is dried over magnesium sulphate, filtered and concentrated. The crude material is taken up in dichloromethane, loaded onto isolute and purified on CombiFlash (40 g silica, dichloromethane to 5% MeOH/dichloromethane) to afford the desired product.

LC/MS ($C_{50}H_{57}N_5O_6$) 824 [M+H]$^+$; RT 1.44 (Method B)

Step B: N-[4-(Benzyloxy)phenyl]-N,1,2-trimethyl-5-{7-[(3S)-3-(morpholin-4-ylmethyl)-1,2,3,4-tetrahydroisoquinoline-2-carbonyl]-1,2,3,4-tetrahydroisoquinolin-6-yl}-1H-pyrrole-3-carboxamide; bis trifluoroacetic acid salt The Boc-protected product from Step A (705 mg, 0.86 mmol) is dissolved in dichloromethane and to this is added trifluoroacetic acid (1.33 ml). The resultant mixture is then allowed to stir at ambient temperature for ca 16 h. The reaction is concentrated in vacuo and the residue triturated with ether to afford a precipitate which is filtered and dried under vacuum to yield the desired product.

LC/MS ($C_{45}H_{49}N_5O_4$) 724 [M+H]$^+$; RT 1.07 (Method B)

Preparation 6bb: N-[4-(Benzyloxy)phenyl]-N,1,2-trimethyl-5-{7-[(3R)-3-methyl-1,2,3,4-tetrahydroisoquinoline-2-carbonyl]-1,2,3,4-tetrahydroisoquinolin-6-yl}-1H-pyrrole-3-carboxamide; trifluoroacetic acid salt The procedure is as in Preparation 6ba, replacing (3S)-3-(morpholin-4-ylmethyl)-1,2,3,4-tetrahydroisoquinoline dihydrochloride in Step A with (3R)-3-methyl-1,2,3,4-tetrahydroisoquinoline from Preparation 2b.

LC/MS ($C_{41}H_{42}N_4O_3$) 639 [M+H]$^+$; RT 1.18 (Method B)

Preparation 6bc: N-[4-(Benzyloxy)phenyl]-N,1,2-trimethyl-5-{7-[(3S)-3-[2-(morpholin-4-yl)ethyl]-1,2,3,4-tetrahydroisoquinoline-2-carbonyl]-1,2,3,4-tetrahydroisoquinolin-6-yl}-1H-pyrrole-3-carboxamide; bis-trifluoroacetic acid salt The procedure is as in Preparation 6ba, replacing (3S)-3-(morpholin-4-ylmethyl)-1,2,3,4-tetrahydroisoquinoline dihydrochloride in Step A with (3S)-3-[2-(morpholin-4-yl)ethyl]-1,2,3,4-tetrahydroisoquinoline dihydrochloride obtained from Preparation 2d.

LC/MS ($C_{46}H_{51}N_5O_4$) 738 [M+H]$^+$; RT 1.07 (Method B)

Preparation 6bd: N-[4-(Benzyloxy)phenyl]-N,1,2-trimethyl-5-{7-[(3R)-3-[3-(morpholin-4-yl)propyl]-1,2,3,4-tetrahydroisoquinoline-2-carbonyl]-1,2,3,4-tetrahydroisoquinolin-6-yl}-1H-pyrrole-3-carboxamide The procedure is as in Preparation 6ba, replacing (3S)-3-(morpholin-4-ylmethyl)-1,2,3,4-tetrahydroisoquinoline dihydrochloride in Step A with (3R)-3-[3-(morpholin-4-yl)propyl]-1,2,3,4-tetrahydroisoquinoline dihydrochloride from Preparation 2f. The intermediate was isolated as the free base.

LC/MS ($C_{47}H_{53}N_5O_4$) 752 [M+H]$^+$; RT 1.03 (Method B)

Preparation 6be: N-[4-(Benzyloxy)phenyl]-5-{7-[(3S)-3-[(dimethylamino)methyl]-1,2,3,4-tetrahydroisoquinoline-2-carbonyl]-1,2,3,4-tetrahydroisoquinolin-6-yl}-N,1,2-trimethyl-1H-pyrrole-3-carboxamide; bis-trifluoroacetic acid salt The procedure is as in Preparation 6ba, replacing (3S)-3-(morpholin-4-ylmethyl)-1,2,3,4-tetrahydroisoquinoline dihydrochloride in Step A with dimethyl[(3S)-1,2,3,4-tetrahydroisoquinolin-3-ylmethyl]amine dihydrochloride from Preparation 2g.

LC/MS ($C_{43}H_{47}N_5O_3$) 682 [M+H]$^+$; RT 1.02 (Method B)

Preparation 6bf: N-[4-(Benzyloxy)phenyl]-N,1,2-trimethyl-5-{7-[(3S)-3-[(4-methylpiperazin-1-yl)methyl]-1,2,3,4-tetrahydroisoquinoline-2-carbonyl]-1,2,3,4-tetrahydroisoquinolin-6-yl}-1H-pyrrole-3-carboxamide; tris-trifluoroacetic acid salt The procedure is as in Preparation 6ba, replacing (3S)-3-(morpholin-4-ylmethyl)-1,2,3,4-tetrahydroisoquinoline dihydrochloride in Step A with (3S)-3-[(4-methylpiperazin-1-yl)methyl]-1,2,3,4-tetrahydroisoquinoline trihydrochloride from Preparation 2h.

LC/MS ($C_{46}H_{52}N_6O_3$) 737 [M+H]$^+$; RT 1.04 (Method B)

Preparation 6ca: N,1,2-Trimethyl-5-{7-[(3S)-3-(morpholin-4-ylmethyl)-1,2,3,4-tetrahydroisoquinoline-2-carbonyl]-1,2,3,4-tetrahydroisoquinolin-6-yl}-N-phenyl-1H-pyrrole-3-carboxamide; bis-trifluoroacetic acid salt The procedure is as in Preparation 6ba, replacing 2-tert-butyl 7-lithio 6-(4-{[4-(benzyloxy)phenyl](methyl)carbamoyl}-1,5-dimethyl-1H-pyrrol-2-yl)-1,2,3,4-tetrahydroisoquinoline-2,7-dicarboxylate in Step A with 2-[(tert-butoxy)

carbonyl]-6-{1,5-dimethyl-4-[methyl(phenyl)carbamoyl]-1H-pyrrol-2-yl}-1,2,3,4-tetrahydroisoquinoline-7-carboxylic acid from Preparation 5c.
LC/MS ($C_{38}H_{43}N_5O_3$) 618 [M+H]$^+$; RT 0.93 (Method B)

Preparation 6cb: N,1,2-Trimethyl-5-{7-[(3R)-3-methyl-1,2,3,4-tetrahydroisoquinoline-2-carbonyl]-1,2,3,4-tetrahydroisoquinolin-6-yl}-N-phenyl-1H-pyrrole-3-carboxamide; trifluoroacetic acid salt The procedure is as in Preparation 6ba, replacing (3S)-3-(morpholin-4-ylmethyl)-1,2,3,4-tetrahydroisoquinoline dihydrochloride in Step A with (3R)-3-methyl-1,2,3,4-tetrahydroisoquinoline from Preparation 2b; and replacing 2-tert-butyl 7-lithio 6-(4-{[4-(benzyloxy)phenyl](methyl)carbamoyl}-1,5-dimethyl-1H-pyrrol-2-yl)-1,2,3,4-tetrahydroisoquinoline-2,7-dicarboxylate in Step A with 2-[(tert-butoxy)carbonyl]-6-{1,5-dimethyl-4-[methyl(phenyl)carbamoyl]-1H-pyrrol-2-yl}-1,2,3,4-tetrahydroisoquinoline-7-carboxylic acid from Preparation 5c.

Preparation 6cd: N,1,2-Trimethyl-5-{7-[(3R)-3-[3-(morpholin-4-yl)propyl]-1,2,3,4-tetrahydroisoquinoline-2-carbonyl]-1,2,3,4-tetrahydroisoquinolin-6-yl}-N-phenyl-1H-pyrrole-3-carboxamide The procedure is as in Preparation 6ba, replacing (3S)-3-(morpholin-4-ylmethyl)-1,2,3,4-tetrahydroisoquinoline dihydrochloride in Step A with (3R)-3-[3-(morpholin-4-yl)propyl]-1,2,3,4-tetrahydroisoquinoline dihydrochloride from Preparation 2f; and replacing 2-tert-butyl 7-lithio 6-(4-{[4-(benzyloxy)phenyl](methyl)carbamoyl}-1,5-dimethyl-1H-pyrrol-2-yl)-1,2,3,4-tetrahydroisoquinoline-2,7-dicarboxylate in Step A with 2-[(tert-Butoxy)carbonyl]-6-{1,5-dimethyl-4-[methyl(phenyl)carbamoyl]-1H-pyrrol-2-yl}-1,2,3,4-tetrahydroisoquinoline-7-carboxylic acid from Preparation 5c. The intermediate was isolated as the free base.
LC/MS ($C_{40}H_{47}N_5O_3$) 646 [M+H]$^+$; RT 0.91 (Method B)

Preparation 6ce: N,1,2-trimethyl-5-{7-[(3S)-3-[(4-methylpiperazin-1-yl)methyl]-1,2,3,4-tetrahydroisoquinoline-2-carbonyl]-1,2,3,4-tetrahydroisoquinolin-6-yl}-N-phenyl-1H-pyrrole-3-carboxamide; tris-trifluoroacetic acid salt The procedure is as in Preparation 6ba, replacing (3S)-3-(morpholin-4-ylmethyl)-1,2,3,4-tetrahydroisoquinoline dihydrochloride in Step A with (3S)-3-[(4-methylpiperazin-1-yl)methyl]-1,2,3,4-tetrahydroisoquinoline trihydrochloride from Preparation 2h, and replacing 2-tert-butyl 7-lithio 6-(4-{[4-(benzyloxy)phenyl](methyl)carbamoyl}-1,5-dimethyl-1H-pyrrol-2-yl)-1,2,3,4-tetrahydroisoquinoline-2,7-dicarboxylate in Step A with 2-[(tert-butoxy)carbonyl]-6-{1,5-dimethyl-4-[methyl(phenyl)carbamoyl]-1H-pyrrol-2-yl}-1,2,3,4-tetrahydroisoquinoline-7-carboxylic acid from Preparation 5c.
LC/MS ($C_{39}H_{46}N_6O_2$) 631 [M+H]$^+$; RT 0.91 (Method B)

Preparation 6da: N,N-Dibutyl-1,2-dimethyl-5-{7-[(3S)-3-(morpholin-4-ylmethyl)-1,2,3,4-tetrahydroisoquinoline-2-carbonyl]-1,2,3,4-tetrahydroisoquinolin-6-yl}-1H-pyrrole-3-carboxamide; bis-trifluoroacetic acid salt The procedure is as in Preparation 6ba, replacing 2-tert-butyl 7-lithio 6-(4-{[4-(benzyloxy)phenyl](methyl)carbamoyl}-1,5-dimethyl-1H-pyrrol-2-yl)-1,2,3,4-tetrahydroisoquinoline-2,7-dicarboxylate in Step A with 2-tert-butyl 7-lithio 6-[4-(dibutylcarbamoyl)-1,5-dimethyl-1H-pyrrol-2-yl]-1,2,3,4-tetrahydroisoquinoline-2,7-dicarboxylate from Preparation 5d.
LC/MS ($C_{39}H_{53}N_5O_3$) 640 [M+H]$^+$; RT 1.10 (Method B)

Preparation 6db: N,N-Dibutyl-1,2-dimethyl-5-{7-[(3R)-3-methyl-1,2,3,4-tetrahydroisoquinoline-2-carbonyl]-1,2,3,4-tetrahydroisoquinolin-6-yl}-1H-pyrrole-3-carboxamide; trifluoroacetic acid salt The procedure is as in Preparation 6ba, replacing (3S)-3-(morpholin-4-ylmethyl)-1,2,3,4-tetrahydroisoquinoline dihydrochloride in Step A with (3R)-3-methyl-1,2,3,4-tetrahydroisoquinoline from Preparation 2b; and replacing 2-tert-butyl 7-lithio 6-(4-{[4-(benzyloxy)phenyl](methyl)carbamoyl}-1,5-dimethyl-1H-pyrrol-2-yl)-1,2,3,4-tetrahydroisoquinoline-2,7-dicarboxylate in Step A with 2-tert-butyl 7-lithio 6-[4-(dibutylcarbamoyl)-1,5-dimethyl-1H-pyrrol-2-yl]-1,2,3,4-tetrahydroisoquinoline-2,7-dicarboxylate from Preparation 5d.

Preparation 6dc: N,N-Dibutyl-1,2-dimethyl-5-[7-(1,2,3,4-tetrahydroisoquinoline-2-carbonyl)-1,2,3,4-tetrahydroisoquinolin-6-yl]-1H-pyrrole-3-carboxamide The procedure is as in Preparation 6ba, replacing (3S)-3-(morpholin-4-ylmethyl)-1,2,3,4-tetrahydroisoquinoline dihydrochloride in Step A with tetrahydroisoquinoline; and neutralising the product solution in Step B with dilute aqueous sodium hydroxide solution.
LC/MS ($C_{34}H_{44}N_4O_2$) 541 [M+H]$^+$; RT 1.14 (Method B)

Preparation 6e: N-(4-Hydroxyphenyl)-N-methyl-3-{7-[(3S)-3-(morpholin-4-ylmethyl)-1,2,3,4-tetrahydroisoquinoline-2-carbonyl]-1,2,3,4-tetrahydroisoquinolin-6-yl}-5,6,7,8-tetrahydroindolizine-1-carboxamide dihydrochloride Step A: tert-Butyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Step A of Preparation 6aa, replacing 6-(1-{[4-(benzyloxy)phenyl](methyl)carbamoyl}-5,6,7,8-tetrahydroindolizin-3-yl)-2-[(tert-butoxy)carbonyl]-1,2,3,4-tetrahydroisoquinoline-7-carboxylic acid in Step A with 2-[(tert-butoxy)carbonyl]-6-{1-[(4-hydroxyphenyl)(methyl)carbamoyl]-5,6,7,8-tetrahydroindolizin-3-yl}-1,2,3,4-tetrahydroisoquinoline-7-carboxylic acid from Preparation 5e.
LC/MS ($C_{45}H_{53}N_5O_6$) 760 [M+H]$^+$; RT 1.25 (Method B)

Step B: N-(4-Hydroxyphenyl)-N-methyl-3-{7-[(3S)-3-(morpholin-4-ylmethyl)-1,2,3,4-tetrahydroisoquinoline-2-carbonyl]-1,2,3,4-tetrahydroisoquinolin-6-yl}-5,6,7,8-tetrahydroindolizine-1-carboxamide dihydrochloride The compound obtained in Step A (135 mg, 0.18 mmol) is dissolved in ethyl acetate (6.75 mL) and to this concentrated HCl (148 uL, 1.78 mmol) is added and allowed to stir for 30 minutes. Minimal IPA is then added dropwise to encourage precipitation. The solid is then filtered off, washed with ethyl acetate and dried under vacuum overnight to afford a solid.

LC/MS ($C_{40}H_{45}N_5O_4$) 660 [M+H]$^+$; RT 0.89 (Method B)

Preparation 6f: N-[4-(Benzyloxy)phenyl]-N-ethyl-1,2-dimethyl-5-{7-[(3S)-3-(morpholin-4-ylmethyl)-1,2,3,4-tetrahydroisoquinoline-2-carbonyl]-1,2,3,4-tetrahydroisoquinolin-6-yl}-1H-pyrrole-3-carboxamide The procedure is as in Preparation 6ba, replacing 2-tert-butyl 7-lithio 6-(4-{[4-(benzyloxy)phenyl](methyl)carbamoyl}-1,5-dimethyl-1H-pyrrol-2-yl)-1,2,3,4-tetrahydroisoquinoline-2,7-dicarboxylate in Step A with 2-tert-butyl 7-lithio 6-(4-{[4-(benzyloxy)phenyl](ethyl)carbamoyl}-1,5-dimethyl-1H-pyrrol-2-yl)-1,2,3,4-tetrahydroisoquinoline-2,7-dicarboxylate from Preparation 5f; and neutralising the product solution in Step B with dilute aqueous sodium hydroxide solution.

LC/MS ($C_{46}H_{51}N_5O_4$) 738 [M+H]$^+$; RT 1.08 (Method B)

Preparation 6g: N-[4-(Benzyloxy)phenyl]-1,2-dimethyl-5-{7-[(3S)-3-(morpholin-4-ylmethyl)-1,2,3,4-tetrahydroisoquinoline-2-carbonyl]-1,2,3,4-tetrahydroisoquinolin-6-yl}-N-propyl-1H-pyrrole-3-carboxamide The procedure is as in Preparation 6ba, replacing 2-tert-butyl 7-lithio 6(4-{[4-(benzyloxy)phenyl](methyl)carbamoyl}-1,5-dimethyl-1H-pyrrol-2-yl)-1,2,3,4-tetrahydroisoquinoline-2,7-dicarboxylate in Step A with 2-tert-butyl 7-lithio 6(4-{[4-(benzyloxy)phenyl](propyl)carbamoyl}-1,5-dimethyl-1H-pyrrol-2-yl)-1,2,3,4-tetrahydroisoquinoline-2,7-dicarboxylate from Preparation 5g; and neutralising the product solution in Step B with dilute aqueous sodium hydroxide solution.

LC/MS ($C_{47}H_{53}N_5O_4$) 752 [M+H]$^+$; RT 1.17 (Method B)

Preparation 6h: N-[4-(Benzyloxy)phenyl]-N-butyl-1,2-dimethyl-5-{7-[(3S)-3-(morpholin-4-ylmethyl)-1,2,3,4-tetrahydroisoquinoline-2-carbonyl]-1,2,3,4-tetrahydroisoquinolin-6-yl}-1H-pyrrole-3-carboxamide Step A: N-[4-(benzyloxy)phenyl]-N-butyl-1,2-dimethyl-5-{7-[(3S)-3-(morpholin-4-ylmethyl)-1,2,3,4-tetrahydroisoquinoline-2-carbonyl]-2-(trifluoroacetyl)-1,2,3,4-tetrahydroisoquinolin-6-yl}-1H-pyrrole-3-carboxamide A solution of tetrahydrofuran/water (5:1, 7 mL) was degassed for 20 min. To a mixture of the boronate ester from Preparation 4i (246 mg, 0.49 mmol) and the bromide from Preparation 1ha (332.78 mg, 0.59 mmol) followed by 7 mL of the stock solution. This was degassed for a further 5 min and to this solution was added cesium carbonate (319.05 mg, 0.98 mmol, 2 eq) and bis(di-tert-butyl(4-dimethylaminophenyl)phosphine) dichloropalladium(ii) (17.33 mg, 0.02 mmol, 0.05 eq) and then heated to 95° C. in the microwave for 40 min. The reaction was diluted in ethyl acetate and washed with brine. The organic extract was dried over magnesium sulfate and concentrated in vacuo, and adsorbed onto isolute and purified on CombiFlash (12 g silica, dichloromethane to 4% methanol in dichloromethane).

LC/MS ($C_{50}H_{54}F_3N_5O_5$) 862 [M+H]$^+$; RT 1.53 (Method B)

Step B: N-[4-(benzyloxy)phenyl]-N-butyl-1,2-dimethyl-5-{7-[(3S)-3-(morpholin-4-ylmethyl)-1,2,3,4-tetrahydroisoquinoline-2-carbonyl]-1,2,3,4-tetrahydroisoquinolin-6-yl}-1H-pyrrole-3-carboxamide To a solution of the product from Step A (138 mg, 0.16 mmol) in ethanol (6 mL) was added a solution of potassium carbonate (132.75 mg, 0.96 mmol) in water (1.2 mL) and the mixture was allowed to stir at reflux for 1 h. The reaction was allowed to cool to ambient temperature and the organic solvent was concentrated in vacuo. The solution left behind was washed with Ethyl Acetate. The organic phase was washed with water and saturated sodium chloride. The organic extract was dried over magnesium sulfate and concentrated in vacuo. The product was used directly in the next step assuming quantitative transformation.

LC/MS ($C_{48}H_{55}N_5O_4$) 766 [M+H]$^+$; RT 1.23 (Method B)

Preparation 7aa: N-[4-(Benzyloxy)phenyl]-N-methyl-3-{6-[(3S)-3-(morpholin-4-ylmethyl)-1,2,3,4-tetrahydroisoquinoline-2-carbonyl]-2,3-dihydro-1H-isoindol-5-yl}-5,6,7,8-tetrahydroindolizine-1-carboxamide Step A: tert-Butyl 5-(1-{[4-(benzyloxy)phenyl](methyl)carbamoyl}-5,6,7,8-tetrahydroindolizin-3-yl)-6-[(3S)-3-(morpholin-4-ylmethyl)-1,2,3,4-tetrahydroisoquinoline-2-carbonyl]-2,3-dihydro-1H-isoindole-2-carboxylate A mixture of bromide from Preparation 1e (845 mg, 1.45 mmol), the boronic ester from Preparation 4a (886 mg, 1.82 mmol) and cesium carbonate (991 mg, 3.04 mmol) in THF (9.0 mL) and water (3.6 mL) is degassed by purging with nitrogen, followed by bubbling nitrogen through for 5 min. The mixture is heated to 60° C., at which point the PdCl$_2$(Ata-Phos)$_2$ catalyst (54 mg, 0.08 mmol) is added and the reaction is allowed to stir for 3 h.

The mixture is allowed to cool to ambient temperature, then diluted with ethyl acetate, and washed sequentially with water and brine. The organic phase is dried over magnesium sulphate, and concentrated in vacuo.

The crude material was purified on by flash column chromatography (40 g silica; dichloromethane to 5% MeOH/dichloromethane) to afford the product as a glassy solid.

LC/MS ($C_{51}H_{57}N_5O_6$) 836 [M+H]$^+$; RT 1.53 (Method B)

Step B: N-[4-(Benzyloxy)phenyl]-N-methyl-3-{6-[(3S)-3-(morpholin-4-ylmethyl)-1,2,3,4-tetrahydroisoquinoline-2-carbonyl]-2,3-dihydro-1H-isoindol-5-yl}-5,6,7,8-tetrahydroindolizine-1-carboxamide To a stirred solution of the product from Step A (850 mg, 1.02 mmol) in dichloromethane (20 mL) is added trifluoroacetic acid (5 mL) and the mixture is stirred for 1 h. Water is added, followed by 2N aqueous sodium hydroxide solution until the aqueous phase was basic. The organic phase is then separated, dried over magnesium sulphate, and concentrated in vacuo to afford the product as a solid.

LC/MS ($C_{46}H_{49}N_5O_4$) 736 [M+H]$^+$; RT 1.12 (Method B)

Preparation 7ab: N-[4-(Benzyloxy)phenyl]-N-methyl-3-{6-[(3R)-3-methyl-1,2,3,4-tetrahydroisoquinoline-2-carbonyl]-2,3-dihydro-1H-isoindol-5-yl}-5,6,7,8-tetrahydroindolizine-1-carboxamide; trifluoroacetic acid salt Step A: tert-Butyl 5-(1-[{4-(benzyloxy)phenyl]methyl)carbamoyl}-5,6,7,8-tetrahydroindolizin-3-yl)-6-[(3R)-3-methyl-1,2,3,4-tetrahydroisoquinoline-2-carbonyl]-2,3-dihydro-1H-isoindole-2-carboxylate A mixture of THF (20 mL) and water (8 mL) is degassed by multiple evacuation/nitrogen purge cycles and bubbling nitrogen through the mix. 20 mL of this mixture is subsequently added via syringe to a mixture of the bromide from Preparation 1f (0.88 g, 1.87 mmol), the boronic ester from Preparation 4a (1.09 g, 2.25 mmol) and cesium carbonate (1.22 g, 3.74 mmol) under nitrogen. $PdCl_2(Ata-Phos)_2$ (66 mg, 0.09 mmol) is then added and the reaction is immediately heated under microwave irradiation at 95° C. for 20 min.

The reaction mixture is diluted with ethyl acetate (100 mL) and sequentially washed with water (2×50 mL), then saturated NaCl (aq) (2×50 mL), dried over magnesium sulphate, filtered and concentrated in vacuo. The crude product was purified by flash chromatography (Combiflash, 80 g, eluting with gradient 0 to 80% ethyl acetate in hexane) to afford the product as a foam.

LC/MS ($C_{47}H_{50}N_4O_5$) 751 [M+H]$^+$; RT 1.61 (Method B)

Step B: N-[4-(Benzyloxy)phenyl]-N-methyl-3-{6-[(3R)-3-methyl-1,2,3,4-tetrahydroisoquinoline-2-carbonyl]-2,3-dihydro-1H-isoindol-5-yl}-5,6,7,8-tetrahydroindolizine-1-carboxamide; trifluoroacetic acid salt To a solution of the product from Step A (152 mg, 0.20 mmol) in dichloromethane (3 mL) is added trifluoroacetic acid (0.7 mL) and the reaction is stirred at ambient temperature for ca 16 h. Solvent was removed in vacuo and the resulting solid is triturated with ether collected by filtration.

LC/MS ($C_{42}H_{42}N_4O_3$) 651 [M+H]$^+$; RT 2.39 (Method A)

Preparation 7ba: N-(4-Benzyloxyphenyl)-N,1,2-trimethyl-5-[6-[(3S)-3-(morpholinomethyl)-3,4-dihydro-1H-isoquinoline-2-carbonyl]isoindolin-5-yl]pyrrole-3-carboxamide hydrochloride Step A: tert-Butyl 5-bromo-6-[(3S)-3-(morpholinomethyl)-3,4-dihydro-1H-isoquinoline-2-carbonyl]isoindoline-2-carboxylate 6-Bromo-2-tert-butoxycarbonyl-isoindoline-5-carboxylic acid (0.70 g), TBTU (0.823 g) and DMAP (25 mg) was dissolved dichloromethane (35 ml) and diisopropylethylamine (1.75 ml) was added. After 3 minutes stirring at room temperature 4-[[(3S)-1,2,3,4-tetrahydroisoquinolin-3-yl]methyl]morpholine hydrochloride (0.656 g) was added and stirred for 1 h. After the completion of the reaction it was diluted with dichloromethane (100 ml) and washed with water (50 ml), dried over sodium sulfate and evaporated. The crude product was purified by flash chromatography over silicagel (dichloromethane/methanol, gradient 1-10%) to give the title compound.

High-Resolution Mass (ESI+):
Empirical formula: $C_{28}H_{34}BrN_3O_4$
[M+H]$^+$ calculated: 556.1813
[M+H]$^+$ measured: 556.1790
IR v: C—H: 2930 cm$^{-1}$; >C=O: 1697, 1635 cm$^{-1}$; C—O—C: 1113 cm$^{-1}$ Step B: tert-Butyl 5-[4-[(4-benzyloxyphenyl)-methyl-carbamoyl]-1,5-dimethyl-pyrrol-2-yl]-6-[(3S)-3-(morpholinomethyl)-3,4-dihydro-1H-isoquinoline-2-carbonyl]isoindoline-2-carboxylate The product from Step A (284 mg, 0.51 mmol) and N-(4-benzyloxyphenyl)-N,1,2-trimethyl-pyrrole-3-carboxamide (205 mg, 0.61 mmol) from Step C of Preparation 4b were dissolved in dimethylacetamide (5 mL) then nitrogen was bubbled through the solution for 5 min. Potassium acetate (0.11 g, 1.12 mmol) and bis(triphenylphosphine)palladium(II) dichloride (20 mg) were added to the mixture then it was heated up to 140° C. then after 20 min stirring water (20 μL) was added. Stirring at 140° C. under nitrogen atmosphere was continued for additional 16 hours. The reaction mixture was allowed to cool to room temperature then evaporated. The residue was partitioned between dichloromethane (50 mL) and water (10 mL). The organic phase was washed with water (10 mL), dried over $Na_2SO_4$ and evaporated. The crude product was purified by flash chromatography over silicagel (dichloromethane/methanol, gradient 1-10%) to give the title compound.

Step C: N-(4-benzyloxyphenyl)-N,1,2-trimethyl-5-[6-[(3S)-3-(morpholinomethyl)-3,4-dihydro-1H-isoquinoline-2-carbonyl]isoindolin-5-yl]pyrrole-3-carboxamide hydrochloride The product from Step B (140 mg) was stirred in a 4M HCl in dioxane (15 ml) solution for 30 min at room temperature. After the completion of the reaction all the solvents were removed to yield 170 mg of the title product.

Preparation 7bb: N-[4-(Benzyloxy)phenyl]-N,1,2-trimethyl-5-{6-[(3R)-3-methyl-1,2,3,4-tetrahydroisoquinoline-2-carbonyl]-2,3-dihydro-1H-isoindol-5-yl}-1H-pyrrole-3-carboxamide Step A: tert-Butyl 5-(4-{[4-(benzyloxy)phenyl](methyl)carbamoyl}-1,5-dimethyl-1H-pyrrol-2-yl)-6-[(3R)-3-methyl-1,2,3,4-tetrahydroisoquinoline-2-carbonyl]-2,3-dihydro-1H-isoindole-2-carboxylate A mixture of N-[4-(Benzyloxy)phenyl]-N,1,2-trimethyl-1H-pyrrole-3-carboxamide from Step C of Preparation 4b (150 mg, 0.45 mmol), the bromide from Preparation 1f (317 mg, 0.67 mmol), potassium acetate (88 mg, 0.9 mmol) in dimethylacetamide (2 mL) is degassed by bubbling with nitrogen gas for 20 min. Bis(triphenylphosphine)palladium dichloride (31.5 mg, 0.04 mmol) is added, and the reaction is heated at 144° C. Over the next 8 h, 2 further 0.1 eq portions of bis(triphenylphosphinepalladium dichloride are added. The reaction is then left stirring for ca 16 h. The reaction is allowed to cool to ambient temperature, and is concentrated in vacuo. The residue is partitioned between ethyl acetate and water, separated, and the organic phase is washed with water, dried (magnesium sulphate), and concentrated in vacuo. The crude material is purified by flash column chromatography (24 g silica, isohexane to ethyl acetate gradient) to afford the desired product.

LC/MS ($C_{45}H_{48}N_4O_5$) 725 [M+H]$^+$; RT 1.57 (Method B)

Step B: N-[4-(Benzyloxy)phenyl]-N,1,2-trimethyl-5-{6-[(3R)-3-methyl-1,2,3,4-tetrahydroisoquinoline-2-carbonyl]-2,3-dihydro-1H-isoindol-5-yl}-1H-pyrrole-3-carboxamide To a solution of the product from Step A (260 mg, 0.36 mmol) in dichloromethane (5 mL) is added trifluoroacetic acid (1 mL) and the mixture is stirred at ambient temperature for ca 16 h. The mixture is partitioned between water and dichloromethane, and basified with 1M aqueous sodium hydroxide. The organic phase is dried (magnesium sulphate), evaporated, and purified on CombiFlash (12 g silica, dichloromethane to 5% methanol/dichloromethane) to afford the product as a glassy solid.

LC/MS ($C_{40}H_{40}N_4O_3$) 625 [M+H]$^+$; RT 1.20 (Method B)

Preparation 7fa: N-(4-Benzyloxyphenyl)-N-methyl-3-[6-[(3S)-3-(morpholinomethyl)-3,4-dihydro-1H-isoquinoline-2-carbonyl]isoindolin-5-yl]indolizine-1-carboxamide hydrochloride

Step A: N-(4-Benzyloxyphenyl)-N-methyl-indolizine-1-carboxamide

Indolizine-1-carboxylic acid (0.4 g, 5.6 mmol) was dissolved in dichloromethane/THF mixture (40/40 ml) then 1-chloro-N,N,2-trimethyl-1-propenylamine (0.8 mL) was added and the mixture was stirred at room temperature for 10 minutes. After the completion of the acyl chloride formation, the mixture was evaporated and redissolved in dry dichloromethane (50 mL). 4-Benzyloxy-N-methylaniline hydrochloride (1.67 g, 6.7 mmol) and triethylamine (2.34 mL, 16.75 mmol) were added and the reaction was stirred at ambient temperature for ca. 16 h. The solution was washed with saturated aqueous NaHCO$_3$ solution, and brine, then dried over Na$_2$SO$_4$ and evaporated. The crude product was purified by flash chromatography over silicagel (dichloromethane/methanol, gradient 1-10%) to give the desired material.

Step B: tert-Butyl 5-[1-[(4-benzyloxyphenyl)-methyl-carbamoyl]indolizin-3-yl]-6-[(3S)-3-(morpholinomethyl)-3,4-dihydro-1H-isoquinoline-2-carbonyl]isoindoline-2-carboxylate The compound of Preparation 1e (278 mg, 0.5 mmol) and the product from Step A (240 mg, 0.70 mmol) were dissolved in dimethylacetamide (5 mL) then nitrogen was bubbled through the solution for 5 min. Potassium acetate (0.11 g, 1.12 mmol) and bis(triphenylphosphine)palladium (II) dichloride (20 mg) were added to the mixture, it was heated to 110° C. then after 20 min stirring water (20 µL) was added. Stirring at 110° C. under a nitrogen atmosphere was continued for additional 5 hours. The reaction mixture was allowed to cool to ambient temperature then evaporated. The residue was dissolved in THF, filtered through a pad of Celite and after removal of solvent by evaporation the crude product was purified by preparative HPLC (H$_2$O-TFA/acetonitrile; gradient elution). The pH of the appropriate combined fractions was adjusted to 10 by Na$_2$CO$_3$ then the acetonitrile was removed under reduced pressure. The precipitated solid was filtered then dried to yield the title compound.

Step C: N-(4-Benzyloxyphenyl)-N-methyl-3-[6-[(3S)-3-(morpholinomethyl)-3,4-dihydro-1H-isoquinoline-2-carbonyl]isoindolin-5-yl]indolizine-1-carboxamide hydrochloride The product from Step B (167 mg) was stirred in a 4M HCl in dioxane (15 ml) solution for 30 min at room temperature. After the completion of the reaction all the solvents were removed to afford the desired product.

Preparation 7fb: N-(4-Benzyloxyphenyl)-N-methyl-3-[6-[(3R)-3-methyl-3,4-dihydro-1H-isoquinoline-2-carbonyl]isoindolin-5-yl]indolizine-1-carboxamide hydrochloride

Step A: tert-Butyl 5-[1-[(4-benzyloxyphenyl)-methyl-carbamoyl]indolizin-3-yl]-6-[(3R)-3-methyl-3,4-dihydro-1H-isoquinoline-2-carbonyl]isoindoline-2-carboxylate The procedure is as in Step B of Preparation 7fa, replacing tert-Butyl 5-bromo-6-[(3S)-3-(morpholinomethyl)-3,4-dihydro-1H-isoquinoline-2-carbonyl]isoindoline-2-carboxylate with the compound of Preparation 1f. The product is purified by preparative HPLC (H$_2$O-TFA/acetonitrile; gradient elution).

Step B: N-(4-benzyloxyphenyl)-N-methyl-3-[6-[(3R)-3-methyl-3,4-dihydro-1H-isoquinoline-2-carbonyl]isoindolin-5-yl]indolizine-1-carboxamide hydrochloride The procedure is as in Step C of Preparation 7fa, replacing tert-butyl 5-[1-[(4-benzyloxyphenyl)-methyl-carbamoyl]indolizin-3-yl]-6-[(3S)-3-(morpholinomethyl)-3,4-dihydro-1H-isoquinoline-2-carbonyl]isoindoline-2-carboxylate with the product from Step A.

The following Examples are obtained using the compounds of the appropriate Preparations described above. When no specific procedure is detailed, the corresponding Example can be obtained by repeating the procedure described for analogues Examples (i.e. whose structure is close) detailed elsewhere in the specification, choosing the appropriate starting materials and using the basic knowledge of the man skilled in the art.

EXAMPLE 1: tert-Butyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is described in Step A of Preparation 6e.

LC/MS ($C_{45}H_{53}N_5O_6$) 760 [M+H]$^+$; RT 1.25 (Method B)

EXAMPLE 2: N-(4-Hydroxyphenyl)-N-methyl-3-{7-[(3S)-3-(morpholin-4-ylmethyl)-1,2,3,4-tetrahydroisoquinoline-2-carbonyl]-1,2,3,4-tetrahydroisoquinolin-6-yl}-5,6,7,8-tetrahydroindolizine-1-carboxamide dihydrochloride The procedure is described in Step B of Preparation 6e.

LC/MS ($C_{40}H_{45}N_5O_4$) 660 [M+H]$^+$; RT 0.89 (Method B)

High-Resolution Mass (ESI+):

Empirical formula: $C_{40}H_{45}N_5O_4$

[M+H]$^+$ calculated: 660.3544

[M+H]$^+$ measured: 660.3522

EXAMPLE 3: 3-[2-(Benzenesulfonyl)-7-[(3S)-3-(morpholin-4-ylmethyl)-1,2,3,4-tetrahydroisoquinoline-2-carbonyl]-1,2,3,4-tetrahydroisoquinolin-6-yl]-N-(4-hydroxyphenyl)-N-methyl-5,6,7,8-tetrahydroindolizine-1-carboxamide Step A: 4-{N-methyl 3-[2-(benzenesulfonyl)-7-[(3S)-3-(morpholin-4-ylmethyl)-1,2,3,4-tetrahydroisoquinoline-2-carbonyl]-1,2,3,4-tetrahydroisoquinolin-6-yl]-5,6,7,8-tetrahydroindolizine-1-amido}phenyl benzenesulfonate To a solution of the product of Preparation 6e (35 mg, 0.05 mmol) in dichloromethane (1 mL) is added triethylamine (52 µL, 0.375 mmol) and the mixture is cooled to 0° C. Benzenesulfonyl chloride (17 µL, 0.13 mmol) is added dropwise, and the resultant mixture is stirred at 0° C. for 1 h. The reaction is diluted with dichloromethane, washed with 1M aqueous sodium hydroxide solution, followed by brine, and dried over magnesium sulphate. The solvent is removed in vacuo, and the crude product is purified on CombiFlash (4 g silica; dichloromethane to 5% MeOH/dichloromethane).
LC/MS ($C_{52}H_{53}N_5O_8S_2$) 798 [M-$C_6H_5SO_2$]$^-$; RT 1.41 (Method B)

Step B: 3-[2-(Benzenesulfonyl)-7-[(3S)-3-(morpholin-4-ylmethyl)-1,2,3,4-tetrahydroisoquinoline-2-carbonyl]-1,2,3,4-tetrahydroisoquinolin-6-yl]-N-(4-hydroxyphenyl)-N-methyl-5,6,7,8-tetrahydroindolizine-1-carboxamide The product from Step A is dissolved in methanol (2 mL), potassium hydroxide (10 eq) is added, and the resultant mixture is allowed to stir at ambient temperature for 7 h. Concentration in vacuo, and purification on CombiFlash (4 g silica; dichloromethane to 5% methanol/dichloromethane) affords the desired product as a solid.
LC/MS ($C_{46}H_{49}N_5O_6S$) 800 [M+H]$^+$; RT 1.21 (Method B)
High-Resolution Mass (ESI+):
Empirical formula: $C_{46}H_{49}N_5O_6S$
[M+H]$^+$ calculated: 800.3476
[M+H]$^+$ measured: 800.3485

EXAMPLE 4: N-(4-Hydroxyphenyl)-N-methyl-3-{7-[(3S)-3-(morpholin-4-ylmethyl)-1,2,3,4-tetrahydroisoquinoline-2-carbonyl]-2-phenylmethanesulfonyl-1,2,3,4-tetrahydroisoquinolin-6-yl}-5,6,7,8-tetrahydroindolizine-1-carboxamide The procedure is as in the process of Example 3, replacing benzenesulfonyl chloride in Step A with phenylmethanesulfonyl chloride.
LC/MS ($C_{47}H_{51}N_5O_6S$) 814 [M+H]$^+$; RT 1.23 (Method B)
High-Resolution Mass (ESI+):
Empirical formula: $C_{47}H_{51}N_5O_6S$
[M+H]$^+$ calculated: 814.3633
[M+H]$^+$ measured: 814.3602

EXAMPLE 5: N-(4-Hydroxyphenyl)-N-methyl-3-{7-[(3S)-3-(morpholin-4-ylmethyl)-1,2,3,4-tetrahydroisoquinoline-2-carbonyl]-2-(naphthalene-2-sulfonyl)-1,2,3,4-tetrahydroisoquinolin-6-yl}-5,6,7,8-tetrahydroindolizine-1-carboxamide The procedure is as in the process of Example 3, replacing benzenesulfonyl chloride in Step A with naphthalene-2-sulfonyl chloride.

LC/MS ($C_{50}H_{51}N_5O_6S$) 850 [M+H]$^+$; RT 1.31 (Method B)
High-Resolution Mass (ESI+):
Empirical formula: $C_{50}H_{51}N_5O_6S$
[M+H]$^+$ calculated: 850.3633
[M+H]$^+$ measured: 850.3624

EXAMPLE 6: tert-Butyl 5-{1-[(4-hydroxyphenyl)(methyl)carbamoyl]-5,6,7,8-tetrahydroindolizin-3-yl}-6-[(3S)-3-(morpholin-4-ylmethyl)-1,2,3,4-tetrahydroisoquinoline-2-carbonyl]-2,3-dihydro-1H-isoindole-2-carboxylate A solution of the product from Step A of Preparation 7aa (16 mg, 0.02 mmol) in ethanol (10 mL) is added to 10% Pd/C (catalytic amount) and the mixture is shaken under an atmosphere of hydrogen for ca 16 h. The mixture is filtered through celite, subsequently eluting with methanol, and removing the solvents under reduced pressure.
LC/MS ($C_{44}H_{51}N_5O_6$) 746 [M+H]$^+$; RT 1.25 (Method B)
High-Resolution Mass (ESI+):
Empirical formula: $C_{44}H_{51}N_5O_6$
[M+H]$^+$ calculated: 746.3912
[M+H]$^+$ measured: 746.3909

EXAMPLE 7: N-(4-Hydroxyphenyl)-N-methyl-3-{6-[(3S)-3-(morpholin-4-ylmethyl)-1,2,3,4-tetrahydroisoquinoline-2-carbonyl]-2,3-dihydro-1H-isoindol-5-yl}-5,6,7,8-tetrahydroindolizine-1-carboxamide; dihydrochloride salt Example 6 (45 mg, 0.05 mmol) was dissolved in a minimal amount of methanol and to this was added 4M solution of HCl in 1,4-dioxane (1 mL), and the mixture was allowed to stir at ambient temperature for ca 1 hr. The reaction was then diluted with dry diethyl ether (ca 5 mL) and the precipitate was collected by filtration and washed with a minimum of cold diethyl ether to afford the product.
LC/MS ($C_{39}H_{43}N_5O_4$) 646 [M+H]$^+$; RT 0.89 (Method B)
High-Resolution Mass (ESI+):
Empirical formula: $C_{39}H_{43}N_5O_4$
[M+H]$^+$ calculated: 646.3388
[M+H]$^+$ measured: 646.3385

EXAMPLE 8: N-(4-Hydroxyphenyl)-N-methyl-3-{6-[(3S)-3-(morpholin-4-ylmethyl)-1,2,3,4-tetrahydroisoquinoline-2-carbonyl]-2-(2-phenylacetyl)-2,3-dihydro-1H-isoindol-5-yl}-5,6,7,8-tetrahydroindolizine-1-carboxamide; hydrochloride salt Step A: N-(4-Hydroxyphenyl)-N-methyl-3-{6-[(3S)-3-(morpholin-4-ylmethyl)-1,2,3,4-tetrahydroisoquinoline-2-carbonyl]-2-(2-phenylacetyl)-2,3-dihydro-1H-isoindol-5-yl}-5,6,7,8-tetrahydroindolizine-1-carboxamide To a solution of product obtained from Preparation 7aa (50 mg, 0.07 mmol) in dichloromethane (2 mL) was added N,N-diisopropylethylamine (0.1 mmol) and the mixture was cooled to 0° C. To the resultant solution was added dropwise 2-phenylacetyl chloride (0.102 mmol) and after 5 min the reaction was diluted with dichloromethane, and washed sequentially with aqueous 1M sodium hydroxide, and brine. The organic extract was dried over magnesium sulfate, filtered and concentrated in vacuo, adsorbed onto isolute, and purified by chromatography (CombiFlash $R_f$, 40 g RediSep™ silica cartridge) eluting in a gradient of isohexane to 25% ethyl acetate. The residue was then dissolved in ethanol (5 mL) and to this was added 10% Pd/C (catalytic amount) and the mixture stirred under a hydrogen atmosphere for ca 16 h. The mixture was filtered through celite, subsequently eluting with methanol, and solvent was removed under reduced pressure. The residue was adsorbed onto isolute and purified by chromatography (CombiFlash $R_f$, 4 g RediSep™ silica cartridge) eluting in a gradient of dichloromethane to 5% methanol in dichloromethane to afford the desired product.

LC/MS ($C_{47}H_{49}N_5O_5$) 764 [M+H]$^+$; RT 1.18 (Method B)

Step B: N-(4-Hydroxyphenyl)-N-methyl-3-{6-[(3S)-3-(morpholin-4-ylmethyl)-1,2,3,4-tetrahydroisoquinoline-2-carbonyl]-2-(2-phenylacetyl)-2,3-dihydro-1H-isoindol-5-yl}-5,6,7,8-tetrahydroindolizine-1-carboxamide; hydrochloride salt The product from Step A was dissolved in isopropyl alcohol (0.5 mL) and ethereal HCl (1M; 0.13 mL) was added. The mixture was stirred for 30 min, then concentrated in vacuo. Trituration of the residue with ether afforded the desired product as a solid.

LC/MS ($C_{47}H_{49}N_5O_5$) 764 [M+H]$^+$; RT 1.16 (Method B)
High-Resolution Mass (ESI+):
Empirical formula: $C_{47}H_{49}N_5O_5$
[M+H]$^+$ calculated: 764.3806
[M+H]$^+$ measured: 764.3807

EXAMPLE 9: N-(4-Hydroxyphenyl)-N-methyl-3-{6-[(3S)-3-(morpholin-4-ylmethyl)-1,2,3,4-tetrahydroisoquinoline-2-carbonyl]-2-(3-phenylpropanoyl)-2,3-dihydro-1H-isoindol-5-yl}-5,6,7,8-tetrahydroindolizine-1-carboxamide hydrochloride The procedure is as in Example 8, replacing 2-phenylacetyl chloride in Step A with 3-phenylpropanoyl chloride.
LC/MS ($C_{48}H_{51}N_5O_5$) 778 [M+H]$^+$; RT 1.19 (Method B)
High-Resolution Mass (ESI+):
Empirical formula: $C_{48}H_{51}N_5O_5$
[M+H]$^+$ calculated: 778.3963
[M+H]$^+$ measured: 778.3973

EXAMPLE 10: N-(4-Hydroxyphenyl)-N-methyl-3-{6-[(3R)-3-methyl-1,2,3,4-tetrahydroisoquinoline-2-carbonyl]-2,3-dihydro-1H-isoindol-5-yl}-5,6,7,8-tetrahydroindolizine-1-carboxamide The procedure is as described in Example 7, replacing Example 6 with product from Preparation 7ab.
LC/MS ($C_{35}H_{36}N_4O_3$) 561 [M+H]$^+$; RT 1.04

EXAMPLE 11: N-(4-Hydroxyphenyl)-N-methyl-3-{6-[(3S)-3-(morpholin-4-ylmethyl)-1,2,3,4-tetrahydroisoquinoline-2-carbonyl]-2-propanoyl-2,3-dihydro-1H-isoindol-5-yl}-5,6,7,8-tetrahydroindolizine-1-carboxamide hydrochloride Step A: N-[4-(Benzyloxy)phenyl]-N-methyl-3-{6-[(3S)-3-(morpholin-4-ylmethyl)-1,2,3,4-tetrahydroisoquinoline-2-carbonyl]-2-propanoyl-2,3-dihydro-1H-isoindol-5-yl}-5,6,7,8-tetrahydroindolizine-1-carboxamide To a solution of the compound from Preparation 7aa (50 mg, 0.068 mmol) in dichloromethane (2 mL) is added DIPEA (17 uL, 0.10 mmol) and the mixture is cooled to 0° C. Propionyl chloride (9 uL, 0.10 mmol) is added dropwise, and after 30 min the mixture is diluted with dichloromethane, washed sequentially with 1M aqueous NaOH and brine, dried over magnesium sulphate, and concentrated in vacuo. Purification by flash column chromatography (4 g silica; dichloromethane to 5% MeOH/dichloromethane) afforded the product as a glassy solid.

LC/MS ($C_{49}H_{53}N_5O_5$) 792 [M+H]$^+$; RT 1.30 (Method B)

Step B: N-(4-Hydroxyphenyl)-N-methyl-3-{6-[(3S)-3-(morpholin-4-ylmethyl)-1,2,3,4-tetrahydroisoquinoline-2-carbonyl]-2-propanoyl-2,3-dihydro-1H-isoindol-5-yl}-5,6,7,8-tetrahydroindolizine-1-carboxamide A solution of the product from Step A (18.7 mg, 0.024 mmol) in ethanol (5 mL) is added to 10% Pd/C (catalytic amount) and the mixture is shaken under an atmosphere of hydrogen for ca 16 h. The mixture is filtered through celite, subsequently eluting with methanol, and removing the solvents under reduced pressure. The crude product is purified by flash column chromatography (4 g silica; dichloromethane to 5% MeOH/dichloromethane) to afford the desired product as a glassy solid.

LC/MS ($C_{42}H_{47}N_5O_5$) 702 [M+H]$^+$; RT 1.08 (Method B)

Step C: N-(4-Hydroxyphenyl)-N-methyl-3-{6-[(3S)-3-(morpholin-4-ylmethyl)-1,2,3,4-tetrahydroisoquinoline-2-carbonyl]-2-propanoyl-2,3-dihydro-1H-isoindol-5-yl}-5,6,7,8-tetrahydroindolizine-1-carboxamide hydrochloride The product from Step B is dissolved in isopropyl alcohol (0.5 mL) and ethereal HCl (1M; 0.13 mL) is added. The mixture is stirred for 30 min, then concentrated in vacuo. Trituration of the residue with ether afforded the desired product as a solid.

LC/MS ($C_{42}H_{47}N_5O_5$) 702 [M+H]$^+$; RT 1.10 (Method B)
High-Resolution Mass (ESI+):
Empirical formula: $C_{42}H_{47}N_5O_5$
[M+H]$^+$ calculated: 702.3650
[M+H]$^+$ measured: 702.3684

EXAMPLE 12: 3-{2-Benzoyl-6-[(3S)-3-(morpholin-4-ylmethyl)-1,2,3,4-tetrahydroisoquinoline-2-carbonyl]-2,3-dihydro-1H-isoindol-5-yl}-N-(4-hydroxyphenyl)-N-methyl-5,6,7,8-tetrahydroindolizine-1-carboxamide hydrochloride The procedure is as in Example 8, replacing 2-phenylacetyl chloride in Step A with benzoyl chloride.
LC/MS ($C_{46}H_{47}N_5O_5$) 750 [M+H]$^+$; RT 1.17 (Method B)
High-Resolution Mass (ESI+):
Empirical formula: $C_{46}H_{47}N_5O_5$
[M+H]$^+$ calculated: 750.3650
[M+H]$^+$ measured: 750.3648

EXAMPLE 13: tert-Butyl 5-{1-[(4-hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxylate The procedure is described in Example 6, replacing the product obtained in Step A of Preparation 7aa with the product obtained in Step A of Preparation 7ab.
LC/MS ($C_{40}H_{44}N_4O_5$) 661 [M+H]$^+$; RT 1.42 (Method B)

High-Resolution Mass (ESI+):
Empirical formula: $C_{40}H_{44}N_4O_5$
[M+H]$^+$ calculated: 661.3384
[M+H]$^+$ measured: 661.3352

EXAMPLE 14: N-(4-Hydroxyphenyl)-N-methyl-3-{6-[(3R)-3-methyl-1,2,3,4-tetrahydroisoquinoline-2-carbonyl]-2-(2-phenylacetyl)-2,3-dihydro-1H-isoindol-5-yl}-5,6,7,8-tetrahydroindolizine-1-carboxamide The procedure is as described in Step A of Example 8, replacing the product from Preparation 7aa in Step A with the product from Preparation 7ab.
LC/MS ($C_{43}H_{42}N_4O_4$) 679 [M+H]$^+$; RT 1.31 (Method B)
High-Resolution Mass (ESI+):
Empirical formula: $C_{43}H_{42}N_4O_4$
[M+H]$^+$ calculated: 679.3279
[M+H]$^+$ measured: 679.3298

EXAMPLE 15: N-(4-Hydroxyphenyl)-N-methyl-3-{6-[(3R)-3-methyl-1,2,3,4-tetrahydroisoquinoline-2-carbonyl]-2-(3-phenylpropanoyl)-2,3-dihydro-1H-isoindol-5-yl}-5,6,7,8-tetrahydroindolizine-1-carboxamide The procedure is as described in Step A of Example 8, replacing the product from Preparation 7aa in Step A with the product from Preparation 7ab, and replacing 2-phenylacetyl chloride in Step A with 3-phenylpropanoyl chloride.
LC/MS ($C_{44}H_{44}N_4O_4$) 693 [M+H]$^+$; RT 2.57 (Method A)
High-Resolution Mass (ESI+):
Empirical formula: $C_{44}H_{44}N_4O_4$
[M+H]$^+$ calculated: 693.3435
[M+H]$^+$ measured: 693.3441

EXAMPLE 16: Phenyl 5-{1-[(4-hydroxyphenyl)(methyl)carbamoyl]-5,6,7,8-tetrahydroindolizin-3-yl}-6-[(3S)-3-(morpholin-4-ylmethyl)-1,2,3,4-tetrahydroisoquinoline-2-carbonyl]-2,3-dihydro-1H-isoindole-2-carboxylate hydrochloride The procedure is as in Example 8, replacing 2-phenylacetyl chloride in Step A with phenyl chloroformate.
LC/MS ($C_{46}H_{47}N_5O_6$) 766 [M+H]$^+$; RT 1.24 (Method B)
High-Resolution Mass (ESI+):
Empirical formula: $C_{46}H_{47}N_5O_6$
[M+H]$^+$ calculated: 766.3599
[M+H]$^+$ measured: 766.3602

EXAMPLE 17: N-tert-Butyl-5-{1-[(4-hydroxyphenyl)(methyl)carbamoyl]-5,6,7,8-tetrahydroindolizin-3-yl}-6-[(3S)-3-(morpholin-4-ylmethyl)-1,2,3,4-tetrahydroisoquinoline-2-carbonyl]-2,3-dihydro-1H-isoindole-2-carboxamide hydrochloride Step A: 5-(1-{[4-(Benzyloxy)phenyl](methyl)carbamoyl}-5,6,7,8-tetrahydroindolizin-3-yl)-N-tert-butyl-6-[(3S)-3-(morpholin-4-ylmethyl)-1,2,3,4-tetrahydroisoquinoline-2-carbonyl]-2,3-dihydro-1H-isoindole-2-carboxamide To a solution of the compound of Preparation 7aa (30 mg, 0.04 mmol) in dichloromethane (2 mL) is added DIPEA (10 uL, 0.06 mmol) and the mixture is cooled to 0° C. tert-Butyl isocyanate (7 uL, 0.06 mmol) is added and the reaction is stirred for 10 min, then diluted with dichloromethane and washed sequentially with 1M aqueous NaOH and brine. The organic phase is dried over magnesium sulphate, filtered and concentrated in vacuo. The crude material is taken-up in dichloromethane, loaded onto isolute and purified on CombiFlash (4 g silica, dichloromethane to 5% methanol/dichloromethane) to afford the desired product as a glassy solid that was used directly in the next step.

Step B: N-tert-Butyl-5-{1-[(4-hydroxyphenyl)(methyl)carbamoyl]-5,6,7,8-tetrahydroindolizin-3-yl}-6-[(3S)-3-(morpholin-4-ylmethyl)-1,2,3,4-tetrahydroisoquinoline-2-carbonyl]-2,3-dihydro-1H-isoindole-2-carboxamide The product from Step A (25 mg) is dissolved in EtOH and to this is added 10% Pd/C (catalytic amount) and the mixture is allowed to stir under an atmosphere of hydrogen for ca 16 h. The reaction is filtered through celite, eluting with methanol and concentrated in vacuo to afford the desired product.
LC/MS ($C_{44}H_{52}N_6O_5$) 745 [M+H]$^+$; RT 2.20 (Method A)

Step C: N-tert-Butyl-5-{1-[(4-hydroxyphenyl)(methyl)carbamoyl]-5,6,7,8-tetrahydroindolizin-3-yl}-6-[(3S)-3-(morpholin-4-ylmethyl)-1,2,3,4-tetrahydroisoquinoline-2-carbonyl]-2,3-dihydro-1H-isoindole-2-carboxamide hydrochloride To a solution of the product from Step B in isopropyl alcohol (0.5 mL) is added ethereal HCl (1M; 0.17 mL, 0.17 mmol) and the mixture is stirred for 30 min. The solvent is removed in vacuo and trituration with ether affords the desired product as a solid.
LC/MS ($C_{44}H_{52}N_6O_5$) 745 [M+H]$^+$; RT 1.10 (Method B)
High-Resolution Mass (ESI+):
Empirical formula: $C_{44}H_{52}N_6O_5$
[M+H]$^+$ calculated: 745.4072
[M+H]$^+$ measured: 745.4081

EXAMPLE 18: 3-[2-(Ethanesulfonyl)-6-[(3S)-3-(morpholin-4-ylmethyl)-1,2,3,4-tetrahydroisoquinoline-2-carbonyl]-2,3-dihydro-1H-isoindol-5-yl]-N-(4-hydroxyphenyl)-N-methyl-5,6,7,8-tetrahydroindolizine-1-carboxamide hydrochloride The procedure is as in Example 8, replacing 2-phenylacetyl chloride in Step A with ethanesulfonyl chloride.
LC/MS ($C_{41}H_{47}N_5O_6S$) 738 [M+H]$^+$; RT 1.07 (Method B)
High-Resolution Mass (ESI+):
Empirical formula: $C_{41}H_{47}N_5O_6S$
[M+H]$^+$ calculated: 738.3320
[M+H]$^+$ measured: 738.3316

EXAMPLE 19: 3-[2-(Benzenesulfonyl)-6-[(3S)-3-(morpholin-4-ylmethyl)-1,2,3,4-tetrahydroisoquinoline-2-carbonyl]-2,3-dihydro-1H-isoindol-5-yl]-N-(4-hydroxyphenyl)-N-methyl-5,6,7,8-tetrahydroindolizine-1-carboxamide hydrochloride The procedure is as in Example 8, replacing 2-phenylacetyl chloride in Step A with benzenesulfonyl chloride.
LC/MS ($C_{45}H_{47}N_5O_6S$) 786 [M+H]$^+$; RT 1.16 (Method B)
High-Resolution Mass (ESI+):
Empirical formula: $C_{45}H_{47}N_5O_6S$
[M+H]$^+$ calculated: 786.3320
[M+H]$^+$ measured: 786.3339

EXAMPLE 20: 3-{2-Cyclopropanecarbonyl-6-[(3R)-3-methyl-1,2,3,4-tetrahydroisoquinoline-2-carbonyl]-2,3-dihydro-1H-isoindol-5-yl}-N-(4-hydroxyphenyl)-N-methyl-5,6,7,8-tetrahydroindolizine-1-carboxamide The procedure is as described in Step A and Step B of Example 8, replacing the product from Preparation 7aa in Step A with the product from Preparation 7ab, and replacing 2-phenylacetyl chloride in Step A with cyclopropanecarbonyl chloride.

LC/MS ($C_{39}H_{40}N_4O_4$) 629.7 [M+H]$^+$; RT 2.41 (Method A)
High-Resolution Mass (ESI+):
Empirical formula: $C_{39}H_{40}N_4O_4$
[M+H]$^+$ calculated: 629.3122
[M+H]$^+$ measured: 629.3129

EXAMPLE 21: N-(4-Hydroxyphenyl)-N-methyl-3-{6-[(3S)-3-(morpholin-4-ylmethyl)-1,2,3,4-tetrahydroisoquinoline-2-carbonyl]-2-(2-phenylethanesulfonyl)-2,3-dihydro-1H-isoindol-5-yl}-5,6,7,8-tetrahydroindolizine-1-carboxamide hydrochloride The procedure is as in Example 8, replacing 2-phenylacetyl chloride in Step A with 2-phenylethane-1-sulfonyl chloride.

LC/MS ($C_{47}H_{51}N_5O_6S$) 814 [M+H]$^+$; RT 1.21 (Method B)

EXAMPLE 22: N-(4-Hydroxyphenyl)-N-methyl-3-{6-[(3S)-3-(morpholin-4-ylmethyl)-1,2,3,4-tetrahydroisoquinoline-2-carbonyl]-2-(pyridine-3-sulfonyl)-2,3-dihydro-1H-isoindol-5-yl}-5,6,7,8-tetrahydroindolizine-1-carboxamide hydrochloride The procedure is as in Example 8, replacing 2-phenylacetyl chloride in Step A with pyridine-3-sulfonyl chloride.

LC/MS ($C_{44}H_{46}N_6O_6S$) 787 [M+H]$^+$; RT 1.09 (Method B)
High-Resolution Mass (ESI+):
Empirical formula: $C_{44}H_{46}N_6O_6S$
[M+H]$^+$ calculated: 787.3272
[M+H]$^+$ measured: 787.3243

EXAMPLE 23: 3-[2-(2-Benzylpropanoyl)-6-[(3R)-3-methyl-1,2,3,4-tetrahydroisoquinoline-2-carbonyl]-2,3-dihydro-1H-isoindol-5-yl]-N-(4-hydroxyphenyl)-N-methyl-5,6,7,8-tetrahydroindolizine-1-carboxamide Step A: N-[4-(benzyloxy)phenyl]-3-[2-(2-benzylpropanoyl)-6-[(3R)-3-methyl-1,2,3,4-tetrahydroisoquinoline-2-carbonyl]-2,3-dihydro-1H-isoindol-5-yl]-N-methyl-5,6,7,8-tetrahydroindolizine-1-carboxamide To a solution of the product from Preparation 7ab (52 mg, 0.07 mmol) in tetrahydrofuran (3 mL) was added N,N-diisopropylethylamine (37 µL, 0.21 mmol) and HBTU (27 mg, 0.07 mmol), followed by 2-methyl-3-phenylpropanoic acid (17 mg, 0.10 mmol). The reaction was stirred at ambient temperature for ca 16 h, then partitioned between ethyl acetate and water, dried over magnesium sulphate, and concentrated in vacuo. Purification by flash column chromatography (silica; iso-hexane to ethyl acetate gradient) afforded the desired product.

LC/MS ($C_{52}H_{52}N_4O_4$) 797 [M+H]$^+$; RT 2.91 (Method A)

Step B: 3-[2-(2-Benzylpropanoyl)-6-[(3R)-3-methyl-1,2,3,4-tetrahydroisoquinoline-2-carbonyl]-2,3-dihydro-1H-isoindol-5-yl]-N-(4-hydroxyphenyl)-N-methyl-5,6,7,8-tetrahydroindolizine-1-carboxamide The product from Step A was dissolved in ethanol (10 mL) and to this was added 10% Pd/C (catalytic amount) and the mixture was allowed to stir under an atmosphere of hydrogen for ca 16 h. The reaction was filtered through celite, eluting with methanol and concentrated in vacuo. Purification by flash column chromatography (silica; iso-hexane to ethyl acetate gradient) afforded the desired product.

LC/MS ($C_{45}H_{46}N_4O_4$) 707 [M+H]$^+$; RT 2.64 (Method A)
High-Resolution Mass (ESI+):
Empirical formula: $C_{45}H_{46}N_4O_4$
[M+H]$^+$ calculated: 707.3592
[M+H]$^+$ measured: 707.3600

EXAMPLE 24: 3-(2-{2-[(4-Chlorophenyl)methyl]propanoyl}-6-[(3R)-3-methyl-1,2,3,4-tetrahydroisoquinoline-2-carbonyl]-2,3-dihydro-1H-isoindol-5-yl)-N-(4-hydroxyphenyl)-N-methyl-5,6,7,8-tetrahydroindolizine-1-carboxamide To a solution of the product from Example 10 (20 mg, 0.03 mmol) in dichloromethane (3 ml) was added TEA (13 ul, 0.09 mmol), HATU (12 mg, 0.03 mmol) and the 3-(4-chlorophenyl)-2-methylpropanoic acid (6 mg, 0.03 mmol), and stirred at ambient temperature for ca 16 h. The reaction was diluted with dichloromethane and washed with water, dried over magnesium sulphate, filtered and concentrated in vacuo. The crude material was purified by column chromatography in a gradient of dichloromethane to 10% methanol/dichloromethane.

LC/MS ($C_{45}H_{45}N_4O_4Cl$) 741 [M+H]$^+$; RT 2.71 (Method A)
High-Resolution Mass (ESI+):
Empirical formula: $C_{45}H_{45}N_4O_4Cl$
[M+H]$^+$ calculated: 741.3202
[M+H]$^+$ measured: 741.3246

EXAMPLE 25: N-(4-Hydroxyphenyl)-N-methyl-3-{6-[(3R)-3-methyl-1,2,3,4-tetrahydroisoquinoline-2-carbonyl]-2-{2-[(4-methylphenyl)methyl]propanoyl}-2,3-dihydro-1H-isoindol-5-yl}-5,6,7,8-tetrahydroindolizine-1-carboxamide The procedure is as described in Example 23, replacing 2-methyl-3-phenylpropanoic acid in Step A with 2-methyl-3-(4-methylphenyl)propanoic acid.

LC/MS ($C_{46}H_{48}N_4O_4$) 721 [M+H]$^+$; RT 2.70 (Method A)
High-Resolution Mass (ESI+):
Empirical formula: $C_{46}H_{48}N_4O_4$
[M+H]$^+$ calculated: 721.3748
[M+H]$^+$ measured: 721.3740

EXAMPLE 26: N-(4-Hydroxyphenyl)-N-methyl-3-{6-[(3R)-3-methyl-1,2,3,4-tetrahydroisoquinoline-2-carbonyl]-2-{2-[4-(trifluoromethoxy)phenyl]acetyl}-2,3-dihydro-1H-isoindol-5-yl}-5,6,7,8-tetrahydroindolizine-1-carboxamide The procedure is as described in Example 23, replacing 2-methyl-3-phenylpropanoic acid in Step A with 2-[4-(trifluoromethoxy)phenyl]acetic acid.

LC/MS ($C_{44}H_{41}N_4O_5F_3$) 763 [M+H]$^+$; RT 2.70 (Method A)

High-Resolution Mass (ESI+):
Empirical formula: $C_{44}H_{41}N_4O_5F_3$
[M+H]$^+$ calculated: 763.3102
[M+H]$^+$ measured: 763.3102

EXAMPLE 27: N-(4-Hydroxyphenyl)-N-methyl-3-{7-[(3R)-3-methyl-1,2,3,4-tetrahydroisoquinoline-2-carbonyl]-1,2,3,4-tetrahydroisoquinolin-6-yl}-5,6,7,8-tetrahydroindolizine-1-carboxamide; trifluoroacetic acid salt Step A: tert-Butyl 6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate The product from Preparation 6ab (95 mg, 0.12 mmol) is dissolved in ethanol (5 mL) and to this is added 10% Pd/C (catalytic amount) and the mixture is allowed to stir under an atmosphere of hydrogen for ca 6 h. The reaction is filtered through celite, eluting with methanol and concentrated in vacuo to afford the desired product.

LC/MS ($C_{41}H_{46}N_4O_5$) 675 [M+H]$^+$; RT 1.43 (Method B)

Step B: N-(4-Hydroxyphenyl)-N-methyl-3-{7-[(3R)-3-methyl-1,2,3,4-tetrahydroisoquinoline-2-carbonyl]-1,2,3,4-tetrahydroisoquinolin-6-yl}-5,6,7,8-tetrahydroindolizine-1-carboxamide; trifluoroacetic acid salt The product from Step A is dissolved in dichloromethane (2 mL) and trifluoroacetic acid (0.1 mL) is added. After stirring at for ca. 16 h at ambient temperature the reaction is concentrated in vacuo and azeotroped with toluene (×3) to afford the desired product as the trifluoroacetic acid salt.

LC/MS ($C_{36}H_{38}N_4O_3$) 575 [M+H]$^+$; RT 1.00 (Method B)

High-Resolution Mass (ESI+):
Empirical formula: $C_{36}H_{38}N_4O_3$
[M+H]$^+$ calculated: 575.3017
[M+H]$^+$ measured: 575.2998

EXAMPLE 28: N-(4-Hydroxyphenyl)-N-methyl-3-{6-[(3R)-3-methyl-1,2,3,4-tetrahydroisoquinoline-2-carbonyl]-2-(pyridin-2-ylmethyl)-2,3-dihydro-1H-isoindol-5-yl}-5,6,7,8-tetrahydroindolizine-1-carboxamide The procedure is as described in Step B of Example 29, replacing the compound from Step A with Example 10, and replacing cyclohexylacetaldehyde with pyridine-2-carbaldehyde.

LC/MS ($C_{41}H_{41}N_5O_3$) 652 [M+H]$^+$; RT 1.06 (Method B)

High-Resolution Mass (ESI+):
Empirical formula: $C_{41}H_{41}N_5O_3$
[M+H]$^+$ calculated: 652.3282
[M+H]$^+$ measured: 652.3269

EXAMPLE 29: 3-[2-(2-Cyclohexylethyl)-6-[(3R)-3-methyl-1,2,3,4-tetrahydroisoquinoline-2-carbonyl]-2,3-dihydro-1H-isoindol-5-yl]-N-(4-hydroxyphenyl)-N-methyl-5,6,7,8-tetrahydroindolizine-1-carboxamide Step A: N-[4-(Benzyloxy)phenyl]-N-methyl-3-{6-[(3R)-3-methyl-1,2,3,4-tetrahydroisoquinoline-2-carbonyl]-2,3-dihydro-1H-isoindol-5-yl}-5,6,7,8-tetrahydroindolizine-1-carboxamide To a solution of the compound of Step A of Preparation 7ab (150 mg, 0.20 mmol) in dichloromethane (5 mL) is added trifluoroacetic acid (0.5 mL) and the reaction is stirred for ca 16 h. The mixture is diluted with dichloromethane, washed with 1N aqueous sodium hydroxide, dried (magnesium sulphate) and condensed under reduced pressure. Purification on CombiFlash (4 g silica, dichloromethane to 10% methanol/dichloromethane) afforded the desired product as a gum.

LC/MS ($C_{42}H_{42}N_4O_3$) 651 [M+H]$^+$; RT 1.2 (Method B)

Step B: N-[4-(Benzyloxy)phenyl]-3-{2-(2-cyclohexylethyl)-6-[(3R)-3-methyl-1,2,3,4-tetrahydroisoquinoline-2-carbonyl]-2,3-dihydro-1H-isoindol-5-yl}-N-methyl-5,6,7,8-tetrahydroindolizine-1-carboxamide To a stirring solution of the product from Step A (57.5 mg, 0.088 mmol) in THF (2 mL) is added cyclohexylacetaldehyde (13.4 mg, 0.11 mmol) followed by sodium triacetoxyborohydride (22.5 mg, 0.106 mmol) and the reaction was stirred for ca 16 h. The mixture is concentrated under reduced pressure, and purified on CombiFlash (4 g silica, dichloromethane to 3% methanol/dichloromethane) to afford the desired product as a gum.

LC/MS ($C_{50}H_{56}N_4O_3$) 761 [M+H]$^+$; RT 1.37 (Method B)

Step C: 3-[2-(2-Cyclohexylethyl)-6-[(3R)-3-methyl-1,2,3,4-tetrahydroisoquinoline-2-carbonyl]-2,3-dihydro-1H-isoindol-5-yl]-N-(4-hydroxyphenyl)-N-methyl-5,6,7,8-tetrahydroindolizine-1-carboxamide To a solution of the product from Step B (13 mg, 0.019 mmol) in dichloromethane (2 mL), cooled to 0° C., is added boron trichloride (2M solution in dichloromethane; 0.1 mL, 0.2 mmol). After 5 h the reaction is quenched by addition of methanol, and concentrated in vacuo. Purification by preparative HPLC afforded the desired product.

LC/MS ($C_{43}H_{50}N_4O_3$) 671 [M+H]$^+$; RT 1.16 (Method B)
High-Resolution Mass (ESI+):
Empirical formula: $C_{43}H_{50}N_4O_3$
[M+H]$^+$ calculated: 671.3956
[M+H]$^+$ measured: 671.3955

EXAMPLE 30: N-(4-Hydroxyphenyl)-N-methyl-3-{6-[(3R)-3-methyl-1,2,3,4-tetrahydroisoquinoline-2-carbonyl]-2-(3-phenylpropyl)-2,3-dihydro-1H-isoindol-5-yl}-5,6,7,8-tetrahydroindolizine-1-carboxamide The procedure is as described in Step B of Example 29, replacing the compound from Step A with Example 10, and replacing cyclohexylacetaldehyde with 3-phenylpropanal.
LC/MS ($C_{44}H_{46}N_4O_3$) 679 [M+H]$^+$; RT 1.16 (Method B)

High-Resolution Mass (ESI+):
Empirical formula: $C_{44}H_{46}N_4O_3$
$[M+H]^+$ calculated: 679.3643
$[M+H]^+$ measured: 679.3612

EXAMPLE 31: N-(4-Hydroxyphenyl)-N-methyl-3-{6-[(3R)-3-methyl-1,2,3,4-tetrahydroisoquinoline-2-carbonyl]-2-{2-[2-(pyrazin-2-yl)-1,3-thiazol-4-yl]acetyl}-2,3-dihydro-1H-isoindol-5-yl}-5,6,7,8-tetrahydroindolizine-1-carboxamide Step A: N-[4-(benzyloxy)phenyl]-N-methyl-3-{6-[(3R)-3-methyl-1,2,3,4-tetrahydroisoquinoline-2-carbonyl]-2-{2-[2-(pyrazin-2-yl)-1,3-thiazol-4-yl]acetyl}-2,3-dihydro-1H-isoindol-5-yl}-5,6,7,8-tetrahydroindolizine-1-carboxamide To a solution of the product from Preparation 7ab (50 mg, 0.07 mmol) in dichloromethane (3 ml) was added triethylamine (29.2 µL, 0.21 mmol) and HATU (27 mg, 0.07 mmol), followed by 2-[2-(pyrazin-2-yl)-1,3-thiazol-4-yl]acetic acid (14.46 mg, 0.07 mmol), and the mixture was stirred at ambient temperature for ca 16 h. The reaction was diluted with dichloromethane and washed with water. The organic phase was dried over magnesium sulphate, filtered and concentrated in vacuo. Purification by flash column chromatography (silica; dichloromethane to 5% methanol in dichloromethane gradient) afforded the desired product.

LC/MS ($C_{51}H_{47}N_7O_4S$) 854 $[M+H]^+$; RT 2.77 (Method A)

Step B: N-(4-Hydroxyphenyl)-N-methyl-3-{6-[(3R)-3-methyl-1,2,3,4-tetrahydroisoquinoline-2-carbonyl]-2-{2-[2-(pyrazin-2-yl)-1,3-thiazol-4-yl]acetyl}-2,3-dihydro-1H-isoindol-5-yl}-5,6,7,8-tetrahydroindolizine-1-carboxamide A solution of the product from Step A (1 eq, 46 mg) in dichloromethane (5 ml) was cooled to 0° C. and to this was added was added boron trichloride (1M in dichloromethane, 100 µL). The reaction was allowed to warm to ambient temperature for ca 16 h, and was then quenched with methanol and partitioned between dichloromethane and water. The organic extract was dried over magnesium sulphate, filtered and concentrated in vacuo. Purification by flash column chromatography (silica; dichloromethane to 10% methanol in dichloromethane gradient) afforded the desired product.

LC/MS ($C_{44}H_{41}N_7O_4S$) 764 $[M+H]^+$; RT 2.44 (Method A)
High-Resolution Mass (ESI+):
Empirical formula: $C_{44}H_{41}N_7O_4S$
$[M+H]^+$ calculated: 764.3014
$[M+H]^+$ measured: 764.2994

EXAMPLE 32: 3-[2-(3-Cyclohexylpropanoyl)-6-[(3R)-3-methyl-1,2,3,4-tetrahydroisoquinoline-2-carbonyl]-2,3-dihydro-1H-isoindol-5-yl]-N-(4-hydroxyphenyl)-N-methyl-5,6,7,8-tetrahydroindolizine-1-carboxamide Step A: N-[4-(Benzyloxy)phenyl]-3-[2-(3-cyclohexylpropanoyl)-6-[(3R)-3-methyl-1,2,3,4-tetrahydroisoquinoline-2-carbonyl]-2,3-dihydro-1H-isoindol-5-yl]-N-methyl-5,6,7,8-tetrahydroindolizine-1-carboxamide To a solution of the compound from Preparation 7ab (52 mg, 0.066 mmol) in THF (3 mL) are added DIPEA (37 µL, 0.21 mmol) and HBTU (27 mg, 0.07 mmol) followed by 3-cyclohexylpropionic acid (18 µL, 0.10 mmol) and the mixture is stirred at ambient temperature for ca 16 h.

The reaction is partitioned between water and ethyl acetate, separated, and the organic phase is dried (magnesium sulphate) and concentrated in vacuo. Purification by flash column chromatography on silica gel, eluting with a gradient of iso-hexane to ethyl acetate afforded the product as a gum.

LC/MS ($C_{51}H_{56}N_4O_4$) 789 $[M+H]^+$; RT 3.00 (Method A)

Step B: 3-[2-(3-Cyclohexylpropanoyl)-6-[(3R)-3-methyl-1,2,3,4-tetrahydroisoquinoline-2-carbonyl]-2,3-dihydro-1H-isoindol-5-yl]-N-(4-hydroxyphenyl)-N-methyl-5,6,7,8-tetrahydroindolizine-1-carboxamide A solution of the product from Step A (50 mg, 0.06 mmol) in ethanol (10 mL) is added to Pd/C (catalytic), and the mixture is shaken under an atmosphere of hydrogen for ca 16 h. The mixture is filtered through celite, eluting with methanol, and then concentrated in vacuo. The crude material is purified by flash column chromatography on silica, eluting with a gradient of dichloromethane to 5% methanol/dichloromethane to afford the product as a solid.

LC/MS ($C_{44}H_{50}N_4O_4$) 699 $[M+H]^+$; RT 2.76 (Method A)
High-Resolution Mass (ESI+):
Empirical formula: $C_{44}H_{50}N_4O_4$
$[M+H]^+$ calculated: 699.3905
$[M+H]^+$ measured: 699.3926

EXAMPLE 33: 3-{2-Benzyl-6-[(3R)-3-methyl-1,2,3,4-tetrahydroisoquinoline-2-carbonyl]-2,3-dihydro-1H-isoindol-5-yl}-N-(4-hydroxyphenyl)-N-methyl-5,6,7,8-tetrahydroindolizine-1-carboxamide The procedure is as described in Step B of Example 29, replacing the compound from Step A with the compound from Example 10, and replacing cyclohexylacetaldehyde with benzaldehyde.

LC/MS ($C_{42}H_{42}N_4O_3$) 651 $[M+H]^+$; RT 1.11 (Method B)
High-Resolution Mass (ESI+):
Empirical formula: $C_{42}H_{42}N_4O_3$
$[M+H]^+$ calculated: 651.3330
$[M+H]^+$ measured: 651.3300

EXAMPLE 34: N-(4-Hydroxyphenyl)-N-methyl-3-{7-[(3R)-3-methyl-1,2,3,4-tetrahydroisoquinoline-2-carbonyl]-2-propanoyl-1,2,3,4-tetrahydroisoquinolin-6-yl}-5,6,7,8-tetrahydroindolizine-1-carboxamide The procedure is as described in Step A of Example 8, replacing the product from Preparation 7aa in Step A with the product from Preparation 6ab, and replacing 2-phenylacetyl chloride in Step A with propanoyl chloride.

LC/MS ($C_{39}H_{42}N_4O_4$) 631 $[M+H]^+$; RT 1.24 (Method B)
High-Resolution Mass (ESI+):
Empirical formula: $C_{39}H_{42}N_4O_4$
$[M+H]^+$ calculated: 631.3279
$[M+H]^+$ measured: 631.3252

EXAMPLE 35: 3-{2-Benzoyl-7-[(3R)-3-methyl-1,2,3,4-tetrahydroisoquinoline-2-carbonyl]-1,2,3,4-tetrahydroisoquinolin-6-yl}-N-(4-hydroxyphenyl)-N-methyl-5,6,7,8-tetrahydroindolizine-1-carboxamide The procedure is as described in Step A of Example 8, replacing the product from Preparation 7aa in Step A with the product from Preparation 6ab, and replacing 2-phenylacetyl chloride in Step A with benzoyl chloride.
LC/MS ($C_{43}H_{42}N_4O_4$) 679 [M+H]$^+$; RT 1.31 (Method B)
High-Resolution Mass (ESI+):
Empirical formula: $C_{43}H_{42}N_4O_4$
[M+H]$^+$ calculated: 679.3279
[M+H]$^+$ measured: 679.3331

EXAMPLE 36: N-(4-Hydroxyphenyl)-N-methyl-3-{7-[(3R)-3-methyl-1,2,3,4-tetrahydroisoquinoline-2-carbonyl]-2-(2-phenylacetyl)-1,2,3,4-tetrahydroisoquinolin-6-yl}-5,6,7,8-tetrahydroindolizine-1-carboxamide The procedure is as described in Step A of Example 8, replacing the product from Preparation 7aa in Step A with the product from Preparation 6ab.
LC/MS ($C_{44}H_{44}N_4O_4$) 693 [M+H]$^+$; RT 1.32 (Method B)
High-Resolution Mass (ESI+):
Empirical formula: $C_{44}H_{44}N_4O_4$
[M+H]$^+$ calculated: 693.3435
[M+H]$^+$ measured: 693.3447

EXAMPLE 37: N-(4-Hydroxyphenyl)-N-methyl-3-{7-[(3R)-3-methyl-1,2,3,4-tetrahydroisoquinoline-2-carbonyl]-2-(3-phenylpropanoyl)-1,2,3,4-tetrahydroisoquinolin-6-yl}-5,6,7,8-tetrahydroindolizine-1-carboxamide The procedure is as described in Step A of Example 8, replacing the product from Preparation 7aa in Step A with the product from Preparation 6ab, and replacing 2-phenylacetyl chloride in Step A with 3-phenylpropanoyl chloride.
LC/MS ($C_{45}H_{46}N_4O_4$) 707 [M+H]$^+$; RT 1.36 (Method B)
High-Resolution Mass (ESI+):
Empirical formula: $C_{45}H_{46}N_4O_4$
[M+H]$^+$ calculated: 707.3592
[M+H]$^+$ measured: 707.3557

EXAMPLE 38: N-(4-Hydroxyphenyl)-N-methyl-3-{6-[(3S)-3-(morpholin-4-ylmethyl)-1,2,3,4-tetrahydroisoquinoline-2-carbonyl]-2-phenylmethanesulfonyl-2,3-dihydro-1H-isoindol-5-yl}-5,6,7,8-tetrahydroindolizine-1-carboxamide The procedure is as described in Step A of Example 8, replacing 2-phenylacetyl chloride in Step A with phenylmethanesulfonyl chloride.
LC/MS ($C_{46}H_{49}N_5O_6S$) 800 [M+H]$^+$; RT 1.15 (Method B)
High-Resolution Mass (ESI+):
Empirical formula: $C_{46}H_{49}N_5O_6S$
[M+H]$^+$ calculated: 800.3476
[M+H]$^+$ measured: 800.3487

EXAMPLE 39: 3-[2-(Benzenesulfonyl)-7-[(3R)-3-methyl-1,2,3,4-tetrahydroisoquinoline-2-carbonyl]-1,2,3,4-tetrahydroisoquinolin-6-yl]-N-(4-hydroxyphenyl)-N-methyl-5,6,7,8-tetrahydroindolizine-1-carboxamide The procedure is as described in Step A of Example 8, replacing the product from Preparation 7aa with the product from Preparation 6ab, and replacing 2-phenylacetyl chloride in Step A with benzenesulfonyl chloride.
LC/MS ($C_{42}H_{42}N_4O_5S$) 715 [M+H]$^+$; RT 1.37 (Method B)
High-Resolution Mass (ESI+):
Empirical formula: $C_{42}H_{42}N_4O_5S$
[M+H]$^+$ calculated: 715.2949
[M+H]$^+$ measured: 715.2937

EXAMPLE 40: N-(4-Hydroxyphenyl)-N-methyl-3-{7-[(3R)-3-methyl-1,2,3,4-tetrahydroisoquinoline-2-carbonyl]-2-phenylmethanesulfonyl-1,2,3,4-tetrahydroisoquinolin-6-yl}-5,6,7,8-tetrahydroindolizine-1-carboxamide The procedure is as described in Step A of Example 8, replacing the product from Preparation 7aa with the product from Preparation 6ab, and replacing 2-phenylacetyl chloride in Step A with phenylmethanesulfonyl chloride.
LC/MS ($C_{43}H_{44}N_4O_5S$) 729 [M+H]$^+$; RT 1.37 (Method B)
High-Resolution Mass (ESI+):
Empirical formula: $C_{43}H_{44}N_4O_5S$
[M+H]$^+$ calculated: 729.3105
[M+H]$^+$ measured: 729.3135

EXAMPLE 41: N-(4-Hydroxyphenyl)-N-methyl-3-{7-[(3R)-3-methyl-1,2,3,4-tetrahydroisoquinoline-2-carbonyl]-2-(naphthalene-2-sulfonyl)-1,2,3,4-tetrahydroisoquinolin-6-yl}-5,6,7,8-tetrahydroindolizine-1-carboxamide The procedure is as described in Step A of Example 8, replacing the product from Preparation 7aa with the product from Preparation 6ab, and replacing 2-phenylacetyl chloride in Step A with naphthalene-2-sulfonyl chloride.
LC/MS ($C_{46}H_{44}N_4O_5S$) 765 [M+H]$^+$; RT 1.44 (Method B)
High-Resolution Mass (ESI+):
Empirical formula: $C_{46}H_{44}N_4O_5S$
[M+H]$^+$ calculated: 765.3105
[M+H]$^+$ measured: 765.3140

EXAMPLE 42: N-(4-Hydroxyphenyl)-N-methyl-3-{6-[(3S)-3-(morpholin-4-ylmethyl)-1,2,3,4-tetrahydroisoquinoline-2-carbonyl]-2-[2-(pyridin-3-yl)acetyl]-2,3-dihydro-1H-isoindol-5-yl}-5,6,7,8-tetrahydroindolizine-1-carboxamide Step A: N-[4-(benzyloxy)phenyl]-N-methyl-3-{6-[(3S)-3-(morpholin-4-ylmethyl)-1,2,3,4-tetrahydroisoquinoline-2-carbonyl]-2-[2-(pyridin-3-yl)acetyl]-2,3-dihydro-1H-isoindol-5-yl}-5,6,7,8-tetrahydroindolizine-1-carboxamide To a solution of the product from Preparation 7aa (40 mg, 0.05 mmol) in DMF (2 mL) was added triethylamine (28 μL, 0.2 mmol), and HBTU (19 mg, 0.05 mmol) followed by 2-(pyridin-3-yl)acetic acid hydrochloride (9.4 mg, 0.05 mmol), and the mixture was stirred at ambient temperature for 1 h. The reaction was concentrated in vacuo and directly used in the next step.
LC/MS ($C_{53}H_{54}N_6O_5$) no ionisation; RT 1.20 (Method B)

Step B: N-(4-Hydroxyphenyl)-N-methyl-3-{6-[(3S)-3-(morpholin-4-ylmethyl)-1,2,3,4-tetrahydroisoquinoline-2-carbonyl]-2-[2-(pyridin-3-yl)acetyl]-2,3-dihydro-1H-isoindol-5-yl}-5,6,7,8-tetrahydroindolizine-1-carboxamide The product from Step A (25 mg, 0.03 mmol) was dissolved in dichloromethane (2 mL) and cooled to 0° C. To this was added boron trichloride (1M; 0.15 mL, 0.15 mmol) and the mixture was stirred at ambient temperature for 2 h. The reaction was poured onto ice/water and extracted with dichloromethane. The organic extract was washed with brine, dried over magnesium sulfate, filtered and concentrated in vacuo. Purification by flash column chromatography (4 g silica; dichloromethane to 5% methanol/dichloromethane) afforded the desired product.

LC/MS ($C_{46}H_{48}N_6O_5$) 765 [M+H]$^+$; RT 0.95 (Method B) High-Resolution Mass (ESI+):
Empirical formula: $C_{46}H_{48}N_6O_5$
[M+2H]$^{2+}$ calculated: 383.1916
[M+2H]$^{2+}$ measured: 383.1952

EXAMPLE 43: tert-Butyl 5-{1-[(4-hydroxyphenyl)(phenyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxylate The procedure is described in Steps A and B of Example 44.

LC/MS ($C_{45}H_{46}N_4O_5$) 723 [M+H]$^+$; RT 1.47 (Method B) High-Resolution Mass (ESI+):
Empirical formula: $C_{45}H_{46}N_4O_5$
[M+H]$^+$ calculated: 723.3541
[M+H]$^+$ measured: 723.3546

EXAMPLE 44: N-(4-Hydroxyphenyl)-3-{6-[(3R)-3-methyl-1,2,3,4-tetrahydroisoquinoline-2-carbonyl]-2,3-dihydro-1H-isoindol-5-yl}-N-phenyl-5,6,7,8-tetrahydroindolizine-1-carboxamide Step A: tert-Butyl 5-(1-{[4-(benzyloxy)phenyl](phenyl)carbamoyl}-5,6,7,8-tetrahydroindolizin-3-yl)-6-[(3R)-3-methyl-1,2,3,4-tetrahydroisoquinoline-2-carbonyl]-2,3-dihydro-1H-isoindole-2-carboxylate A mix of THF (20 mL) and water (8 mL) is degassed by multiple evacuation/nitrogen purge cycles and bubbling nitrogen through. 4 mL of this mixture is added via syringe to a mixture of the boronic ester from Preparation 4f (117 mg, 0.28 mmol), the bromide from Preparation 1f (169 mg, 0.36 mmol) and cesium carbonate (182 mg, 0.56 mmol). Nitrogen is bubbled through the mix for another 3 mins. Bis(di-tert-butyl(4-dimethylaminophenyl)phosphine)dichloropalladium(II) (10 mg, 5 mole %) is added and the reaction is immediately heated at 95° C. under microwave irradiation for 30 mins.

The reaction mixture is diluted with ethyl acetate (30 mL) and washed sequentially with water (2×30 mL) and saturated NaCl (aq) (1×50 mL), dried over magnesium sulphate, filtered and evaporated. The crude material is purified by flash chromatography (Combiflash, 12 g silica, eluting with gradient 0 to 100% ethyl acetate in hexane) to afford the product as an oil.

LC/MS ($C_{52}H_{52}N_4O_5$) 813 [M+H]$^+$; RT 1.66 (Method B)

Step B: tert-Butyl 5-{1-[(4-hydroxyphenyl)(phenyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxylate A solution of the product from Step A (94 mg, 0.12 mmol) in ethanol (5 mL) is hydrogenated over 10% Pd/C catalyst under an atmosphere of hydrogen for ca 16 h. The mixture was filtered through celite, eluting with ethanol, and concentrated in vacuo. Purification by flash chromatography on silica gel (CombiFlash Rf, 4 g SiO2 silica column) eluting with 0 to 100% ethyl acetate in hexane afforded the product as a solid.

LC/MS ($C_{45}H_{46}N_4O_5$) 723 [M+H]$^+$; RT 1.47 (Method B)

Step C: N-(4-Hydroxyphenyl)-3-{6-[(3R)-3-methyl-1,2,3,4-tetrahydroisoquinoline-2-carbonyl]-2,3-dihydro-1H-isoindol-5-yl}-N-phenyl-5,6,7,8-tetrahydroindolizine-1-carboxamide To a solution of the product from Step B (40 mg, 0.055 mmol) in anhydrous dichloromethane (4 mL) under nitrogen is added trifluoroacetic acid (180 uL, 2.33 mmol) and the reaction is stirred for ca 16 h. The mixture is diluted with dichloromethane (25 mL) and washed sequentially with 1M NaOH (aq) solution (20 mL) and saturated NaCl (aq) solution (20 mL). The organic phase is dried over sodium sulphate, filtered and evaporated. The crude material is purified by flash chromatography on silica gel (CombiFlash Rf, 4 g, SilaSep column) eluting with 0 to 15% Methanol in dichloromethane to afford a glassy solid. Trituration with diethyl ether and evaporation afforded the desired product as a solid.

LC/MS ($C_{40}H_{38}N_4O_3$) 623 [M+H]$^+$; RT 1.08 (Method B) High-Resolution Mass (ESI+):
Empirical formula: $C_{40}H_{38}N_4O_3$
[M+H]$^+$ calculated: 623.3017
[M+H]$^+$ measured: 623.3028

EXAMPLE 45: Phenyl 5-{1-[(4-hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxylate The procedure is as in Step A of Example 8, replacing the product from Preparation 7aa with the product from Preparation 7ab, and replacing 2-phenylacetyl chloride with phenyl chloroformate.

LC/MS ($C_{42}H_{40}N_4O_5$) 681 [M+H]$^+$; RT 1.36 (Method B) High-Resolution Mass (ESI+):
Empirical formula: $C_{42}H_{40}N_4O_5$
[M+H]$^+$ calculated: 681.3071
[M+H]$^+$ measured: 681.3057

EXAMPLE 46: Phenyl 6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate The procedure is as in Step A of Example 8, replacing the product from Preparation 7aa with the product from Preparation 6ab, and replacing 2-phenylacetyl chloride with phenyl chloroformate.

LC/MS ($C_{43}H_{42}N_4O_5$) 695 [M+H]$^+$; RT 1.41 (Method B) High-Resolution Mass (ESI+):
Empirical formula: $C_{43}H_{42}N_4O_5$
[M+H]$^+$ calculated: 695.3228
[M+H]$^+$ measured: 695.3193

EXAMPLE 47: tert-Butyl 6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate Step A: tert-Butyl 6-(1-[{4-(benzyloxy)phenyl](methyl)carbamoyl}-5,6,7,8-tetrahydroindolizin-3-yl)-7-[(3R)-3-methyl-1,2,3,4-tetrahydroisoquinoline-2-carbonyl]-1,2,3,4-tetrahydroisoquinoline-2-carboxylate The procedure is described in Step A of Preparation 6ab.
LC/MS ($C_{48}H_{52}N_4O_5$) 765 [M+H]$^+$; RT 1.62 (Method B)

Step B: tert-Butyl 6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate A solution of the product from Step A (50 mg, 0.07 mmol) in ethanol (5 mL) is added to Pd/C (catalytic), and the mixture is shaken under an atmosphere of hydrogen for ca 16 h. The mixture is filtered through celite, eluting with methanol, and then concentrated in vacuo. The crude material is purified by flash column chromatography on silica, eluting with a gradient of dichloromethane to 5% methanol/dichloromethane to afford the product as a solid.
LC/MS ($C_{41}H_{46}N_4O_5$) 675 [M+H]$^+$; RT 1.42 (Method B)
High-Resolution Mass (ESI+):
Empirical formula: $C_{41}H_{46}N_4O_5$
[M+H]$^+$ calculated: 675.3541
[M+H]$^+$ measured: 675.3571

EXAMPLE 48: N-tert-Butyl-6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxamide The procedure is as in Step A of Example 8, replacing the product from Preparation 7aa with the product from Preparation 6ab, and replacing 2-phenylacetyl chloride with 2-isocyanato-2-methylpropane.
LC/MS ($C_{41}H_{47}N_5O_4$) 674 [M+H]$^+$; RT 1.33 (Method B)
High-Resolution Mass (ESI+):
Empirical formula: $C_{41}H_{47}N_5O_4$
[M+H]$^+$ calculated: 674.3701
[M+H]$^+$ measured: 674.3706

EXAMPLE 49: 3-{2-[2-(4-Chlorophenoxy)acetyl]-6-[(3R)-3-methyl-1,2,3,4-tetrahydroisoquinoline-2-carbonyl]-2,3-dihydro-1H-isoindol-5-yl}-N-(4-hydroxyphenyl)-N-methyl-5,6,7,8-tetrahydroindolizine-1-carboxamide Step A: N-[4-(Benzyloxy)phenyl]-3-{2-[2-(4-chlorophenoxy)acetyl]-6-[(3R)-3-methyl-1,2,3,4-tetrahydroisoquinoline-2-carbonyl]-2,3-dihydro-1H-isoindol-5-yl}-N-methyl-5,6,7,8-tetrahydroindolizine-1-carboxamide The procedure is as in Step A of Example 8, replacing the product from Preparation 7aa with the product from Preparation 7ab, and replacing 2-phenylacetyl chloride with 2-(4-chlorophenoxy)acetyl chloride.
LC/MS ($C_{50}H_{47}N_4O_5Cl$) 819 [M+H]$^+$; RT 1.56 (Method B)

Step B: 3-{2-[2-(4-Chlorophenoxy)acetyl]-6-[(3R)-3-methyl-1,2,3,4-tetrahydroisoquinoline-2-carbonyl]-2,3-dihydro-1H-isoindol-5-yl}-N-(4-hydroxyphenyl)-N-methyl-5,6,7,8-tetrahydroindolizine-1-carboxamide The procedure is as in Step B of Example 42, replacing with the product from Step A of Example 42 with the product from Step A of Example 49.
LC/MS ($C_{43}H_{41}N_4O_5Cl$) 729 [M+H]$^+$; RT 1.37 (Method B)
High-Resolution Mass (ESI+):
Empirical formula: $C_{43}H_{41}N_4O_5Cl$
[M+H]$^+$ calculated: 729.2838
[M+H]$^+$ measured: 729.2809

EXAMPLE 50: 3-{2-[2-(3-Chlorophenoxy)acetyl]-6-[(3R)-3-methyl-1,2,3,4-tetrahydroisoquinoline-2-carbonyl]-2,3-dihydro-1H-isoindol-5-yl}-N-(4-hydroxyphenyl)-N-methyl-5,6,7,8-tetrahydroindolizine-1-carboxamide The procedure is as in Example 49, replacing 2-(4-chlorophenoxy)acetyl chloride in Step A with 2-(3-chlorophenoxy)acetyl chloride.
LC/MS ($C_{43}H_{41}N_4O_5Cl$) 729 [M+H]$^+$; RT 1.37 (Method B)
High-Resolution Mass (ESI+):
Empirical formula: $C_{43}H_{41}N_4O_5Cl$
[M+H]$^+$ calculated: 729.2838
[M+H]$^+$ measured: 729.2871

EXAMPLE 51: N-(4-Hydroxyphenyl)-3-{2-[2-(4-methoxyphenyl)acetyl]-6-[(3R)-3-methyl-1,2,3,4-tetrahydroisoquinoline-2-carbonyl]-2,3-dihydro-1H-isoindol-5-yl}-N-methyl-5,6,7,8-tetrahydroindolizine-1-carboxamide High-Resolution Mass (ESI+):
Empirical formula: $C_{44}H_{44}N_4O_5$
[M+H]$^+$ calculated: 709.3392
[M+H]$^+$ measured: 709.3382

EXAMPLE 52: N-(4-Hydroxyphenyl)-N-methyl-3-{6-[(3R)-3-methyl-1,2,3,4-tetrahydroisoquinoline-2-carbonyl]-2-(2-phenoxyacetyl)-2,3-dihydro-1H-isoindol-5-yl}-5,6,7,8-tetrahydroindolizine-1-carboxamide The procedure is as described in Step A of Example 8, replacing the product from Preparation 7aa in Step A with the product from Preparation 7ab, and replacing 2-phenylacetyl chloride in Step A with 2-phenoxyacetyl chloride.
LC/MS ($C_{43}H_{42}N_4O_5$) 695 [M+H]$^+$; RT 1.31 (Method B)
High-Resolution Mass (ESI+):
Empirical formula: $C_{43}H_{42}N_4O_5$
[M+H]$^+$ calculated: 695.3228
[M+H]$^+$ measured: 695.3252

EXAMPLE 53: 3-{2-[2-(4-Cyanophenyl)acetyl]-7-[(3R)-3-methyl-1,2,3,4-tetrahydroisoquinoline-2-carbonyl]-1,2,3,4-tetrahydroisoquinolin-6-yl}-N-(4-hydroxyphenyl)-N-methyl-5,6,7,8-tetrahydroindolizine-1-carboxamide The procedure is as in Example 24, replacing the product from Example 10 with the product from Example 27, and replacing 3-(4-chlorophenyl)-2-methylpropanoic acid with 2-(4-cyanophenyl)acetic acid.

LC/MS ($C_{45}H_{43}N_5O_4$) 718 [M+H]$^+$; RT 1.29

EXAMPLE 54: N-(4-Hydroxyphenyl)-N-methyl-3-{7-[(3R)-3-methyl-1,2,3,4-tetrahydroisoquinoline-2-carbonyl]-2-[2-(4-methylphenyl)acetyl]-1,2,3,4-tetrahydroisoquinolin-6-yl}-5,6,7,8-tetrahydroindolizine-1-carboxamide LC/MS ($C_{45}H_{46}N_4O_4$) 707 [M+H]$^+$; RT 2.65 (Method A)
High-Resolution Mass (ESI+):
Empirical formula: $C_{45}H_{46}N_4O_4$
[M+H]$^+$ calculated: 707.3592
[M+H]$^+$ measured: 707.3556

EXAMPLE 55: 5-{1-[(4-Hydroxyphenyl)(methyl)carbamoyl]-5,6,7,8-tetrahydroindolizin-3-yl}-N-methyl-6-[(3R)-3-methyl-1,2,3,4-tetrahydroisoquinoline-2-carbonyl]-2,3-dihydro-1H-isoindole-2-carboxamide Step A: tert-Butyl 5-{1-[(4-hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxylate To a solution of the compound of Step A of Preparation 7ab (400 mg, 0.53 mmol) in ethanol (10 mL) is added 10% Pd/C (catalytic), and the mixture is stirred under an atmosphere of hydrogen for ca 16 h. The mixture is filtered through celite, concentrated under reduced pressure, and purified by flash column chromatography on silica to afford the product as a glassy solid.

LC/MS ($C_{40}H_{44}N_4O_5$) 661 [M+H]$^+$; RT 1.41 (Method B)

Step B: N-(4-Hydroxyphenyl)-N-methyl-3-{6-[(3R)-3-methyl-1,2,3,4-tetrahydroisoquinoline-2-carbonyl]-2,3-dihydro-1H-isoindol-5-yl}-5,6,7,8-tetrahydroindolizine-1-carboxamide; trifluoroacetic acid salt To a solution of the product from Step A (300 mg) in dichloromethane (5 mL) is added trifluoroacetic acid (excess) and the mixture is allowed to stir at ambient temperature for ca 16 h. The reaction is concentrated in vacuo and triturated with ether to afford the product as a solid.

LC/MS ($C_{35}H_{36}N_4O_3$) 561 [M+H]$^+$; RT 1.01 (Method B)

Step C: 5-{1-[(4-Hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carbonyl chloride To a solution of the product from Step B (100 mg, 0.15 mmol) in dichloromethane (2 mL), cooled to 0° C., is added DIPEA (61 uL, 0.37 mmol) followed by portion-wise addition of triphosgene (44 mg, 0.15 mmol). The reaction is allowed to warm to ambient temperature and stirred for 1 h, then partitioned between dichloromethane and 1M aqueous HCl. The organic phase is dried over magnesium sulphate and concentrated in vacuo to afford the product as a mixture of trichloromethyl 5-{1-[(4-hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxylate and 5-{1-[(4-hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carbonyl chloride that was used directly in the next step without further purification.

LC/MS ($C_{37}H_{35}Cl_3N_4O_5$) 721 [M+H]$^+$; RT 1.44, ($C_{36}H_{35}ClN_4O_4$) 623 [M+H]$^+$; RT 1.32 (Method B)

Step D: 5-{1-[(4-Hydroxyphenyl)(methyl)carbamoyl]-5,6,7,8-tetrahydroindolizin-3-yl}-N-methyl-6-[(3R)-3-methyl-1,2,3,4-tetrahydroisoquinoline-2-carbonyl]-2,3-dihydro-1H-isoindole-2-carboxamide To a solution of the product from Step C (50 mg, 0.07 mmol) in acetonitrile (2 mL) is added methylamine (2M in THF; 346 uL, 0.69 mmol) and DIPEA (61 uL, 0.31 mmol) and the mixture is stirred for ca 16 h. Solvent is removed in vacuo and the residue is partitioned between ethyl acetate and water, the organic phase is dried over magnesium sulphate, and the solvent is removed in vacuo. The residue is dissolved in 1,4-dioxane (2 mL) and a 1M aqueous solution of NaOH (5 mL) was added dropwise. After 1 h the mixture is diluted with water, acidified with 1M aqueous HCl, and extracted with ethyl acetate. The organic extracts are dried over magnesium sulphate and concentrated under reduced pressure. Purification on CombiFlash (4 g silica, dichloromethane to 5% MeOH/dichloromethane) afforded the desired product as a solid.

LC/MS ($C_{37}H_{39}N_5O_4$) 618 [M+H]$^+$; RT 2.27 (Method A)
High-Resolution Mass (ESI+):
Empirical formula: $C_{37}H_{39}N_5O_4$
[M+H]$^+$ calculated: 618.3075
[M+H]$^+$ measured: 618.3069

EXAMPLE 56: 3-[2-(Ethanesulfonyl)-7-[(3R)-3-methyl-1,2,3,4-tetrahydroisoquinoline-2-carbonyl]-1,2,3,4-tetrahydroisoquinolin-6-yl]-N-(4-hydroxyphenyl)-N-methyl-5,6,7,8-tetrahydroindolizine-1-carboxamide The procedure is as described in Step A and Step B of Example 8, replacing the product from Preparation 7aa in Step A with the product from Preparation 6ab, and replacing 2-phenylacetyl chloride in Step A with ethanesulfonyl chloride.

LC/MS ($C_{38}H_{42}N_4O_5S$) 667 [M+H]$^+$; RT 1.27 (Method B)
High-Resolution Mass (ESI+):
Empirical formula: $C_{38}H_{42}N_4O_5S$
[M+H]$^+$ calculated: 667.2949
[M+H]$^+$ measured: 667.2935

EXAMPLE 57: 3-{2-Ethyl-7-[(3R)-3-methyl-1,2,3,4-tetrahydroisoquinoline-2-carbonyl]-1,2,3,4-tetrahydroisoquinolin-6-yl}-N-(4-hydroxyphenyl)-N-methyl-5,6,7,8-tetrahydroindolizine-1-carboxamide LC/MS ($C_{38}H_{42}N_4O_3$) 603 [M+H]$^+$; RT 1.05 (Method B)
High-Resolution Mass (ESI+):

Empirical formula: $C_{38}H_{42}N_4O_3$
[M+H]$^+$ calculated: 603.3330
[M+H]$^+$ measured: 603.3270

EXAMPLE 58: 4-Aminophenyl 6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate Step A: 4-nitrophenyl 6-(1-{[4-(benzyloxy)phenyl](methyl)carbamoyl}-5,6,7,8-tetrahydroindolizin-3-yl)-7-[(3R)-3-methyl-1,2,3,4-tetrahydroisoquinoline-2-carbonyl]-1,2,3,4-tetrahydroisoquinoline-2-carboxylate To a solution of the product from Preparation 7ab (43 mg, 0.07 mmol) in dichloromethane (5 mL) was added 4-nitrophenyl chloroformate (18 mg, 0.09 mmol) and allowed to stir at ambient temperature ca 16 h. The reaction was diluted with dichloromethane and washed with 1N HCl, NaHCO$_3$ and brine. The organic phase was dried over magnesium sulphate, filtered and concentrated in vacuo, and taken forward assuming quantitative transformation.
LC/MS ($C_{50}H_{47}N_5O_7$) 830 [M+H]$^+$; RT 1.58 (Method B)

Step B: 4-Aminophenyl 6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate To a solution of the compound of Step A (54 mg, 0.07 mmol) in ethanol (10 mL) is added 10% Pd/C (catalytic), and the mixture is stirred under an atmosphere of hydrogen for ca 16 h. The reaction mixture was filtered through celite and concentrated under reduced pressure.
LC/MS ($C_{43}H_{43}N_5O_5$) 708 [M−H]$^−$; RT 1.26 (Method B)
High-Resolution Mass (ESI+):
Empirical formula: $C_{43}H_{43}N_5O_5$
[M+H]$^+$ calculated: 710.3337
[M+H]$^+$ measured: 710.3302

EXAMPLE 59: 4-Acetamidophenyl 6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate 4-Aminophenyl 6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate [Example 58] (23 mg, 0.03 mmol) is dissolved in dichloromethane (5 mL) followed by the addition of DIPEA (0.17 mL, 1 mmol) and cooled to 0° C. Acetyl chloride (3 µL, 0.04 mmol) is added and the reaction mixture is stirred for ca 16 h at ambient temperature. Ammonia in methanol (7 N; 1 mL) is added, and the resultant mixture is washed with saturated NaHCO$_3$ solution and brine, dried over magnesium sulphate, filtered and concentrated. The product is purified by FlashChrom (24 g silica, dichloromethane to 5% methanol/dichloromethane).
LC/MS ($C_{45}H_{45}N_5O_6$) 752 [M+H]$^+$; RT 1.25 (Method B)
High-Resolution Mass (ESI+):
Empirical formula: $C_{45}H_{45}N_5O_6$
[M+H]$^+$ calculated: 752.3443
[M+H]$^+$ measured: 752.3461

EXAMPLE 60: 5-{1-[(4-Hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-N-phenyl-2,3-dihydro-1H-isoindole-2-carboxamide The procedure is as described in Step A and Step B of Example 8, replacing the product from Preparation 7aa in Step A with the product from Preparation 7ab, and replacing 2-phenylacetyl chloride in Step A with phenyl isocyanate.
LC/MS ($C_{42}H_{41}N_5O_4$) 680 [M+H]$^+$; RT 1.29 (Method B)
High-Resolution Mass (ESI+):
Empirical formula: $C_{42}H_{41}N_5O_4$
[M+H]$^+$ calculated: 680.3231
[M+H]$^+$ measured: 680.3225

EXAMPLE 61: N-Benzyl-5-{1-[(4-hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxamide The procedure is as described in Step A and Step B of Example 8, replacing the product from Preparation 7aa in Step A with the product from Preparation 7ab, and replacing 2-phenylacetyl chloride in Step A with benzyl isocyanate.
LC/MS ($C_{43}H_{43}N_5O_4$) 694 [M+H]$^+$; RT 1.28 (Method B)
High-Resolution Mass (ESI+):
Empirical formula: $C_{43}H_{43}N_5O_4$
[M+H]$^+$ calculated: 694.3388
[M+H]$^+$ measured: 694.3392

EXAMPLE 62: Benzyl 5-{1-[(4-hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxylate A solution of the product obtained from Example 10 (53 mg, 0.08 mmol) in dichloromethane (5 mL) was cooled to 0° C. and to this was added N,N-diisopropylethylamine (0.18 mmol) and benzyl chloroformate (14.7 mg, 0.09 mmol). The reaction was stirred at ambient temperature for 15 min, then diluted with dichloromethane and washed successively with 1M aqueous sodium hydroxide, and brine. The organic extract was dried over magnesium sulphate, filtered and concentrated in vacuo. Purification by flash column chromatography (CombiFlash R$_f$, 4 g RediSep™ silica cartridge; gradient of dichloromethane to 5% methanol in dichloromethane) afforded the desired product.
LC/MS ($C_{43}H_{42}N_4O_5$) 695 [M+H]$^+$; RT 1.40 (Method B)
High-Resolution Mass (ESI+):
Empirical formula: $C_{43}H_{42}N_4O_5$
[M+H]$^+$ calculated: 695.3228
[M+H]$^+$ measured: 695.3241

EXAMPLE 63: Phenyl 5-{4-[(4-hydroxyphenyl)(methyl)carbamoyl]-1,5-dimethyl-1H-pyrrol-2-yl}-6-[(3R)-3-methyl-1,2,3,4-tetrahydroisoquinoline-2-carbonyl]-2,3-dihydro-1H-isoindole-2-carboxylate The procedure is as in Example 8, replacing the product from Preparation 7aa with the product from Preparation 7bb, and replacing 2-phenylacetyl chloride in Step A with phenyl chloroformate.
LC/MS ($C_{40}H_{38}N_4O_5$) 655 [M+H]$^+$; RT 1.33 (Method B)

High-Resolution Mass (ESI+):
Empirical formula: $C_{40}H_{38}N_4O_5$
$[M+H]^+$ calculated: 655.2915
$[M+H]^+$ measured: 655.2897

EXAMPLE 64: 1H-pyrrolo[2,3-b]pyridin-5-ylmethyl 5-{1-[(4-hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxylate Step A: 4-Nitrophenyl 1H-pyrrolo[2,3-b]pyridin-5-ylmethyl carbonate To a solution of 1H-pyrrolo[2,3-b]pyridin-5-ylmethanol (148 mg, 1 mmol) and N,N-diisopropylethylamine (261 μL, 1.5 mmol) in DCM (10 mL) was added 4-nitrophenyl chloroformate (202 mg, 1 mmol) and the mixture was stirred at ambient temperature. After concentrating in vacuo, purification by flash column chromatography (silica; ethyl acetate) afforded the desired material.
LC/MS ($C_{15}H_{11}N_3O_5$) 314 $[M+H]^+$; RT 1.19 (Method B)

Step B: 1H-pyrrolo[2,3-b]pyridin-5-ylmethyl 5-{1-[(4-hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxylate To a solution of the product from Example 10 (10 mg, 0.02 mmol) in tetrahydrofuran (1 ml) was added N,N-diisopropylethylamine (11 μL, 0.06 mmol) followed by the product from Step A (6 mg, 0.02 mmol), and the mixture was stirred at ambient temperature for ca 16 h. After this time, further N,N-diisopropylethylamine (11 μL, 0.06 mmol) and product from Step A (6 mg, 0.02 mmol) were added to affect full conversion. Purification by flash column chromatography (silica; gradient of iso-hexane to ethyl acetate) followed by evaporation and trituration with diethyl ether afforded the desired product.
LC/MS ($C_{44}H_{42}N_6O_5$) 735 $[M+H]^+$; RT 2.48 (Method A)

EXAMPLE 65: 5-{1-[(4-Hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-N-[4-(4-methylpiperazin-1-yl)phenyl]-2,3-dihydro-1H-isoindole-2-carboxamide The procedure is as in Example 8, replacing the product from Preparation 7aa with the product from Preparation 7ab, and replacing 2-phenylacetyl chloride in Step A with 1-(4-isocyanatophenyl)-4-methylpiperazine.
LC/MS ($C_{47}H_{51}N_7O_4$) 776 $[M-H]^-$; RT 2.18 (Method A)
High-Resolution Mass (ESI+):
Empirical formula: $C_{47}H_{51}N_7O_4$
$[M+2H]^{2+}$ calculated: 389.7074
$[M+2H]^{2+}$ measured: 389.7107

EXAMPLE 66: N-(4-Hydroxyphenyl)-N-methyl-3-{6-[(3R)-3-methyl-1,2,3,4-tetrahydroisoquinoline-2-carbonyl]-2-(3-phenylpyrrolidine-1-carbonyl)-2,3-dihydro-1H-isoindol-5-yl}-5,6,7,8-tetrahydroindolizine-1-carboxamide Step A: 3-Phenylpyrrolidine-1-carbonyl chloride A solution of the 3-phenylpyrrolidine hydrochloride (50 mg, 0.27 mmol) and N,N-diisopropylethylamine (0.14 mL, 0.81 mmol) in dichloromethane (2 ml) was cooled to 0° C. To this was added triphosgene (81 mg, 0.27 mmol) and the mixture was stirred at ambient temperature. The reaction was subsequently diluted with water and the product extracted into dichloromethane, dried over magnesium sulphate and purified by flash column chromatography (silica; gradient of iso-hexane to 10% ethyl acetate in iso-hexane) to afford the desired product.
LC/MS ($C_{11}H_2NOCl$) 210 $[M+H]^+$; RT 2.56 (Method A)

Step B: N-(4-Hydroxyphenyl)-N-methyl-3-{6-[(3R)-3-methyl-1,2,3,4-tetrahydroisoquinoline-2-carbonyl]-2-(3-phenylpyrrolidine-1-carbonyl)-2,3-dihydro-1H-isoindol-5-yl}-5,6,7,8-tetrahydroindolizine-1-carboxamide The procedure is as for Example 8, replacing the product from Preparation 7aa with the product from Preparation 7ab, and replacing 2-phenylacetyl chloride with the acid chloride obtained in Step A of Example 66.
LC/MS ($C_{46}H_{47}N_5O_4$) 734 $[M+H]^+$; RT 2.68 (Method A)
High-Resolution Mass (ESI+):
Empirical formula: $C_{46}H_{47}N_5O_4$
$[M+H]^+$ calculated: 734.3701
$[M+H]^+$ measured: 734.3673

EXAMPLE 67: N-(4-Hydroxyphenyl)-N-methyl-3-{7-[(3R)-3-methyl-1,2,3,4-tetrahydroisoquinoline-2-carbonyl]-2-(3-phenylpyrrolidine-1-carbonyl)-1,2,3,4-tetrahydroisoquinolin-6-yl}-5,6,7,8-tetrahydroindolizine-1-carboxamide The procedure is as for Step A from Example 11, replacing the product from Preparation 7aa with the product from Example 27, and replacing propionyl chloride with the acid chloride obtained in Step A of Example 66.
LC/MS ($C_{47}H_{49}N_5O_4$) 748 $[M+H]^+$; RT 2.71 (Method A)
High-Resolution Mass (ESI+):
Empirical formula: $C_{47}H_{49}N_5O_4$
$[M+H]^+$ calculated: 748.3857
$[M+H]^+$ measured: 748.3815

EXAMPLE 68: Phenyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 8, replacing the product from Preparation 7aa with the product from Preparation 6bb, and replacing 2-phenylacetyl chloride in Step A with phenyl chloroformate.
LC/MS ($C_{41}H_{40}N_4O_5$) 669 $[M+H]^+$; RT 1.35 (Method B)
High-Resolution Mass (ESI+):
Empirical formula: $C_{41}H_{40}N_4O_5$
$[M+H]^+$ calculated: 669.3071
$[M+H]^+$ measured: 669.3045

EXAMPLE 69: Phenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate hydrochloride Step A: N-[4-(Benzyloxy)phenyl]-N-methyl-3-{7-[(3S)-3-(morpholin-4-ylmethyl)-1,2,3,4-tetrahydroisoquinoline-2-carbonyl]-1,2,3,4-tetrahydroisoquinolin-6-yl}-5,6,7,8-tetrahydroindolizine-1-carboxamide dihydrochloride The product from Step A of Preparation 6aa (549 mg, 0.65 mmol) is dissolved in methanol (5 mL), then a solution of HCl in dioxane (4 M; 10 mL) is added and the mixture is allowed to stir for ca 16 h. Ether is added, resulting in the precipitation of a solid which is collected by filtration and washed with ether to afford the desired product.

LC/MS ($C_{47}H_{51}N_5O_4$) 750[M+H]$^+$; RT 1.09 (Method B)

Step B: Phenyl 6-(1-[{4-(benzyloxy)phenyl](methyl)carbamoyl}-5,6,7,8-tetrahydroindolizin-3-yl)-7-[(3S)-3-(morpholin-4-ylmethyl)-1,2,3,4-tetrahydroisoquinoline-2-carbonyl]-1,2,3,4-tetrahydroisoquinoline-2-carboxylate The product from Step A (100 mg, 0.12 mmol) is dissolved in dichloromethane (5 mL) and to this is added DIPEA (174 uL, 1 mmol) and the solution cooled to 0° C. Phenyl chloroformate (18 uL, 0.14 mmol) is added and the mixture is stirred for 30 minutes before diluting with dichloromethane, washing sequentially with 1M NaOH and brine, and then drying over magnesium sulphate. The solvent is removed in vacuo, and the residue is taken up in dichloromethane and purified on CombiFlash (12 g silica; dichloromethane to 5% methanol/dichloromethane) to afford the product as a solid.

LC/MS ($C_{54}H_{55}N_5O_6$) 870[M+H]$^+$; RT 1.45 (Method B)

Step C: Phenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate hydrochloride A solution of the product from Step B (96.6 mg, 0.11 mmol) in ethanol (5 mL) is added to a catalytic amount of 10% Pd/C, and the mixture is shaken under an atmosphere of hydrogen gas for ca 16 h. The mixture is filtered through celite and evaporated, whereby the residue is dissolved in a minimum amount of isopropyl alcohol. To the resultant solution is added ethereal HCl (1M, 0.5 mL), followed by ether, and the solid product is collected by vacuum filtration.

LC/MS ($C_{47}H_{49}N_5O_6$) 780[M+H]$^+$; RT 1.21 (Method B)
High-Resolution Mass (ESI+):
Empirical formula: $C_{47}H_{49}N_5O_6$
[M+H]$^+$ calculated: 780.3756
[M+H]$^+$ measured: 780.3791

EXAMPLE 70: N-(4-Hydroxyphenyl)-N-methyl-3-{7-[(3S)-3-(morpholin-4-ylmethyl)-1,2,3,4-tetrahydroisoquinoline-2-carbonyl]-2-(2-phenylacetyl)-1,2,3,4-tetrahydroisoquinolin-6-yl}-5,6,7,8-tetrahydroindolizine-1-carboxamide The procedure is as in Example 8, replacing the product from Preparation 7aa in Step A with the product from Preparation 6aa.

LC/MS ($C_{48}H_{51}N_5O_5$) 778 [M+H]$^+$; RT 1.14 (Method B)

EXAMPLE 71: 6-{1-[(4-Hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-N-phenyl-1,2,3,4-tetrahydroisoquinoline-2-carboxamide The procedure is as in Step A of Example 8, replacing the product from Preparation 7aa in Step A with the product from Preparation 6aa, and replacing 2-phenylacetyl chloride with phenyl isocyanate.

LC/MS ($C_{43}H_{43}N_5O_4$) 694 [M+H]$^+$; RT 1.31 (Method B)
High-Resolution Mass (ESI+):
Empirical formula: $C_{43}H_{43}N_5O_4$
[M+H]$^+$ calculated: 694.3388
[M+H]$^+$ measured: 694.3356

EXAMPLE 72: N-(4-Hydroxyphenyl)-N-methyl-3-{6-[(3R)-3-methyl-1,2,3,4-tetrahydroisoquinoline-2-carbonyl]-2-(2-phenylethyl)-2,3-dihydro-1H-isoindol-5-yl}-5,6,7,8-tetrahydroindolizine-1-carboxamide LC/MS ($C_{43}H_{44}N_4O_3$) 665 [M+H]+; RT 1.10 (Method B)
High-Resolution Mass (ESI+):
Empirical formula: $C_{43}H_{44}N_4O_3$
[M+H]$^+$ calculated: 665.3486
[M+H]$^+$ measured: 665.3477

EXAMPLE 73: N-Benzyl-6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxamide The procedure is as in Example 8, replacing the product from Preparation 7aa in Step A with the product from Preparation 6aa, and replacing 2-phenylacetyl chloride with benzyl isocyanate.

LC/MS ($C_{44}H_{45}N_5O_4$) 708 [M+H]$^+$; RT 1.3 (Method B)
High-Resolution Mass (ESI+):
Empirical formula: $C_{44}H_{45}N_5O_4$
[M+H]$^+$ calculated: 708.3544
[M+H]$^+$ measured: 708.3556

EXAMPLE 74: 6-{1-[(4-Hydroxyphenyl)(methyl)carbamoyl]-5,6,7,8-tetrahydroindolizin-3-yl}-N-methyl-7-[(3R)-3-methyl-1,2,3,4-tetrahydroisoquinoline-2-carbonyl]-N-phenyl-1,2,3,4-tetrahydroisoquinoline-2-carboxamide Step A: 6-(1-{[4-(benzyloxy)phenyl](methyl)carbamoyl}-5,6,7,8-tetrahydroindolizin-3-yl)-7-[(3R)-3-methyl-1,2,3,4-tetrahydroisoquinoline-2-carbonyl]-1,2,3,4-tetrahydroisoquinoline-2-carbonyl chloride A solution of the product from Preparation 6ab (50 mg, 0.08 mmol) in dichloromethane (5 mL) was cooled to 0° C. and to this was added N,N-diisopropylethylamine (0.3 mmol) followed by triphosgene (22.3 mg, 0.08 mmol), and the mixture was allowed to stir at ambient temperature for 1 h. The reaction was partitioned between dichloromethane and 1M aqueous HCl, and the organic extract was dried over magnesium sulphate. After concentration in vacuo, the material was used directly in the next step assuming quantitative transformation.

LC/MS ($C_{44}H_{43}N_4O_4Cl$) 727 [M+H]$^+$; RT 1.54 (Method B)

Step B: 6-(1-{[4-(benzyloxy)phenyl](methyl)carbamoyl}-5,6,7,8-tetrahydroindolizin-3-yl)-N-methyl-7-[(3R)-3-methyl-1,2,3,4-tetrahydroisoquinoline-2-carbonyl]-N-phenyl-1,2,3,4-tetrahydroisoquinoline-2-carboxamide To a solution of product obtained from Step A (62 mg, 0.08 mmol) in Acetonitrile (5 mL) was added N,N-diisopropylethylamine (0.40 mmol) and N-methylaniline (80.4 mg, 0.75 mmol), and the mixture was stirred at ambient temperature for ca 16 h. The reaction mixture was diluted with ethyl acetate and successively washed with aqueous sodium bicarbonate, and brine. The organic extract was dried over magnesium sulfate, filtered, and concentrated in vacuo. Purification by flash column chromatography (4 g silica, dichloromethane to 5% methanol in dichloromethane) afforded the desired product.

LC/MS ($C_{51}H_{51}N_5O_4$) 798 [M+H]$^+$; RT 1.56 (Method B)

Step C: 6-{1-[(4-Hydroxyphenyl)(methyl)carbamoyl]-5,6,7,8-tetrahydroindolizin-3-yl}-N-methyl-7-[(3R)-3-methyl-1,2,3,4-tetrahydroisoquinoline-2-carbonyl]-N-phenyl-1,2,3,4-tetrahydroisoquinoline-2-carboxamide To a solution of product obtained in Step B (60 mg, 0.08 mmol) in ethanol (5 mL) was added 10% Pd/C (catalytic amount) and the mixture was shaken under an atmosphere of hydrogen for ca 16 h. The mixture was filtered through celite, subsequently eluting with methanol, and the solvent was removed in vacuo. Purification by flash column chromatography (4 g silica; dichloromethane to 5% methanol in dichloromethane) afforded the desired product as a solid.

LC/MS ($C_{44}H_{45}N_5O_4$) 708 [M+H]$^+$; RT 1.35 (Method B)
High-Resolution Mass (ESI+):
Empirical formula: $C_{44}H_{45}N_5O_4$
[M+H]$^+$ calculated: 708.3544
[M+H]$^+$ measured: 708.3543

EXAMPLE 75: N-(4-Hydroxyphenyl)-N,1,2-trimethyl-5-{7-[(3R)-3-methyl-1,2,3,4-tetrahydroisoquinoline-2-carbonyl]-2-(2-phenylacetyl)-1,2,3,4-tetrahydroisoquinolin-6-yl}-1H-pyrrole-3-carboxamide The procedure is as in Example 8, replacing the product from Preparation 7aa in Step A with the product from Preparation 6bb.

LC/MS ($C_{42}H_{42}N_4O_4$) 667 [M+H]$^+$; RT 1.27 (Method B)

EXAMPLE 76: N-tert-Butyl-5-{1-[(4-hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxamide The procedure is as in Example 8, replacing the product from Preparation 7aa with the product from Preparation 7ab, and replacing 2-phenylacetyl chloride with tert-butyl isocyanate.

LC/MS ($C_{40}H_{45}N_5O_4$) 660 [M+H]$^+$; RT 1.29 (Method B)
High-Resolution Mass (ESI+):
Empirical formula: $C_{40}H_{45}N_5O_4$
[M+H]$^+$ calculated: 660.3544
[M+H]$^+$ measured: 660.3529

EXAMPLE 77: 6-{1-[(4-Hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-N-phenyl-1,2,3,4-tetrahydroisoquinoline-2-carboxamide The procedure is as in Example 8, replacing the product from Preparation 7aa with the product from Preparation 6aa, and replacing 2-phenylacetyl chloride with phenyl isocyanate.

LC/MS ($C_{47}H_{50}N_6O_5$) 779 [M+H]$^+$; RT 1.12

EXAMPLE 78: N-Benzyl-6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxamide The procedure is as in Example 8, replacing the product from Preparation 7aa with the product from Preparation 6aa, and replacing 2-phenylacetyl chloride with benzyl isocyanate.

LC/MS ($C_{48}H_{52}N_6O_5$) 793 [M+H]$^+$; RT 1.12
High-Resolution Mass (ESI+):
Empirical formula: $C_{48}H_{52}N_6O_5$
[M+H]$^+$ calculated: 793.4072
[M+H]$^+$ measured: 793.4067

EXAMPLE 79: 6-{1-[(4-Hydroxyphenyl)(methyl)carbamoyl]-5,6,7,8-tetrahydroindolizin-3-yl}-N-methyl-7-[(3R)-3-methyl-1,2,3,4-tetrahydroisoquinoline-2-carbonyl]-1,2,3,4-tetrahydroisoquinoline-2-carboxamide The procedure is as in Example 74, replacing N-methylaniline in Step B with N-benzylmethylamine.

LC/MS ($C_{38}H_{41}N_5O_4$) 632 [M+H]$^+$; RT 1.16 (Method B)
High-Resolution Mass (ESI+):
Empirical formula: $C_{38}H_{41}N_5O_4$
[M+H]$^+$ calculated: 632.3231
[M+H]$^+$ measured: 632.3232

EXAMPLE 80: N-(4-Hydroxyphenyl)-N,1,2-trimethyl-5-{6-[(3R)-3-methyl-1,2,3,4-tetrahydroisoquinoline-2-carbonyl]-2-(2-phenylacetyl)-2,3-dihydro-1H-isoindol-5-yl}-1H-pyrrole-3-carboxamide Step A: N-[4-(Benzyloxy)phenyl]-N,1,2-trimethyl-5-{6-[(3R)-3-methyl-1,2,3,4-tetrahydroisoquinoline-2-carbonyl]-2-(2-phenylacetyl)-2,3-dihydro-1H-isoindol-5-yl}-1H-pyrrole-3-carboxamide To a solution of the compound from Preparation 7bb (50 mg, 0.08 mmol) in dichloromethane (2 mL), cooled to 0° C., are added DIPEA (28 uL, 0.16 mmol) and phenylacetyl chloride (13 uL, 0.10 mmol). After stirring for 10 min, the reaction is diluted with dichloromethane, sequentially washed with 1M aqueous NaOH and brine, dried (magnesium sulphate), and concentrated in vacuo. The crude material is purified on CombiFlash (4 g silica, dichloromethane to 3% methanol/dichloromethane) to afford the product.

LC/MS ($C_{48}H_{46}N_4O_4$) 743 [M+H]$^+$; RT 1.47 (Method B)

Step B: N-(4-Hydroxyphenyl)-N,1,2-trimethyl-5-{6-[(3R)-3-methyl-1,2,3,4-tetrahydroisoquinoline-2-carbonyl]-2-(2-phenylacetyl)-2,3-dihydro-1H-isoindol-5-yl}-1H-pyrrole-3-carboxamide A solution of the product from Step A (59 mg, 0.08 mmol) in ethanol was added to 10% Pd/C (catalytic) and the mixture was shaken at ambient temperature under an atmosphere of hydrogen for ca 16 h. Filtration through celite, evaporation of solvents under vacuum, and purification on CombiFlash (4 g silica, dichloromethane to 5% methanol/dichloromethane) afforded the desired product.

LC/MS ($C_{41}H_{40}N_4O_4$) 653 [M+H]$^+$; RT 1.25 (Method B)
High-Resolution Mass (ESI+):

Empirical formula: $C_{41}H_{40}N_4O_4$
[M+H]$^+$ calculated: 653.3122
[M+H]$^+$ measured: 653.3137

EXAMPLE 81: N-tert-Butyl-5-{1-[(4-hydroxyphenyl)(methyl)carbamoyl]-5,6,7,8-tetrahydroindolizin-3-yl}-N-methyl-6-[(3R)-3-methyl-1,2,3,4-tetrahydroisoquinoline-2-carbonyl]-2,3-dihydro-1H-isoindole-2-carboxamide The procedure is as in Example 74, replacing the product from Preparation 6ab in Step A with the product from Preparation 7ab, and replacing N-methyl aniline in Step B with N-tert-butylmethylamine.
LC/MS ($C_{41}H_{47}N_5O_4$) 674 [M+H]$^+$; RT 1.38 (Method B)
High-Resolution Mass (ESI+):
Empirical formula: $C_{41}H_{47}N_5O_4$
[M+H]$^+$ calculated: 674.3701
[M+H]$^+$ measured: 674.3720

EXAMPLE 82: 5-{1-[(4-Hydroxyphenyl)(methyl)carbamoyl]-5,6,7,8-tetrahydroindolizin-3-yl}-N-methyl-6-[(3R)-3-methyl-1,2,3,4-tetrahydroisoquinoline-2-carbonyl]-N-phenyl-2,3-dihydro-1H-isoindole-2-carboxamide The procedure is as in Example 74, replacing the product from Preparation 6ab with the product from Preparation 7ab.
LC/MS ($C_{43}H_{43}N_5O_4$) 694 [M+H]$^+$; RT 1.33 (Method B)
High-Resolution Mass (ESI+):
Empirical formula: $C_{43}H_{43}N_5O_4$
[M+H]$^+$ calculated: 694.3388
[M+H]$^+$ measured: 694.3395

EXAMPLE 83: N-(4-Hydroxyphenyl)-N-methyl-3-{6-[(3R)-3-methyl-1,2,3,4-tetrahydroisoquinoline-2-carbonyl]-2-(3-phenylazetidine-1-carbonyl)-2,3-dihydro-1H-isoindol-5-yl}-5,6,7,8-tetrahydroindolizine-1-carboxamide The procedure is as in Example 74, replacing the product from Preparation 7aa with the product from Preparation 7ab, and replacing N-methylaniline with 3-phenylazetidine hydrochloride.
LC/MS ($C_{45}H_{45}N_5O_4$) 720 [M+H]$^+$; RT 2.62 (Method A)
High-Resolution Mass (ESI+):
Empirical formula: $C_{45}H_{45}N_5O_4$
[M+H]$^+$ calculated: 720.3544
[M+H]$^+$ measured: 720.3536

EXAMPLE 84: N-(4-Hydroxyphenyl)-N-methyl-3-{7-[(3R)-3-methyl-1,2,3,4-tetrahydroisoquinoline-2-carbonyl]-2-(3-phenylazetidine-1-carbonyl)-1,2,3,4-tetrahydroisoquinolin-6-yl}-5,6,7,8-tetrahydroindolizine-1-carboxamide The procedure is as in Example 74, replacing the product from Preparation 7aa with the product from Preparation 6ab, and replacing N-methylaniline with 3-phenylazetidine hydrochloride.
LC/MS ($C_{46}H_{47}N_5O_4$) 734 [M+H]$^+$; RT 2.66 (Method A)
High-Resolution Mass (ESI+):
Empirical formula: $C_{46}H_{47}N_5O_4$
[M+H]$^+$ calculated: 734.3701
[M+H]$^+$ measured: 734.3668

EXAMPLE 85: N-Benzyl-5-{1-[(4-hydroxyphenyl)(methyl)carbamoyl]-5,6,7,8-tetrahydroindolizin-3-yl}-N-methyl-6-[(3R)-3-methyl-1,2,3,4-tetrahydroisoquinoline-2-carbonyl]-2,3-dihydro-1H-isoindole-2-carboxamide Step A: N-Benzyl-5-(1-{[4-(benzyloxy)phenyl](methyl)carbamoyl}-5,6,7,8-tetrahydroindolizin-3-yl)-N-methyl-6-[(3R)-3-methyl-1,2,3,4-tetrahydroisoquinoline-2-carbonyl]-2,3-dihydro-1H-isoindole-2-carboxamide The procedure is as in Step A and Step B of Example 74, replacing the product from Preparation 6ab in Step A with the product from Preparation 7ab, and replacing N-methylaniline in Step B with N-benzylmethylamine.
LC/MS ($C_{51}H_{51}N_5O_4$) 798 [M+H]$^+$; RT 1.55 (Method B)

Step B: N-Benzyl-5-{1-[(4-hydroxyphenyl)(methyl)carbamoyl]-5,6,7,8-tetrahydroindolizin-3-yl}-N-methyl-6-[(3R)-3-methyl-1,2,3,4-tetrahydroisoquinoline-2-carbonyl]-2,3-dihydro-1H-isoindole-2-carboxamide The product from Step A (46 mg, 0.06 mmol) was dissolved in dichloromethane (5 mL) and cooled to 0° C. To this was added boron trichloride (1M in dichloromethane; 0.18 mmol) dropwise. The reaction was stirred at ambient temperature for 1 h, then quenched by the addition of methanol (5 mL) and concentrated in vacuo. The crude material was partitioned between ethyl acetate and water, and the organic extract was washed with brine, dried (magnesium sulphate) and concentrated in vacuo. Purification by flash column chromatography (4 g silica, dichloromethane to 5% methanol in dichloromethane) afforded the desired product.
LC/MS ($C_{44}H_{45}N_5O_4$) 708 [M+H]$^+$; RT 1.36 (Method B)
High-Resolution Mass (ESI+):
Empirical formula: $C_{44}H_{45}N_5O_4$
[M+H]$^+$ calculated: 708.3544
[M+H]$^+$ measured: 708.3542

EXAMPLE 86: 3-{2-[2-(2-Chlorophenoxy)acetyl]-6-[(3R)-3-methyl-1,2,3,4-tetrahydroisoquinoline-2-carbonyl]-2,3-dihydro-1H-isoindol-5-yl}-N-(4-hydroxyphenyl)-N-methyl-5,6,7,8-tetrahydroindolizine-1-carboxamide Step A: N-[4-(Benzyloxy)phenyl]-3-{2-[2-(2-chlorophenoxy)acetyl]-6-[(3R)-3-methyl-1,2,3,4-tetrahydroisoquinoline-2-carbonyl]-2,3-dihydro-1H-isoindol-5-yl}-N-methyl-5,6,7,8-tetrahydroindolizine-1-carboxamide The procedure is as in Step A of Example 11, replacing the product from Preparation 7aa with the product from Preparation 7ab, and replacing propionyl chloride with 2-(2-chlorophenoxy)acetyl chloride.
LC/MS ($C_{50}H_{47}N_4O_5Cl$) 819 [M+H]$^+$; RT 1.53 (Method B)

Step B: 3-{2-[2-(2-Chlorophenoxy)acetyl]-6-[(3R)-3-methyl-1,2,3,4-tetrahydroisoquinoline-2-carbonyl]-2,3-dihydro-1H-isoindol-5-yl}-N-(4-hydroxyphenyl)-N-methyl-5,6,7,8-tetrahydroindolizine-1-carboxamide The procedure is as in Step B of Example 85, replacing the product in Step A of Example 85 with the product of Step A in Example 86.

LC/MS ($C_{43}H_{41}N_4O_5Cl$) 729 [M+H]$^+$; RT 1.35 (Method B)
High-Resolution Mass (ESI+):
  Empirical formula: $C_{43}H_{41}N_4O_5Cl$
  [M+H]$^+$ calculated: 729.2838
  [M+H]$^+$ measured: 729.2820

EXAMPLE 87: N-(4-Hydroxyphenyl)-N-methyl-3-{6-[(3R)-3-methyl-1,2,3,4-tetrahydroisoquinoline-2-carbonyl]-2-[2-(phenylamino)acetyl]-2,3-dihydro-1H-isoindol-5-yl}-5,6,7,8-tetrahydroindolizine-1-carboxamide The procedure is as described in Example 23, replacing 2-methyl-3-phenylpropanoic acid in Step A with 2-(phenylamino)acetic acid.
LC/MS ($C_{43}H_{43}N_5O_4$) 694 [M+H]$^+$; RT 2.58 (Method A)
High-Resolution Mass (ESI+):
  Empirical formula: $C_{43}H_{43}N_5O_4$
  [M+H]$^+$ calculated: 694.3388
  [M+H]$^+$ measured: 694.3357

EXAMPLE 88: Phenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate hydrochloride The procedure was as described for Example 69, replacing the compound from Preparation 6aa with the compound from Preparation 6ba.
LC/MS ($C_{45}H_{47}N_5O_6$) 754 [M+H]$^+$; RT 1.17 (Method B)
High-Resolution Mass (ESI+):
  Empirical formula: $C_{45}H_{47}N_5O_6$
  [M+H]$^+$ calculated: 754.3599
  [M+H]$^+$ measured: 754.3598

EXAMPLE 89: N-(4-Hydroxyphenyl)-N,1,2-trimethyl-5-{7-[(3S)-3-(morpholin-4-ylmethyl)-1,2,3,4-tetrahydroisoquinoline-2-carbonyl]-2-(2-phenylacetyl)-1,2,3,4-tetrahydroisoquinolin-6-yl}-1H-pyrrole-3-carboxamide The procedure is as in Example 8, replacing the product from Preparation 7aa with the product from Preparation 6aa.
LC/MS ($C_{46}H_{49}N_5O_5$) 752 [M+H]$^+$; RT 1.10 (Method B)
High-Resolution Mass (ESI+):
  Empirical formula: $C_{46}H_{49}N_5O_5$
  [M+H]$^+$ calculated: 752.3806
  [M+H]$^+$ measured: 752.3797

EXAMPLE 90: N-(4-Hydroxyphenyl)-N-methyl-3-{7-[(3R)-3-methyl-1,2,3,4-tetrahydroisoquinoline-2-carbonyl]-2-[(2S)-2-phenylpropanoyl]-1,2,3,4-tetrahydroisoquinolin-6-yl}-5,6,7,8-tetrahydroindolizine-1-carboxamide The procedure is as described in Example 23, replacing the product of 7ab with the product of Preparation 6ab, and replacing 2-methyl-3-phenylpropanoic acid in Step A with (2S)-2-phenylpropanoic acid.
LC/MS ($C_{45}H_{46}N_4O_4$) 707 [M+H]$^+$; RT 2.65 (Method A)
High-Resolution Mass (ESI+):
  Empirical formula: $C_{45}H_{46}N_4O_4$
  [M+H]$^+$ calculated: 707.3592
  [M+H]$^+$ measured: 707.3589

EXAMPLE 91: N-(4-Hydroxyphenyl)-N-methyl-3-{7-[(3R)-3-methyl-1,2,3,4-tetrahydroisoquinoline-2-carbonyl]-2-[(2R)-2-phenylpropanoyl]-1,2,3,4-tetrahydroisoquinolin-6-yl}-5,6,7,8-tetrahydroindolizine-1-carboxamide The procedure is as described in Example 23, replacing the product of 7ab with the product of Preparation 6ab, and replacing 2-methyl-3-phenylpropanoic acid in Step A with (2R)-2-phenylpropanoic acid.
LC/MS ($C_{45}H_{46}N_4O_4$) 707 [M+H]$^+$; RT 2.66 (Method A)
High-Resolution Mass (ESI+):
  Empirical formula: $C_{45}H_{46}N_4O_4$
  [M+H]$^+$ calculated: 707.3592
  [M+H]$^+$ measured: 707.3589

EXAMPLE 92: N-(4-Hydroxyphenyl)-N-methyl-3-{6-[(3R)-3-methyl-1,2,3,4-tetrahydroisoquinoline-2-carbonyl]-2-[(phenylcarbamoyl)methyl]-2,3-dihydro-1H-isoindol-5-yl}-5,6,7,8-tetrahydroindolizine-1-carboxamide The procedure is as in Example 8, replacing the product from Preparation 7aa in Step A with the product from Preparation 7ab, and replacing 2-phenylacetyl chloride in Step A with 2-chloro-N-phenylacetamide
LC/MS ($C_{43}H_{43}N_5O_4$) 694 [M+H]$^+$; RT 1.18 (Method B)

EXAMPLE 93: Benzyl 6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate The procedure is as in Example 62, replacing the product from Example 10 with the product from Example 27.
LC/MS ($C_{44}H_{44}N_4O_5$) 709 [M+H]$^+$; RT 1.41 (Method B)
High-Resolution Mass (ESI+):
  Empirical formula: $C_{44}H_{44}N_4O_5$
  [M+H]$^+$ calculated: 709.3384
  [M+H]$^+$ measured: 709.3387

EXAMPLE 94: Benzyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate Step A: N-(4-Hydroxyphenyl)-N-methyl-3-{7-[(3S)-3-(morpholin-4-ylmethyl)-1,2,3,4-tetrahydroisoquinoline-2-carbonyl]-1,2,3,4-tetrahydroisoquinolin-6-yl}-5,6,7,8-tetrahydroindolizine-1-carboxamide, trifluoroacetic acid salt To a solution of the product from Step A of Preparation 6aa (43 mg, 0.065 mmol) in dichloromethane (5 mL) is added trifluoroacetic acid (0.4 mL), and the mixture is stirred at ambient temperature for ca 16 h. The solvent is removed in vacuo to afford the desired product which is used directly in the next step without further purification.
LC/MS ($C_{40}H_{45}N_5O_4$) 660 [M+H]$^+$; RT 0.87 (Method B)

Step B: Benzyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The product from Step A (43 mg, 0.06 mmol) is dissolved in dichloromethane (2 mL) and cooled to 0° C. To this is added triethylamine (42 uL, 0.3 mmol) followed by benzyl chloroformate (9 uL) and the mixture is stirred for 15 minutes. The reaction mixture is diluted with dichloromethane and washed sequentially with 1M aqueous NaOH, and brine. The organics are dried over magnesium sulphate, filtered and concentrated and the residue taken-up in methanol. To the methanolic solution is added 1M aqueous NaOH and the mixture is heated for 2 hours at 50° C. The reaction mixture is concentrated in vacuo, partitioned between ethyl acetate and brine, and the organics dried over magnesium sulphate. After evaporation, the crude product is purified by flash column chromatography over silica (4 g), eluting with a gradient of dichloromethane to 5% methanol/dichloromethane.
LC/MS ($C_{48}H_{51}N_5O_6$) 794 [M+H]$^+$; RT 1.21 (Method B)
High-Resolution Mass (ESI+):
Empirical formula: $C_{48}H_{51}N_5O_6$
[M+H]$^+$ calculated: 794.3912
[M+H]$^+$ measured: 794.3908

EXAMPLE 95: N-(4-Hydroxyphenyl)-N-methyl-3-{7-[(3R)-3-methyl-1,2,3,4-tetrahydroisoquinoline-2-carbonyl]-2-(2-phenylbutanoyl)-1,2,3,4-tetrahydroisoquinolin-6-yl}-5,6,7,8-tetrahydroindolizine-1-carboxamide The procedure is as described in Example 23, replacing the product of 7ab with the product of Preparation 6ab, and replacing 2-methyl-3-phenylpropanoic acid in Step A with 1-phenylcyclopropane-1-carboxylic acid.
LC/MS ($C_{46}H_{48}N_4O_4$) 721 [M+H]$^+$; RT 2.72 (Method A)
High-Resolution Mass (ESI+):
Empirical formula: $C_{46}H_{48}N_4O_4$
[M+H]$^+$ calculated: 721.3748
[M+H]$^+$ measured: 721.3740

EXAMPLE 96: N-(4-Hydroxyphenyl)-N-methyl-3-{7-[(3R)-3-methyl-1,2,3,4-tetrahydroisoquinoline-2-carbonyl]-2-[2-(4-{[2-(morpholin-4-yl)ethyl]amino}phenyl)acetyl]-1,2,3,4-tetrahydroisoquinolin-6-yl}-5,6,7,8-tetrahydroindolizine-1-carboxamide Step A: Ethyl 2-(4-{[2-(morpholin-4-yl)ethyl]amino}phenyl)acetate To a boiling tube was added ethyl 2-(4-bromophenyl)acetate (317 mg, 1.3 mmol), the 2-(morpholin-4-yl)ethan-1-amine (257 μL, 1.96 mmol), potassium phosphate tribasic (386 mg, 1.82 mmol) and (2-biphenyl)di-tert-butylphosphine (0.1 mol %) followed by toluene (6 mL). The reaction was degassed with nitrogen followed by the addition of bis(dibenzylideneacetone)palladium(0) (0.05 mol %). The reaction was then heated at 100° C. under nitrogen for ca 6 h. The reaction was diluted with dichloromethane and washed with water. The organic extract was dried over magnesium sulphate, filtered and loaded onto a column for purification on silica in a gradient of iso-hexane to ethyl acetate.
LC/MS ($C_{16}H_{24}N_2O_3$) 293 [M+H]$^+$; RT 1.74 (Method A)

Step B: Sodium 2-(4-{[2-(morpholin-4-yl)ethyl]amino}phenyl)acetate

To a solution of the product obtained in Step A (61 mg, 0.21 mmol) in methanol (5 ml) was added 2M NaOH (21 μL, 0.42 mmol). The reaction was stirred at ambient temperature for ca 16 h. The reaction was then filtered through a cotton wool plug and concentrated in vacuo, then triturated with ether, filtered and solvents removed in vacuo.
LC/MS ($C_{14}H_{20}N_2O_3$) 265 [M+H]$^+$; RT 0.50 (Method A)

Step C: N-[4-(Benzyloxy)phenyl]-N-methyl-3-{7-[(3R)-3-methyl-1,2,3,4-tetrahydroisoquinoline-2-carbonyl]-2-[2-(4-{[2-(morpholin-4-yl)ethyl]amino}phenyl)acetyl]-1,2,3,4-tetrahydroisoquinolin-6-yl}-5,6,7,8-tetrahydroindolizine-1-carboxamide To a solution of the product from Preparation 6ab (40 mg, 0.05 mmol) in dichloromethane (3 ml) was added N,N-diisopropylethylamine (20 μL, 0.15 mmol) and HBTU (20 mg, 0.5 mmol) followed by the sodium salt from Step B (23 mg, 0.8 mmol). The reaction was stirred at ambient temperature for ca 16 h. The reaction was diluted with dichloromethane and washed with water. The organic extract was dried over magnesium sulphate, filtered and concentrated in vacuo. Purification by flash column chromatography (silica; dichloromethane to 5% methanol in dichloromethane) followed by trituration with ether afforded the desired product as a cream powder.
LC/MS ($C_{57}H_{62}N_6O_5$) 911 [M+H]$^+$; RT 2.51 (Method A)

Step D: N-(4-Hydroxyphenyl)-N-methyl-3-{7-[(3R)-3-methyl-1,2,3,4-tetrahydroisoquinoline-2-carbonyl]-2-[2-(4-{[2-(morpholin-4-yl)ethyl]amino}phenyl)acetyl]-1,2,3,4-tetrahydroisoquinolin-6-yl}-5,6,7,8-tetrahydroindolizine-1-carboxamide A solution of the product from Step C (68 mg, 0.07 mmol) in ethanol (5 mL) was added to 10% Pd/C (catalytic) and the mixture was shaken at ambient temperature under an atmosphere of hydrogen for ca 16 h. Filtration through celite, evaporation of solvents under vacuum, and purification on CombiFlash (4 g silica, dichloromethane to 5% methanol in dichloromethane) afforded the desired product.
LC/MS ($C_{50}H_{56}N_6O_5$) 819 [M−H]$^-$; RT 2.21 (Method A)

EXAMPLE 97: N-(4-Hydroxyphenyl)-N-methyl-3-{7-[(3R)-3-methyl-1,2,3,4-tetrahydroisoquinoline-2-carbonyl]-2-{2-[4-(4-methylpiperazin-1-yl)phenyl]acetyl}-1,2,3,4-tetrahydroisoquinolin-6-yl}-5,6,7,8-tetrahydroindolizine-1-carboxamide The procedure is as in Example 96, replacing 2-(morpholin-4-yl)ethan-1-amine in Step A with 1-methylpiperazine.
LC/MS ($C_{49}H_{54}N_6O_4$) 791 [M+H]$^+$; RT 2.20 (Method A)
High-Resolution Mass (ESI+):
Empirical formula: $C_{49}H_{54}N_6O_4$
[M+H]$^+$ calculated: 791.4279
[M+H]$^+$ measured: 791.4268

EXAMPLE 98: 4-Methylphenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate hydrochloride The procedure was as described for Example 99, replacing 3-methylphenol in Step B with 4-methylphenol.
LC/MS ($C_{48}H_{51}N_5O_6$) 794 [M+H]$^+$; RT 1.25 (Method B)

EXAMPLE 99: 3-Methylphenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate Step A: 6-(1-{[4-(Benzyloxy)phenyl](methyl)carbamoyl}-5,6,7,8-tetrahydroindolizin-3-yl)-7-[(3S)-3-(morpholin-4-ylmethyl)-1,2,3,4-tetrahydroisoquinoline-2-carbonyl]-1,2,3,4-tetrahydroisoquinoline-2-carbonyl chloride To a solution of the compound from Preparation 6aa (150 mg, 0.17 mmol) in dichloromethane (5 mL), cooled to 0° C., is added DIPEA (89 uL, 0.51 mmol) followed by the portion-wise addition of triphosgene (52 mg, 0.17 mmol). After stirring for 1 h, the reaction mixture is partitioned between dichloromethane and 1M aqueous HCl, and the phase is dried over magnesium sulphate, filtered and concentrated to afford a mixture of trichloromethyl 6-(1-{[4-(benzyloxy)phenyl](methyl)carbamoyl}-5,6,7,8-tetrahydroindolizin-3-yl)-7-[(3S)-3-(morpholin-4-ylmethyl)-1,2,3,4-tetrahydroisoquinoline-2-carbonyl]-1,2,3,4-tetrahydroisoquinoline-2-carboxylate and 6-(1-{[4-(benzyloxy)phenyl](methyl)carbamoyl}-5,6,7,8-tetrahydroindolizin-3-yl)-7-[(3S)-3-(morpholin-4-ylmethyl)-1,2,3,4-tetrahydroisoquinoline-2-carbonyl]-1,2,3,4-tetrahydroisoquinoline-2-carbonyl chloride that is used directly in the next step without further purification, and assuming quantitative transformation.

Step B: 3-Methylphenyl 6-(1-[{4-(benzyloxy)phenyl](methyl)carbamoyl}-5,6,7,8-tetrahydroindolizin-3-yl)-7-[(3S)-3-(morpholin-4-ylmethyl)-1,2,3,4-tetrahydroisoquinoline-2-carbonyl]-1,2,3,4-tetrahydroisoquinoline-2-carboxylate To a solution of the product from Step A (30 mg) in acetonitrile (5 ml) is added potassium carbonate (17 mg, 0.123 mmol) and 3-methylphenol (13 uL, 0.123 mmol) and the mixture is heated at 65° C. for 2 hours. The reaction is cooled to room temperature, diluted in ethyl acetate and washed with brine. The organics are dried over magnesium sulphate, filtered and concentrated. The crude material is taken-up in dichloromethane, loaded onto isolute and purified on CombiFlash (4 g silica, dichloromethane to 5% methanol/dichloromethane).

Step C: 3-Methylphenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate A solution of the product from Step B (30 mg, 0.03 mmol) in ethanol is added to 10% Pd/C (catalytic) and the mixture is shaken under an atmosphere of hydrogen for ca 16 h. Filtration through celite, evaporation, and purification on CombiFlash (4 g silica, dichloromethane to 5% MeOH/dichloromethane) afforded the desired product. The appropriate fractions were combined and concentrated to obtain the desired product.
LC/MS ($C_{48}H_{51}N_5O_6$) 794 [M+H]$^+$; RT 1.25 (Method B)
High-Resolution Mass (ESI+):
Empirical formula: $C_{48}H_{51}N_5O_6$
[M+H]$^+$ calculated: 794.3912
[M+H]$^+$ measured: 794.3925

EXAMPLE 100: 2-Methylphenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure was as described for Example 99, replacing 3-methylphenol in Step B with 2-methylphenol.
LC/MS ($C_{48}H_{51}N_5O_6$) 794 [M+H]$^+$; RT 1.25 (Method B)
High-Resolution Mass (ESI+):
Empirical formula: $C_{48}H_{51}N_5O_6$
[M+H]$^+$ calculated: 794.3912
[M+H]$^+$ measured: 794.3877

EXAMPLE 101: N-(4-Hydroxyphenyl)-5-{2-[2-(4-methoxyphenyl)acetyl]-6-[(3R)-3-methyl-1,2,3,4-tetrahydroisoquinoline-2-carbonyl]-2,3-dihydro-1H-isoindol-5-yl}-N,1,2-trimethyl-1H-pyrrole-3-carboxamide High-Resolution Mass (ESI+):
Empirical formula: $C_{42}H_{42}N_4O_5$
[M+H]$^+$ calculated: 683.3235
[M+H]$^+$ measured: 683.3213

EXAMPLE 102: 5-{2-[2-(4-Fluorophenyl)acetyl]-6-[(3R)-3-methyl-1,2,3,4-tetrahydroisoquinoline-2-carbonyl]-2,3-dihydro-1H-isoindol-5-yl}-N-(4-hydroxyphenyl)-N,1,2-trimethyl-1H-pyrrole-3-carboxamide High-Resolution Mass (ESI+):
Empirical formula: $C_{41}H_{39}FN_4O_4$
[M+H]$^+$ calculated: 671.3035
[M+H]$^+$ measured: 671.3039

EXAMPLE 103: N-(4-Hydroxyphenyl)-N,1,2-trimethyl-5-{6-[(3R)-3-methyl-1,2,3,4-tetrahydroisoquinoline-2-carbonyl]-2-(2-phenoxyacetyl)-2,3-dihydro-1H-isoindol-5-yl}-1H-pyrrole-3-carboxamide High-Resolution Mass (ESI+):
Empirical formula: $C_{41}H_{40}N_4O_5$
[M+H]$^+$ calculated: 669.3079
[M+H]$^+$ measured: 669.3084

EXAMPLE 104: N-(4-hydroxyphenyl)-N,1,2-trimethyl-5-{6-[(3R)-3-methyl-1,2,3,4-tetrahydroisoquinoline-2-carbonyl]-2-(2-phenoxypropanoyl)-2,3-dihydro-1H-isoindol-5-yl}-1H-pyrrole-3-carboxamide High-Resolution Mass (ESI+):
Empirical formula: $C_{42}H_{42}N_4O_5$
[M+H]$^+$ calculated: 683.3235
[M+H]$^+$ measured: 683.3210

EXAMPLE 105: 4-Chlorophenyl 5-{4-[(4-hydroxyphenyl)(methyl)carbamoyl]-1,5-dimethyl-1H-pyrrol-2-yl}-6-[(3R)-3-methyl-1,2,3,4-tetrahydroisoquinoline-2-carbonyl]-2,3-dihydro-1H-isoindole-2-carboxylate High-Resolution Mass (ESI+):
Empirical formula: $C_{40}H_{37}ClN_4O_5$
[M+H]$^+$ calculated: 689.2532
[M+H]$^+$ measured: 689.2539

EXAMPLE 106: 4-Fluorophenyl 5-{4-[(4-hydroxyphenyl)(methyl)carbamoyl]-1,5-dimethyl-1H-pyrrol-2-yl}-6-[(3R)-3-methyl-1,2,3,4-tetrahydroisoquinoline-2-carbonyl]-2,3-dihydro-1H-isoindole-2-carboxylate High-Resolution Mass (ESI+):
Empirical formula: $C_{40}H_{37}FN_4O_5$
$[M+H]^+$ calculated: 673.2828
$[M+H]^+$ measured: 673.2832

EXAMPLE 107: 4-Methylphenyl 5-{4-[(4-hydroxyphenyl)(methyl)carbamoyl]-1,5-dimethyl-1H-pyrrol-2-yl}-6-[(3R)-3-methyl-1,2,3,4-tetrahydroisoquinoline-2-carbonyl]-2,3-dihydro-1H-isoindole-2-carboxylate High-Resolution Mass (ESI+):
Empirical formula: $C_{41}H_{40}N_4O_5$
$[M+H]^+$ calculated: 669.3079
$[M+H]^+$ measured: 669.3065

EXAMPLE 108: 3-{2-[2-(4-{[2-(Dimethylamino)ethyl]amino}phenyl)acetyl]-7-[(3R)-3-methyl-1,2,3,4-tetrahydroisoquinoline-2-carbonyl]-1,2,3,4-tetrahydroisoquinolin-6-yl}-N-(4-hydroxyphenyl)-N-methyl-5,6,7,8-tetrahydroindolizine-1-carboxamide hydrochloride The procedure is as in Example 96, replacing 2-(morpholin-4-yl)ethan-1-amine in Step A with (2-aminoethyl)dimethylamine.
LC/MS ($C_{48}H_{54}N_6O_4$) 777 $[M-H]^-$; RT 2.20 (Method A)

EXAMPLE 109: N-(4-Hydroxyphenyl)-N-methyl-3-{7-[(3R)-3-methyl-1,2,3,4-tetrahydroisoquinoline-2-carbonyl]-2-(1-phenylcyclopropanecarbonyl)-1,2,3,4-tetrahydroisoquinolin-6-yl}-5,6,7,8-tetrahydroindolizine-1-carboxamide Step A: N-[4-(benzyloxy)phenyl]-N-methyl-3-{7-[(3R)-3-methyl-1,2,3,4-tetrahydroisoquinoline-2-carbonyl]-2-(1-phenylcyclopropanecarbonyl)-1,2,3,4-tetrahydroisoquinolin-6-yl}-5,6,7,8-tetrahydroindolizine-1-carboxamide To a solution of the product from Preparation 6ab (43 mg, 0.06 mmol) in dichloromethane (5 ml) was added Hunig's Base (32 µL, 0.18 mmol) and HBTU (23 mg, 0.06 mmol) followed by 1-phenylcyclopropane-1-carboxylic acid (9 mg, 0.06 mmol), and stirred at ambient temperature for ca 16 h. The reaction was diluted with dichloromethane and washed with water, followed by aqueous 1M HCl and then brine. The organic extract was dried over magnesium sulfate, filtered and loaded onto a column and purified in ethyl acetate to obtain the desired product.
LC/MS ($C_{53}H_{52}N_4O_4$) 809 $[M+H]^+$; RT 2.92 (Method A)

Step B: N-(4-Hydroxyphenyl)-N-methyl-3-{7-[(3R)-3-methyl-1,2,3,4-tetrahydroisoquinoline-2-carbonyl]-2-(1-phenylcyclopropanecarbonyl)-1,2,3,4-tetrahydroisoquinolin-6-yl}-5,6,7,8-tetrahydroindolizine-1-carboxamide A solution of the product from Step A (47.6 mg, 0.06 mmol) in anhydrous dichloromethane (5 ml) was cooled to 0° C. and to this was added boron trichloride (1M in DCM, 120 µL, 0.12 mmol). The reaction was stirred at ambient temperature for ca 16 h. The reaction was quenched with methanol (5 mL), and the reaction was diluted with dichloromethane. The organic phase was washed with water, dried over magnesium sulfate, filtered and concentrated in vacuo. The crude product was purified by column chromatography in a gradient of dichloromethane to 5% methanol in dichloromethane followed by trituration with ether and dried in vacuo.
LC/MS ($C_{46}H_{46}N_4O_4$) 719 $[M+H]^+$; RT 2.65 (Method A)
High-Resolution Mass (ESI+):
Empirical formula: $C_{46}H_{46}N_4O_4$
$[M+H]^+$ calculated: 719.3592
$[M+H]^+$ measured: 719.3556

EXAMPLE 110: N-Ethyl-5-{4-[(4-hydroxyphenyl)(methyl)carbamoyl]-1,5-dimethyl-1H-pyrrol-2-yl}-6-[(3R)-3-methyl-1,2,3,4-tetrahydroisoquinoline-2-carbonyl]-2,3-dihydro-1H-isoindole-2-carboxamide High-Resolution Mass (ESI+):
Empirical formula: $C_{36}H_{39}N_5O_4$
$[M+H]^+$ calculated: 606.3082
$[M+H]^+$ measured: 606.3078

EXAMPLE 111: N-Benzyl-5-{4-[(4-hydroxyphenyl)(methyl)carbamoyl]-1,5-dimethyl-1H-pyrrol-2-yl}-6-[(3R)-3-methyl-1,2,3,4-tetrahydroisoquinoline-2-carbonyl]-2,3-dihydro-1H-isoindole-2-carboxamide High-Resolution Mass (ESI+):
Empirical formula: $C_{41}H_{41}N_5O_4$
$[M+H]^+$ calculated: 668.3239
$[M+H]^+$ measured: 668.3203

EXAMPLE 112: 5-{2-Acetyl-6-[(3R)-3-methyl-1,2,3,4-tetrahydroisoquinoline-2-carbonyl]-2,3-dihydro-1H-isoindol-5-yl}-N-(4-hydroxyphenyl)-N,1,2-trimethyl-1H-pyrrole-3-carboxamide High-Resolution Mass (ESI+):
Empirical formula: $C_{35}H_{36}N_4O_4$
$[M+H]^+$ calculated: 577.2817
$[M+H]^+$ measured: 577.2782

EXAMPLE 113: N-(4-Hydroxyphenyl)-N-methyl-3-{7-[(3R)-3-methyl-1,2,3,4-tetrahydroisoquinoline-2-carbonyl]-2-(2-{4-[(4-methylpiperazin-1-yl)methyl]phenyl}acetyl)-1,2,3,4-tetrahydroisoquinolin-6-yl}-5,6,7,8-tetrahydroindolizine-1-carboxamide Step A: 2-{4-[(4-methylpiperazin-1-yl)methyl]phenyl}acetic acid To a suspension of 4(bromomethyl)phenyl acetic acid (100 mg, 0.44 mmol) in acetonitrile (2 ml) was added potassium carbonate (126 mg, 0.88 mmol) and N-methylpiperazine (100 µL, 0.88 mmol), and the reaction stirred at ambient temperature for ca 16 h. The reaction was filtered and washed with ethyl acetate. The filtrate was basified with methanolic sodium hydroxide and then concentrated in vacuo. The crude material was dissolved in methanol and loaded onto a PE-AX column which had been pre-wetted with dichloromethane. The column was then washed with dichloromethane and methanol, and the product eluted with 10% formic acid/dichloromethane.
LC/MS ($C_{14}H_{20}N_2O_2$) 249 $[M+H]^+$; RT 0.42 (Method A)

Step B: N-[4-(benzyloxy)phenyl]-N-methyl-3-{7-[(3R)-3-methyl-1,2,3,4-tetrahydroisoquinoline-2-carbonyl]-2-(2-{4-[(4-methylpiperazin-1-yl)methyl]phenyl}acetyl)-1,2,3,4-tetrahydroisoquinolin-6-yl}-5,6,7,8-tetrahydroindolizine-1-carboxamide To a solution of the product from Preparation 6ab (50 mg, 0.08 mmol) in dichloromethane (3 mL) was added triethylamine (56 µL, 0.4 mmol) and HBTU (30 mg, 0.08 mmol) followed by the acid obtained in Step A (30 mg, 0.1 mmol) in dichloromethane (2 mL). The reaction was stirred at ambient temperature for ca 2 h. The reaction was diluted with dichloromethane and washed with water, dried over magnesium sulphate, filtered and concentrated in vacuo. The reaction was purified by column chromatography on 10 g silica column in a gradient of dichloromethane to 5% methanol in dichloromethane.

LC/MS ($C_{57}H_{62}N_6O_4$) 448 $[M+2H]^{2+}$; RT 2.51 (Method A)

Step C: N-(4-Hydroxyphenyl)-N-methyl-3-{7-[(3R)-3-methyl-1,2,3,4-tetrahydroisoquinoline-2-carbonyl]-2-(2-{4-[(4-methylpiperazin-1-yl)methyl]phenyl}acetyl)-1,2,3,4-tetrahydroisoquinolin-6-yl}-5,6,7,8-tetrahydroindolizine-1-carboxamide A solution of the product from Step B (44 mg, 0.05 mmol) in ethanol (10 mL) is added to 10% Pd/C (catalytic) and the mixture is shaken under an atmosphere of hydrogen for ca 16 h. Filtration through celite, evaporation, and purification on column chromatography (4 g silica, dichloromethane to 5% methanol in dichloromethane) afforded the desired product. Trituration with diethyl ether afforded the desired product.

LC/MS ($C_{50}H_{56}N_6O_4$) 803 $[M-H]^-$; RT 2.20 (Method A)
High-Resolution Mass (ESI+):
  Empirical formula: $C_{50}H_{56}N_6O_4$
  $[M+2H]^{2+}$ calculated: 403.2254
  $[M+2H]^{2+}$ measured: 403.2252

EXAMPLE 114: Phenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate A solution of the product obtained from Preparation 6cb (50 mg, 0.08 mmol) and N,N-diisopropylethylamine (70 µL, 0.4 mmol) was dissolved in dichloromethane (5 mL) and cooled to 0° C. To this was added phenylchloroformate (11 µL, 0.09 mmol), and the mixture was stirred at ambient temperature for 15 min. The reaction was diluted with dichloromethane, then washed with aqueous 1M sodium hydroxide, and brine. The organic extract was dried over magnesium sulfate, filtered and concentrated in vacuo. Purification by flash column chromatography (4 g silica, dichloromethane to 4% methanol in dichloromethane) afforded the desired product.

LC/MS ($C_{41}H_{40}N_4O_4$) 653 $[M+H]^+$; RT 1.48 (Method B)
High-Resolution Mass (ESI+):
  Empirical formula: $C_{41}H_{40}N_4O_4$
  $[M+H]^+$ calculated: 653.3122
  $[M+H]^+$ measured: 653.3159

EXAMPLE 115: Phenyl 6-{1,5-dimethyl-4-[methyl(phenyl)carbamoyl]-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 114, replacing the product from Preparation 6cb with the product from Preparation 6ca.
LC/MS ($C_{45}H_{47}N_5O_5$) 738 $[M+H]^+$; RT 1.28 (Method B)
High-Resolution Mass (ESI+):
  Empirical formula: $C_{45}H_{47}N_5O_5$
  $[M+H]^+$ calculated: 738.3650
  $[M+H]^+$ measured: 738.3655

EXAMPLE 116: N-(4-Hydroxyphenyl)-5-{2-[3-(4-methoxyphenyl)propyl]-6-[(3R)-3-methyl-1,2,3,4-tetrahydroisoquinoline-2-carbonyl]-2,3-dihydro-1H-isoindol-5-yl}-N,1,2-trimethyl-1H-pyrrole-3-carboxamide High-Resolution Mass (ESI+):
  Empirical formula: $C_{43}H_{46}N_4O_4$
  $[M+H]^+$ calculated: 683.3599
  $[M+H]^+$ measured: 683.3608

EXAMPLE 117: N,1,2-trimethyl-5-{7-[(3S)-3-(morpholin-4-ylmethyl)-1,2,3,4-tetrahydroisoquinoline-2-carbonyl]-2-(2-phenylacetyl)-1,2,3,4-tetrahydroisoquinolin-6-yl}-N-phenyl-1H-pyrrole-3-carboxamide The procedure is as in Example 114, replacing the product from Preparation 6cb with the product from preparation 6ca, and replacing phenyl chloroformate with phenylacetyl chloride.
LC/MS ($C_{46}H_{49}N_5O_4$) 736 $[M+H]^+$; RT 1.23 (Method B)
High-Resolution Mass (ESI+):
  Empirical formula: $C_{46}H_{49}N_5O_4$
  $[M+H]^+$ calculated: 736.3857
  $[M+H]^+$ measured: 736.3828

EXAMPLE 118: N,1,2-Trimethyl-5-{7-[(3R)-3-methyl-1,2,3,4-tetrahydroisoquinoline-2-carbonyl]-2-(2-phenylacetyl)-1,2,3,4-tetrahydroisoquinolin-6-yl}-N-phenyl-1H-pyrrole-3-carboxamide The procedure is as in Example 114, replacing phenyl chloroformate with phenylacetyl chloride.
LC/MS ($C_{42}H_{42}N_4O_3$) 651 $[M+H]^+$; RT 1.40 (Method B)
High-Resolution Mass (ESI+):
  Empirical formula: $C_{42}H_{42}N_4O_3$
  $[M+H]^+$ calculated: 651.3330
  $[M+H]^+$ measured: 651.3344

EXAMPLE 119: N,1,2-Trimethyl-5-{7-[(3R)-3-methyl-1,2,3,4-tetrahydroisoquinoline-2-carbonyl]-1,2,3,4-tetrahydroisoquinolin-6-yl}-N-phenyl-1H-pyrrole-3-carboxamide hydrochloride The product from Preparation 6cb (22 mg, 0.03 mmol) was dissolved in ethyl acetate (10 mL) and washed with saturated sodium bicarbonate (10 mL). The organic phase was separated, dried over magnesium sulfate and concentrated in vacuo. The solid was then dissolved in methanol (2 mL) and to this was added 1M HCl in diethyl ether (0.15 mL, 5 eq.), stirred for 30 min, and then concentrated in vacuo. The solid was then triturated in a small amount of diethyl ether and the solids were isolated by filtration. They were washed with cold ether before being dried under vacuum for 1 h.

LC/MS ($C_{34}H_{36}N_4O_2$) 533 [M+H]$^+$; RT 1.08 (Method B)

EXAMPLE 120: 4-Fluorophenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as described in Step A of Example 8, replacing the product from Preparation 7aa in Step A with the product from Preparation 6aa, and replacing 2-phenylacetyl chloride in Step A with 4-fluorophenyl chloroformate.

LC/MS ($C_{47}H_{48}N_5O_6F$) 798 [M+H]$^+$; RT 1.22 (Method B)
High-Resolution Mass (ESI+):
Empirical formula: $C_{47}H_{48}N_5O_6F$
[M+H]$^+$ calculated: 798.3661
[M+H]$^+$ measured: 798.3663

EXAMPLE 121: 4-Methoxyphenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as described in Step A of Example 8, replacing the product from Preparation 7aa in Step A with the product from Preparation 6aa, and replacing 2-phenylacetyl chloride in Step A with 4-methoxyphenyl chloroformate.

LC/MS ($C_{48}H_{51}N_5O_7$) 810 [M+H]$^+$; RT 1.21 (Method B)
High-Resolution Mass (ESI+):
Empirical formula: $C_{48}H_{51}N_5O_7$
[M+H]$^+$ calculated: 810.3861
[M+H]$^+$ measured: 810.3826

EXAMPLE 122: 4-Chlorophenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate Step A: 4-Chlorophenyl 6-(1-[{4-(benzyloxy)phenyl](methyl)carbamoyl}-5,6,7,8-tetrahydroindolizin-3-yl)-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Step A of Example 11, replacing the product from Preparation 7aa in Step A with the product from Preparation 6aa, and replacing propionyl chloride with 4-chlorophenyl chloroformate.

LC/MS ($C_{54}H_{54}ClN_5O_6$) 904 [M+H]$^+$; RT 1.51 (Method B)

Step B: 4-Chlorophenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Step B of Example 85, replacing the product of Step A in Example 85 with the product of Step A in Example 122.

LC/MS ($C_{47}H_{48}ClN_5O_6$) 814 [M+H]$^+$; RT 1.27 (Method B)

EXAMPLE 123: 3-{2-[2-(3-{[2-(Dimethylamino)ethyl]amino}phenyl)acetyl]-7-[(3R)-3-methyl-1,2,3,4-tetrahydroisoquinoline-2-carbonyl]-1,2,3,4-tetrahydroisoquinolin-6-yl}-N-(4-hydroxyphenyl)-N-methyl-5,6,7,8-tetrahydroindolizine-1-carboxamide The procedure is as in Example 96, replacing 2-(morpholin-4-yl)ethan-1-amine in Step A with (2-aminoethyl)dimethylamine, and replacing ethyl 2-(4-bromophenyl)acetate in Step A with methyl 2-(3-bromophenyl)acetate.

LC/MS ($C_{48}H_{54}N_6O_4$) 777 [M−H]$^-$; RT 2.23 (Method A)

EXAMPLE 124: 4-(Trifluoromethyl)phenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 74, replacing the product from Preparation 6ab in Step A with the product from Preparation 6aa, and replacing N-methylaniline in Step B with 4-(trifluoromethyl)phenol.

LC/MS ($C_{48}H_{48}N_5O_6F_3$) 848 [M+H]$^+$; RT 1.31 (Method B)
High-Resolution Mass (ESI+):
Empirical formula: $C_{48}H_{48}N_5O_6F_3$
[M+H]$^+$ calculated: 848.3629
[M+H]$^+$ measured: 848.3615

EXAMPLE 125: 4-(Trifluoromethoxy)phenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 74, replacing the product from Preparation 6ab in Step A with the product from Preparation 6aa, and replacing N-methylaniline in Step B with 4-(trifluoromethoxy)phenol.

LC/MS ($C_{48}H_{48}N_5O_7F_3$) 864 [M+H]$^+$; RT 1.31 (Method B)
High-Resolution Mass (ESI+):
Empirical formula: $C_{48}H_{48}N_5O_7F_3$
[M+H]$^+$ calculated: 864.3579
[M+H]$^+$ measured: 864.3576

EXAMPLE 126: 4-Ethylphenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 74, replacing the product from Preparation 6ab in Step A with the product from Preparation 6aa, and replacing N-methylaniline in Step B with 4-ethylphenol.

LC/MS ($C_{49}H_{53}N_5O_6$) 808 [M+H]$^+$; RT 1.32 (Method B)
High-Resolution Mass (ESI+):
Empirical formula: $C_{49}H_{53}N_5O_6$
[M+H]$^+$ calculated: 808.4069
[M+H]$^+$ measured: 808.4026

EXAMPLE 127: 4-Cyanophenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 74, replacing the product from Preparation 6ab in Step A with the product from Preparation 6aa, and replacing N-methylaniline in Step B with 4-hydroxybenzonitrile.

LC/MS ($C_{48}H_{48}N_6O_6$) 805 [M+H]$^+$; RT 1.18 (Method B)

EXAMPLE 128: 2-Methoxyphenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Step A of Example 8, replacing the product from Preparation 7aa in Step A with the product from Preparation 6aa, and replacing 2-phenylacetyl chloride with 2-methoxyphenyl chloroformate.

LC/MS ($C_{48}H_{51}N_5O_7$) 810 [M+H]$^+$; RT 1.20 (Method B)

EXAMPLE 129: N-(4-Hydroxyphenyl)-N-methyl-3-{7-[(3R)-3-methyl-1,2,3,4-tetrahydroisoquinoline-2-carbonyl]-2-{2-[4-(morpholin-4-ylmethyl)phenyl]acetyl}-1,2,3,4-tetrahydroisoquinolin-6-yl}-5,6,7,8-tetrahydroindolizine-1-carboxamide Step A: N-[4-(Benzyloxy)phenyl]-N-methyl-3-{7-[(3R)-3-methyl-1,2,3,4-tetrahydroisoquinoline-2-carbonyl]-2-{2-[4-(morpholin-4-ylmethyl)phenyl]acetyl}-1,2,3,4-tetrahydroisoquinolin-6-yl}-5,6,7,8-tetrahydroindolizine-1-carboxamide The procedure is as in Step A and B of Example 113, replacing N-methylpiperazine in Step A with morpholine.

LC/MS ($C_{56}H_{59}N_5O_5$) 882 [M+H]$^+$; RT 2.51 (Method A)

Step B: N-(4-Hydroxyphenyl)-N-methyl-3-{7-[(3R)-3-methyl-1,2,3,4-tetrahydroisoquinoline-2-carbonyl]-2-{2-[4-(morpholin-4-ylmethyl)phenyl]acetyl}-1,2,3,4-tetrahydroisoquinolin-6-yl}-5,6,7,8-tetrahydroindolizine-1-carboxamide A solution of the product from Step A (49 mg, 0.06 mmol) in anhydrous dichloromethane (5 ml) was cooled to 0° C. and to this was added boron trichloride (1M in DCM, 170 µL, 0.17 mmol). The reaction was stirred at ambient temperature for ca 16 h. The reaction was quenched with methanol (5 mL), and the reaction was diluted with dichloromethane. The organic phase was washed with water, dried over magnesium sulfate, filtered and concentrated in vacuo. The crude product was purified by column chromatography in a gradient of dichloromethane to 7% methanol in dichloromethane followed by trituration with ether and dried in vacuo.

LC/MS ($C_{49}H_{53}N_5O_5$) 792 [M+H]$^+$; RT 2.20 (Method A)
High-Resolution Mass (ESI+):
 Empirical formula: $C_{49}H_{53}N_5O_5$
 [M+2H]$^{2+}$ calculated: 396.7096
 [M+2H]$^{2+}$ measured: 396.7104

EXAMPLE 130: N-(4-Hydroxyphenyl)-N,1,2-trimethyl-5-{7-[(3S)-3-(morpholin-4-ylmethyl)-1,2,3,4-tetrahydroisoquinoline-2-carbonyl]-2-(3-phenylpropanoyl)-1,2,3,4-tetrahydroisoquinolin-6-yl}-1H-pyrrole-3-carboxamide The procedure was as in Example 23, replacing the product from Preparation 7ab in Step A with the product from Preparation 6ba, and replacing 2-methyl-3-phenylpropanoic acid in Step A with 3-phenylpropanoic acid.

LC/MS ($C_{47}H_{51}N_5O_5$) 766 [M+H]$^+$; RT 1.14 (Method B)
High-Resolution Mass (ESI+):
 Empirical formula: $C_{47}H_{51}N_5O_5$
 [M+H]$^+$ calculated: 766.3963
 [M+H]$^+$ measured: 766.3955

EXAMPLE 131: N-(4-Hydroxyphenyl)-N,1,2-trimethyl-5-{7-[(3S)-3-(morpholin-4-ylmethyl)-1,2,3,4-tetrahydroisoquinoline-2-carbonyl]-2-[(2E)-3-phenylprop-2-enoyl]-1,2,3,4-tetrahydroisoquinolin-6-yl}-1H-pyrrole-3-carboxamide The procedure was as in Example 109, replacing the product from Preparation 6ab with the product from Preparation 6ba, and replacing 2-methyl-3-phenylpropanoic acid with (2E)-3-phenylprop-2-enoic acid.

LC/MS ($C_{47}H_{49}N_5O_5$) 764 [M+H]$^+$; RT 1.15 (Method B)
High-Resolution Mass (ESI+):
 Empirical formula: $C_{47}H_{49}N_5O_5$
 [M+H]$^+$ calculated: 764.3806
 [M+H]$^+$ measured: 764.3779

EXAMPLE 132: 5-[2-(3-Cyclohexylpropanoyl)-7-[(3S)-3-(morpholin-4-ylmethyl)-1,2,3,4-tetrahydroisoquinoline-2-carbonyl]-1,2,3,4-tetrahydroisoquinolin-6-yl]-N-(4-hydroxyphenyl)-N,1,2-trimethyl-1H-pyrrole-3-carboxamide The procedure was as in Example 23, replacing the product from Preparation 7ab in Step A with the product from Preparation 6ba, and replacing 2-methyl-3-phenylpropanoic acid in Step A with 3-cyclohexylpropanoic acid.

LC/MS ($C_{47}H_{57}N_5O_5$) 772 [M+H]$^+$; RT 1.25 (Method B)

EXAMPLE 133: Phenyl 5-{1-[(4-hydroxyphenyl)(phenyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxylate High-Resolution Mass (ESI+):
 Empirical formula: $C_{47}H_{43}N_4O_5$
 [M+H]$^+$ calculated: 743.3228
 [M+H]$^+$ measured: 743.3234

EXAMPLE 134: N-(4-hydroxyphenyl)-3-{7-[(3R)-3-methyl-1,2,3,4-tetrahydroisoquinoline-2-carbonyl]-2-(2-phenylacetyl)-1,2,3,4-tetrahydroisoquinolin-6-yl}-N-phenyl-5,6,7,8-tetrahydroindolizine-1-carboxamide High-Resolution Mass (ESI+):
 Empirical formula: $C_{49}H_{47}N_4O_4$
 [M+H]$^+$ calculated: 755.3592
 [M+H]$^+$ measured: 755.3595

EXAMPLE 135: N-(4-Hydroxyphenyl)-5-{2-[3-(3-methoxyphenyl)propanoyl]-7-[(3S)-3-(morpholin-4-ylmethyl)-1,2,3,4-tetrahydroisoquinoline-2-carbonyl]-1,2,3,4-tetrahydroisoquinolin-6-yl}-N,1,2-trimethyl-1H-pyrrole-3-carboxamide The procedure was as in Example 23, replacing the product from Preparation 7ab in Step A with the product from Preparation 6ba, and replacing 2-methyl-3-phenylpropanoic acid in Step A with 3-(2-methoxyphenyl)propanoic acid.

LC/MS ($C_{48}H_{53}N_5O_6$) 796 [M+H]$^+$; RT 1.14 (Method B)
High-Resolution Mass (ESI+):
Empirical formula: $C_{48}H_{53}N_5O_6$
[M+H]$^+$ calculated: 796.4069
[M+H]$^+$ measured: 796.4068

EXAMPLE 136: N-(4-Hydroxyphenyl)-5-{2-[(2E)-3-(3-methoxyphenyl)prop-2-enoyl]-7-[(3S)-3-(morpholin-4-ylmethyl)-1,2,3,4-tetrahydroisoquinoline-2-carbonyl]-1,2,3,4-tetrahydroisoquinolin-6-yl}-N,1,2-trimethyl-1H-pyrrole-3-carboxamide The procedure was as in Example 109, replacing the product from Preparation 6ab with the product from Preparation 6ba, and replacing 2-methyl-3-phenylpropanoic acid with (2E)-3-(2-methoxyphenyl)prop-2-enoic acid.

LC/MS ($C_{48}H_{51}N_5O_6$) 794 [M+H]$^+$; RT 1.16 (Method B)
High-Resolution Mass (ESI+):
Empirical formula: $C_{48}H_{51}N_5O_6$
[M+H]$^+$ calculated: 794.3912
[M+H]$^+$ measured: 794.3908

EXAMPLE 137: 5-{2-[(2E)-3-(3,4-dichlorophenyl)prop-2-enoyl]-7-[(3S)-3-(morpholin-4-ylmethyl)-1,2,3,4-tetrahydroisoquinoline-2-carbonyl]-1,2,3,4-tetrahydroisoquinolin-6-yl}-N-(4-hydroxyphenyl)-N,1,2-trimethyl-1H-pyrrole-3-carboxamide The procedure was as in Example 109, replacing the product from Preparation 6ab with the product from Preparation 6ba, and replacing 2-methyl-3-phenylpropanoic acid with (2E)-3-(3,4-dichlorophenyl)prop-2-enoic acid.

LC/MS ($C_{47}H_{47}N_5O_5Cl_2$) 832 [M+H]$^+$; RT 1.27 (Method B)
High-Resolution Mass (ESI+):
Empirical formula: $C_{47}H_{47}N_5O_5Cl_2$
[M+H]$^+$ calculated: 832.3027
[M+H]$^+$ measured: 832.3000

EXAMPLE 138: 3-{2-[3-(4-{[2-(Dimethylamino)ethyl]amino}phenyl)propanoyl]-7-[(3R)-3-methyl-1,2,3,4-tetrahydroisoquinoline-2-carbonyl]-1,2,3,4-tetrahydroisoquinolin-6-yl}-N-(4-hydroxyphenyl)-N-methyl-5,6,7,8-tetrahydroindolizine-1-carboxamide The procedure is as described in Example 96, replacing 2-(morpholin-4-yl)ethan-1-amine in Step A with (2-aminoethyl)dimethylamine, and replacing ethyl 2-(4-bromophenyl)acetate in Step A with methyl 3-(4-bromophenyl)propanoate.

LC/MS ($C_{49}H_{56}N_6O_4$) 791 [M−H]$^−$; RT 2.22 (Method A)
High-Resolution Mass (ESI+):
Empirical formula: $C_{49}H_{56}N_6O_4$
[M+H]$^+$ calculated: 793.4436
[M+H]$^+$ measured: 793.4411

EXAMPLE 139: 4-Methylphenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 11, replacing the product from Preparation 7aa with the Product from Preparation 6ba, and replacing propionyl chloride with 4-methylphenyl chloroformate.

LC/MS ($C_{46}H_{49}N_5O_6$) 768 [M+H]$^+$; RT 1.22 (Method B)
High-Resolution Mass (ESI+):
Empirical formula: $C_{46}H_{49}N_5O_6$
[M+H]$^+$ calculated: 768.3756
[M+H]$^+$ measured: 768.3723

EXAMPLE 140: 4-Chlorophenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate Step A: 4-Chlorophenyl 6-(4-{[4-(benzyloxy)phenyl](methyl)carbamoyl}-1,5-dimethyl-1H-pyrrol-2-yl)-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Step A of Example 11, replacing the product from Preparation 7aa in Step A with the product from Preparation 6ba, and replacing propionyl chloride with 4-chlorophenyl chloroformate.

LC/MS ($C_{52}H_{52}N_5O_6Cl$) 878[M+H]$^+$; RT 1.48 (Method B)

Step B: 4-Chlorophenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Step B of Example 85, replacing product in Step A of Example 85 with product of Step A in Example 140.

LC/MS ($C_{45}H_{46}N_5O_6Cl$) 788 [M+H]$^+$; RT 1.24 (Method B)
High-Resolution Mass (ESI+):
Empirical formula: $C_{45}H_{46}N_5O_6Cl$
[M+H]$^+$ calculated: 788.3209
[M+H]$^+$ measured: 788.3191

EXAMPLE 141: 4-Carbamoylphenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 74, replacing the product from Preparation 7aa in Step A with the product from Preparation 6aa, and replacing N-methylaniline with 4-hydroxybenzamide.

LC/MS ($C_{48}H_{50}N_6O_7$) 823 [M+H]$^+$; RT 1.06 (Method B)

High-Resolution Mass (ESI+):
Empirical formula: $C_{48}H_{50}N_6O_7$
$[M+H]^+$ calculated: 823.3814
$[M+H]^+$ measured: 823.3788

EXAMPLE 142: 4-(Dimethylcarbamoyl)phenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 74, replacing the product from Preparation 7aa in Step A with the product from Preparation 6aa, and replacing N-methylaniline with 4-hydroxy-N,N-dimethylbenzamide.
LC/MS ($C_{50}H_{54}N_6O_7$) 851 $[M+H]^+$; RT 1.11 (Method B)
High-Resolution Mass (ESI+):
Empirical formula: $C_{50}H_{54}N_6O_7$
$[M+H]^+$ calculated: 851.4127
$[M+H]^+$ measured: 851.4094

EXAMPLE 143: 4-(1H-imidazol-1-yl)phenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 74, replacing the product from Preparation 7aa in Step A with the product from Preparation 6aa, and replacing N-methylaniline with 4-(1H-imidazol-1-yl)phenol.
LC/MS ($C_{50}H_{51}N_7O_6$) 846 $[M+H]^+$; RT 1.03 (Method B)
High-Resolution Mass (ESI+):
Empirical formula: $C_{50}H_{51}N_7O_6$
$[M+2H]^{2+}$ calculated: 423.7023
$[M+2H]^{2+}$ measured: 423.7023

EXAMPLE 144: 3-[2-(2-{4-[(Dimethylamino)methyl]phenyl}acetyl)-7-[(3R)-3-methyl-1,2,3,4-tetrahydroisoquinoline-2-carbonyl]-1,2,3,4-tetrahydroisoquinolin-6-yl]-N-(4-hydroxyphenyl)-N-methyl-5,6,7,8-tetrahydroindolizine-1-carboxamide The procedure is as in Example 113, replacing N-methylpiperazine in Step A with dimethylamine.
LC/MS ($C_{47}H_{51}N_5O_4$) 748 $[M-H]^-$; RT 2.18 (Method A)
High-Resolution Mass (ESI+):
Empirical formula: $C_{47}H_{51}N_5O_4$
$[M+H]^+$ calculated: 750.4014
$[M+H]^+$ measured: 750.3984

EXAMPLE 145: 5-{2-[2-(4-Cyanophenyl)acetyl]-7-[(3R)-3-methyl-1,2,3,4-tetrahydroisoquinoline-2-carbonyl]-1,2,3,4-tetrahydroisoquinolin-6-yl}-N-(4-hydroxyphenyl)-N,1,2-trimethyl-1H-pyrrole-3-carboxamide The procedure is as in Example 109, replacing the product from Preparation 6ab in Step A with the product from Preparation 6bb, and replacing 1-phenylcyclopropane-1-carboxylic acid in Step A with 2-(4-cyanophenyl)acetic acid.
LC/MS ($C_{43}H_{41}N_5O_4$) 692 $[M+H]^+$; RT 1.24 (Method B)
High-Resolution Mass (ESI+):
Empirical formula: $C_{43}H_{41}N_5O_4$
$[M+H]^+$ calculated: 692.3231
$[M+H]^+$ measured: 692.3199

EXAMPLE 146: 4-Cyanophenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 573, replacing 3,4-dichlorophenol in Step B with 4-hydroxybenzonitrile.
LC/MS ($C_{46}H_{46}N_6O_6$) 779 $[M+H]^+$; RT 1.14 (Method B)

EXAMPLE 147: 4-Cyanophenyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 573, replacing the product from Preparation 6ba with the product from Preparation 6bb, and replacing 3,4-dichlorophenol in Step B with 4-hydroxybenzonitrile.
LC/MS ($C_{42}H_{39}N_5O_5$) 694 $[M+H]^+$; RT 1.29 (Method B)
High-Resolution Mass (ESI+):
Empirical formula: $C_{42}H_{39}N_5O_5$
$[M+H]^+$ calculated: 694.3024
$[M+H]^+$ measured: 694.3044

EXAMPLE 148: 4-Cyano-2-methoxyphenyl 6-{1-[(4-hydroxyphenyl)(methyl)carbamoyl]-5,6,7,8-tetrahydroindolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 573, replacing the product from Preparation 6ba with the product from Preparation 7aa, and replacing 3,4-dichlorophenol in Step B with 4-hydroxybenzonitrile.
LC/MS ($C_{49}H_{50}N_6O_7$) 835 $[M+H]^+$; RT 1.19 (Method B)
High-Resolution Mass (ESI+):
Empirical formula: $C_{49}H_{50}N_6O_7$
$[M+H]^+$ calculated: 835.3814
$[M+H]^+$ measured: 835.3833

EXAMPLE 149: 5-{2-[2-(4-{[2-(Dimethylamino)ethyl]amino}phenyl)acetyl]-7-[(3R)-3-methyl-1,2,3,4-tetrahydroisoquinoline-2-carbonyl]-1,2,3,4-tetrahydroisoquinolin-6-yl}-N,1,2-trimethyl-N-phenyl-1H-pyrrole-3-carboxamide The procedure is as in Example 96, replacing 2-(morpholin-4-yl)ethan-1-amine in Step A with (2-aminoethyl)dimethylamine, and replacing the product from Preparation 6ba in Step C with the product obtained from Preparation 6cb.
LC/MS ($C_{46}H_{52}N_6O_3$) 737 $[M+H]^+$; RT 1.13 (Method B)
High-Resolution Mass (ESI+):
Empirical formula: $C_{46}H_{52}N_6O_3$
$[M+H]^+$ calculated: 737.4174
$[M+H]^+$ measured: 737.4173

EXAMPLE 150: 5-{2-[2-(4-Cyanophenyl)acetyl]-7-[(3R)-3-methyl-1,2,3,4-tetrahydroisoquinoline-2-carbonyl]-1,2,3,4-tetrahydroisoquinolin-6-yl}-N,1,2-trimethyl-N-phenyl-1H-pyrrole-3-carboxamide The procedure is as in Example 109, replacing the product from Preparation 6ab in Step A with the product from Preparation 6cb, and replacing 1-phenylcyclopropane-1-carboxylic acid in Step A with 2-(4-cyanophenyl)acetic acid.
LC/MS ($C_{43}H_{41}N_5O_3$) 676 [M+H]$^+$; RT 1.36 (Method B)
High-Resolution Mass (ESI+):
Empirical formula: $C_{43}H_{41}N_5O_3$
[M+H]$^+$ calculated: 676.3282
[M+H]$^+$ measured: 676.3249

EXAMPLE 151: 5-{2-[2-(4-Cyanophenyl)acetyl]-7-[(3S)-3-(morpholin-4-ylmethyl)-1,2,3,4-tetrahydroisoquinoline-2-carbonyl]-1,2,3,4-tetrahydroisoquinolin-6-yl}-N,1,2-trimethyl-N-phenyl-1H-pyrrole-3-carboxamide The procedure is as in Example 109, replacing the product from Preparation 6ab in Step A with the product from Preparation 6ca, and replacing 1-phenylcyclopropane-1-carboxylic acid in Step A with 2-(4-cyanophenyl)acetic acid.
LC/MS ($C_{47}H_{48}N_6O_4$) 761 [M+H]$^+$; RT 1.19 (Method B)
High-Resolution Mass (ESI+):
Empirical formula: $C_{47}H_{48}N_6O_4$
[M+H]$^+$ calculated: 761.3810
[M+H]$^+$ measured: 761.3811

EXAMPLE 152: 4-Cyanophenyl 6-{1,5-dimethyl-4-[methyl(phenyl)carbamoyl]-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Step A and B Example 573, replacing 3,4-dichlorophenol in Step B with 4-hydroxybenzonitrile.
LC/MS ($C_{46}H_{46}N_6O_5$) 763 [M+H]$^+$; RT 1.26 (Method B)
High-Resolution Mass (ESI+):
Empirical formula: $C_{46}H_{46}N_6O_5$
[M+H]$^+$ calculated: 763.3602
[M+H]$^+$ measured: 763.3572

EXAMPLE 153: 4-{[2-(Dimethylamino)ethyl]amino}phenyl 6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate The procedure is as in Example 489, replacing the product from Preparation 6cb with the product from Preparation 6ab.
LC/MS ($C_{47}H_{52}N_6O_5$) 779 [M−H]$^-$; RT 2.27 (Method A)
High-Resolution Mass (ESI+):
Empirical formula: $C_{47}H_{52}N_6O_5$
[M+2H]$^{2+}$ calculated: 391.2072
[M+2H]$^{2+}$ measured: 391.2081

EXAMPLE 154: 3-[2-(2-{4-[2-(Dimethylamino)ethoxy]phenyl}acetyl)-7-[(3R)-3-methyl-1,2,3,4-tetrahydroisoquinoline-2-carbonyl]-1,2,3,4-tetrahydroisoquinolin-6-yl]-N-(4-hydroxyphenyl)-N-methyl-5,6,7,8-tetrahydroindolizine-1-carboxamide Step A: methyl 2-{4-[2-(dimethylamino)ethoxy]phenyl}acetate To a solution of methyl 4-hydroxyphenylacetate (50 mg, 0.3 mmol) in acetone (5 mL) was added cesium carbonate (196 mg, 0.6 mmol) followed by 2-dimethylaminoethyl chloride hydrochloride (45 mg, 0.31 mmol) and the reaction stirred at ambient temperature for ca 16 h. To this was added sodium iodide (45 mg, 0.3 mmol) and the mixture was heated at 60° C. for ca 48 h. The reaction was cooled to ambient temperature, diluted with dichloromethane and washed with water, dried over magnesium sulphate, filtered and concentrated in vacuo and loaded onto a pre-packed 10 g silica column and purified by column chromatography in a gradient of dichloromethane to 10% methanol in dichloromethane to afford the desired product.
LC/MS ($C_{13}H_{19}NO_3$) 238 [M+H]$^+$; RT 1.49 (Method A)

Step B: sodium 2-{4-[2-(dimethylamino)ethoxy]phenyl}acetate

To a solution of methyl 2-{4-[2-(dimethylamino)ethoxy]phenyl}acetate (19 mg, 0.08 mmol) in methanol (3 mL) was added sodium hydroxide (2M, 80 μL, 0.16 mmol) and the reaction stirred at ambient temperature for ca 48 h. The reaction was concentrated in vacuo to afford the desired product and taken on assuming quantitative transformation.
LC/MS ($C_{12}H_{17}NO_3$) 224 [M+H]$^+$; RT 0.53 (Method A)

Step C: N-[4-(benzyloxy)phenyl]-3-[2-(2-{4-[2-(dimethylamino)ethoxy]phenyl}acetyl)-7-[(3R)-3-methyl-1,2,3,4-tetrahydroisoquinoline-2-carbonyl]-1,2,3,4-tetrahydroisoquinolin-6-yl]-N-methyl-5,6,7,8-tetrahydroindolizine-1-carboxamide To a suspension of the product from Step B (16 mg, 0.06 mmol) in dichloromethane (5 mL) was added the product from Preparation 6ab (50 mg, 0.06 mmol) followed by triethylamine (27 μL, 0.19 mmol) and HBTU (24 mg, 0.06 mmol) and the reaction stirred at ambient temperature for ca 16 h. The reaction was diluted with dichloromethane and washed with water, dried over magnesium sulphate, filtered and concentrated in vacuo and loaded onto a pre-packed 10 g silica column in dichloromethane and purified by column chromatography in a gradient of dichloromethane to 10% methanol in dichloromethane
LC/MS ($C_{55}H_{59}N_5O_5$) 435.5 [M+2H]$^{2+}$; RT 2.54 (Method A)

Step D: 3-[2-(2-{4-[2-(Dimethylamino)ethoxy]phenyl}acetyl)-7-[(3R)-3-methyl-1,2,3,4-tetrahydroisoquinoline-2-carbonyl]-1,2,3,4-tetrahydroisoquinolin-6-yl]-N-(4-hydroxyphenyl)-N-methyl-5,6,7,8-tetrahydroindolizine-1-carboxamide To a solution of the product obtained from Step C (51.8 mg, 0.04 mmol, 1 eq) in ethanol (5 mL) was added 10% Pd/C (catalytic). The reaction was stirred under a hydrogen atmosphere for ca 48. The reaction was filtered through a celite cartridge and washed with methanol and concentrated in vacuo and purified by reverse phase preparative HPLC (H$_2$O-TFA/acetonitrile; gradient elution).
LC/MS ($C_{48}H_{53}N_5O_5$) 778 [M−H]$^-$; RT 2.20 (Method A)

EXAMPLE 155: 4-[2-(Dimethylcarbamoyl)ethyl]phenyl 6-{1-[(4-hydroxyphenyl)(methyl)carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate The procedure is as in Example 786, replacing the product from Preparation 6cb in Step A with the product from Preparation 6ab, and 4-hydroxybenzonitrile in Step B with 3-(4-hydroxyphenyl)-N,N-dimethylpropanamide.
LC/MS ($C_{48}H_{51}N_5O_6$) 794 [M+H]$^+$; RT 2.57 (Method A)

High-Resolution Mass (ESI+):
Empirical formula: $C_{48}H_{51}N_5O_6$
[M+H]$^+$ calculated: 794.3912
[M+H]$^+$ measured: 794.3950

EXAMPLE 156: N-(4-Hydroxyphenyl)-N-methyl-3-{6-[(3S)-3-(morpholin-4-ylmethyl)-1,2,3,4-tetrahydroisoquinoline-2-carbonyl]-2-(2-phenoxyacetyl)-2,3-dihydro-1H-isoindol-5-yl}-5,6,7,8-tetrahydroindolizine-1-carboxamide High-Resolution Mass (ESI+):
Empirical formula: $C_{47}H_{49}N_5O_6$
[M+H]$^+$ calculated: 780.3763
[M+H]$^+$ measured: 780.3759

EXAMPLE 157: 1,1-Dioxo-1$\lambda^6$-thiolan-3-yl 5-{4-[(4-hydroxyphenyl)(methyl)carbamoyl]-1,5-dimethyl-1H-pyrrol-2-yl}-6-[(3R)-3-methyl-1,2,3,4-tetrahydroisoquinoline-2-carbonyl]-2,3-dihydro-1H-isoindole-2-carboxylate High-Resolution Mass (ESI+):
Empirical formula: $C_{38}H_{40}N_4O_7S$
[M+H]$^+$ calculated: 697.2698
[M+H]$^+$ measured: 697.2696

EXAMPLE 158: N-(4-Hydroxyphenyl)-3-{6-[(3R)-3-methyl-1,2,3,4-tetrahydroisoquinoline-2-carbonyl]-2-(2-phenoxyacetyl)-2,3-dihydro-1H-isoindol-5-yl}-N-{1-methyl-1H-pyrrolo[2,3-b]pyridin-5-yl}-5,6,7,8-tetrahydroindolizine-1-carboxamide EXAMPLE 159: N-(4-Hydroxyphenyl)-N,1,2-trimethyl-5-{6-[(3S)-3-(morpholin-4-ylmethyl)-1,2,3,4-tetrahydroisoquinoline-2-carbonyl]-2-(2-phenoxyacetyl)-2,3-dihydro-1H-isoindol-5-yl}-1H-pyrrole-3-carboxamide High-Resolution Mass (ESI+):
Empirical formula: $C_{45}H_{47}N_5O_6$
[M+H]$^+$ calculated: 754.3606
[M+H]$^+$ measured: 754.3574

EXAMPLE 160: 5-{2-[2-(Benzyloxy)acetyl]-6-[(3R)-3-methyl-1,2,3,4-tetrahydroisoquinoline-2-carbonyl]-2,3-dihydro-1H-isoindol-5-yl}-N-(4-hydroxyphenyl)-N,1,2-trimethyl-1H-pyrrole-3-carboxamide High-Resolution Mass (ESI+):
Empirical formula: $C_{42}H_{42}N_4O_5$
[M+H]$^+$ calculated: 683.3235
[M+H]$^+$ measured: 683.3238

EXAMPLE 161: Phenyl 6-[4-(dibutylcarbamoyl)-1,5-dimethyl-1H-pyrrol-2-yl]-7-(1,2,3,4-tetrahydroisoquinoline-2-carbonyl)-1,2,3,4-tetrahydroisoquinoline-2-carboxylate The product from Preparation 6dc (81 mg, 0.15 mmol, 1 eq) in dichloromethane (5 mL) was cooled to 0° C. To this was added N,N-diisopropylethylamine (52 µL, 0.3 mmol) followed by phenyl chloroformate (21 µL, 0.16 mmol) and the mixture was allowed to stir for 15 min. The reaction was diluted with dichloromethane and washed sequentially with 1M aqueous NaOH, and brine. The organic extracts were dried over magnesium sulphate, filtered and concentrated in vacuo. Purification by flash column chromatography (CombiFlash R$_f$, 12 g RediSep™ silica cartridge; gradient of dichloromethane to 5% methanol in dichloromethane) afforded the desired product.
LC/MS ($C_{41}H_{48}N_4O_4$) 661 [M+H]$^+$; RT 1.57 (Method B)
High-Resolution Mass (ESI+):
Empirical formula: $C_{41}H_{48}N_4O_4$
[M+H]$^+$ calculated: 661.3748
[M+H]$^+$ measured: 661.3769

EXAMPLE 162: N,N-Dibutyl-1,2-dimethyl-5-[2-(2-phenylacetyl)-7-(1,2,3,4-tetrahydroisoquinoline-2-carbonyl)-1,2,3,4-tetrahydroisoquinolin-6-yl]-1H-pyrrole-3-carboxamide The procedure is as in Example 161, replacing phenyl chloroformate with phenylacetyl chloride.
LC/MS ($C_{42}H_{50}N_4O_3$) 659 [M+H]$^+$; RT 1.52 (Method B)
High-Resolution Mass (ESI+):
Empirical formula: $C_{42}H_{50}N_4O_3$
[M+H]$^+$ calculated: 659.3956
[M+H]$^+$ measured: 659.3969

EXAMPLE 163: Phenyl 6-[4-(dibutylcarbamoyl)-1,5-dimethyl-1H-pyrrol-2-yl]-7-[(3R)-3-methyl-1,2,3,4-tetrahydroisoquinoline-2-carbonyl]-1,2,3,4-tetrahydroisoquinoline-2-carboxylate The procedure is as in Example 161, replacing the product from Preparation 6dc with product from Preparation 6db.
LC/MS ($C_{42}H_{50}N_4O_4$) 675 [M+H]$^+$; RT 1.52 (Method B)
High-Resolution Mass (ESI+):
Empirical formula: $C_{42}H_{50}N_4O_4$
[M+H]$^+$ calculated: 675.3905
[M+H]$^+$ measured: 675.3900

EXAMPLE 164: N,N-Dibutyl-1,2-dimethyl-5-{7-[(3R)-3-methyl-1,2,3,4-tetrahydroisoquinoline-2-carbonyl]-2-(2-phenylacetyl)-1,2,3,4-tetrahydroisoquinolin-6-yl}-1H-pyrrole-3-carboxamide The procedure is as in Example 161, replacing the product from Preparation 6dc with product from Preparation 6db, and replacing phenyl chloroformate with phenylacetyl chloride.
LC/MS ($C_{43}H_{52}N_4O_3$) 673 [M+H]$^+$; RT 1.51 (Method B)
High-Resolution Mass (ESI+):
Empirical formula: $C_{43}H_{52}N_4O_3$
[M+H]$^+$ calculated: 673.4112
[M+H]$^+$ measured: 673.4087

EXAMPLE 165: N,N-Dibutyl-1,2-dimethyl-5-{7-[(3S)-3-(morpholin-4-ylmethyl)-1,2,3,4-tetrahydroisoquinoline-2-carbonyl]-2-(2-phenylacetyl)-1,2,3,4-tetrahydroisoquinolin-6-yl}-1H-pyrrole-3-carboxamide To a solution of the product of Preparation 6da (112 mg, 0.13 mmol) in dichloromethane (5 mL) was added N,N-diisopropylethylamine (112 µL, 0.64 mmol) followed by phenylacetyl chloride (17 µL, 0.14 mmol) and the mixture was allowed to stir for 15 min. The reaction was diluted with dichloromethane and washed sequentially with 1M aqueous sodium hydroxide, and brine. The organic extracts were dried over magnesium sulphate, filtered and concentrated.

Purification by flash column chromatography (CombiFlash R$_f$, 12 g RediSep™ silica cartridge) eluting with a gradient of dichloromethane to 5% methanol in dichloromethane afforded the desired product.

LC/MS (C$_{47}$H$_{59}$N$_5$O$_4$) 758 [M+H]$^+$; RT 1.40 (Method B)
High-Resolution Mass (ESI+):
Empirical formula: C$_{47}$H$_{59}$N$_5$O$_4$
[M+H]$^+$ calculated: 758.4640
[M+H]$^+$ measured: 758.4648

EXAMPLE 166: N-(4-Hydroxyphenyl)-N-methyl-3-{6-[(3S)-3-(morpholin-4-ylmethyl)-1,2,3,4-tetrahydroisoquinoline-2-carbonyl]-2-(2-phenoxyacetyl)-2,3-dihydro-1H-isoindol-5-yl}indolizine-1-carboxamide High-Resolution Mass (ESI+):
Empirical formula: C$_{47}$H$_{45}$N$_5$O$_6$
[M+H]$^+$ calculated: 776.3450
[M+H]$^+$ measured: 776.3430

EXAMPLE 167: N-(4-Hydroxyphenyl)-N-methyl-3-{6-[(3R)-3-methyl-1,2,3,4-tetrahydroisoquinoline-2-carbonyl]-2-(2-phenoxyacetyl)-2,3-dihydro-1H-isoindol-5-yl}indolizine-1-carboxamide High-Resolution Mass (ESI+):
Empirical formula: C$_{43}$H$_{38}$N$_4$O$_5$
[M+H]$^+$ calculated: 691.2922
[M+H]$^+$ measured: 691.2913

EXAMPLE 168: 4-Methylphenyl 5-{1-[(4-hydroxyphenyl)(methyl)carbamoyl]-5,6,7,8-tetrahydroindolizin-3-yl}-6-[(3R)-3-methyl-1,2,3,4-tetrahydroisoquinoline-2-carbonyl]-2,3-dihydro-1H-isoindole-2-carboxylate High-Resolution Mass (ESI+):
Empirical formula: C$_{43}$H$_{42}$N$_4$O$_5$
[M+H]$^+$ calculated: 695.3235
[M+H]$^+$ measured: 695.3230

EXAMPLE 169: N-(4-Hydroxyphenyl)-N-methyl-3-{7-[(3R)-3-methyl-1,2,3,4-tetrahydroisoquinoline-2-carbonyl]-2-{2-[3-(4-methylpiperazin-1-yl)phenyl]acetyl}-1,2,3,4-tetrahydroisoquinolin-6-yl}-5,6,7,8-tetrahydroindolizine-1-carboxamide Step A: methyl 2-[3-(4-methylpiperazin-1-yl)phenyl]acetate To a boiling tube was added methyl 2-(3-bromophenyl)acetate (250 mg, 1.09 mmol), 1-methylpiperazine (0.18 mL, 1.64 mmol), di-tert-butyl(2-phenylphenyl)phosphane, (32.57 mg, 0.11 mmol) and potassium phosphate tribasic (463.32 mg, 2.18 mmol) which were then suspended in toluene (5 mL) and degassed by sparging with nitrogen for 5 min. Tris(Dibenzylideneacetone)Dipalladium(0) (49.97 mg, 0.05 mmol) was then added to the reaction and stirred at 90° C. under nitrogen for ca 16 h. The reaction was filtered and solids washed with dichloromethane and concentrated in vacuo, and then loaded onto a pre-packed 10 g silica column in dichloromethane and purified by column chromatography in a gradient of dichloromethane to 5% methanol in dichloromethane.

LC/MS (C$_{14}$H$_{20}$N$_2$O$_2$) 249 [M+H]$^+$; RT 1.56 (Method B)

Step B: sodium 2-[3-(4-methylpiperazin-1-yl)phenyl]acetate

To a solution of the product from Step A (39.3 mg, 0.16 mmol) in methanol (5 mL) was added sodium hydroxide (2M, 0.16 mL, 0.32 mmol) and the reaction stirred at ambient temperature for ca 16 h. The reaction was concentrated in vacuo and triturated with diethyl ether to afford the desired product.

LC/MS (C$_{13}$H$_{18}$N$_2$O$_2$) 235 [M+H]$^+$; RT 0.69 (Method B)

Step C: N-[4-(benzyloxy)phenyl]-N-methyl-3-{7-[(3R)-3-methyl-1,2,3,4-tetrahydroisoquinoline-2-carbonyl]-2-{2-[3-(4-methylpiperazin-1-yl)phenyl]acetyl}-1,2,3,4-tetrahydroisoquinolin-6-yl}-5,6,7,8-tetrahydroindolizine-1-carboxamide To a solution of the product from Preparation 6ab (50 mg, 0.06 mmol) in dichloromethane (3 mL) was added HBTU (24.35 mg, 0.06 mmol) and triethylamine (26.79 µL, 0.19 mmol) followed by the product from Step B (24.68 mg, 0.1 mmol) and the reaction stirred at ambient temperature for ca 16 h. The reaction was diluted with dichloromethane and washed with water and brine. The organic extract was dried over magnesium sulphate, filtered and concentrated in vacuo, and loaded onto a pre-packed 5 g silica column in dichloromethane and purified by column chromatography in a gradient of dichloromethane in 5% methanol in dichloromethane.

LC/MS (C$_{56}$H$_{60}$N$_6$O$_4$) 881 [M+H]$^+$; RT 2.52 (Method B)

Step D: N-(4-Hydroxyphenyl)-N-methyl-3-{7-[(3R)-3-methyl-1,2,3,4-tetrahydroisoquinoline-2-carbonyl]-2-{2-[3-(4-methylpiperazin-1-yl)phenyl]acetyl}-1,2,3,4-tetrahydroisoquinolin-6-yl}-5,6,7,8-tetrahydroindolizine-1-carboxamide To a solution the product from Step C (45 mg, 0.05 mmol) in ethanol (10 mL) was added 10% Pd/C (catalytic), and stirred under a hydrogen atmosphere at ambient temperature for ca 16 h. The reaction was filtered through a celite cartridge, which was washed with methanol and the filtrate was concentrated in vacuo, and loaded onto a pre-packed 5 g silica column in dichloromethane and purified by column chromatography in a gradient of dichloromethane to 5% methanol in dichloromethane.

LC/MS (C$_{49}$H$_{54}$N$_6$O$_4$) 791 [M+H]$^+$; RT 2.21 (Method B)
High-Resolution Mass (ESI+):
Empirical formula: C$_{49}$H$_{54}$N$_6$O$_4$
[M+2H]$^{2+}$ calculated: 396.2176
[M+2H]$^{2+}$ measured: 396.2176

EXAMPLE 170: 5-{4-[(4-Hydroxyphenyl)(methyl)carbamoyl]-1,5-dimethyl-1H-pyrrol-2-yl}-N-methyl-6-[(3R)-3-methyl-1,2,3,4-tetrahydroisoquinoline-2-carbonyl]-2,3-dihydro-1H-isoindole-2-carboxamide High-Resolution Mass (ESI+):
Empirical formula: C$_{35}$H$_{37}$N$_5$O$_4$
[M+H]$^+$ calculated: 592.2926
[M+H]$^+$ measured: 592.2925

EXAMPLE 171: N-(4-Hydroxyphenyl)-N-methyl-3-{6-[(3R)-3-methyl-1,2,3,4-tetrahydroisoquinoline-2-carbonyl]-2-[2-(phenylsulfanyl)acetyl]-2,3-dihydro-1H-isoindol-5-yl}-5,6,7,8-tetrahydroindolizine-1-carboxamide High-Resolution Mass (ESI+):
Empirical formula: $C_{43}H_{42}N_4O_4S$
$[M+H]^+$ calculated: 711.3007
$[M+H]^+$ measured: 711.3001

EXAMPLE 172: 5-{2-[2-(2H-1,3-Benzodioxol-5-yl)acetyl]-6-[(3R)-3-methyl-1,2,3,4-tetrahydroisoquinoline-2-carbonyl]-2,3-dihydro-1H-isoindol-5-yl}-N-(4-hydroxyphenyl)-N,1,2-trimethyl-1H-pyrrole-3-carboxamide High-Resolution Mass (ESI+):
Empirical formula: $C_{42}H_{40}N_4O_6$
$[M+H]^+$ calculated: 697.3028
$[M+H]^+$ measured: 697.2994

EXAMPLE 173: 5-(2-[(2S)-2-Amino-2-phenylacetyl]-6-{[(3R)-3-methyl-3,4-dihydroisoquinolin-2(1H)-yl]carbonyl}-2,3-dihydro-1H-isoindol-5-yl)-N-(4-hydroxyphenyl)-N,1,2-trimethyl-1H-pyrrole-3-carboxamide High-Resolution Mass (ESI+):
Empirical formula: $C_{41}H_{41}N_5O_4$
$[M+H]^+$ calculated: 668.3239
$[M+H]^+$ measured: 668.3238

EXAMPLE 174: 5-(2-[(2R)-2-Amino-2-phenylacetyl]-6-{[(3R)-3-methyl-3,4-dihydroisoquinolin-2(1H)-yl]carbonyl}-2,3-dihydro-1H-isoindol-5-yl)-N-(4-hydroxyphenyl)-N,1,2-trimethyl-1H-pyrrole-3-carboxamide High-Resolution Mass (ESI+):
Empirical formula: $C_{41}H_{41}N_5O_4$
$[M+H]^+$ calculated: 668.3239
$[M+H]^+$ measured: 668.3247

EXAMPLE 175: N-(4-Hydroxyphenyl)-5-(2-[(2R)-2-hydroxy-2-phenylacetyl]-6-{[(3R)-3-methyl-3,4-dihydroisoquinolin-2(1H)-yl]carbonyl}-2,3-dihydro-1H-isoindol-5-yl)-N,1,2-trimethyl-1H-pyrrole-3-carboxamide High-Resolution Mass (ESI+):
Empirical formula: $C_{41}H_{40}N_4O_5$
$[M+H]^+$ calculated: 669.3079
$[M+H]^+$ measured: 669.3063

EXAMPLE 176: 5-{2-[2-(1-Piperidyl)acetyl]-6-[(3R)-3-methyl-1,2,3,4-tetrahydro isoquinoline-2-carbonyl]-2,3-dihydro-1H-isoindol-5-yl}-N-(4-hydroxyphenyl)-N,1,2-trimethyl-1H-pyrrole-3-carboxamide High-Resolution Mass (ESI+):
Empirical formula: $C_{40}H_{45}N_5O_4$
$[M+H]^+$ calculated: 660.3552
$[M+H]^+$ measured: 660.3512

EXAMPLE 177: 5-[2-[2-(1,3-Benzodioxol-5-yl)acetyl]-6-[(3R)-3-methyl-3,4-dihydro-1H-isoquinoline-2-carbonyl]isoindolin-5-yl]-N,1,2-trimethyl-N-(1-methylpyrrolo[2,3-h]pyridin-5-yl)pyrrole-3-carboxamide EXAMPLE 178: 5-[2-[2-(1,3-Benzodioxol-5-yl)acetyl]-6-[(3R)-3-methyl-3,4-dihydro-1H-isoquinoline-2-carbonyl]isoindolin-5-yl]-N-(4-hydroxyphenyl)-1,2-dimethyl-N-(1-methyl-1H-pyrazol-4-yl)pyrrole-3-carboxamide EXAMPLE 179: N-(4-Hydroxyphenyl)-N,1,2-trimethyl-5-[6-[(3R)-3-methyl-3,4-dihydro-1H-isoquinoline-2-carbonyl]-2-[(2R)-2-phenylpropanoyl]isoindolin-5-yl]pyrrole-3-carboxamide EXAMPLE 180: N-(4-Hydroxyphenyl)-N,1,2-trimethyl-5-[6-[(3R)-3-methyl-3,4-dihydro-1H-isoquinoline-2-carbonyl]-2-[2-(3-thienyl)acetyl]isoindolin-5-yl]pyrrole-3-carboxamide EXAMPLE 181: N-(4-Hydroxyphenyl)-N,1,2-trimethyl-5-[6-[(3R)-3-methyl-3,4-dihydro-1H-isoquinoline-2-carbonyl]-2-[(2S)-2-phenylpropanoyl]isoindolin-5-yl]pyrrole-3-carboxamide EXAMPLE 182: 5-[2-[3-(4-Chlorophenoxy)propanoyl]-6-[(3R)-3-methyl-3,4-dihydro-1H-isoquinoline-2-carbonyl]isoindolin-5-yl]-N-(4-hydroxyphenyl)-N,1,2-trimethyl-pyrrole-3-carboxamide EXAMPLE 183: N-(4-Hydroxyphenyl)-N,1,2-trimethyl-5-[6-[(3R)-3-methyl-3,4-dihydro-1H-isoquinoline-2-carbonyl]-2-(2-pyrrol-1-ylacetyl)isoindolin-5-yl]pyrrole-3-carboxamide EXAMPLE 184: Phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 185: Phenyl 6-{4-[ethyl(4-hydroxyphenyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 777, replacing the compound from Preparation 6be in Step A with product from Preparation 6f, and replacing phenylacetyl chloride in Step A with phenyl chloroformate.
LC/MS ($C_{46}H_{49}N_5O_6$) 768 $[M+H]^+$; RT 1.21 (Method B)
High-Resolution Mass (ESI+):
Empirical formula: $C_{46}H_{49}N_5O_6$
$[M+H]^+$ calculated: 768.3756
$[M+H]^+$ measured: 768.3741

EXAMPLE 186: Phenyl 6-{4-[(4-hydroxyphenyl)(propyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 777, replacing the product from Preparation 6be in Step A with the product from Preparation 6g, and replacing phenylacetyl chloride in Step A with phenyl chloroformate.

LC/MS ($C_{47}H_{51}N_5O_6$) 782 [M+H]$^+$; RT 1.24 (Method B)

High-Resolution Mass (ESI+):

Empirical formula: $C_{47}H_{51}N_5O_6$

[M+H]$^+$ calculated: 782.3912

[M+H]$^+$ measured: 782.3927

EXAMPLE 187: Phenyl 6-{4-[butyl(4-hydroxyphenyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 777, replacing the product from Preparation 6be in Step A with the product from Preparation 6h, and replacing phenylacetyl chloride in Step A with phenyl chloroformate.

LC/MS ($C_{48}H_{53}N_5O_6$) 796 [M+H]$^+$; RT 1.29 (Method B)

High-Resolution Mass (ESI+):

Empirical formula: $C_{48}H_{53}N_5O_6$

[M+2H]$^{2+}$ calculated: 398.7071

[M+2H]$^{2+}$ measured: 398.7075

EXAMPLE 188: Phenyl 6-{4-[(4-hydroxyphenyl)(phenyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 189: Phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 190: Phenyl 6-{4-[ethyl(phenyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 191: Phenyl 6-{1,5-dimethyl-4-[phenyl(propyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 192: Phenyl 6-{4-[butyl(phenyl)carbamoyl]-1,5-dimethyl-1H-pyrrol-2-yl}-7-{[(1S)-3-(morpholin-4-ylmethyl)-3,4-dihydroisoquinolin-2(1H)-yl]carbonyl}-3,4-dihydroisoquinoline-2(1H)-carboxylate EXAMPLE 193: Phenyl 6-{4-(diphenylcarbamoyl)-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 194: Phenyl 6-{4-[butyl(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 195: Phenyl 6-{4-[butyl(ethyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 196: Phenyl 6-{4-[butyl(propyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 197: Phenyl 6-[4-(dibutylcarbamoyl)-1,5-dimethyl-1H-pyrrol-2-yl]-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 165, replacing phenylacetyl chloride with phenyl chloroformate.

LC/MS ($C_{46}H_{57}N_5O_5$) 760 [M+H]$^+$; RT 1.40 (Method B)

High-Resolution Mass (ESI+):

Empirical formula: $C_{46}H_{57}N_5O_5$

[M+H]$^+$ calculated: 760.4432

[M+H]$^+$ measured: 760.4449

EXAMPLE 198: Phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 199: Phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 200: Phenyl 6-{4-[(4-hydroxyphenyl)(phenyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 201: Phenyl 6-[4-(diphenylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 202: Phenyl 6-{4-[butyl(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 203: Phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 204: Phenyl 7-(3,4-dihydroisoquinolin-2(1H)-ylcarbonyl)-6-{4-[(4-hydroxyphenyl)(methyl)carbamoyl]-1,5-dimethyl-1H-pyrrol-2-yl}-3,4-dihydroisoquinoline-2(1H)-carboxylate EXAMPLE 205: Phenyl 7-(3,4-dihydroisoquinolin-2(1H)-ylcarbonyl)-6-{1,5-dimethyl-4-[methyl(phenyl)carbamoyl]-1H-pyrrol-2-yl}-3,4-dihydroisoquinoline-2(1H)-carboxylate EXAMPLE 206: Phenyl 7-(3,4-dihydroisoquinolin-2(1H)-ylcarbonyl)-6-{4-[(4-hydroxyphenyl)(phenyl)carbamoyl]-1,5-dimethyl-1H-pyrrol-2-yl}-3,4-dihydroisoquinoline-2(1H)-carboxylate EXAMPLE 207: Phenyl 7-(3,4-dihydroisoquinolin-2(1H)-ylcarbonyl)-6-[4-(diphenylcarbamoyl)-1,5-dimethyl-1H-pyrrol-2-1]-3,4-dihydroisoquinoline-2(1H)-carboxylate EXAMPLE 208: Phenyl 6-{4-[butyl(methyl)carbamoyl]-1,5-dimethyl-1H-pyrrol-2-yl}-7-(3,4-dihydroisoquinolin-2(1H)-ylcarbonyl)-3,4-dihydroisoquinoline-2(1H)-carboxylate EXAMPLE 209: Phenyl 6-[4-(dibutylcarbamoyl)-1,5-dimethyl-1H-pyrrol-2-yl]-7-(3,4-dihydroisoquinolin-2(1H)-ylcarbonyl)-3,4-dihydroisoquinoline-2(1H)-carboxylate EXAMPLE 210: Phenyl 7-{[(3S)-3-(aminomethyl)-3,4-dihydroisoquinolin-2(1H)-yl]carbonyl}-6-{4-[(4-hydroxyphenyl)(methyl)carbamoyl]-1,5-dimethyl-1H-pyrrol-2-yl}-3,4-dihydroisoquinoline-2(1H)-carboxylate EXAMPLE 211: Phenyl 7-[(3S)-3-[(dimethylamino)methyl]-1,2,3,4-tetrahydroisoquinoline-2-carbonyl]-6-{4-[(4-hydroxyphenyl)(methyl)carbamoyl]-1,5-dimethyl-1H-pyrrol-2-yl}-1,2,3,4-tetrahydroisoquinoline-2-carboxylate Step A: Phenyl 6-(4-{[4-(benzyloxy)phenyl](methyl)carbamoyl}-1,5-dimethyl-1H-pyrrol-2-yl)-7-[(3S)-3-[(dimethylamino)methyl]-1,2,3,4-tetrahydroisoquinoline-2-carbonyl]-1,2,3,4-tetrahydroisoquinoline-2-carboxylate The procedure is as in Step A of Example 777, replacing phenylacetyl chloride with phenyl chloroformate.
LC/MS ($C_{50}H_{51}N_5O_5$) 802 [M+H]$^+$; RT 1.34 (Method B)

Step B: Phenyl 7-[(3S)-3-[(dimethylamino)methyl]-1,2,3,4-tetrahydroisoquinoline-2-carbonyl]-6-{4-[(4-hydroxyphenyl)(methyl)carbamoyl]-1,5-dimethyl-1H-pyrrol-2-yl}-1,2,3,4-tetrahydroisoquinoline-2-carboxylate The procedure is as in Step B of Example 777, but purification was via preparative HPLC (H$_2$O-TFA/acetonitrile; gradient elution).
LC/MS ($C_{43}H_{45}N_5O_5$) 712 [M+H]$^+$; RT 1.13 (Method B)
High-Resolution Mass (ESI+):
Empirical formula: $C_{43}H_{45}N_5O_5$
[M+H]$^+$ calculated: 712.3493
[M+H]$^+$ measured: 712.3496

EXAMPLE 212: Phenyl 6-{4-[(4-hydroxyphenyl)(methyl)carbamoyl]-1,5-dimethyl-1H-pyrrol-2-yl}-7-{[(1S)-3-(pyrrolidin-1-ylmethyl)-3,4-dihydroisoquinolin-2(1H)-yl]carbonyl}-3,4-dihydroisoquinoline-2(1H)-carboxylate EXAMPLE 213: Phenyl 6-{4-[(4-hydroxyphenyl)(methyl)carbamoyl]-1,5-dimethyl-1H-pyrrol-2-yl}-7-{[(1S)-3-(piperidin-1-ylmethyl)-3,4-dihydroisoquinolin-2(1H)-yl]carbonyl}-3,4-dihydroisoquinoline-2(1H)-carboxylate EXAMPLE 214: Phenyl 6-{4-[(4-hydroxyphenyl)(methyl)carbamoyl]-1,5-dimethyl-1H-pyrrol-2-yl}-7-[(3S)-3-[(4-methylpiperazin-1-yl)methyl]-1,2,3,4-tetrahydroisoquinoline-2-carbonyl]-1,2,3,4-tetrahydroisoquinoline-2-carboxylate Step A: Phenyl 6-(4-{[4-(benzyloxy)phenyl](methyl)carbamoyl}-1,5-dimethyl-1H-pyrrol-2-yl)-7-[(3S)-3-[(4-methylpiperazin-1-yl)methyl]-1,2,3,4-tetrahydroisoquinoline-2-carbonyl]-1,2,3,4-tetrahydroisoquinoline-2-carboxylate The procedure is as in Step A of Example 777, replacing the compound from Preparation 6be with the compound from Preparation 6bf, and replacing phenylacetyl chloride with phenyl chloroformate.
LC/MS ($C_{53}H_{56}N_6O_5$) 857 [M+H]$^+$; RT 1.34 (Method B)

Step B: Phenyl 6-{4-[(4-hydroxyphenyl)(methyl)carbamoyl]-1,5-dimethyl-1H-pyrrol-2-yl}-7-[(3S)-3-[(4-methylpiperazin-1-yl)methyl]-1,2,3,4-tetrahydroisoquinoline-2-carbonyl]-1,2,3,4-tetrahydroisoquinoline-2-carboxylate The procedure is as in Step B of Example 777, but purification was via preparative HPLC (H$_2$O-TFA/acetonitrile; gradient elution).
LC/MS ($C_{46}H_{50}N_6O_5$) 767 [M+H]$^+$; RT 1.14 (Method B)
High-Resolution Mass (ESI+):
Empirical formula: $C_{46}H_{50}N_6O_5$
[M+2H]$^{2+}$ calculated: 384.1994
[M+2H]$^{2+}$ measured: 384.1995

EXAMPLE 215: Phenyl 7-{[(3S)-3-[2-(dimethylamino)ethyl]-3,4-dihydroisoquinolin-2(1H)-yl]carbonyl}-6-{4-[(4-hydroxyphenyl)(methyl)carbamoyl]-1,5-dimethyl-1H-pyrrol-2-yl}-3,4-dihydroisoquinoline-2(1H)-carboxylate EXAMPLE 216: Phenyl 6-{4-[(4-hydroxyphenyl)(methyl)carbamoyl]-1,5-dimethyl-1H-pyrrol-2-yl}-7-[(3S)-3-[2-(morpholin-4-yl)ethyl]-1,2,3,4-tetrahydroisoquinoline-2-carbonyl]-1,2,3,4-tetrahydroisoquinoline-2-carboxylate The procedure is as in Example 777, replacing the compound from Preparation 6be in Step A with product from Preparation 6bc, and replacing phenylacetyl chloride in Step A with phenyl chloroformate.
LC/MS ($C_{46}H_{49}N_5O_6$) 768 [M+H]$^+$; RT 1.14 (Method B)
High-Resolution Mass (ESI+):
Empirical formula: $C_{46}H_{49}N_5O_6$
[M+H]$^+$ calculated: 768.3756
[M+H]$^+$ measured: 768.3756

EXAMPLE 217: Phenyl 7-{[(3S)-3-(aminomethyl)-3,4-dihydroisoquinolin-2(1H)-yl]carbonyl}-6-{1,5-dimethyl-4-[methyl(phenyl)carbamoyl]-1H-pyrrol-2-yl}-3,4-dihydroisoquinoline-2(1H)-carboxylate EXAMPLE 218: Phenyl 7-{[(3S)-3-[(dimethylamino)methyl]-3,4-dihydroisoquinolin-2(1H)-yl]carbonyl}-6-{1,5-dimethyl-4-[methyl(phenyl)carbamoyl]-1H-pyrrol-2-yl}-3,4-dihydroisoquinoline-2(1H)-carboxylate EXAMPLE 219: Phenyl 6-{1,5-dimethyl-4-[methyl(phenyl)carbamoyl]-1H-pyrrol-2-yl}-7-{[(3S)-3-(pyrrolidin-1-ylmethyl)-3,4-dihydroisoquinolin-2(1H)-yl]carbonyl}-3,4-dihydroisoquinoline-2(1H)-carboxylate EXAMPLE 220: Phenyl 6-{1,5-dimethyl-4-[methyl(phenyl)carbamoyl]-1H-pyrrol-2-yl}-7-{[(3S)-3-(piperidin-1-ylmethyl)-3,4-dihydroisoquinolin-2(1H)-yl]carbonyl}-3,4-dihydroisoquinoline-2(1H)-carboxylate EXAMPLE 221: Phenyl 6-{1,5-dimethyl-4-[methyl(phenyl)carbamoyl]-1H-pyrrol-2-yl}-7-{[(3S)-3-[(4-methylpiperazin-1-yl)methyl]-3,4-dihydroisoquinolin-2(1H)-yl]carbonyl}-3,4-dihydroisoquinoline-2(1H)-carboxylate EXAMPLE 222: Phenyl 7-{[(3S)-3-[2-(dimethylamino)ethyl]-3,4-dihydroisoquinolin-2(1H)-yl]carbonyl}-6-{1,5-dimethyl-4-[methyl(phenyl)carbamoyl]-1H-pyrrol-2-yl}-3,4-dihydroisoquinoline-2(1H)-carboxylate EXAMPLE 223: Phenyl 6-{1,5-dimethyl-4-[methyl(phenyl)carbamoyl]-1H-pyrrol-2-yl}-7-{[(3S)-3-[2-(morpholin-4-yl)ethyl]-3,4-dihydroisoquinolin-2(1H)-yl]carbonyl}-3,4-dihydroisoquinoline-2(1H)-carboxylate EXAMPLE 224: Phenyl 7-{[(3S)-3-(aminomethyl)-3,4-dihydroisoquinolin-2(1H)-yl]carbonyl}-6-[4-(dibutylcarbamoyl)-1,5-dimethyl-1H-pyrrol-2-yl]-3,4-dihydroisoquinoline-2(1H)-carboxylate EXAMPLE 225: Phenyl 6-[4-(dibutylcarbamoyl)-1,5-dimethyl-1H-pyrrol-2-yl]-7-{[(3S)-3-[(dimethylamino)methyl]-3,4-dihydroisoquinolin-2(1H)-yl]carbonyl}-3,4-dihydroisoquinoline-2(1H)-carboxylate EXAMPLE 226: Phenyl 6-[4-(dibutylcarbamoyl)-1,5-dimethyl-1H-pyrrol-2-yl]-7-{[(3S)-3-(pyrrolidin-1-ylmethyl)-3,4-dihydroisoquinolin-2(1H)-yl]carbonyl}-3,4-dihydroisoquinoline-2(1H)-carboxylate EXAMPLE 227: phenyl 6-[4-(dibutylcarbamoyl)-1,5-dimethyl-1H-pyrrol-2-yl]-7-{[(3S)-3-(piperidin-1-ylmethyl)-3,4-dihydroisoquinolin-2(1H)-yl]carbonyl}-3,4-dihydroisoquinoline-2(1H)-carboxylate EXAMPLE 228: Phenyl 6-[4-(dibutylcarbamoyl)-1,5-dimethyl-1H-pyrrol-2-yl]-7-{[(3S)-3-[(4-methylpiperazin-1-yl)methyl]-3,4-dihydroisoquinolin-2(1H)-yl]carbonyl}-3,4-dihydroisoquinoline-2(1H)-carboxylate EXAMPLE 229: Phenyl 6-[4-(dibutylcarbamoyl)-1,5-dimethyl-1H-pyrrol-2-yl]-7-{[(3S)-3-[2-(dimethylamino)ethyl]-3,4-dihydroisoquinolin-2(1H)-yl]carbonyl}-3,4-dihydroisoquinoline-2(1H)-carboxylate EXAMPLE 230: Phenyl 6-[4-(dibutylcarbamoyl)-1,5-dimethyl-1H-pyrrol-2-yl]-7-{[(3S)-3-[2-(morpholin-4-yl)ethyl]-3,4-dihydroisoquinolin-2(1H)-yl]carbonyl}-3,4-dihydroisoquinoline-2(1H)-carboxylate EXAMPLE 231: N-(4-Hydroxyphenyl)-N,1,2-trimethyl-5-[7-{[(3S)-3-(morpholin-4-ylmethyl)-3,4-dihydroisoquinolin-2(1H)-yl]carbonyl}-2-(phenylacetyl)-1,2,3,4-tetrahydroisoquinolin-6-yl]-1H-pyrrole-3-carboxamide EXAMPLE 232: N-Butyl-N-(4-hydroxyphenyl)-1,2-dimethyl-5-{7-[(3S)-3-(morpholin-4-ylmethyl)-1,2,3,4-tetrahydroisoquinoline-2-carbonyl]-2-(2-phenylacetyl)-1,2,3,4-tetrahydroisoquinolin-6-yl}-1H-pyrrole-3-carboxamide The procedure is as in Example 777, replacing the product from Preparation 6be in Step A with the product from Preparation 6h.

LC/MS ($C_{49}H_{55}N_5O_5$) 794 [M+H]$^+$; RT 1.23 (Method B)
High-Resolution Mass (ESI+):
  Empirical formula: $C_{49}H_{55}N_5O_5$
  [M+2H]$^{2+}$ calculated: 397.7174
  [M+2H]$^{2+}$ measured: 397.7178

EXAMPLE 233: N-(4-Hydroxyphenyl)-1,2-dimethyl-5-[7-{[(3S)-3-(morpholin-4-ylmethyl)-3,4-dihydroisoquinolin-2(1H)-yl]carbonyl}-2-(phenylacetyl)-1,2,3,4-tetrahydroisoquinolin-6-yl]-N-phenyl-1H-pyrrole-3-carboxamide EXAMPLE 234: N,1,2-Trimethyl-5-[7-{[(3S)-3-(morpholin-4-ylmethyl)-3,4-dihydroisoquinolin-2(1H)-yl]carbonyl}-2-(phenylacetyl)-1,2,3,4-tetrahydroisoquinolin-6-yl]-N-phenyl-1H-pyrrole-3-carboxamide EXAMPLE 235: N-Butyl-1,2-dimethyl-5-[7-{[(3S)-3-(morpholin-4-methyl)-3,4-dihydroisoquinolin-2(1H)-yl]carbonyl}-2-(phenylacetyl)-1,2,3,4-tetrahydroisoquinolin-6-yl]-N-phenyl-1H-pyrrole-3-carboxamide EXAMPLE 236: 1,2-Dimethyl-5-[7-{[(3S)-3-(morpholin-4-ylmethyl)-3,4-dihydroisoquinolin-2(1H)-yl]carbonyl}-2-(phenylacetyl)-1,2,3,4-tetrahydroisoquinolin-6-yl]-N,N-diphenyl-1H-pyrrole-3-carboxamide EXAMPLE 237: N-Butyl-N,1,2-trimethyl-5-[7-{[(3S)-3-(morpholin-4-ylmethyl)-3,4-dihydroisoquinolin-2(1H)-yl]carbonyl}-2-(phenylacetyl)-1,2,3,4-tetrahydroisoquinolin-6-yl]-1H-pyrrole-3-carboxamide EXAMPLE 238: N,N-Dibutyl-1,2-dimethyl-5-[7-{[(3S)-3-(morpholin-4-ylmethyl)-3,4-dihydroisoquinolin-2(1H)-yl]carbonyl}-2-(phenylacetyl)-1,2,3,4-tetrahydroisoquinolin-6-yl]-1H-pyrrole-3-carboxamide EXAMPLE 239: N-(4-Hydroxyphenyl)-N,1,2-trimethyl-5-{7-{[(3R)-3-methyl-4-dihydroisoquinolin-2(1H)-yl]carbonyl}-2-(phenylacetyl)-1,2,3,4-tetrahydroisoquinolin-6-yl}-1H-pyrrole-3-carboxamide EXAMPLE 240: N,1,2-Trimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-N-phenyl-1H-pyrrole-3-carboxamide EXAMPLE 241: N-(4-Hydroxyphenyl)-1,2-dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-N-phenyl-1H-pyrrole-3-carboxamide EXAMPLE 242: 1,2-Dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-N,N-diphenyl-1H-pyrrole-3-carboxamide EXAMPLE 243: N-Butyl-N,1,2-trimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-1H-pyrrole-3-carboxamide EXAMPLE 244: N,N-Dibutyl-1,2-dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-1H-pyrrole-3-carboxamide EXAMPLE 245: 6-{4-[(4-Hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-N-phenyl-1,2,3,4-tetrahydroisoquinoline-2-carboxamide The procedure is as in Example 777, replacing the compound from Preparation 6be in Step A with the compound from Preparation 6ba, and replacing phenylacetyl chloride with benzyl iscocyanate.

LC/MS ($C_{45}H_{48}N_6O_5$) 753 [M+H]$^+$; RT 1.14 (Method B) High-Resolution Mass (ESI+):

Empirical formula: $C_{45}H_{48}N_6O_5$
[M+H]$^+$ calculated: 753.3740
[M+H]$^+$ measured: 753.3759

EXAMPLE 246: 6-{4-[Butyl(4-hydroxyphenyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 247: 6-{4-[(4-Hydroxyphenyl)(phenyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 248: 6-{1,5-Dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 249: 6-{4-[Butyl(phenyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 250: 6-[4-(Diphenylcarbamoyl)-1,5-dimethyl-1H-pyrrol-2-yl]-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 251: 6-{4-[Butyl(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 252: 6-[4-(Dibutylcarbamoyl)-1,5-dimethyl-1H-pyrrol-2-yl]-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 253: 6-{4-[(4-Hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-N-phenyl-1,2,3,4-tetrahydroisoquinoline-2-carboxamide The procedure is as in Example 777, replacing the compound from Preparation 6be in Step A with the compound from Preparation 6bb, and replacing phenylacetyl chloride with benzyl iscocyanate.

LC/MS ($C_{41}H_{41}N_5O_4$) 668 [M+H]$^+$; RT 1.31 (Method B) High-Resolution Mass (ESI+):

Empirical formula: $C_{41}H_{41}N_5O_4$
[M+H]$^+$ calculated: 668.3231
[M+H]$^+$ measured: 668.3211

EXAMPLE 254: 6-{1,5-Dimethyl-4-[methyl(phenyl)carbamoyl]-1H-pyrrol-2-yl}-7-{[(3R)-3-methyl-3,4-dihydroisoquinolin-2(1H)-yl]carbonyl}-N-phenyl-3,4-dihydroisoquinoline-2(1H)-carboxamide EXAMPLE 255: 6-{4-[(4-Hydroxyphenyl)(phenyl)carbamoyl]-1,5-dimethyl-1H-pyrrol-2-yl}-7-{[(3R)-3-methyl-3,4-dihydroisoquinolin-2(1H)-yl]carbonyl}-N-phenyl-3,4-dihydroisoquinoline-2(1H)-carboxamide EXAMPLE 256: 6-[4-(Diphenylcarbamoyl)-1,5-dimethyl-1H-pyrrol-2-yl]-7-{[(3R)-3-methyl-3,4-dihydroisoquinolin-2(1H)-yl]carbonyl}-N-phenyl-3,4-dihydroisoquinoline-2(1H)-carboxamide EXAMPLE 257: 6-{4-[Butyl(methyl)carbamoyl]-1,5-dimethyl-1H-pyrrol-2-yl}-7-{[(3R)-3-methyl-3,4-dihydroisoquinolin-2(1H)-yl]carbonyl}-N-phenyl-3,4-dihydroisoquinoline-2(1H)-carboxamide EXAMPLE 258: 6-[4-(Dibutylcarbamoyl)-1,5-dimethyl-1H-pyrrol-2-yl]-7-{[(3R)-3-methyl-3,4-dihydroisoquinolin-2(1H)-yl]carbonyl}-N-phenyl-3,4-dihydroisoquinoline-2(1H)-carboxamide EXAMPLE 259: N-(4-Hydroxyphenyl)-N,1,2-trimethyl-5-[7-{[(3R)-3-methyl-3,4-dihydroisoquinolin-2(1H)-yl]carbonyl}-2-(2-phenylethyl)-1,2,3,4-tetrahydroisoquinolin-6-yl]-1H-pyrrole-3-carboxamide EXAMPLE 260: Benzyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 261: N-(4-Hydroxyphenyl)-N,1,2-trimethyl-5-[7-{[(3S)-3-(morpholin-4-ylmethyl)-3,4-dihydroisoquinolin-2(1H)-yl]carbonyl}-2-(phenoxyacetyl)-1,2,3,4-tetrahydroisoquinolin-6-yl]-1H-pyrrole-3-carboxamide EXAMPLE 262: N-(4-Hydroxyphenyl)-N,1,2-trimethyl-5-(7-{[(3R)-3-methyl-3,4-dihydroisoquinolin-2(1H)-yl]carbonyl}-2-[2-oxo-2-(phenylamino)ethyl]-1,2,3,4-tetrahydroisoquinolin-6-yl)-1H-pyrrole-3-carboxamide EXAMPLE 263: 5-(2-Benzoyl-7-{[(3S)-3-(morpholin-4-ylmethyl)-3,4-dihydroisoquinolin-2(1H)-yl]carbonyl}-1,2,3,4-tetrahydroisoquinolin-6-yl)-N-(4-hydroxyphenyl)-N,1,2-trimethyl-1H-pyrrole-3-carboxamide EXAMPLE 264: N-(4-Hydroxyphenyl)-N,1,2-trimethyl-5-(7-{[(3S)-3-(morpholin-4-ylmethyl)-3,4-dihydroisoquinolin-2(1H)-yl]carbonyl}-2-[(2E)-3-phenylprop-2-enoyl]-1,2,3,4-tetrahydroisoquinolin-6-yl)-1H-pyrrole-3-carboxamide EXAMPLE 265: N-(4-Hydroxyphenyl)-N,1,2-trimethyl-5-[7-{[(3S)-3-(morpholin-4-ylmethyl)-3,4-dihydroisoquinolin-2(1H)-yl]carbonyl}-2-(3-phenylpropanoyl)-1,2,3,4-tetrahydroisoquinolin-6-yl]-1H-pyrrole-3-carboxamide EXAMPLE 266: 6-{4-[(4-Hydroxyphenyl)(methyl)carbamoyl]-1,5-dimethyl-1H-pyrrol-2-yl}-N-methyl-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 267: 6-{4-[Butyl(4-hydroxyphenyl)carbamoyl]-1,5-dimethyl-1H-pyrrol-2-yl}-N-methyl-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 268: 6-{4-[(4-Hydroxyphenyl)(phenyl)carbamoyl]-1,5-dimethyl-1H-pyrrol-2-yl}-N-methyl-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 269: 6-{1,5-Dimethyl-4-[methyl(phenyl)carbamoyl]-1H-pyrrol-2-yl}-N-methyl-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 270: 6-{4-[Butyl(phenyl)carbamoyl]-1,5-dimethyl-1H-pyrrol-2-yl}-N-methyl-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 271: 6-[4-(Diphenylcarbamoyl)-1,5-dimethyl-1H-pyrrol-2-yl]-N-methyl-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 272: 6-{4-[Butyl(methyl)carbamoyl]-1,5-dimethyl-1H-pyrrol-2-yl}-N-methyl-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 273: 6-[4-(Dibutylcarbamoyl)-1,5-dimethyl-1H-pyrrol-2-yl]-N-methyl-7-{[(3S)-3-(morpholin-4-ylmethyl)-3,4-dihydroisoquinolin-2(1H)-yl]carbonyl}-N-phenyl-3,4-dihydroisoquinoline-2(1H)-carboxamide EXAMPLE 274: 6-{4-[(4-Hydroxyphenyl)(methyl)carbamoyl]-1,5-dimethyl-1H-pyrrol-2-yl}-N-methyl-7-{[(3R)-3-methyl-3,4-dihydroisoquinolin-2(1H)-yl]carbonyl}-N-phenyl-3,4-dihydroisoquinoline-2(1H)-carboxamide EXAMPLE 275: 6-{1,5-Dimethyl-4-[methyl(phenyl)carbamoyl]-1H-pyrrol-2-yl}-N-methyl-7-{[(3R)-3-methyl-3,4-dihydroisoquinolin-2(1H)-yl]carbonyl}-N-phenyl-3,4-dihydroisoquinoline-2(1H)-carboxamide EXAMPLE 276: 6-{4-[(4-Hydroxyphenyl)(phenyl)carbamoyl]-1,5-dimethyl-1H-pyrrol-2-yl}-N-methyl-7-{[(3R)-3-methyl-3,4-dihydroisoquinolin-2(1H)-yl]carbonyl}-N-phenyl-3,4-dihydroisoquinoline-2(1H)-carboxamide EXAMPLE 277: 6-[4-(Diphenylcarbamoyl)-1,5-dimethyl-1H-pyrrol-2-yl]-N-methyl-7-{[(3R)-3-methyl-3,4-dihydroisoquinolin-2(1H)-yl]carbonyl}-N-phenyl-3,4-dihydroisoquinoline-2(1H)-carboxamide EXAMPLE 278: 6-{4-[Butyl(methyl)carbamoyl]-1,5-dimethyl-1H-pyrrol-2-yl}-N-methyl-7-{[(3R)-3-methyl-3,4-dihydroisoquinolin-2(1H)-yl]carbonyl}-N-phenyl-3,4-dihydroisoquinoline-2(1H)-carboxamide EXAMPLE 279: 6-[4-(Dibutylcarbamoyl)-1,5-dimethyl-1H-pyrrol-2-yl]-N-methyl-7-{[(3R)-3-methyl-3,4-dihydroisoquinolin-2(1H)-yl]carbonyl}-N-phenyl-3,4-dihydroisoquinoline-2(1H)-carboxamide EXAMPLE 280: 5-[2-(Benzylsulfonyl)-7-{[(3S)-3-(morpholin-4-ylmethyl)-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide EXAMPLE 281: 5-[2-(Benzylsulfonyl)-7-{[(3S)-3-(morpholin-4-ylmethyl)-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 282: 5-[2-(Benzylsulfonyl)-7-{[(3S)-3-(morpholin-4-ylmethyl)-3,4-dihydroisoquinolin-2(1H)-yl]carbonyl}-1,2,3,4-tetrahydroisoquinolin-6-yl]-N-(4-hydroxyphenyl)-1,2-dimethyl-N-phenyl-1H-pyrrole-3-carboxamide EXAMPLE 283: 5-[2-(Benzylsulfonyl)-7-{[(3S)-3-(morpholin-4-ylmethyl)-3,4-dihydroisoquinolin-2(1H)-yl]carbonyl}-1,2,3,4-tetrahydroisoquinolin-6-yl]-N,N-dibutyl-1,2-dimethyl-1H-pyrrole-3-carboxamide EXAMPLE 284: 5-[2-(Benzylsulfonyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide EXAMPLE 285: 5-[2-(Benzylsulfonyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 286: 5-[2-(Benzylsulfonyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-1,2-dimethyl-N-phenyl-1H-pyrrole-3-carboxamide EXAMPLE 287: 5-[2-(Benzylsulfonyl)-7-{[(3R)-3-methyl-3,4-dihydroisoquinolin-2(1H)-yl]carbonyl}-1,2,3,4-tetrahydroisoquinolin-6-yl]-N,N-dibutyl-1,2-dimethyl-1H-pyrrole-3-carboxamide EXAMPLE 288: N-(4-Hydroxyphenyl)-N,1,2-trimethyl-5-[7-{[(3R)-3-methyl-3,4-dihydroisoquinolin-2(1H)-yl]carbonyl}-2-(phenylsulfamoyl)-1,2,3,4-tetrahydroisoquinolin-6-yl]-1H-pyrrole-3-carboxamide EXAMPLE 289: N,1,2-Trimethyl-5-[7-{[(3R)-3-methyl-3,4-dihydroisoquinolin-2(1H)-yl]carbonyl}-2-(phenylsulfamoyl)-1,2,3,4-tetrahydroisoquinolin-6-yl]-N-phenyl-1H-pyrrole-3-carboxamide EXAMPLE 290: N-(4-Hydroxyphenyl)-1,2-dimethyl-5-[7-{[(3R)-3-methyl-3,4-dihydroisoquinolin-2(1H)-yl]carbonyl}-2-(phenylsulfamoyl)-1,2,3,4-tetrahydroisoquinolin-6-yl]-N-phenyl-1H-pyrrole-3-carboxamide EXAMPLE 291: N,N-Dibutyl-1,2-dimethyl-5-[7-{[(3R)-3-methyl-3,4-dihydroisoquinolin-2(1H)-yl]carbonyl}-2-(phenylsulfamoyl)-1,2,3,4-tetrahydroisoquinolin-6-yl]-1H-pyrrole-3-carboxamide EXAMPLE 292: N-(4-Hydroxyphenyl)-N,1,2-trimethyl-5-(2-[methyl(phenyl)sulfamoyl]7-{[(3S)-3-(morpholin-4-ylmethyl)-3,4-dihydroisoquinolin-2(1H)-yl]carbonyl}-1,2,3,4-tetrahydroisoquinolin-6-yl)-1H-pyrrole-3-carboxamide EXAMPLE 293: N,1,2-Trimethyl-5-(2-[methyl(phenyl)sulfamoyl]-7-{[(3S)-3-(morpholin-4-ylmethyl)-3,4-dihydroisoquinolin-2(1H)-yl]carbonyl}-1,2,3,4-tetrahydroisoquinolin-6-yl)-N-phenyl-1H-pyrrole-3-carboxamide EXAMPLE 294: N-(4-Hydroxyphenyl)-1,2-dimethyl-5-(2-[methyl(phenyl)sulfamoyl]-7-{[(3S)-3-(morpholin-4-ylmethyl)-3,4-dihydroisoquinolin-2(1H)-yl]carbonyl}-1,2,3,4-tetrahydroisoquinolin-6-yl)-N-phenyl-1H-pyrrole-3-carboxamide EXAMPLE 295: N,N-Dibutyl-1,2-dimethyl-5-(2-[methyl(phenyl)sulfamoyl]-7-{[(3S)-3-(morpholin-4-ylmethyl)-3,4-dihydroisoquinolin-2(1H)-yl]carbonyl}-1,2,3,4-tetrahydroisoquinolin-6-yl)-1H-pyrrole-3-carboxamide EXAMPLE 296: N-(4-Hydroxyphenyl)-N,1,2-trimethyl-5-(7-{[(3R)-3-methyl-3,4-dihydroisoquinolin-2(1H)-yl]carbonyl}-2-[methyl(phenyl)sulfamoyl]-1,2,3,4-tetrahydroisoquinolin-6-yl)-1H-pyrrole-3-carboxamide EXAMPLE 297: N,1,2-Trimethyl-5-(7-{[(3R)-3-methyl-3,4-dihydroisoquinolin-2(1H)-yl]carbonyl}-2-[methyl(phenyl)sulfamoyl]-1,2,3,4-tetrahydroisoquinolin-6-yl)-N-phenyl-1H-pyrrole-3-carboxamide EXAMPLE 298: N-(4-Hydroxyphenyl)-1,2-dimethyl-5-(7-{[(3R)-3-methyl-3,4-dihydroisoquinolin-2(1H)-yl]carbonyl}-2-[methyl(phenyl)sulfamoyl]-1,2,3,4-tetrahydroisoquinolin-6-yl)-N-phenyl-1H-pyrrole-3-carboxamide EXAMPLE 299: N,N-Dibutyl-1,2-dimethyl-5-(7-{[(3R)-3-methyl-3,4-dihydroisoquinolin-2(1H)-yl]carbonyl}-2-[methyl(phenyl)sulfamoyl]-1,2,3,4-tetrahydroisoquinolin-6-yl)-1H-pyrrole-3-carboxamide EXAMPLE 300: N-(4-Hydroxyphenyl)-N,1,2-trimethyl-5-[7-{[(3S)-3-(morpholin-4-ylmethyl)-3,4-dihydroisoquinolin-2(1H)-yl]carbonyl}-2-(phenylsulfonyl)-1,2,3,4-tetrahydroisoquinolin-6-yl]-1H-pyrrole-3-carboxamide EXAMPLE 301: N,1,2-Trimethyl-5-[7-{[(3S)-3-(morpholin-4-ylmethyl)-3,4-dihydroisoquinolin-2(1H)-yl]carbonyl}-2-(phenylsulfanyl)-1,2,3,4-tetrahydroisoquinolin-6-yl]-N-phenyl-1H-pyrrole-3-carboxamide EXAMPLE 302: N-(4-Hydroxyphenyl)-1,2-dimethyl-5-[7-{[(3S)-3-(morpholin-4-ylmethyl)-3,4-dihydroisoquinolin-2(1H)-yl]carbonyl}-2-(phenylsulfonyl)-1,2,3,4-tetrahydroisoquinolin-6-yl]-N-phenyl-1H-pyrrole-3-carboxamide EXAMPLE 303: N,N-Dibutyl-1,2-dimethyl-5-[7-{[(3S)-3-(morpholin-4-ylmethyl)-3,4-dihydroisoquinolin-2(1H)-yl]carbonyl}-2-(phenylsulfonyl)-1,2,3,4-tetrahydroisoquinolin-6-yl]-1H-pyrrole-3-carboxamide EXAMPLE 304: N-(4-Hydroxyphenyl)-N,1,2-trimethyl-5-[7-{[(3R)-3-methyl-3,4-dihydroisoquinolin-2(1H)-yl]carbonyl}-2-(phenylsulfonyl)-1,2,3,4-tetrahydroisoquinolin-6-yl]-1H-pyrrole-3-carboxamide EXAMPLE 305: N,1,2-Trimethyl-5-[7-{[(3R)-3-methyl-3,4-dihydroisoquinolin-2(1H)-yl]carbonyl}-2-(phenylsulfonyl)-1,2,3,4-tetrahydroisoquinolin-6-yl]-N-phenyl-1H-pyrrole-3-carboxamide EXAMPLE 306: N-(4-Hydroxyphenyl)-1,2-dimethyl-S-[7-{[(3R)-3-methyl-3,4-dihydroisoquinolin-2(1H)-yl]carbonyl}-2-(phenylsulfonyl)-1,2,3,4-tetrahydroisoquinolin-6-yl]-N-phenyl-1H-pyrrole-3-carboxamide EXAMPLE 307: N,N-Dibutyl-1,2-dimethyl-5-[7-{[(3R)-3-methyl-3,4-dihydroisoquinolin-2(1H)-yl]carbonyl}-2-(phenylsulfonyl)-1,2,3,4-tetrahydroisoquinolin-6-yl]-1H-pyrrole-3-carboxamide EXAMPLE 308: Phenyl 6-{1-[(4-hydroxyphenyl)(methyl)carbamoyl]tetrahydroindolizin-3-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 309: Phenyl 6-{1-[methyl(phenyl)carbamoyl]-5,6,7,8-tetrahydroindolizin-3-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 310: Phenyl 6-{1-[(4-hydroxyphenyl)(phenyl)carbamoyl]-5,6,7,8-tetrahydroindolizin-3-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 311: Phenyl 6-[1-(diphenylcarbamoyl)-5,6,7,8-tetrahydroindolizin-3-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 312: Phenyl 6-{1-[butyl(methyl)carbamoyl]-5,6,7,8-tetrahydroindolizin-3-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 313: Phenyl 6-[1-(dibutylcarbamoyl)-5,6,7,8-tetrahydroindolizin-3-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 314: Phenyl 6-{1-[(4-hydroxyphenyl)(methyl)carbamoyl]-5,6,7,8-tetrahydroindolizin-3-yl}-7-{[(3R)-3-methyl-3,4-dihydroisoquinolin-2(1H)-yl]carbonyl}-3,4-dihydroisoquinoline-2(1H)-carboxylate EXAMPLE 315: Phenyl 6-{1-[(4-hydroxyphenyl)(methyl)carbamoyl]indolizin-3-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 316: Phenyl 6-{1-[methyl(phenyl)carbamoyl]indolizin-3-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 317: Phenyl 6-{1-[(4-hydroxyphenyl)(phenyl)carbamoyl]indolizin-3-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 318: Phenyl 6-[1-(diphenylcarbamoyl)indolizin-3-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 319: Phenyl 6-{1-[butyl(methyl)carbamoyl]indolizin-3-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 320: Phenyl 6-[1-(dibutylcarbamoyl)indolizin-3-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 321: Phenyl 6-{1-[(4-hydroxyphenyl)(methyl)carbamoyl]indolizin-3-yl}-7-{[(3R)-3-methyl-3,4-dihydroisoquinolin-2(1H)-yl]carbonyl}-3,4-dihydroisoquinoline-2(1H)-carboxylate EXAMPLE 322: Phenyl 6-{3-[(4-hydroxyphenyl)(methyl)carbamoyl]-1H-indol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 323: Phenyl 6-{3-[methyl(phenyl)carbamoyl]-1H-indol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 324: Phenyl 6-{3-[(4-hydroxyphenyl)(phenyl)carbamoyl]-1H-indol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 325: Phenyl 6-[3-(diphenylcarbamoyl)-1H-indol-1-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 326: Phenyl 6-{3-[butyl(methyl)carbamoyl]-1H-indol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 327: Phenyl 6-[3-(dibutylcarbamoyl)-1H-indol-1-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 328: Phenyl 6-{3-[(4-hydroxyphenyl)(methyl)carbamoyl]-1H-indol-1-yl}-7-{[(3R)-3-methyl-3,4-dihydroisoquinolin-2(1H)-yl]carbonyl}-3,4-dihydroisoquinoline-2(1H)-carboxylate EXAMPLE 329: Phenyl 6-{3-[(4-hydroxyphenyl)(methyl)carbamoyl]-1H-indazol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 330: Phenyl 6-{3-[methyl(phenyl)carbamoyl]-1H-indazol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 331: Phenyl 6-{3-[(4-hydroxyphenyl)(phenyl)carbamoyl]-1H-indazol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 332: Phenyl 6-[3-(diphenylcarbamoyl)-1H-indazol-1-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 333: Phenyl 6-{3-[butyl(methyl)carbamoyl]-1H-indazol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 334: Phenyl 6-[3-(dibutylcarbamoyl)-1H-indazol-1-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 335: Phenyl 6-{3[(4-hydroxyphenyl)(methyl)carbamoyl]-1H-indazol-1-yl}-7-{[(3R)-3-methyl-3,4-dihydroisoquinolin-2(1H)-yl]carbonyl}-3,4-dihydroisoquinoline-2(1H)-carboxylate EXAMPLE 336: Phenyl 6-{4-chloro-3-[(4-hydroxyphenyl)(methyl)carbamoyl]-5-methyl-1H-pyrazol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 337: Phenyl 6-{4-chloro-5-methyl-3-[methyl(phenyl)carbamoyl]-1H-pyrazol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 338: Phenyl 6-{4-chloro-3-[(4-hydroxyphenyl)(phenyl)carbamoyl]-5-methyl-1H-pyrazol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 339: Phenyl 6-[4-chloro-3-(diphenylcarbamoyl)-5-methyl-1H-pyrazol-1-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 340: Phenyl 6-{3-[butyl(methyl)carbamoyl]-4-chloro-5-methyl-1H-pyrazol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 341: Phenyl 6-[4-chloro-3-(dibutylcarbamoyl)-5-methyl-1H-pyrazol-1-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 342: Phenyl 6-{4-chloro-3-[(4-hydroxyphenyl)(methyl)carbamoyl]-5-methyl-1H-pyrazol-1-yl}-7-{[(3R)-3-methyl-3,4-dihydroisoquinolin-2(1H)-yl]carbonyl}-3,4-dihydroisoquinoline-2(1H)-carboxylate EXAMPLE 343: Phenyl 6-{4-[(4-hydroxyphenyl)(methyl)carbamoyl]-2,3-dimethyl-1H-pyrrol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 344: Phenyl 6-{2,3-dimethyl-4-[methyl(phenyl)carbamoyl]-1H-pyrrol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 345: Phenyl 6-{4-[(4-hydroxyphenyl)(phenyl)carbamoyl]-2,3-dimethyl-1H-pyrrol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 346: Phenyl 6-[4-(diphenylcarbamoyl)-2,3-dimethyl-1H-pyrrol-1-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 347: Phenyl 6-{4-[butyl(methyl)carbamoyl]-2,3-dimethyl-1H-pyrrol-1-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 348: Phenyl 6-[4-(dibutylcarbamoyl)-2,3-dimethyl-1H-pyrrol-1-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 349: Phenyl 6-{4-[(4-hydroxyphenyl)(methyl)carbamoyl]-2,3-dimethyl-1H-pyrrol-1-yl}-7-{[(3R)-3-methyl-3,4-dihydroisoquinolin-2(1H)-yl]carbonyl}-3,4-dihydroisoquinoline-2(1H)-carboxylate EXAMPLE 350: Phenyl 6-{2-[(4-hydroxyphenyl)(methyl)carbamoyl]-5-methyl-1,3-thiazol-4-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 351: Phenyl 6-{5-methyl-2-[methyl(phenyl)carbamoyl]-1,3-thiazol-4-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 352: Phenyl 6-{2-[(4-hydroxyphenyl)(phenyl)carbamoyl]-5-methyl-1,3-thiazol-4-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 353: Phenyl 6-[2-(diphenylcarbamoyl)-5-methyl-1,3-thiazol-4-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 354: Phenyl 6-{2-[butyl(methyl)carbamoyl]-5-methyl-1,3-thiazol-4-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 355: Phenyl 6-[2-(dibutylcarbamoyl)-5-methyl-1,3-thiazol-4-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 356: Phenyl 6-{2-[(4-hydroxyphenyl)(methyl)carbamoyl]-5-methyl-1,3-thiazol-4-yl}-7-{[(3R)-3-methyl-3,4-dihydroisoquinolin-2(1H)-yl]carbonyl}-3,4-dihydroisoquinoline-2(1H)-carboxylate EXAMPLE 357: Phenyl 5-{4-[(4-hydroxyphenyl)(methyl)carbamoyl]-1,5-dimethyl-1H-pyrrol-2-yl}-6-{[(3S)-3-(morpholin-4-ylmethyl)-3,4-dihydroisoquinolin-2(1H)-yl]carbonyl}-1,3-dihydro-2H-isoindole-2-carboxylate EXAMPLE 358: Phenyl 7-{4-[(4-hydroxyphenyl)(methyl)carbamoyl]-1,5-dimethyl-1H-pyrrol-2-yl}-8-{[(3S)-3-(morpholin-4-ylmethyl)-3,4-dihydroisoquinolin-2(1H)-yl]carbonyl}-1,3,4,5-tetrahydro-2H-2-benzazepine-2-carboxylate EXAMPLE 359: Phenyl 7-{4-[(4-hydroxyphenyl)(methyl)carbamoyl]-1,5-dimethyl-1H-pyrrol-2-yl}-8-{[(3S)-3-(morpholin-4-ylmethyl)-3,4-dihydroisoquinolin-2(1H)-yl]carbonyl}-1,2,4,5-tetrahydro-3H-3-benzazepine-3-carboxylate EXAMPLE 360: N-(4-Hydroxyphenyl)-N,1,2-trimethyl-5-[7-{[(3S)-3-(morpholin-4-ylmethyl)-3,4-dihydroisoquinolin-2(1H)-yl]carbonyl}-1-oxo-2-(2-phenylethyl)-1,2,3,4-tetrahydroisoquinolin-6-yl]-1H-pyrrole-3-carboxamide EXAMPLE 361: N-(4-Hydroxyphenyl)-N,1,2-trimethyl-5-[6-{[(3S)-3-(morpholin-4-ylmethyl)-3,4-dihydroisoquinolin-2(1H)-yl]carbonyl}-1-oxo-2-(2-phenylethyl)-2,3-dihydro-1H-isoindol-5-yl]-1H-pyrrole-3-carboxamide EXAMPLE 362: Phenyl 1,1-difluoro-6-{4-[(4-hydroxyphenyl)(methyl)carbamoyl]-1,5-dimethyl-1H-pyrrol-2-yl}-5-{[(3S)-3-(morpholin-4-ylmethyl)-3,4-dihydroisoquinolin-2(1H)-yl]carbonyl}-1,3-dihydro-2H-isoindole-2-carboxylate EXAMPLE 363: Phenyl 1,1,3,3-tetrafluoro-5-{4-[(4-hydroxyphenyl)(methyl)carbamoyl]-1,5-dimethyl-1H-pyrrol-2-yl}-6-{[(3S)-3-(morpholin-4-ylmethyl)-3,4-dihydroisoquinolin-2(1H)-yl]carbonyl}-1,3-dihydro-2H-isoindole-2-carboxylate EXAMPLE 364: 5-[3,3-Difluoro-6-{[(3S)-3-(morpholin-4-ylmethyl)-3,4-dihydroisoquinolin-2(1H)-yl]carbonyl}-1-oxo-2-(2-phenylethyl)-2,3-dihydro-1H-isoindol-5-yl]-N-(4-hydroxyphenyl)-N,1,2-trimethyl-1H-pyrrole-3-carboxamide EXAMPLE 365: Phenyl 6-(4-{[2-(dimethylamino)ethyl](4-hydroxyphenyl)carbamoyl}-1,5-dimethyl-1H-pyrrol-2-yl)-7-{[(3R)-3-methyl-3,4-dihydroisoquinolin-2(1H)-yl]carbonyl}-3,4-dihydroisoquinoline-2(1H)-carboxylate EXAMPLE 366: Phenyl 6-(4-{(4-hydroxyphenyl)[2-(morpholin-4-yl)ethyl]carbamoyl}-1,5-dimethyl-1H-pyrrol-2-yl)-7-{[(3R)-3-methyl-3,4-dihydroisoquinolin-2(1H)-yl]carbonyl}-3,4-dihydroisoquinoline-2(1H)-carboxylate EXAMPLE 367: N-[2-(Dimethylamino)ethyl]-N-(4-hydroxyphenyl)-1,2-dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-1H-pyrrole-3-carboxamide EXAMPLE 368: N-(4-Hydroxyphenyl)-1,2-dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-N-[2-(morpholin-4-yl)ethyl]-1H-pyrrole-3-carboxamide EXAMPLE 369: Phenyl 6-(4-{[2-(dimethylamino)ethyl](phenyl)carbamoyl}-1,5-dimethyl-1H-pyrrol-2-yl)-7-{[(3R)-3-methyl-3,4-dihydroisoquinolin-2(1H)-yl]carbonyl}-3,4-dihydroisoquinoline-2(1H)-carboxylate EXAMPLE 370: Phenyl 6-(1,5-dimethyl-4-{[2-(morpholin-4-yl)ethyl](phenyl)carbamoyl}-1H-pyrrol-2-yl)-7-{[(3R)-3-methyl-3,4-dihydroisoquinolin-2(1H)-yl]carbonyl}-3,4-dihydroisoquinoline-2(1H)-carboxylate EXAMPLE 371: N-[2-(Dimethylamino)ethyl]-1,2-dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-N-phenyl-1H-pyrrole-3-carboxamide EXAMPLE 372: 1,2-Dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-N-[2-(morpholin-4-yl)ethyl]-N-phenyl-1H-pyrrole-3-carboxamide EXAMPLE 373: Phenyl 6-(4-{butyl[2-(dimethylamino)ethyl]carbamoyl}-1,5-dimethyl-1H-pyrrol-2-yl)-7-{[(3R)-3-methyl-3,4-dihydroisoquinolin-2(1H)-yl]carbonyl}-3,4-dihydroisoquinoline-2(1H)-carboxylate EXAMPLE 374: Phenyl 6-(4-{butyl[2-(morpholin-4-yl)ethyl]carbamoyl}-1,5-dimethyl-1H-pyrrol-2-yl)-7-{[(3R)-3-methyl-3,4-dihydroisoquinolin-2(1H)-yl]carbonyl}-3,4-dihydroisoquinoline-2(1H)-carboxylate EXAMPLE 375: N-Butyl-N-[2-(dimethylamino)ethyl]-1,2-dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-1H-pyrrole-3-carboxamide EXAMPLE 376: N-Butyl-1,2-dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-N-[2-(morpholin-4-yl)ethyl]-1H-pyrrole-3-carboxamide EXAMPLE 377: Phenyl 6-{1-[2-(dimethylamino)ethyl]-4-[(4-hydroxyphenyl)(methyl)carbamoyl]-5-methyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 378: Phenyl 6-{4-[(4-hydroxyphenyl)(methyl)carbamoyl]-5-methyl-1-[2-(morpholin-4-yl)ethyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 379: 1-[2-(Dimethylamino)ethyl]-N-(4-hydroxyphenyl)-N,2-dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-1H-pyrrole-3-carboxamide EXAMPLE 380: N-(4-Hydroxyphenyl)-N,2-dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-1-[2-(morpholin-4-yl)ethyl]-1H-pyrrole-3-carboxamide EXAMPLE 381: Phenyl 6-{1-[2-(dimethylamino)ethyl]-5-methyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 382: Phenyl 7-{[(3R)-3-methyl-3,4-dihydroisoquinolin-2(1H)-yl]carbonyl}-6-{5-methyl-4-[methyl(phenyl)carbamoyl]-1-[2-(morpholin-4-yl)ethyl]-1H-pyrrol-2-yl}-3,4-dihydroisoquinoline-2(1H)-carboxylate EXAMPLE 383: 1-[2-(Dimethylamino)ethyl]-N,2-dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-N-phenyl-1H-pyrrole-3-carboxamide EXAMPLE 384: N,2-Dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-1-[2-(morpholin-4-yl)ethyl]-N-phenyl-1H-pyrrole-3-carboxamide EXAMPLE 385: Phenyl 6-{4-(dibutylcarbamoyl)-1-[2-(dimethylamino)ethyl]-5-methyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 386: Phenyl 6-{4-(dibutylcarbamoyl)-5-methyl-1-[2-(morpholin-4-yl)ethyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 387: N,N-Dibutyl-1-[2-(dimethylamino)ethyl]-2-methyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-1H-pyrrole-3-carboxamide EXAMPLE 388: N,N-Dibutyl-2-methyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-1-[2-(morpholin-4-yl)ethyl]-1H-pyrrole-3-carboxamide EXAMPLE 389: 2-(4-Methylpiperazin-1-yl)phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 390: 2-{[2-(Dimethylamino)ethyl](methyl)amino}phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 391: 2-{[2-(Dimethylamino)ethyl]amino}phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 392: 2-[2-(Dimethylamino)ethoxy]phenyl 6-{4-[(4-hydroxyphenyl) (methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 709, replacing the product from Preparation 6ba in Step A with the product from Preparation 6bb, and replacing benzyl 3-hydroxybenzoate from Step B with 3-[2-(dimethylamino)ethoxy]phenol.

LC/MS ($C_{45}H_{49}N_5O_6$) 754 [M–H]⁻; RT 2.27 (Method A)
High-Resolution Mass (ESI+):
Empirical formula: $C_{45}H_{49}N_5O_6$
[M+2H]²⁺ calculated: 378.6914
[M+2H]²⁺ measured: 378.6926

EXAMPLE 393: 2-[2-(Dimethylamino)ethyl]phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 394: 2-[(Dimethylamino)methyl]phenyl 6-{4-[(4-hydroxyphenyl) (methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 395: 2-[3-(Dimethylamino)prop-1-yn-1-yl]phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 396: N-(4-Hydroxyphenyl)-N,1,2-trimethyl-5-(7-{[(3R)-3-methyl-3,4-dihydroisoquinolin-2(1H)-yl]carbonyl}-2-{[2-(4-methylpiperazin-1-yl)phenyl]acetyl}-1,2,3,4-tetrahydroisoquinolin-6-yl)-1H-pyrrole-3-carboxamide EXAMPLE 397: 5-(2-[(2-{[2-(Dimethylamino)ethyl](methyl)amino}phenyl)acetyl]-7-{[(3R)-3-methyl-3,4-dihydroisoquinolin-2(1H)-yl]carbonyl}-1,2,3,4-tetrahydroisoquinolin-6-yl)-N-(4-hydroxyphenyl)-N,1,2-trimethyl-1H-pyrrole-3-carboxamide EXAMPLE 398: 5-(2-[(2-{[2-(Dimethylamino)ethyl]amino}phenyl)acetyl]-7-{[(3R)-3-methyl-3,4-dihydroisoquinolin-2(1H)-yl]carbonyl}-1,2,3,4-tetrahydroisoquinolin-6-yl)-N-(4-hydroxyphenyl)-N,1,2-trimethyl-1H-pyrrole-3-carboxamide EXAMPLE 399: 5-[2-({2-[2-(Dimethylamino)ethoxy]phenyl}acetyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide EXAMPLE 400: 5-[2-({2-[2-(Dimethylamino)ethyl]phenyl}acetyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide EXAMPLE 401: 5-[2-({2-[(Dimethylamino)methyl]phenyl}acetyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide EXAMPLE 402: 5-[2-({2-[3-(Dimethylamino)prop-1-yn-1-yl]phenyl}acetyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide EXAMPLE 403: 2-(4-Methylpiperazin-1-yl)phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 404: 2-{[2-(Dimethylamino)ethyl](methyl)amino}phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 405: 2-{[2-(Dimethylamino)ethyl]amino}phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1)-carboxylate EXAMPLE 406: 2-[2-(Dimethylamino)ethoxy]phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 407: 2-[2-(Dimethylamino)ethyl]phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 408: 2-[(Dimethylamino)methyl]phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 409: 2-[3-(Dimethylamino)prop-1-yn-1-yl]phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 410: N,1,2-Trimethyl-5-(7-{[(3R)-3-methyl-3,4-dihydroisoquinolin-2(1H)-yl]carbonyl}-2-{[2-(4-methylpiperazin-1-yl)phenyl]acetyl}-1,2,3,4-tetrahydroisoquinolin-6-yl)-N-phenyl-1H-pyrrole-3-carboxamide EXAMPLE 411: 5-(2-[(2-{[2-(Dimethylamino)ethyl](methyl)amino}phenyl)acetyl]-7-{[(3R)-3-methyl-3,4-dihydroisoquinolin-2(1H)-yl]carbonyl}-1,2,3,4-tetrahydroisoquinolin-6-yl)-N,1,2-trimethyl-N-phenyl-1H-pyrrole-3-carboxamide EXAMPLE 412: 5-(2-[(2-{[2-(Dimethylamino)ethyl]amino}phenyl)acetyl]-7-{[(3R)-3-methyl-3,4-dihydroisoquinolin-2(1H)-yl]carbonyl}-1,2,3,4-tetrahydroisoquinolin-6-yl)-N,1,2-trimethyl-N-phenyl-1H-pyrrole-3-carboxamide EXAMPLE 413: 5-[2-({2-[2-(Dimethylamino)ethoxy]phenyl}acetyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 414: 5-[2-({2-[2-(Dimethylamino)ethyl]phenyl}acetyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 415: 5-[2-({2-[(Dimethylamino)methyl]phenyl}acetyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 416: 5-[2-({2-[3-(Dimethylamino)prop-1-yn-1-yl]phenyl}acetyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 417: 2-(4-Methylpiperazin-1-yl)phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 418: 2-{[2-(Dimethylamino)ethyl](methyl)amino}phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 419: 2-{[2-(Dimethylamino)ethyl]amino}phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 420: 2-[2-(Dimethylamino)ethoxy]phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 421: 2-[2-(Dimethylamino)ethyl]phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 422: 2-[(Dimethylamino)methyl]phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 423: 2-[3-(Dimethylamino)prop-1-yn-1-yl]phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 424: N,N-Dibutyl-1,2-dimethyl-5-(7-{[(3R)-3-methyl-3,4-dihydroisoquinolin-2(1H)-yl]carbonyl}-2-{[2-(4-methylpiperazin-1-yl)phenyl]acetyl}-1,2,3,4-tetrahydroisoquinolin-6-yl)-1H-pyrrole-3-carboxamide EXAMPLE 425: N,N-Dibutyl-5-(2-[(2-{[2-(dimethylamino)ethyl](methyl)amino}phenyl)acetyl]-7-{[(3R)-3-methyl-3,4-dihydroisoquinolin-2(1H)-yl]carbonyl}-1,2,3,4-tetrahydroisoquinolin-6-yl)-1,2-dimethyl-1H-pyrrole-3-carboxamide EXAMPLE 426: N,N-Dibutyl-5-(2-[(2-{[2-(dimethylamino)ethyl]amino}phenyl)acetyl]-7-{[(3R)-3-methyl-3,4-dihydroisoquinolin-2(1H)-yl]carbonyl}-1,2,3,4-tetrahydroisoquinolin-6-yl)-1,2-dimethyl-1H-pyrrole-3-carboxamide EXAMPLE 427: N,N-Dibutyl-5-[2-({2-[2-(dimethylamino)ethoxy]phenyl}acetyl)-7-{[(3R)-3-methyl-3,4-dihydroisoquinolin-2(1H)-yl]carbonyl}-1,2,3,4-tetrahydroisoquinolin-6-yl]-1,2-dimethyl-1H-pyrrole-3-carboxamide EXAMPLE 428: N,N-Dibutyl-5-[2-({2-[2-(dimethylamino)ethyl]phenyl}acetyl)-7-{[(3R)-3-methyl-3,4-dihydroisoquinolin-2(1H)-yl]carbonyl}-1,2,3,4-tetrahydroisoquinolin-6-yl]-1,2-dimethyl-1H-pyrrole-3-carboxamide EXAMPLE 429: N,N-Dibutyl-5-[2-({2-[(dimethylamino)methyl]phenyl}acetyl)-7-{[(3R)-3-methyl-3,4-dihydroisoquinolin-2(1H)-yl]carbonyl}-1,2,3,4-tetrahydroisoquinolin-6-yl]-1,2-dimethyl-1H-pyrrole-3-carboxamide EXAMPLE 430: N,N-Dibutyl-5-[2-({2-[3-(dimethylamino)prop-1-yn-1-yl]phenyl}acetyl)-7-{[(3R)-3-methyl-3,4-dihydroisoquinolin-2(1H)-yl]carbonyl}-1,2,3,4-tetrahydroisoquinolin-6-yl]-1,2-dimethyl-1H-pyrrole-3-carboxamide EXAMPLE 431: 3-(4-Methylpiperazin-1-yl)phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 432: 3-{[2-(Dimethylamino)ethyl](methyl)amino}phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 433: 3-{[2-(Dimethylamino)ethyl]amino}phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 434: 3-[2-(Dimethylamino)ethoxy]phenyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 709, replacing the product from Preparation 6ba in Step A with product from Preparation 6bb, and replacing benzyl 3-hydroxybenzoate from Step B with 3-[2-(dimethylamino)ethoxy]phenol.

LC/MS ($C_{45}H_{49}N_5O_6$) 754 [M−H]$^−$; RT 2.24 (Method A)

High-Resolution Mass (ESI+):

Empirical formula: $C_{45}H_{49}N_5O_6$

[M+2H]$^{2+}$ calculated: 378.6914

[M+2H]$^{2+}$ measured: 378.6918

EXAMPLE 435: 3-[2-(Dimethylamino)ethyl]phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate

EXAMPLE 436: 3-[(Dimethylamino)methyl]phenyl 6-{4-[(4-hydroxyphenyl) (methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate

EXAMPLE 437: 3-[3-(Dimethylamino)prop-1-yn-1-yl]phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate

EXAMPLE 438: N-(4-Hydroxyphenyl)-N,1,2-trimethyl-5-(7-{[(3R)-3-methyl-3,4-dihydroisoquinolin-2(1H)-yl]carbonyl}-2-{[3-(4-methylpiperazin-1-yl)phenyl]acetyl}-1,2,3,4-tetrahydroisoquinolin-6-yl)-1H-pyrrole-3-carboxamide

EXAMPLE 439: 5-(2-[(3-{[2-(Dimethylamino)ethyl](methyl)amino}phenyl)acetyl]-7-{[(3R)-3-methyl-3,4-dihydroisoquinolin-2(1H)-yl]carbonyl}-1,2,3,4-tetrahydroisoquinolin-6-yl)-N-(4-hydroxyphenyl)-N,1,2-trimethyl-1H-pyrrole-3-carboxamide

EXAMPLE 440: 5-(2-[(3-{[2-(Dimethylamino)ethyl]amino}phenyl)acetyl]-7-{[(3R)-3-methyl-3,4-dihydroisoquinolin-2(1H)-yl]carbonyl}-1,2,3,4-tetrahydroisoquinolin-6-yl)-N-(4-hydroxyphenyl)-N,1,2-trimethyl-1H-pyrrole-3-carboxamide

EXAMPLE 441: 5-[2-({3-[2-(Dimethylamino)ethoxy]phenyl}acetyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide

EXAMPLE 442: 5-[2-({3-[2-(Dimethylamino)ethyl]phenyl}acetyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide

EXAMPLE 443: 5-[2-({3-[(Dimethylamino)methyl]phenyl}acetyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide

EXAMPLE 444: 5-[2-({3-[3-(Dimethylamino)prop-1-yn-1-yl]phenyl}acetyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide

EXAMPLE 445: 3-(4-Methylpiperazin-1-yl)phenyl 6-{1,5-dimethyl-4-[methyl(phenyl) carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate

EXAMPLE 446: 3-{[2-(Dimethylamino)ethyl](methyl)amino}phenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 786, replacing 4-hydroxybenzonitrile in Step B with 3-{[2-(dimethylamino)ethyl](methyl)amino}phenol.
LC/MS ($C_{46}H_{52}N_6O_4$) no ionisation; RT 2.44 (Method A)
High-Resolution Mass (ESI+):
Empirical formula: $C_{46}H_{52}N_6O_4$
$[M+2H]^{2+}$ calculated: 377.2098
$[M+2H]^{2+}$ measured: 377.2100

EXAMPLE 447: 3-{[2-(Dimethylamino)ethyl]amino}phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate

EXAMPLE 448: 3-[2-(Dimethylamino)ethoxy]phenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 786, replacing 4-hydroxybenzonitrile in Step B with 3-[2-(dimethylamino)ethoxy]phenol.
LC/MS ($C_{45}H_{49}N_5O_5$) 740 $[M+H]^+$; RT 1.20 (Method B)
High-Resolution Mass (ESI+):
Empirical formula: $C_{45}H_{49}N_5O_5$
$[M+2H]^{2+}$ calculated: 370.6940
$[M+2H]^{2+}$ measured: 370.6954

EXAMPLE 449: 3-[2-(Dimethylamino)ethyl]phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate

EXAMPLE 450: 3-[(Dimethylamino)methyl]phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate

EXAMPLE 451: 3-[3-(Dimethylamino)prop-1-yn-1-yl]phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 452: N,1,2-Trimethyl-5-(7-{[(3R)-3-methyl-3,4-dihydroisoquinolin-2(1H)-yl]carbonyl}-2-{[3-(4-methylpiperazin-1-yl)phenyl]acetyl}-1,2,3,4-tetrahydroisoquinolin-6-yl)-N-phenyl-1H-pyrrole-3-carboxamide EXAMPLE 453: 5-(2-[(3-{[2-(Dimethylamino)ethyl](methyl)amino}phenyl)acetyl]-7-{[(3R)-3-methyl-3,4-dihydroisoquinolin-2(1H)-yl]carbonyl}-1,2,3,4-tetrahydroisoquinolin-6-yl)-N,1,2-trimethyl-N-phenyl-1H-pyrrole-3-carboxamide EXAMPLE 454: 5-(2-[(3-{[2-(Dimethylamino)ethyl]amino}phenyl)acetyl]-7-{[(3R)-3-methyl-3,4-dihydroisoquinolin-2(1H)-yl]carbonyl}-1,2,3,4-tetrahydroisoquinolin-6-yl)-N,1,2-trimethyl-N-phenyl-1H-pyrrole-3-carboxamide EXAMPLE 455: 5-[2-({3-[2-(Dimethylamino)ethoxy]phenyl}acetyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 456: 5-[2-({3-[2-(Dimethylamino)ethyl]phenyl}acetyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 457: 5-[2-({3-[(Dimethylamino)methyl]phenyl}acetyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 458: 5-[2-({3-[3-(Dimethylamino)prop-1-yn-1-yl]phenyl}acetyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 459: 3-(4-Methylpiperazin-1-yl)phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 460: 3-{[2-(Dimethylamino)ethyl](methyl)amino}phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 461: 3-{[2-(Dimethylamino)ethyl]amino}phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 462: 3-[2-(Dimethylamino)ethoxy]phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 463: 3-[2-(Dimethylamino)ethyl]phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 464: 3-[(Dimethylamino)methyl]phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 465: 3-[3-(Dimethylamino)prop-1-yn-1-yl]phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 466: N,N-Dibutyl-1,2-dimethyl-5-(7-{[(3R)-3-methyl-3,4-dihydroisoquinolin-2(1H)-yl]carbonyl}-2-{[3-(4-methylpiperazin-1-yl)phenyl]acetyl}-1,2,3,4-tetrahydroisoquinolin-6-yl)-1H-pyrrole-3-carboxamide EXAMPLE 467: N,N-Dibutyl-5-(2-[(3-{[2-(dimethylamino)ethyl](methyl)amino}phenyl)acetyl]-7-{[(3R)-3-methyl-3,4-dihydroisoquinolin-2(1H)-yl]carbonyl}-1,2,3,4-tetrahydroisoquinolin-6-yl)-1,2-dimethyl-1H-pyrrole-3-carboxamide EXAMPLE 468: N,N-Dibutyl-5-(2-[(3-{[2-(dimethylamino)ethyl]amino}phenyl)acetyl]-7-{[(3R)-3-methyl-3,4-dihydroisoquinolin-2(1H)-yl]carbonyl}-1,2,3,4-tetrahydroisoquinolin-6-yl)-1,2-dimethyl-IR-pyrrole-3-carboxamide EXAMPLE 469: N,N-Dibutyl-5-[2-({3-[2-(dimethylamino)ethoxy]phenyl}acetyl)-7-{[(3R)-3-methyl-3,4-dihydroisoquinolin-2(1H)-yl]carbonyl}-1,2,3,4-tetrahydroisoquinolin-6-yl]-1,2-dimethyl-1H-pyrrole-3-carboxamide EXAMPLE 470: N,N-Dibutyl-5-[2-({3-[2-(dimethylamino)ethyl]phenyl}acetyl)-7-{[(3R)-3-methyl-3,4-dihydroisoquinolin-2(1H)-yl]carbonyl}-1,2,3,4-tetrahydroisoquinolin-6-yl]-1,2-dimethyl-1H-pyrrole-3-carboxamide EXAMPLE 471: N,N-Dibutyl-5-[2-({3-[(dimethylamino)methyl]phenyl}acetyl)-7-{[(3R)-3-methyl-3,4-dihydroisoquinolin-2(1H)-yl]carbonyl}-1,2,3,4-tetrahydroisoquinolin-6-yl]-1,2-dimethyl-1H-pyrrole-3-carboxamide EXAMPLE 472: N,N-Dibutyl-5-[2-({3-[3-(dimethylamino)prop-1-yn-1-yl]phenyl}acetyl)-7-{[(3R)-3-methyl-3,4-dihydroisoquinolin-2(1H)-yl]carbonyl}-1,2,3,4-tetrahydroisoquinolin-6-yl]-1,2-dimethyl-1H-pyrrole-3-carboxamide EXAMPLE 473: 4-(4-Methylpiperazin-1-yl)phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 474: 4-{[2-(Dimethylamino)ethyl](methyl)amino}phenyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 709, replacing the product from Preparation 6ba in Step A with the product from Preparation 6bb, and replacing benzyl 3-hydroxybenzoate from Step B with 4-{[2-(dimethylamino)ethyl](methyl)amino}phenol.
LC/MS ($C_{46}H_{52}N_6O_5$) 767 [M–H]$^-$; RT 2.26 (Method A)

EXAMPLE 475: 4-{[2-(Dimethylamino)ethyl]amino}phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 476: 4-[2-(Dimethylamino)ethoxy]phenyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 709, replacing the product from Preparation 6ba in Step A with the product from Preparation 6bb, and replacing benzyl 3-hydroxybenzoate from Step B with 4-[2-(dimethylamino)ethoxy]phenol.
LC/MS ($C_{45}H_{49}N_5O_6$) 754 [M-1-1]$^-$; RT 2.21 (Method A)
High-Resolution Mass (ESI+):
Empirical formula: $C_{45}H_{49}N_5O_6$
[M+2H]$^{2+}$ calculated: 378.6914
[M+2H]$^{2+}$ measured: 378.6926

EXAMPLE 477: 4-[2-(Dimethylamino)ethyl]phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 478: 4-[(Dimethylamino)methyl]phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 479: 4-[3-(Dimethylamino)prop-1-yn-1-yl]phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 480: N-(4-Hydroxyphenyl)-N,1,2-trimethyl-5-(7-{[(3R)-3-methyl-3,4-dihydroisoquinolin-2(1H)-yl]carbonyl}-2-{[4-(4-methylpiperazin-1-yl)phenyl]acetyl}-1,2,3,4-tetrahydroisoquinolin-6-yl)-1H-pyrrole-3-carboxamide EXAMPLE 481: 5-(2-[(4-{[2-(Dimethylamino)ethyl](methyl)amino}phenyl)acetyl]-7-{[(3R)-3-methyl-3,4-dihydroisoquinolin-2(1H)-yl]carbonyl}-1,2,3,4-tetrahydroisoquinolin-6-yl)-N-(4-hydroxyphenyl)-N,1,2-trimethyl-1H-pyrrole-3-carboxamide EXAMPLE 482: 5-(2-[(4-{[2-(Dimethylamino)ethyl]amino}phenyl)acetyl]-7-{[(3R)-3-methyl-3,4-dihydroisoquinolin-2(1H)-yl]carbonyl}-1,2,3,4-tetrahydroisoquinolin-6-yl)-N-(4-hydroxyphenyl)-N,1,2-trimethyl-1H-pyrrole-3-carboxamide EXAMPLE 483: 5-[2-({4-[2-(Dimethylamino)ethoxy]phenyl}acetyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide EXAMPLE 484: 5-[2-({4-[2-(Dimethylamino)ethyl]phenyl}acetyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide EXAMPLE 485: 5-[2-({4-[(Dimethylamino)methyl]phenyl}acetyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide EXAMPLE 486: 5-[2-({4-[3-(Dimethylamino)prop-1-yn-1-yl]phenyl}acetyl)-7-{[(3R)-3-methyl-3,4-dihydroisoquinolin-2(1H)-yl]carbonyl}-1,2,3,4-tetrahydroisoquinolin-6-yl]-N-(4-hydroxyphenyl)-N,1,2-trimethyl-1H-pyrrole-3-carboxamide EXAMPLE 487: 4-(4-Methylpiperazin-1-yl)phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 488: 4-{[2-(Dimethylamino)ethyl](methyl)amino}phenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate Step A: 6-{1,5-Dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carbonyl chloride The procedure is as in Step A of Example 573, replacing the product from Preparation 6ba with the product from Preparation 6cb.
LC/MS ($C_{35}H_{35}ClN_4O_3$) 595 [M+H]$^+$; RT 2.73 (Method A)

Step B: 4-{[2-(Dimethylamino)ethyl](methyl)amino}phenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate To a solution of the carbamoyl chloride obtained from Step A (55 mg, 0.09 mmol) in acetonitrile (5 mL) was added potassium carbonate (128 mg, 0.92 mmol) and 4-(dimethylamino)ethyl](methyl)amino}phenol (22 mg, 0.11 mmol), and the reaction was stirred at 60° C. for ca 16 h. The reaction was allowed to cool to ambient temperature, diluted with dichloromethane and washed with water. The organic extract was dried over magnesium sulphate, filtered and concentrated in vacuo. Purification by flash column chromatography (silica; dichloromethane to 10% methanol/dichloromethane) afforded the desired product as a cream solid.
LC/MS ($C_{46}H_{52}N_6O_4$) 753 [M+H]$^+$; RT 2.42 (Method A)
High-Resolution Mass (ESI+):
Empirical formula: $C_{46}H_{52}N_6O_4$
[M+2H]$^{2+}$ calculated: 377.2098
[M+2H]$^{2+}$ measured: 377.2102

EXAMPLE 489: 4-{[2-(Dimethylamino)ethyl]amino}phenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate Step A: 6-{1,5-Dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carbonyl chloride The procedure is as in Step A of Example 573, replacing the product from Preparation 6ba with the product from Preparation 6cb.
LC/MS ($C_{35}H_{35}ClN_4O_3$) 595 [M+H]$^+$; RT 2.73 (Method A)

Step B: 4-{[(tert-Butoxy)carbonyl][2-(dimethylamino)ethyl]amino}phenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Step B of Example 573, replacing the product of Step A in Example 573 with the product of Step A in Example 489, and replacing 3,4-dichlorophenol with tert-butyl N-[2-(dimethylamino)ethyl]-N-(4-hydroxyphenyl)carbamate.
LC/MS ($C_{50}H_{58}N_6O_6$) no ionisation; RT 2.54 (Method A)

Step C: 4-{[2-(Dimethylamino)ethyl]amino}phenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate To a solution of product obtained in Step B (31 mg, 0.04 mmol, 1 eq) in dichloromethane (5 mL) was added trifluoroacetic acid (0.5 mL) and the mixture was stirred at ambient temperature for ca 4 h. The reaction was diluted with water and basified with aqueous 2M sodium hydroxide. The phases were separated and the aqueous phase was extracted with dichloromethane. The combined organic phases were dried over magnesium sulphate, filtered and concentrated in vacuo. Purification by flash column chromatography (10 g silica; dichloromethane to 10% methanol in dichloromethane) afforded the desired product as a white powder.
LC/MS ($C_{45}H_{50}N_6O_4$) no ionisation; RT 2.38 (Method A)
High-Resolution Mass (ESI+):
Empirical formula: $C_{45}H_{50}N_6O_4$
[M+2H]$^{2+}$ calculated: 370.2020
[M+2H]$^{2+}$ measured: 370.2038

EXAMPLE 490: 4-[2-(Dimethylamino)ethoxy]phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 491: 4-[2-(Dimethylamino)ethyl]phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1-carboxylate EXAMPLE 492: 4-[(Dimethylamino)methyl]phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 493: 4-[3-(Dimethylamino)prop-1-yn-1-yl]phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 494: N,1,2-Trimethyl-5-(7-{[(3R)-3-methyl-3,4-dihydroisoquinolin-2(1H)-yl]carbonyl}-2-{[4-(4-methylpiperazin-1-yl)phenyl]acetyl}-1,2,3,4-tetrahydroisoquinolin-6-yl)-N-phenyl-1H-pyrrole-3-carboxamide EXAMPLE 495: 5-(2-[(4-{[2-(Dimethylamino)ethyl](methyl)amino}phenyl)acetyl]-7-{[(3R)-3-methyl-3,4-dihydroisoquinolin-2(1H)-yl]carbonyl}-1,2,3,4-tetrahydroisoquinolin-6-yl)-N,1,2-trimethyl-N-phenyl-1H-pyrrole-3-carboxamide EXAMPLE 496: 5-(2-[(4-{[2-(Dimethylamino)ethyl]amino}phenyl)acetyl]-7-{[(3R)-3-methyl-3,4-dihydroisoquinolin-2(1H)-yl]carbonyl}-1,2,3,4-tetrahydroisoquinolin-6-yl)-N,1,2-trimethyl-N-phenyl-1H-pyrrole-3-carboxamide EXAMPLE 497: 5-[2-({4-[2-(Dimethylamino)ethoxy]phenyl}acetyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 498: 5-[2-({4-[2-(Dimethylamino)ethyl]phenyl}acetyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 499: 5-[2-({4-[(Dimethylamino)methyl]phenyl}acetyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 500: 5-[2-({4-[3-(Dimethylamino)prop-1-yn-1-yl]phenyl}acetyl)-7-{[(3R)-3-methyl-3,4-dihydroisoquinolin-2(1H)-yl]carbonyl}-1,2,3,4-tetrahydroisoquinolin-6-yl]-N,1,2-trimethyl-N-phenyl-1H-pyrrole-3-carboxamide EXAMPLE 501: 4-(4-Methylpiperazin-1-yl)phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 502: 4-{[2-(Dimethylamino)ethyl](methyl)amino}phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 503: 4-{[2-(Dimethylamino)ethyl]amino}phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 504: 4-[2-(Dimethylamino)ethoxy]phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 505: 4-[2-(Dimethylamino)ethyl]phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 506: 4-[(Dimethylamino)methyl]phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 507: 4-[3-(Dimethylamino)prop-1-yn-1-yl]phenyl 6-[4-(dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinoline-2(1H)-carboxylate EXAMPLE 508: N,N-Dibutyl-1,2-dimethyl-5-(7-{[(3R)-3-methyl-3,4-dihydroisoquinolin-2(1H)-yl]carbonyl}-2-{[4-(4-methylpiperazin-1-yl)phenyl]acetyl}-1,2,3,4-tetrahydroisoquinolin-6-yl)-1H-pyrrole-3-carboxamide EXAMPLE 509: N,N-Dibutyl-5-(2-[(4-{[2-(dimethylamino)ethyl](methyl)amino}phenyl)acetyl]-7-{[(3R)-3-methyl-3,4-dihydroisoquinolin-2(1H)-yl]carbonyl}-1,2,3,4-tetrahydroisoquinolin-6-yl)-1,2-dimethyl-1H-pyrrole-3-carboxamide EXAMPLE 510: N,N-Dibutyl-5-(2-[(4-{[2-(dimethylamino)ethyl]amino}phenyl)acetyl]-7-{[(3R)-3-methyl-3,4-dihydroisoquinolin-2(1H)-yl]carbonyl}-1,2,3,4-tetrahydroisoquinolin-6-yl)-1,2-dimethyl-1H-pyrrole-3-carboxamide EXAMPLE 511: N,N-Dibutyl-5-[2-({4-[2-(dimethylamino)ethoxy]phenyl}acetyl)-7-{[(3R)-3-methyl-3,4-dihydroisoquinolin-2(1H)-yl]carbonyl}-1,2,3,4-tetrahydroisoquinolin-6-yl]-1,2-dimethyl-1H-pyrrole-3-carboxamide EXAMPLE 512: N,N-Dibutyl-5-[2-({4-[2-(dimethylamino)ethyl]phenyl}acetyl)-7-{[(3R)-3-methyl-3,4-dihydroisoquinolin-2(1H)-yl]carbonyl}-1,2,3,4-tetrahydroisoquinolin-6-yl]-1,2-dimethyl-1H-pyrrole-3-carboxamide EXAMPLE 513: N,N-Dibutyl-5-[2-({4-[(dimethylamino)methyl]phenyl}acetyl)-7-{[(3R)-3-methyl-3,4-dihydroisoquinolin-2(1H)-yl]carbonyl}-1,2,3,4-tetrahydroisoquinolin-6-yl]-1,2-dimethyl-1H-pyrrole-3-carboxamide EXAMPLE 514: N,N-Dibutyl-5-[2-({4-[3-(dimethylamino)prop-1-yn-1-yl]phenyl}acetyl)-7-{[(3R)-3-methyl-3,4-dihydroisoquinolin-2(1H)-yl]carbonyl}-1,2,3,4-tetrahydroisoquinolin-6-yl]-1,2-dimethyl-1H-pyrrole-3-carboxamide EXAMPLE 515: Disodium 4-[({1,2-Dimethyl-5-[7-{[(3S)-3-(morpholin-4-ylmethyl)-3,4-dihydroisoquinolin-2(1H)-yl]carbonyl}-2-(phenoxycarbonyl)-1,2,3,4-tetrahydroisoquinolin-6-yl]-1H-pyrrol-3-yl}carbonyl)(methyl)amino]phenyl phosphate EXAMPLE 516: Disodium 4-[({1,2-dimethyl-5-[7-{[(3S)-3-(morpholin-4-ylmethyl)-3,4-dihydroisoquinolin-2(1H)-yl]carbonyl}-2-(phenylacetyl)-1,2,3,4-tetrahydroisoquinolin-6-yl]-1H-pyrrol-3-yl}carbonyl)(methyl)amino]phenyl phosphate EXAMPLE 517: Disodium 4-[methyl({3-[7-{[(3S)-3-(morpholin-4-ylmethyl)-3,4-dihydroisoquinolin-2(1H)-yl]carbonyl]-2-(phenoxycarbonyl)-1,2,3,4-tetrahydroisoquinolin-6-yl]-5,6,7,8-tetrahydroindolizin-1-yl}carbonyl)amino]phenyl phosphate EXAMPLE 518: Disodium 4-[methyl({3-[7-{[(3S)-3-(morpholin-4-ylmethyl)-3,4-dihydroisoquinolin-2(1H)-yl]carbonyl]-2-(phenylacetyl)-1,2,3,4-tetrahydroisoquinolin-6-yl]-5,6,7,8-tetrahydroindolizin-1-yl}carbonyl)amino]phenyl phosphate EXAMPLE 519: Disodium 4-[({1,2-dimethyl-5-[7-{[(3R)-3-methyl-3,4-dihydroisoquinolin-2(1H)-yl]carbonyl}-2-(phenoxycarbonyl)-1,2,3,4-tetrahydroisoquinolin-6-yl]-1H-pyrrol-3-yl}carbonyl)(methyl)amino]phenyl phosphate EXAMPLE 520: Disodium 4-[({1,2-dimethyl-5-[7-{[(3R)-3-methyl-3,4-dihydroisoquinolin-2(1H)-yl]carbonyl}-2-(phenylacetyl)-1,2,3,4-tetrahydroisoquinolin-6-yl]-1H-pyrrol-3-yl}carbonyl)(methyl)amino]phenyl phosphate EXAMPLE 521: Disodium 4-[methyl({3-[7-{[(3R)-3-methyl-3,4-dihydroisoquinolin-2(1H)-yl]carbonyl}-2-(phenoxycarbonyl)-1,2,3,4-tetrahydroisoquinolin-6-yl]-5,6,7,8-tetrahydroindolizin-1-yl}carbonyl)amino]phenyl phosphate EXAMPLE 522: Disodium 4-[methyl({3-[7-{[(3R)-3-methyl-3,4-dihydroisoquinolin-2(1H)-yl]carbonyl}-2-(phenylacetyl)-1,2,3,4-tetrahydroisoquinolin-6-yl]-5,6,7,8-tetrahydroindolizin-1-yl}carbonyl)amino]phenyl phosphate EXAMPLE 523: Phenyl 6-{1-ethyl-4-[(4-hydroxyphenyl)(methyl)carbamoyl]-5-methyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 524: Phenyl 6-{1-(2-hydroxyethyl)-4-[(4-hydroxyphenyl)(methyl)carbamoyl]-5-methyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 525: Phenyl 6-{4-[(4-hydroxyphenyl)(methyl)carbamoyl]-1-(2-methoxyethyl)-5-methyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 526: Phenyl 6-{4-[(4-hydroxyphenyl)(methyl)carbamoyl]-5-methyl-1-(2,2,2-trifluoroethyl)-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 527: Phenyl 6-{1-ethyl-5-methyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 528: Phenyl 6-{1-(2-hydroxyethyl)-5-methyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 529: Phenyl 6-{1-(2-methoxyethyl)-5-methyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 530: Phenyl 6-{5-methyl-4-[methyl(phenyl)carbamoyl]-1-(2,2,2-trifluoroethyl)-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 531: Phenyl 6-[4-(dibutylcarbamoyl)-1-ethyl-5-methyl-1H-pyrrol-2-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 532: Phenyl 6-[4-(dibutylcarbamoyl)-1-(2-hydroxyethyl)-5-methyl-1H-pyrrol-2-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 533: Phenyl 6-[4-(dibutylcarbamoyl)-1-(2-methoxyethyl)-5-methyl-1H-pyrrol-2-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 534: Phenyl 6-[4-(dibutylcarbamoyl)-5-methyl-1-(2,2,2-trifluoroethyl)-pyrrol-2-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 535: 2-Methylphenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 536: 3-Methylphenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 537: 4-Methylphenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 538: 2-Chlorophenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 539: 3-Chlorophenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 540: 4-Chlorophenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 541: 2-Hydroxyphenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 542: 3-Hydroxyphenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 543: 4-Hydroxyphenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 544: 2-Methoxyphenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 545: 3-Methoxyphenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 546: 4-Methoxyphenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 547: 2-(Methylamino)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 548: 3-(Methylamino)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 549: 4-(Methylamino)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 550: 2-(Dimethylamino)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 551: 3-(Dimethylamino)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 552: 4-(Dimethylamino)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 553: 2-(Acetylamino)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 554: 3-(Acetylamino)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 555: 4-(Acetylamino)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 556: 2-(Trifluoromethyl)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 557: 3-(Trifluoromethyl)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 558: 4-(Trifluoromethyl)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 559: 2-Cyanophenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 560: 3-Cyanophenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]'-1,2,3,4-tetrahydroisoquinoline-2-carboxylate The procedure is an in Example 573, replacing 3,4-dichlorophenol in Step B with 3-hydroxybenzonitrile.

LC/MS ($C_{46}H_{46}N_6O_6$) 779 [M+H]$^+$; RT 1.14 (Method B)
High-Resolution Mass (ESI+):
Empirical formula: $C_{46}H_{46}N_6O_6$
[M+H]$^+$ calculated: 779.3552
[M+H]$^+$ measured: 779.3515

EXAMPLE 561: 4-Cyanophenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 562: 2-Ethynylphenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 563: 3-Ethynylphenyl 6-{4-[(4-hydroxyphenyl)(methyl)carbamoyl]dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 564: 4-Ethynylphenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate To a solution of the product obtained from Example 784 (53 mg, 0.06 mmol, 1 eq) and triethylamine (10 µL, 0.1 mmol) in THF (1 mL) were added bis(triphenylphosphine)palladium(II) dichloride (5 mg, 0.01 mmol, 0.12 eq), copper (I) iodide (0.7 mg, 3.84 µmol), and trimethylsilylacetylene (36 µL, 0.26 mmol, 4 eq) and the mixture was heated at 60° C. for ca 16 h. The reaction was allowed to cool to ambient temperature, then evaporated and purified preparative HPLC ($H_2O$-TFA/acetonitrile; gradient elution) to afford the desired product.

LC/MS ($C_{47}H_{47}N_5O_6$) 778 [M+H]$^+$; RT 1.24 (Method B) High-Resolution Mass (ESI+):

Empirical formula: $C_{47}H_{47}N_5O_6$

[M+H]$^+$ calculated: 778.3599

[M+H]$^+$ measured: 778.3635

EXAMPLE 565: 2,3-Dichlorophenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 566: Naphthalen-1-yl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 567: 1H-Indol-7-yl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 568: 1-Methyl-1H-indol-7-yl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 569: 1H-Indol-4-yl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 570: 1-Methyl-1H-indol-4-yl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 571: 1H-Pyrrolo[2,3-b]pyridin-4-yl 6-{4-[(4-hydroxyphenyl)(methyl) carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 572: 1-Methyl-1H-pyrrolo[2,3-b]pyridin-4-yl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 573: 3,4-Dichlorophenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate Step A: 6-(4-{[4-(Benzyloxy)phenyl](methyl)carbamoyl}-1,5-dimethyl-1H-pyrrol-2-yl)-7-[(3S)-3-(morpholin-4-ylmethyl)-1,2,3,4-tetrahydroisoquinoline-2-carbonyl]-1,2,3,4-tetrahydroisoquinoline-2-carbonyl chloride To a solution of the compound from Preparation 6ba (450 mg, 0.47 mmol) and N,N-diisopropylethylamine (0.41 mL, 2.36 mmol) in dichloromethane (45 mL), cooled to 0° C., was added triphosgene (139 mg, 0.47 mmol) and the mixture was stirred for 1 h at ambient temperature. The reaction was diluted with dichloromethane and was washed with 1M aqueous HCl. The organic extract was dried over magnesium sulfate, filtered and concentrated in vacuo to afford a yellow solid that was used directly in the next step without further purification, and assuming quantitative transformation.

LC/MS ($C_{46}H_{48}ClN_5O_5$) 786 [M+H]$^+$; RT 1.33 (Method B)

Step B: 3,4-Dichlorophenyl 6-(4-{[4-(benzyloxy)phenyl](methyl)carbamoyl}-1,5-dimethyl-1H-pyrrol-2-yl)-7-[(3S)-3-(morpholin-4-ylmethyl)-1,2,3,4-tetrahydroisoquinoline-2-carbonyl]-1,2,3,4-tetrahydroisoquinoline-2-carboxylate To a solution of the compound from Step A (41 mg, 0.05 mmol) in acetonitrile (5 mL) was added potassium carbonate (72 mg, 0.52 mmol), DMAP (0.052 mmol) and 3,4-dichlorophenol (0.52 mmol) and the mixture heated at 60° C. for ca 16 h. The reaction mixture was diluted with ethyl acetate and was washed with saturated aqueous sodium bicarbonate, and brine. The organic extract was dried over magnesium sulfate and concentrated in vacuo. Purification by flash column chromatography (CombiFlash R$_f$, 4 g RediSep™ silica cartridge; dichloromethane to 5% methanol in dichloromethane) afforded the desired product.

LC/MS ($C_{52}H_{51}Cl_2N_5O_6$) 912 [M+H]$^+$; RT 1.48 (Method B)

Step C: 3,4-Dichlorophenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate To a solution of the compound from Step A in dichloromethane (5 mL), cooled to 0° C., was added drop-wise boron trichloride (1 M in dichloromethane; 5 eq.). The reaction was then allowed to warm to ambient temperature and continue stirring for ca 16 h. The reaction was quenched by the addition of water (10 mL) and the phases were separated. The organic phase was washed successively with aqueous sodium bicarbonate, and brine. The organic extract was dried over magnesium sulphate, filtered and concentrated in vacuo. Purification by flash column chromatography (CombiFlash R$_f$, 4 g RediSep™ silica cartridge; dichloromethane to 5% methanol in dichloromethane) afforded the desired product.

LC/MS ($C_{45}H_{45}Cl_2N_5O_6$) 822 [M+H]$^+$; RT 1.28 (Method B)
High-Resolution Mass (ESI+):
Empirical formula: $C_{45}H_{45}N_5O_6Cl_2$
[M+H]$^+$ calculated: 822.2820
[M+H]$^+$ measured: 822.2832

EXAMPLE 574: Naphthalen-2-yl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is an in Example 573, replacing 3,4-dichlorophenol in Step B with naphthalen-2-ol.
LC/MS ($C_{49}H_{49}N_5O_6$) 804 [M+H]$^+$; RT 1.24 (Method B)
High-Resolution Mass (ESI+):
Empirical formula: $C_{49}H_{49}N_5O_6$
[M+H]$^+$ calculated: 804.3756
[M+H]$^+$ measured: 804.3767

EXAMPLE 575: 1H-Indol-6-yl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is an in Example 573, replacing 3,4-dichlorophenol in Step B with 3H-indol-6-ol.
LC/MS ($C_{47}H_{48}N_6O_6$) 793 [M+H]$^+$; RT 1.15 (Method B)
High-Resolution Mass (ESI+):
Empirical formula: $C_{47}H_{48}N_6O_6$
[M+H]$^+$ calculated: 793.3708
[M+H]$^+$ measured: 793.3690

EXAMPLE 576: 1-Methyl-1H-indol-6-yl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 577: 1H-Indol-5-yl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is an in Example 573, replacing 3,4-dichlorophenol in Step B with 1H-indol-5-ol.
LC/MS ($C_{47}H_{48}N_6O_6$) 793 [M+H]$^+$; RT 1.13 (Method B)
High-Resolution Mass (ESI+):
Empirical formula: $C_{47}H_{48}N_6O_6$
[M+2H]$^{2+}$ calculated: 397.1890
[M+2H]$^{2+}$ measured: 397.1879

EXAMPLE 578: 1-Methyl-1H-indol-5-yl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 579: 1H-Pyrrolo[2,3-b]pyridin-5-yl 6-{4-[(4-hydroxyphenyl)(methyl) carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is an in Example 573, replacing 3,4-dichlorophenol in Step B with 1H-pyrrolo[2,3-b]pyridin-5-ol.
LC/MS ($C_{46}H_{47}N_7O_6$) 794 [M+H]$^+$; RT 1.07 (Method B)
High-Resolution Mass (ESI+):
Empirical formula: $C_{46}H_{47}N_7O_6$
[M+2H]$^{2+}$ calculated: 397.6867
[M+2H]$^{2+}$ measured: 397.6880

EXAMPLE 580: 1-Methyl-1H-pyrrolo[2,3-b]pyridin-5-yl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 581: 1H-Pyrrolo[2,3-b]pyridin-4-yl 6-{4-[(4-hydroxyphenyl)(methyl) carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 582: 1H-Pyrrolo[2,3-b]pyridin-5-yl 6-{4-[(4-hydroxyphenyl)(methyl) carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 583: 2-(Methylsulfanyl)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 584: 3-(Methylsulfanyl)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 585: 4-(Methylsulfanyl)phenyl 6-{4-[(4-hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 586: 2-(Dimethylcarbamoyl)phenyl 6-{4-[(4-hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 587: 3-(Dimethylcarbamoyl)phenyl 6-{4-[(4-hydroxyphenyl)(methyl) carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 588: 4-(Dimethylcarbamoyl)phenyl 6-{4-[(4-hydroxyphenyl)(methyl) carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 589: 2-Methylphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 590: 3-Methylphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 591: 4-Methylphenyl 6-{1,5-dimethyl-4-[methyl(phenyl)carbamoyl]-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 785, replacing the product from Preparation 6cb with the product from Preparation 6ca.
LC/MS ($C_{46}H_{49}N_5O_5$) 752 [M+H]$^+$; RT 1.34 (Method B)
High-Resolution Mass (ESI+):

Empirical formula: $C_{46}H_{49}N_5O_5$
[M+H]$^+$ calculated: 752.3806
[M+H]$^+$ measured: 752.3836

EXAMPLE 592: 2-Chlorophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 593: 3-Chlorophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 594: 4-Chlorophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 595: 2-Hydroxyphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 596: 3-Hydroxyphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 597: 4-Hydroxyphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 598: 2-Methoxyphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 599: 3-Methoxyphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 600: 4-Methoxyphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 601: 2-(Methylamino)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 602: 3-(Methylamino)phenyl 6-{1,5-dimethyl-4-[methyl(phenyl)carbamoyl]-1R-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 603: 4-(Methylamino)phenyl 6-{1,5-dimethyl-4-[methyl(phenyl)carbamoyl]-1H-pyrrol-2-yl}-7-{[(1S)-3-(morpholin-4-ylmethyl)-3,4-dihydroisoquinolin-2(1H)-yl]carbonyl}-3,4-dihydroisoquinoline-2(1H)-carboxylate EXAMPLE 604: 2-(Dimethylamino)phenyl 6-{1,5-dimethyl-4-[methyl(phenyl) carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 605: 3-(Dimethylamino)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 606: 4-(Dimethylamino)phenyl 6-{1,5-dimethyl-4-[methyl(phenyl) carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 607: 2-(Acetylamino)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 608: 3-(Acetylamino)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 609: 4-(Acetylamino)phenyl 6-{1,5-dimethyl-4-[methyl(phenyl)carbamoyl]-1H-pyrrol-2-yl}-7-{[(1S)-3-(morpholin-4-ylmethyl)-3,4-dihydroisoquinolin-2(1H)-yl]carbonyl}-3,4-dihydroisoquinoline-2(1H)-carboxylate EXAMPLE 610: 2-(Trifluoromethyl)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 611: 3-(Trifluoromethyl)phenyl 6-{1,5-dimethyl-4 [methyl(phenyl) carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 612: 4-(Trifluoromethyl)phenyl 6-{1,5-dimethyl-4 [methyl(phenyl) carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 613: 2-Cyanophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 614: 3-Cyanophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 615: 4-Cyanophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 616: 2-Ethynylphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 617: 3-Ethynylphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 618: 4-Ethynylphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 619: 2,3-Dichlorophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 620: Naphthalen-1-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 621: 1H-Indol-7-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 622: 1-Methyl-1H-indol-7-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 623: 1H-Indol-4-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 624: 1-Methyl-1H-indol-4-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 625: 1H-Pyrrolo[2,3-b]pyridin-4-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 626: 1-Methyl-1H-pyrrolo[2,3-b]pyridin-4-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 627: 3,4-Dichlorophenyl 6-{1,5-dimethyl-4-[methyl(phenyl)carbamoyl]-1H-pyrrol-2-yl}-7-{[(1S)-3-(morpholin-4-ylmethyl)-3,4-dihydroisoquinolin-2(1H)-yl]carbonyl}-3,4-dihydroisoquinoline-2(1H)-carboxylate EXAMPLE 628: Naphthalen-2-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 629: 1H-Indol-6-yl 6-{1,5-dimethyl-4-[methyl(phenyl)carbamoyl]-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate Step A: 6-{1,5-Dimethyl-4-[methyl(phenyl)carbamoyl]-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carbonyl chloride and Trichloromethyl 6-{1,5-dimethyl-4-[methyl(phenyl)carbamoyl]-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate To a solution of product from Preparation 6ca (200 mg, 0.32 mmol) and N,N-diisopropylethylamine (0.17 mL, 0.97 mmol) in dichloromethane (10 mL), cooled to 0° C., was added triphosgene (96 mg, 0.32 mmol) and the mixture was stirred at ambient temperature 1 h. The reaction was diluted with dichloromethane and washed with 1M aqueous HCl. The organic extract was dried with magnesium sulfate, filtered and concentrated in vacuo to afford the desired products as a mixture.

LC/MS ($C_{39}H_{42}ClN_5O_4$) 680 [M+H]$^+$; RT 1.27, and ($C_{40}R_{42}Cl_3N_5O_5$) 778 [M+H]$^+$; RT 1.36 (Method B)

Step B: 1H-Indol-6-yl 6-{1,5-dimethyl-4-[methyl(phenyl)carbamoyl]-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate To a solution of the material from Step A (50 mg, 0.06 mmol) in acetonitrile (5 mL) was added potassium carbonate (44 mg, 0.32 mmol) followed by 1H-indol-6-ol (1.5 eq) and the mixture was heated at 60° C. for ca 16 h. The reaction was allowed to cool to ambient temperature, and was diluted with ethyl acetate (20 mL) and washed successively with 1M aqueous sodium hydroxide, and brine. The organic extract was dried over magnesium sulfate, filtered and concentrated in vacuo. Purification by flash column chromatography (CombiFlash R$_f$, 4 g RediSep™ silica cartridge; dichloromethane to 10% methanol in dichloromethane) afforded the desired product.

LC/MS ($C_{47}H_{48}N_6O_5$) 777 [M+H]$^+$; RT 1.26 (Method B)
High-Resolution Mass (ESI+):

Empirical formula: $C_{47}H_{48}N_6O_5$

[M+H]$^+$ calculated: 777.3759

[M+H]$^+$ measured: 777.3795

EXAMPLE 630: 1-Methyl-1H-indol-6-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate

EXAMPLE 631: 1H-Indol-5-yl 6-{1,5-dimethyl-4-[methyl(phenyl)carbamoyl]-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 629, replacing 1H-indol-6-ol in Step B with 1H-indol-5-ol, and purifying via preparative HPLC (H$_2$O-TFA/acetonitrile; gradient elution).

LC/MS (C$_{47}$H$_{48}$N$_6$O$_5$) 777 [M+H]$^+$; RT 1.28 (Method B)
High-Resolution Mass (ESI+):
Empirical formula: C$_{47}$H$_{48}$N$_6$O$_5$
[M+H]$^+$ calculated: 777.3759
[M+H]$^+$ measured: 777.3742

EXAMPLE 632: 1-Methyl-1H-indol-5-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate

EXAMPLE 633: 1H-Pyrrolo[2,3-b]pyridin-5-yl 6-{1,5-dimethyl-4-[methyl(phenyl)carbamoyl]-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 629, replacing 1H-indol-6-ol in Step B with 1H-pyrrolo[2,3-b]pyridin-5-ol.

LC/MS (C$_{46}$H$_{47}$N$_7$O$_5$) 778 [M+H]$^+$; RT 1.18 (Method B)
High-Resolution Mass (ESI+):
Empirical formula: C$_{46}$H$_{47}$N$_7$O$_5$
[M+2H]$^{2+}$ calculated: 389.6892
[M+2H]$^{2+}$ measured: 389.6874

EXAMPLE 634: 1-Methyl-1H-pyrrolo[2,3-b]pyridin-5-yl 6-{1,5-dimethyl-4-[methyl(phenyl)carbamoyl]-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 629, replacing 1H-indol-6-ol in Step B with 1-methyl-1H-pyrrolo[2,3-b]pyridin-5-ol, and purifying via preparative HPLC (H$_2$O-TFA/acetonitrile; gradient elution).

LC/MS (C$_{47}$H$_{49}$N$_7$O$_5$) 792 [M+H]$^+$; RT 1.25 (Method B)
High-Resolution Mass (ESI+):
Empirical formula: C$_{47}$H$_{49}$N$_7$O$_5$
[M+2H]$^{2+}$ calculated: 396.6970
[M+2H]$^{2+}$ measured: 396.6978

EXAMPLE 635: 1H-Pyrrolo[2,3-b]pyridin-4-yl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate

EXAMPLE 636: 1H-Pyrrolo[2,3-b]pyridin-5-yl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 786, replacing 4-hydroxybenzonitrile in Step B with 1H-pyrrolo[2,3-b]pyridin-5-ol.

LC/MS (C$_{42}$H$_{40}$N$_6$O$_4$) 693 [M+H]$^+$; RT 1.34 (Method B)
High-Resolution Mass (ESI+):
Empirical formula: C$_{42}$H$_{40}$N$_6$O$_4$
[M+2H]$^{2+}$ calculated: 347.1628
[M+2H]$^{2+}$ measured: 347.1639

EXAMPLE 637: 2-(Methylsulfanyl)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate

EXAMPLE 638: 3-(Methylsulfanyl)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate

EXAMPLE 639: 4-(Methylsulfanyl)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate

EXAMPLE 640: 2-(Dimethylcarbamoyl)phenyl 6-{1,5-dimethyl-4-[methylphenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1-carboxylate

EXAMPLE 641: 3-(Dimethylcarbamoyl)phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1-carboxylate

EXAMPLE 642: 4-(Dimethylcarbamoyl)phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 643: 2-Methylphenyl 6-[4-(dibutylcarbamoyl)-1,5-dimethyl-1H-pyrrol-2-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 644: 3-Methylphenyl 6-[4-(dibutylcarbamoyl)-1,5-dimethyl-1H-pyrrol-2-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 645: 4-Methylphenyl 6-[4-(dibutylcarbamoyl)-1,5-dimethyl-1H-pyrrol-2-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 646: 2-Chlorophenyl 6-[4-(dibutylcarbamoyl)-1,5-dimethyl-1H-pyrrol-2-yl]-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 647: 3-Chlorophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 648: 4-Chlorophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 649: 2-Hydroxyphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 650: 3-Hydroxyphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 651: 4-Hydroxyphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 652: 2-methoxyphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 653: 3-Methoxyphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 654: 4-Methoxyphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 655: 2-(Methylamino)phenyl 6-{1,5-dimethyl-4-[methyl(phenyl)carbamoyl]-1R-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 656: 3-(Methylamino)phenyl 6-{1,5-dimethyl-4-[methyl(phenyl)carbamoyl]-1H-pyrrol-2-yl}-7-{[(1S)-3-(morpholin-4-ylmethyl)-3,4-dihydroisoquinolin-2(1H)-yl]carbonyl}-3,4-dihydroisoquinoline-2(1H)-carboxylate EXAMPLE 657: 4-(Methylamino)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 658: 2-(Dimethylamino)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 659: 3-(Dimethylamino)phenyl 6-{1,5-dimethyl-4-[methyl(phenyl) carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 660: 4-(Dimethylamino)phenyl 6-{1,5-dimethyl-4-[methyl(phenyl) carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 661: 2-(Acetylamino)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 662: 3-(Acetylamino)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 663: 4-(Acetylamino)phenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 664: 2-(Trifluoromethyl)phenyl 6-{1,5-dimethyl-4 [methyl(phenyl) carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 665: 3-(Trifluoromethyl)phenyl 6-{1,5-dimethyl-4 [methyl(phenyl) carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 666: 4-(Trifluoromethyl)phenyl 6-{1,5-dimethyl-4-[methyl(phenyl) carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 667: 2-Cyanophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 668: 3-Cyanophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 669: 4-Cyanophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 670: 2-Ethynylphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 671: 3-Ethynylphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 672: 4-Ethynylphenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 673: 2,3-Dichlorophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 674: Naphthalen-1-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 675: 1H-indol-7-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 676: 1-Methyl-1H-indol-7-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 677: 1H-Indol-4-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 678: 1-Methyl-1H-indol-4-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 679: 1H-Pyrrolo[2,3-b]pyridin-4-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 680: 1-Methyl-1H-pyrrolo[2,3-b]pyridin-4-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 681: 3,4-Dichlorophenyl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 682: Naphthalen-2-yl 6-{1,5-dimethyl-4-[methyl(phenyl)carbamoyl]-1H-pyrrol-2-yl}-7{-[(3S)-3-(morpholin-4-ylmethyl)-3,4-dihydroisoquinolin-2(1H)-yl]carbonyl}-3,4-dihydroisoquinoline-2(1H)-carboxylate EXAMPLE 683: 1H-Indol-6-yl 6-{1,5-dimethyl-4-[methyl(phenyl)carbamoyl]-1H-pyrrol-2-yl}-7{-[(3S)-3-(morpholin-4-ylmethyl)-3,4-dihydroisoquinolin-2(1H)-yl]carbonyl}-3,4-dihydroisoquinoline-2(1H)-carboxylate EXAMPLE 684: 1-Methyl-1H-indol-6-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 685: 1H-Indol-5-yl 6-{1,5-dimethyl-4-[methyl(phenyl)carbamoyl]-1H-pyrrol-2-yl}-7{-[(3S)-3-(morpholin-4-ylmethyl)-3,4-dihydroisoquinolin-2(1H)-yl]carbonyl}-3,4-dihydroisoquinoline-2(1H)-carboxylate EXAMPLE 686: 1-Methyl-1H-indol-5-yl 6-{1,5-dimethyl-4-[methyl(phenyl)carbamoyl]-1H-pyrrol-2-yl}-7-{[(1S)-3-(morpholin-4-ylmethyl)-3,4-dihydroisoquinolin-2(1H)-yl]carbonyl}-3,4-dihydroisoquinoline-2(1H)-carboxylate EXAMPLE 687: 1H-Pyrrolo[2,3-b]pyridin-5-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 688: 1-Methyl-1H-pyrrolo[2,3-b]pyridin-5-yl 6-{1,5-dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 689: 1H-Pyrrolo[2,3-b]pyridin-4-yl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1-carboxylate EXAMPLE 690: 1H-Pyrrolo[2,3-b]pyridin-5-yl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 691: 2-(Methylsulfanyl)phenyl 6-{1,5-dimethyl-4-[methyl(phenyl) carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 692: 3-(Methylsulfanyl)phenyl 6-{1,5-dimethyl-4-[methyl(phenyl) carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 693: 4-(Methylsulfanyl)phenyl 6-{1,5-dimethyl-4-[methyl(phenyl) carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 694: 2-(Dimethylcarbamoyl)phenyl 6-{1,5-dimethyl-4-[methyl(phenyl) carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 695: 3-(Dimethylcarbamoyl)phenyl 6-{1,5-dimethyl-4-[methyl(phenyl) carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 696: 4-(Dimethylcarbamoyl)phenyl 6-{1,5-dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinoline-2(1H)-carboxylate EXAMPLE 697: Phenyl 7-{[(3S)-3-(hydroxymethyl)-3,4-dihydroisoquinolin-2(1H)-yl]carbonyl}-6-{4-[(4-hydroxyphenyl)(methyl)carbamoyl]-1,5-dimethyl-1H-pyrrol-2-yl}-3,4-dihydroisoquinoline-2(1H)-carboxylate EXAMPLE 698: 5-[7-{[(3S)-3-(Hydroxymethyl)-3,4-dihydroisoquinolin-2(1H)-yl]carbonyl}-2-(phenylacetyl)-1,2,3,4-tetrahydroisoquinolin-6-yl]-N-(4-hydroxyphenyl)-N,1,2-trimethyl-1H-pyrrole-3-carboxamide EXAMPLE 699: Phenyl 6-{1,5-dimethyl-4-[methyl(phenyl)carbamoyl]-1H-pyrrol-2-yl}-7-{[(3S)-3-(hydroxymethyl)-3,4-dihydroisoquinolin-2(1H)-yl]carbonyl}-3,4-dihydroisoquinoline-2(1H)-carboxylate EXAMPLE 700: 5-[7-{[(3S)-3-(Hydroxymethyl)-3,4-dihydroisoquinolin-2(1H)-yl]carbonyl}-2-(phenylacetyl)-1,2,3,4-tetrahydroisoquinolin-6-yl]-N,1,2-trimethyl-N-phenyl-1H-pyrrole-3-carboxamide EXAMPLE 701: Phenyl 6-[4-(dibutylcarbamoyl)-1,5-dimethyl-1H-pyrrol-2-yl]-7-{[(3S)-3-(hydroxymethyl)-3,4-dihydroisoquinolin-2(1H)-yl]carbonyl}-3,4-dihydroisoquinoline-2(1H)-carboxylate EXAMPLE 702: N,N-Dibutyl-5-[7-{[(3S)-3-(hydroxymethyl)-3,4-dihydroisoquinolin-2(1H)-yl]carbonyl}-2-(phenylacetyl)-1,2,3,4-tetrahydroisoquinolin-6-yl]-1,2-dimethyl-1H-pyrrole-3-carboxamide EXAMPLE 703: Phenyl 6-{4-[(4-hydroxyphenyl)(methyl)carbamoyl]-1,5-dimethyl-1H-pyrrol-2-yl}-7-{[(3S)-3-(methoxymethyl)-3,4-dihydroisoquinolin-2(1H)-yl]carbonyl}-3,4-dihydroisoquinoline-2(1H)-carboxylate EXAMPLE 704: N-(4-Hydroxyphenyl)-5-[7-{[(3S)-3-(methoxymethyl)-3,4-dihydroisoquinolin-2(1H)-yl]carbonyl}-2-(phenylacetyl)-1,2,3,4-tetrahydroisoquinolin-6-yl]-N,1,2-trimethyl-1H-pyrrole-3-carboxamide EXAMPLE 705: Phenyl 6-{1,5-dimethyl-4-[methyl(phenyl)carbamoyl]-1H-pyrrol-2-yl}-7-{[(3S)-3-(methoxymethyl)-3,4-dihydroisoquinolin-2(1H)-yl]carbonyl}-3,4-dihydroisoquinoline-2(1H)-carboxylate EXAMPLE 706: 5-[7-{[(3S)-3-(Methoxymethyl)-3,4-dihydroisoquinolin-2(1H)-yl]carbonyl}-2-(phenylacetyl)-1,2,3,4-tetrahydroisoquinolin-6-yl]-N,1,2-trimethyl-N-phenyl-1H-pyrrole-3-carboxamide EXAMPLE 707: Phenyl 6-[4-(dibutylcarbamoyl)-1,5-dimethyl-1H-pyrrol-2-yl]-7-{[(3S)-3-(methoxymethyl)-3,4-dihydroisoquinolin-2(1H)-yl]carbonyl}-3,4-dihydroisoquinoline-2(1H)-carboxylate EXAMPLE 708: N,N-Dibutyl-5-[7-{[(3S)-3-(methoxymethyl)-3,4-dihydroisoquinolin-2(1H)-yl]carbonyl}-2-(phenylacetyl)-1,2,3,4-tetrahydroisoquinolin-6-yl]-1,2-dimethyl-1H-pyrrole-3-carboxamide EXAMPLE 709: 3-(6-{4-[(4-Hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carbonyloxy)benzoic acid Step A: 6-(4-{[4-(Benzyloxy)phenyl](methyl)carbamoyl}-1,5-dimethyl-1H-pyrrol-2-yl)-7-[(3S)-3-(morpholin-4-ylmethyl)-1,2,3,4-tetrahydroisoquinoline-2-carbonyl]-1,2,3,4-tetrahydroisoquinoline-2-carbonyl chloride To a solution of the product from Preparation 6ba (450 mg, 0.47 mmol, 1 eq) in dichloromethane (45 mL), cooled to 0° C., was added N,N-diisopropylethylamine (0.41 mL, 2.36 mmol, 5 eq) and triphosgene (139 mg, 0.47 mmol, 0.99 eq), and the mixture was stirred for 1 h at ambient temperature. The reaction was diluted with dichloromethane and washed with 1M aqueous HCl. The organic phase was dried over magnesium sulfate and concentrated in vacuo to afford a yellow solid that was used directly in the next step without further purification, and assuming quantitative transformation.

LC/MS ($C_{46}H_{48}ClN_5O_5$) 786 [M+H]$^+$; RT 1.33 (Method B)

Step B: 3-[(Benzyloxy)carbonyl]phenyl 6-(4-{[4-(benzyloxy)phenyl](methyl)carbamoyl}-1,5-dimethyl-1H-pyrrol-2-yl)-7-[(3S)-3-(morpholin-4-ylmethyl)-1,2,3,4-tetrahydroisoquinoline-2-carbonyl]-1,2,3,4-tetrahydroisoquinoline-2-carboxylate To a solution of product obtained from Step A (41 mg, 0.05 mmol) in Acetonitrile (5 mL) was added potassium carbonate (71.87 mg, 0.52 mmol), DMAP (0.052 mmol) and benzyl 3-hydroxybenzoate (0.52 mmol) and the mixture was heated at 60° C. for 16 h.

The reaction mixture was diluted with ethyl acetate, and washed successively with aqueous sodium bicarbonate, and brine. The organic extracts were dried (MgSO$_4$) and concentrated in vacuo. Purification by flash column chromatography (4 g silica; dichloromethane to 5% MeOH/dichloromethane) afforded the desired product.

LC/MS ($C_{60}H_{59}N_5O_8$) no ionisation; RT 1.46 (Method B)

Step C: 3-(6-{4-[(4-Hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carbonyloxy)benzoic acid To a solution of the product obtained in Step B (42 mg, 0.04 mmol, 1 eq) in ethanol (8 mL) was added 10% Pd/C (50 mg) and the mixture was shaken under an atmosphere of hydrogen for ca 4 h. The reaction was filtered through celite, subsequently eluting with methanol, and concentrated in vacuo. Purification by flash column chromatography (4 g silica; dichloromethane to 5% methanol/dichloromethane) afforded the desired product as a solid.

LC/MS ($C_{46}H_{47}N_5O_8$) 798 [M+H]$^+$; RT 1.07 (Method B)
High-Resolution Mass (ESI+):
Empirical formula: $C_{46}H_{47}N_5O_8$
[M+H]$^+$ calculated: 798.3497
[M+H]$^+$ measured: 798.3438

EXAMPLE 710: 3-{2-[6-{4-[(4-Hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinolin-2(1H)-yl]-2-oxoethyl}benzoic acid EXAMPLE 711: 3-({[6-{1,5-Dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinolin-2(1H)-yl]carbonyl}oxy)benzoic acid EXAMPLE 712: 3-{2-[6-{1,5-Dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinolin-2(1H)-yl]-2-oxoethyl}benzoic acid EXAMPLE 713: 3-[({6-[4-(Dibutylcarbamoyl)-1,5-dimethyl-1H-pyrrol-2-yl]-7-{[(3S)-3-(morpholin-4-ylmethyl)-3,4-dihydroisoquinolin-2(1H)-yl]carbonyl}-3,4-dihydroisoquinolin-2(1H)-yl}carbonyl)oxy]benzoic acid EXAMPLE 714: 3-(2-{6-[4-(Dibutylcarbamoyl)-1,5-dimethyl-1H-pyrrol-2-yl]-7-{[(3S)-3-(morpholin-4-ylmethyl)-3,4-dihydroisoquinolin-2(1H)-yl]carbonyl}-3,4-dihydroisoquinolin-2(1H)-yl}-2-oxoethyl)benzoic acid EXAMPLE 715: 3-(6-{4-[(4-Hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carbonyloxy)benzoic acid The procedure is as in Example 709, replacing the product from Preparation 6bb with the product from Preparation 6bf, in Step A.

LC/MS ($C_{42}H_{40}N_4O_7$) 711 RT 1.27 (Method B)
High-Resolution Mass (ESI+):
Empirical formula: $C_{42}H_{40}N_4O_7$
[M+2H]$^{2+}$ calculated: 713.2970
[M+2H]$^{2+}$ measured: 713.2962

EXAMPLE 716: 3-{2-[6-{4-[(4-Hydroxyphenyl)(methyl)carbamoyl]-1,5-dimethyl-1H-pyrrol-2-yl}-7-{[(3R)-3-methyl-3,4-dihydroisoquinolin-2(1H)-yl]carbonyl}-3,4-dihydroisoquinolin-2(1H)-yl]-2-oxoethyl}benzoic acid EXAMPLE 717: 3-({[6-{1,5-Dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinolin-2(1H)-yl]carbonyl}oxy)benzoic acid EXAMPLE 718: 3-{2-[6-{1,5-Dimethyl-4-[methyl(phenyl)carbamoyl]-1H-pyrrol-2-yl}-7-{[(3R)-3-methyl-3,4-dihydroisoquinolin-2(1H)-yl]carbonyl}-3,4-dihydroisoquinolin-2(1H)-yl]-2-oxoethyl}benzoic acid EXAMPLE 719: 3-[({6-[4-(Dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinolin-2(1H)-yl}carbonyl)oxy]benzoic acid EXAMPLE 720: 3-(2-{6-[4-(Dibutylcarbamoyl)-1,5-dimethyl-1H-pyrrol-2-yl]-7-{[(3R)-3-methyl-3,4-dihydroisoquinolin-2(1H)-yl]carbonyl}-3,4-dihydroisoquinolin-2(1H)-yl}-2-oxoethyl)benzoic acid EXAMPLE 721: 4-(6-{4-[(4-Hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carbonyloxy)benzoic acid The procedure is as in Example 709, replacing benzyl 3-hydroxybenzoate from Step B with benzyl 4-hydroxybenzoate.

LC/MS ($C_{46}H_{47}N_5O_8$) 798 [M+H]$^+$; RT 1.07 (Method B)
High-Resolution Mass (ESI+):
Empirical formula: $C_{46}H_{47}N_5O_8$
[M+H]$^+$ calculated: 798.3497
[M+H]$^+$ measured: 798.3475

EXAMPLE 722: 4-{2-[6-{4-[(4-Hydroxyphenyl)(methyl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinolin-2(1H)-yl]-2-oxoethyl}benzoic acid EXAMPLE 723: 4-({[6-{1,5-Dimethyl-4-[methyl(phenyl)carbamoyl]-1H-pyrrol-2-yl}-7-{[(3S)-3-(morpholin-4-ylmethyl)-3,4-dihydroisoquinolin-2(1H)-yl]carbonyl}-3,4-dihydroisoquinolin-2(1H)-yl]carbonyl}oxy)benzoic acid EXAMPLE 724: 4-{2-[6-{1,5-Dimethyl-4-[methyl
(phenyl)carbamoyl]-1H-pyrrol-2-yl}-7-{[(3S)-3-
(morpholin-4-ylmethyl)-3,4-dihydroisoquinolin-2
(1H)-yl]carbonyl}-3,4-dihydroisoquinolin-2(1H)-yl]-
2-oxoethyl}benzoic acid EXAMPLE 725: 4-[({6-[4-(Dibutylcarbamoyl)-1,5-
dimethyl-1H-pyrrol-2-yl]-7-{[(3S)-3-(morpholin-4-
ylmethyl)-3,4-dihydroisoquinolin-2(1H)-yl]carbo-
nyl}-3,4-dihydroisoquinolin-2(1H)-yl]carbonyl)oxy]
benzoic acid EXAMPLE 726: 4-(2-{6-[4-(Dibutylcarbamoyl)-1,
5-dimethyl-1H-pyrrol-2-yl]-7-{[(3S)-3-(morpholin-
4-ylmethyl)-3,4-dihydroisoquinolin-2(1H)-yl]carbo-
nyl}-3,4-dihydroisoquinolin-2(1H)-yl}-2-oxoethyl)
benzoic acid EXAMPLE 727: 4-({[6-{4-[(4-Hydroxyphenyl)
(methyl)carbamoyl]-1,5-dimethyl-1H-pyrrol-2-yl}-
7-{[(3R)-3-methyl-3,4-dihydroisoquinolin-2(1H)-yl]
carbonyl}-3,4-dihydroisoquinolin-2(1H)-yl]
carbonyl}oxy)benzoic acid EXAMPLE 728: 4-{2-[6-{4-[(4-Hydroxyphenyl)
(methyl)carbamoyl]-1,5-dimethyl-1H-pyrrol-2-yl}-
7-{[(3R)-3-methyl-3,4-dihydroisoquinolin-2(1H)-yl]
carbonyl}-3,4-dihydroisoquinolin-2(1H)-yl]-2-
oxoethyl}benzoic acid EXAMPLE 729: 4-({[6-{1,5-Dimethyl-4-[methyl
(phenyl)carbamoyl]-1H-pyrrol-2-}-7-{[(3R)-3-
methyl-3,4-dihydroisoquinolin-2(1H)-yl]carbonyl}-
3,4-dihydroisoquinolin-2(1H)-yl]carbonyl}oxy)
benzoic acid EXAMPLE 730: 4-{2-[6-{1,5-Dimethyl-4-[methyl
(phenyl)carbamoyl]-1H-pyrrol-2-yl}-7-{[(3R)-3-
methyl-3,4-dihydroisoquinolin-2(1H)-yl]carbonyl}-
3,4-dihydroisoquinolin-2(1H)-yl]-2-
oxoethyl}benzoic acid EXAMPLE 731: 4-[({6-[4-(Dibutylcarbamoyl)-1,5-
dimethyl-1H-pyrrol-2-yl]-7-{[(3R)-3-methyl-3,4-
dihydroisoquinolin-2(1H)-yl]carbonyl}-3,4-dihy-
droisoquinolin-2(1H)-yl}carbonyl)oxy]benzoic acid EXAMPLE 732: 4-(2-{6-[4-(Dibutylcarbamoyl)-1,
5-dimethyl-1H-pyrrol-2-yl]-7-{[(3R)-3-methyl-3,4-
dihydroisoquinolin-2(1H)-yl]carbonyl}-3,4-dihy-
droisoquinolin-2(1H)-yl}-2-oxoethyl)benzoic acid EXAMPLE 733: 3-(6-{4-[(4-Hydroxyphenyl)
(methyl)carbamoyl]-1,5-dimethyl-1H-pyrrol-2-yl}-
7-[(3S)-3-[(4-methylpiperazin-1-yl)methyl]-1,2,3,4-
tetrahydroisoquinoline-2-carbonyl]-1,2,3,4-
tetrahydroisoquinoline-2-carbonyloxy)benzoic acid The procedure is as in Example 709, replacing the product from Preparation 6ba with the product from Preparation 6bf, in Step A.

LC/MS ($C_{47}H_{50}N_6O_7$) 811 [M+H]$^+$; RT 2.16 (Method A)

High-Resolution Mass (ESI+):

Empirical formula: $C_{47}H_{50}N_6O_7$

[M+2H]$^{2+}$ calculated: 406.1943

[M+2H]$^{2+}$ measured: 406.1944

EXAMPLE 734: 3-{2-[6-{4-[(4-Hydroxyphenyl)
(methyl)carbamoyl]-1,5-dimethyl-1H-pyrrol-2-yl}-
7-{[(3S)-3-[(4-methylpiperazin-1-yl)methyl]-3,4-
dihydroisoquinolin-2(1H)-yl]carbonyl}-3,4-
dihydroisoquinolin-2(1H)-yl]-2-oxoethyl}benzoic
acid EXAMPLE 735: 3-(6-{1,5-Dimethyl-4-[methyl
(phenyl)carbamoyl]-1H-pyrrol-2-yl}-7-[(3S)-3-[(4-
methylpiperazin-1-yl)methyl]-1,2,3,4-tetrahydroiso-
quinoline-2-carbonyl]-1,2,3,4-
tetrahydroisoquinoline-2-carbonyloxy)benzoic acid The procedure is as in Example 709, replacing the product from Preparation 6ba with the product from Preparation 6ce, in Step A.

LC/MS ($C_{47}H_{50}N_6O_6$) 795 [M+H]$^+$; RT 1.4 (Method B)

High-Resolution Mass (ESI+):

Empirical formula: $C_{47}H_{50}N_6O_6$

[M+2H]$^{2+}$ calculated: 398.1969

[M+2H]$^{2+}$ measured: 398.1985

EXAMPLE 736: 3-{2-[6-{1,5-Dimethyl-4-[methyl
(phenyl)carbamoyl]-1H-pyrrol-2-yl}-7-{[(3S)-3-[(4-
methylpiperazin-1-yl)methyl]-3,4-dihydroisoquino-
lin-2(1H)-yl]carbonyl}-3,4-dihydroisoquinolin-2
(1H)-yl]-2-oxoethyl}benzoic acid EXAMPLE 737: 3-[({6-[4-(Dibutylcarbamoyl)-1,5-
dimethyl-1H-pyrrol-2-yl]-7-{[(3S)-3-[(4-methylpip-
erazin-1-yl)methyl]-3,4-dihydroisoquinolin-2(1H)-
yl]carbonyl}-3,4-dihydroisoquinolin-2(1H)-
yl}carbonyl)oxy]benzoic acid EXAMPLE 738: 3-(2-{6-[4-(Dibutylcarbamoyl)-1,
5-dimethyl-1H-pyrrol-2-yl]-7-{[(3S)-3-[(4-methyl-
piperazin-1-yl)methyl]-3,4-dihydroisoquinolin-2
(1H)-yl]carbonyl}-3,4-dihydroisoquinolin-2(1H)-
yl}-2-oxoethyl)benzoic acid EXAMPLE 739: 4-({[6-{4-[(4-Hydroxyphenyl)
(methyl)carbamoyl]-1,5-dimethyl-1H-pyrrol-2-yl}-
7-{[(3S)-3-[(4-methylpiperazin-1-yl)methyl]-3,4-
dihydroisoquinolin-2(1H)-yl]carbonyl}-3,4-
dihydroisoquinolin-2(1H)-yl]carbonyl}oxy)benzoic
acid EXAMPLE 740: 4-{2-[6-{4-[(4-Hydroxyphenyl)(methyl)carbamoyl]-1,5-dimethyl-1H-pyrrol-2-yl}-7-{[(3S)-3-[(4-methylpiperazin-1-yl)methyl]-3,4-dihydroisoquinolin-2(1H)-yl]carbonyl}-3,4-dihydroisoquinolin-2(1H)-yl]-2-oxoethyl}benzoic acid EXAMPLE 741: 4-({[6-{1,5-Dimethyl-4-[methyl(phenyl)carbamoyl]-1H-pyrrol-2-yl}-7-{[(3S)-3-[(4-methylpiperazin-1-yl)methyl]-3,4-dihydroisoquinolin-2(1H)-yl]carbonyl}-3,4-dihydroisoquinolin-2(1H)-yl]carbonyl}oxy)benzoic acid EXAMPLE 742: 4-{2-[6-{1,5-Dimethyl-4-[methyl(phenyl)carbamoyl]-1H-pyrrol-2-yl}-7-{[(3S)-3-[(4-methylpiperazin-1-yl)methyl]-3,4-dihydroisoquinolin-2(1H)-yl]carbonyl}-3,4-dihydroisoquinolin-2(1H)-yl]-2-oxoethyl}benzoic acid EXAMPLE 743: 4-[({6-[4-(Dibutylcarbamoyl)-1,5-dimethyl-1H-pyrrol-2-yl]-7-{[(3S)-3-[(4-methylpiperazin-1-yl)methyl]-3,4-dihydroisoquinolin-2(1H)-yl]carbonyl}-3,4-dihydroisoquinolin-2(1H)-yl}carbonyl)oxy]benzoic acid EXAMPLE 744: 4-(2-{6-[4-(Dibutylcarbamoyl)-1,5-dimethyl-1H-pyrrol-2-yl]-7-{[(3S)-3-[(4-methylpiperazin-1-yl)methyl]-3,4-dihydroisoquinolin-2(1H)-yl]carbonyl}-3,4-dihydroisoquinolin-2(1H)-yl}-2-oxoethyl)benzoic acid EXAMPLE 745: 5-(2-Acetyl-7-{[(3S)-3-(morpholin-4-ylmethyl)-3,4-dihydroisoquinolin-2(1H)-yl]carbonyl}-1,2,3,4-tetrahydroisoquinolin-6-yl)-N-(4-hydroxyphenyl)-1,2-dimethyl-N-phenyl-1H-pyrrole-3-carboxamide EXAMPLE 746: 5-(2-Acetyl-7-{[(3R)-3-methyl-3,4-dihydroisoquinolin-2(1H)-yl]carbonyl}-1,2,3,4-tetrahydroisoquinolin-6-yl)-N-(4-hydroxyphenyl)-1,2-dimethyl-N-phenyl-1H-pyrrole-3-carboxamide EXAMPLE 747: N-(4-Hydroxyphenyl)-1,2-dimethyl-5-(2-methyl-7-{[(3R)-3-methyl-3,4-dihydroisoquinolin-2(1H)-yl]carbonyl}-1,2,3,4-tetrahydroisoquinolin-6-yl)-N-phenyl-1H-pyrrole-3-carboxamide EXAMPLE 748: 5-(2-Acetyl-7-{[(3S)-3-(morpholin-4-ylmethyl)-3,4-dihydroisoquinolin-2(1H)-yl]carbonyl}-1,2,3,4-tetrahydroisoquinolin-6-yl)-N-(4-hydroxyphenyl)-1,2-dimethyl-N-(1-methyl-1H-pyrrolo[2,3-b]pyridin-5-yl)-1H-pyrrole-3-carboxamide EXAMPLE 749: 5-(2-Acetyl-7-{[(3R)-3-methyl-3,4-dihydroisoquinolin-2(1H)-yl]carbonyl}-1,2,3,4-tetrahydroisoquinolin-6-yl)-N-(4-hydroxyphenyl)-1,2-dimethyl-N-(1-methyl-1H-pyrrolo[2,3-b]pyridin-5-yl)-1H-pyrrole-3-carboxamide EXAMPLE 750: N-(4-Hydroxyphenyl)-1,2-dimethyl-5-(2-methyl-7-{[(3R)-3-methyl-3,4-dihydroisoquinolin-2(1H)-yl]carbonyl}-1,2,3,4-tetrahydroisoquinolin-6-yl)-N-(1-methyl-1H-pyrrolo[2,3-b]pyridin-5-yl)-1H-pyrrole-3-carboxamide EXAMPLE 751: 5-(2-Acetyl-7-{[(3S)-3-(morpholin-4-ylmethyl)-3,4-dihydroisoquinolin-2(1H)-yl]carbonyl}-1,2,3,4-tetrahydroisoquinolin-6-yl)-N-(4-hydroxyphenyl)-1,2-dimethyl-N-(pyridin-4-yl)-1H-pyrrole-3-carboxamide EXAMPLE 752: 5-(2-Acetyl-7-{[(3R)-3-methyl-3,4-dihydroisoquinolin-2(1H)-yl]carbonyl}-1,2,3,4-tetrahydroisoquinolin-6-yl)-N-(4-hydroxyphenyl)-1,2-dimethyl-N-(pyridin-4-yl)-1H-pyrrole-3-carboxamide EXAMPLE 753: N-(4-Hydroxyphenyl)-1,2-dimethyl-5-(2-methyl-7-{[(3R)-3-methyl-3,4-dihydroisoquinolin-2(1H)-yl]carbonyl}-1,2,3,4-tetrahydroisoquinolin-6-yl)-N-(pyridin-4-yl)-1H-pyrrole-3-carboxamide EXAMPLE 754: 5-(2-Acetyl-7-{[(3S)-3-(morpholin-4-ylmethyl)-3,4-dihydroisoquinolin-2(1H)-yl]carbonyl}-1,2,3,4-tetrahydroisoquinolin-6-yl)-1,2-dimethyl-N,N-diphenyl-1H-pyrrole-3-carboxamide EXAMPLE 755: 5-(2-Acetyl-7-{[(3R)-3-methyl-3,4-dihydroisoquinolin-2(1H)-yl]carbonyl}-1,2,3,4-tetrahydroisoquinolin-6-yl)-1,2-dimethyl-N,N-diphenyl-1H-pyrrole-3-carboxamide EXAMPLE 756: 1,2-Dimethyl-5-(2-methyl-7-{[(3R)-3-methyl-3,4-dihydroisoquinolin-2(1H)-yl]carbonyl}-1,2,3,4-tetrahydroisoquinolin-6-yl)-N,N-diphenyl-1H-pyrrole-3-carboxamide EXAMPLE 757: 5-(2-Acetyl-7-{[(3S)-3-(morpholin-4-ylmethyl)-3,4-dihydroisoquinolin-2(1H)-yl]carbonyl}-1,2,3,4-tetrahydroisoquinolin-6-yl)-1,2-dimethyl-N-(1-methyl-1H-pyrrolo[2,3-b]pyridin-5-yl)-N-phenyl-1H-pyrrole-3-carboxamide EXAMPLE 758: 5-(2-Acetyl-7-{[(3R)-3-methyl-3,4-dihydroisoquinolin-2(1H)-yl]carbonyl}-1,2,3,4-tetrahydroisoquinolin-6-yl)-1,2-dimethyl-N-(1-methyl-1H-pyrrolo[2,3-b]pyridin-5-yl)-N-phenyl-1H-pyrrole-3-carboxamide EXAMPLE 759: 1,2-Dimethyl-5-(2-methyl-7-{[(3R)-3-methyl-3,4-dihydroisoquinolin-2(1H)-yl]carbonyl}-1,2,3,4-tetrahydroisoquinolin-6-yl)-N-(1-methyl-1H-pyrrolo[2,3-b]pyridin-5-yl)-N-phenyl-1H-pyrrole-3-carboxamide EXAMPLE 760: 5-(2-Acetyl-7-{[(3S)-3-(morpholin-4-ylmethyl)-3,4-dihydroisoquinolin-2(1H)-yl]carbonyl}-1,2,3,4-tetrahydroisoquinolin-6-yl)-1,2-dimethyl-N-phenyl-N-(pyridin-4-yl)-1H-pyrrole-3-carboxamide EXAMPLE 761: 5-(2-Acetyl-7-{[(3R)-3-methyl-3,4-dihydroisoquinolin-2(1H)-yl]carbonyl}-1,2,3,4-tetrahydroisoquinolin-6-yl)-1,2-dimethyl-N-phenyl-N-(pyridin-4-yl)-1H-pyrrole-3-carboxamide EXAMPLE 762: 1,2-Dimethyl-5-(2-methyl-7-{[(3R)-3-methyl-3,4-dihydroisoquinolin-2(1H)-yl]carbonyl}-1,2,3,4-tetrahydroisoquinolin-6-yl)-N-phenyl-N-(pyridin-4-yl)-1H-pyrrole-3-carboxamide EXAMPLE 763: 4-Methylphenyl 6-{4-[(4-hydroxyphenyl)(1-methyl-1H-pyrazol-4-yl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 764: 4-Methylphenyl 6-{1-[(4-hydroxyphenyl)(1-methyl-1H-pyrazol-4-yl)carbamoyl]-5,6,7,8-tetrahydroindolizin-3-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 765: 4-Methylphenyl 6-{4-[(4-hydroxyphenyl)(pyridin-4-yl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 766: 4-Methylphenyl 6-{1-[(4-hydroxyphenyl)(pyridin-4-yl)carbamoyl]-5,6,7,8-tetrahydroindolizin-3-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 767: 4-Methylphenyl 6-{4-[(4-hydroxyphenyl)(1-methyl-1H-pyrrolo[2,3-b]pyridin-5-yl)carbamoyl]-1,5-dimethyl-1H-pyrrol-2-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 768: 4-Methylphenyl 6-{1-[(4-hydroxyphenyl)(1-methyl-1H-pyrrolo[2,3-b]pyridin-5-yl)carbamoyl]-5,6,7,8-tetrahydroindolizin-3-yl}-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 769: 4-Methylphenyl 6-(1,5-dimethyl-4-{(1-methyl-1H-pyrazol-4-yl)[4-(phosphonooxy)phenyl]carbamoyl}-1H-pyrrol-2-yl)-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 770: 4-Methylphenyl 6-(1-{(1-methyl-1H-pyrazol-4-yl)[4-(phosphonooxy)phenyl]carbamoyl}-5,6,7,8-tetrahydroindolizin-3-yl)-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 771: 4-Methylphenyl 6-(1,5-dimethyl-4-{[4-(phosphonooxy)phenyl](pyridin-4-yl)carbamoyl}-1H-pyrrol-2-yl)-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 772: 4-Methylphenyl 7-{[(3S)-3-(morpholin-4-ylmethyl)-3,4-dihydroisoquinolin-2(1H)-yl]carbonyl}-6-(1-{[4-(phosphonooxy)phenyl](pyridin-4-yl)carbamoyl}-5,6,7,8-tetrahydroindolizin-3-yl)-3,4-dihydroisoquinoline-2(1H)-carboxylate EXAMPLE 773: 4-Methylphenyl 6-(1,5-dimethyl-4-{(1-methyl-1H-pyrrolo[2,3-b]pyridin-5-yl)[4-(phosphonooxy)phenyl]carbamoyl}-1H-pyrrol-2-yl)-7-{[(3S)-3-(morpholin-4-ylmethyl)-3,4-dihydroisoquinolin-2(1H)-yl]carbonyl}-3,4-dihydroisoquinoline-2(1H)-carboxylate EXAMPLE 774: 4-Methylphenyl 6-(1-{(1-methyl-1H-pyrrolo[2,3-b]pyridin-5-yl)[4-(phosphonooxy)phenyl]carbamoyl}-5,6,7,8-tetrahydroindolizin-3-yl)-7-{[(3S)-3-(morpholin-4-ylmethyl)-3,4-dihydroisoquinolin-2(1H)-yl]carbonyl}-4-dihydroisoquinoline-2(1H)-carboxylate EXAMPLE 775: 2-[2-(Dimethylcarbamoyl)ethyl]phenyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 709, replacing the product from Preparation 6ba in Step A with the product from Preparation 6bb, and replacing benzyl 3-hydroxybenzoate from Step B with 3-(2-hydroxyphenyl)-N,N-dimethylpropanamide.

LC/MS ($C_{46}H_{49}N_5O_6$) 768 [M+H]$^+$; RT 2.51 (Method A) High-Resolution Mass (ESI+):

Empirical formula: $C_{46}H_{49}N_5O_6$
[M+2H]$^{2+}$ calculated: 384.6914
[M+2H]$^{2+}$ measured: 384.6929

EXAMPLE 776: 3-[2-(Dimethylcarbamoyl)ethyl]
phenyl 6-{4-[(4-hydroxyphenyl)(methyl)carbamoyl]-1,5-dimethyl-1H-pyrrol-2-yl}-7-[(3R)-3-ethyl-1,2,3,4-tetrahydroisoquinoline-2-carbonyl]-1,2,3,4-tetrahydroisoquinoline-2-carboxylate The procedure is as in Example 709, replacing the product from Preparation 6ba in Step A with the product from Preparation 6bb, and replacing benzyl 3-hydroxybenzoate from Step B with 3-(3-hydroxyphenyl)-N,N-dimethylpropanamide.
LC/MS ($C_{46}H_{49}N_5O_6$) 768 [M+H]$^+$; RT 2.50 (Method A)
High-Resolution Mass (ESI+):
Empirical formula: $C_{46}H_{49}N_5O_6$
[M+2H]$^{2+}$ calculated: 384.6914
[M+2H]$^{2+}$ measured: 384.6913

EXAMPLE 777: 5-{7-[(3S)-3-[(Dimethylamino)methyl]-1,2,3,4-tetrahydroisoquinoline-2-carbonyl]-2-(2-phenylacetyl)-1,2,3,4-tetrahydroisoquinolin-6-yl}-N-(4-hydroxyphenyl)-N,1,2-trimethyl-1H-pyrrole-3-carboxamide Step A: N-[4-(Benzyloxy)phenyl]-5-{7-[(3S)-3-[(dimethylamino)methyl]-1,2,3,4-tetrahydroisoquinoline-2-carbonyl]-2-(2-phenylacetyl)-1,2,3,4-tetrahydroisoquinolin-6-yl}-N,1,2-trimethyl-1H-pyrrole-3-carboxamide A solution of the compound from Preparation 6be (50 mg, 0.05 mmol) and N,N-diisopropylethylamine (48 μL, 0.27 mmol) in dichloromethane (5 mL) was cooled to 0° C. To this was added phenylacetyl chloride (8 μL, 0.06 mmol) and the reaction was then stirred at ambient temperature for 1 h. The reaction mixture was diluted with dichloromethane, washed with 1M aqueous sodium hydroxide, and then brine. The organic extract was dried over magnesium sulphate, filtered and concentrated in vacuo. Purification by flash column chromatography (CombiFlash R$_f$, 4 g RediSep™ silica cartridge; dichloromethane to 10% methanol in dichloromethane) afforded the desired product.
LC/MS ($C_{51}H_{53}N_5O_4$) 800 [M+H]$^+$; RT 1.26 (Method B)

Step B: 5-{7-[(3S)-3-[(dimethylamino)methyl]-1,2,3,4-tetrahydroisoquinoline-2-carbonyl]-2-(2-phenylacetyl)-1,2,3,4-tetrahydroisoquinolin-6-yl}-N-(4-hydroxyphenyl)-N,1,2-trimethyl-1H-pyrrole-3-carboxamide To a solution of the material from Step A (30 mg, 0.04 mmol) in ethanol (5 mL) was added 10% Pd/C (catalytic amount) and the mixture was shaken under an atmosphere of hydrogen for ca 16 h. The mixture is filtered through celite, subsequently eluting with methanol, and concentrated under reduced pressure. Purification by flash column chromatography (CombiFlash R$_f$, 4 g RediSep™ silica cartridge; dichloromethane to 7% methanol in dichloromethane) afforded the desired product.
LC/MS ($C_{44}H_{47}N_5O_4$) 710 [M+H]$^+$; RT 1.07 (Method B)

High-Resolution Mass (ESI+):
Empirical formula: $C_{44}H_{47}N_5O_4$
[M+H]$^+$ calculated: 710.3701
[M+H]$^+$ measured: 710.3702

EXAMPLE 778: N-(4-Hydroxyphenyl)-N,1,2-trimethyl-5-{7-[(3S)-3-[(4-methylpiperazin-1-yl)methyl]-1,2,3,4-tetrahydroisoquinoline-2-carbonyl]-2-(2-phenylacetyl)-1,2,3,4-tetrahydroisoquinolin-6-yl}-1H-pyrrole-3-carboxamide The procedure is as in Example 777, replacing the compound from Preparation 6be in Step A with the compound from Preparation 6bf.
LC/MS ($C_{47}H_{52}N_6O_4$) 765 [M+H]$^+$; RT 1.08 (Method B)
High-Resolution Mass (ESI+):
Empirical formula: $C_{47}H_{52}N_6O_4$
[M+H]$^+$ calculated: 765.4123
[M+H]$^+$ measured: 765.4141

EXAMPLE 779: N-(4-Hydroxyphenyl)-N,1,2-trimethyl-5-{7-[(3S)-3-[2-(morpholin-4-yl)ethyl]-1,2,3,4-tetrahydroisoquinoline-2-carbonyl]-2-(2-phenylacetyl)-1,2,3,4-tetrahydroisoquinolin-6-yl}-1H-pyrrole-3-carboxamide The procedure is as in Example 777, replacing the compound from Preparation 6be in Step A with product from Preparation 6bc.
LC/MS ($C_{47}H_{51}N_5O_5$) 766 [M+H]$^+$; RT 1.08 (Method B)
High-Resolution Mass (ESI+):
Empirical formula: $C_{47}H_{51}N_5O_5$
[M+H]$^+$ calculated: 766.3963
[M+H]$^+$ measured: 766.3982

EXAMPLE 780: N-Ethyl-N-(4-hydroxyphenyl)-1,2-dimethyl-5-{7-[(3S)-3-(morpholin-4-ylmethyl)-1,2,3,4-tetrahydroisoquinoline-2-carbonyl]-2-(2-phenylacetyl)-1,2,3,4-tetrahydroisoquinolin-6-yl}-1H-pyrrole-3-carboxamide The procedure is as in Example 777, replacing the compound from Preparation 6be in Step A with product from Preparation 6f.
LC/MS ($C_{47}H_{51}N_5O_5$) 766 [M+H]$^+$; RT 1.15 (Method B)
High-Resolution Mass (ESI+):
Empirical formula: $C_{47}H_{51}N_5O_5$
[M+H]$^+$ calculated: 766.3963
[M+H]$^+$ measured: 766.3967

EXAMPLE 781: N-(4-Hydroxyphenyl)-1,2-dimethyl-5-{7-[(3S)-3-(morpholin-4-ylmethyl)-1,2,3,4-tetrahydroisoquinoline-2-carbonyl]-2-(2-phenylacetyl)-1,2,3,4-tetrahydroisoquinolin-6-yl}-N-propyl-1H-pyrrole-3-carboxamide The procedure is as in Example 777, replacing the product from Preparation 6be in Step A with the product from Preparation 6g.
LC/MS ($C_{48}H_{53}N_5O_5$) 780 [M+H]$^+$; RT 1.19 (Method B)
High-Resolution Mass (ESI+):
Empirical formula: $C_{48}H_{53}N_5O_5$
[M+H]$^+$ calculated: 780.4119
[M+H]$^+$ measured: 780.4101

EXAMPLE 782: 5-{7-[(3S)-3-[(Dimethylamino)methyl]-1,2,3,4-tetrahydroisoquinoline-2-carbonyl]-2-(trifluoroacetyl)-1,2,3,4-tetrahydroisoquinolin-6-yl}-N-(4-hydroxyphenyl)-N,1,2-trimethyl-1H-pyrrole-3-carboxamide LC/MS ($C_{38}H_{40}F_3N_5O_4$) 688 [M+H]$^+$; RT 1.07 (Method B)
High-Resolution Mass (ESI+):
  Empirical formula: $C_{38}H_{40}N_5O_4F_3$
  [M+H]$^+$ calculated: 688.3105
  [M+H]$^+$ measured: 688.3094

EXAMPLE 783: N-(4-Hydroxyphenyl)-N,1,2-trimethyl-5-{7-[(3S)-3-[(4-methylpiperazin-1-yl)methyl]-1,2,3,4-tetrahydroisoquinoline-2-carbonyl]-2-(trifluoroacetyl)-1,2,3,4-tetrahydroisoquinolin-6-yl}-1H-pyrrole-3-carboxamide LC/MS ($C_{41}H_{45}N_6O_4F_3$) 743 [M+H]$^+$; RT 1.09 (Method B)
High-Resolution Mass (ESI+):
  Empirical formula: $C_{41}H_{45}N_6O_4F_3$
  [M+2H]$^{2+}$ calculated: 372.1800
  [M+2H]$^{2+}$ measured: 372.1801

EXAMPLE 784: 4-Bromophenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate Step A: 4-Bromophenyl 6-(4-{[4-(benzyloxy)phenyl](methyl)carbamoyl}-1,5-dimethyl-1H-pyrrol-2-yl)-7-[(3S)-3-(morpholin-4-ylmethyl)-1,2,3,4-tetrahydroisoquinoline-2-carbonyl]-1,2,3,4-tetrahydroisoquinoline-2-carboxylate To a solution of the compound from Preparation 6ba (108 mg, 0.11 mmol) and N,N-diisopropylethylamine (0.1 mL, 0.57 mmol) in dichloromethane (15 mL), cooled to 0° C., was added triphosgene (34 mg, 0.11 mmol) and the mixture was stirred for 1 h at ambient temperature. The reaction was diluted with dichloromethane and washed with 1M aqueous HCl. The organic extract was dried over magnesium sulfate, filtered and concentrated in vacuo to afford a yellow solid. To a solution of this solid in acetonitrile (10 mL) was added potassium carbonate (152 mg, 1.1 mmol), DMAP (13 mg, 0.11 mmol) and 4-bromophenol (98 mg, 0.57 mmol) and the mixture was heated at 60° C. for ca 16 h. The reaction was diluted with ethyl acetate and washed successively with saturated aqueous sodium bicarbonate, and brine. The organic extract was dried over magnesium sulfate and concentrated in vacuo. Purification by flash column chromatography (CombiFlash R$_f$, 4 g RediSep™ silica cartridge; dichloromethane to 5% methanol in dichloromethane) afforded the desired product (79 mg, 0.09 mmol).

LC/MS ($C_{52}H_{52}BrN_5O_6$) 922 [M+H]$^+$; RT 1.50 (Method B)

Step B: 4-Bromophenyl 6-{4-[(4-hydroxyphenyl)(methyl)carbamoyl]-1,5-dimethyl-M-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The product from Step A was dissolved in dichloromethane (10 mL) and cooled to 0° C. To this was added boron trichloride (5 eq.) drop-wise. The reaction was then allowed to warm to ambient temperature for 1 h. The reaction mixture was adsorbed onto isolute and purified by chromatography (CombiFlash R$_f$, 12 g RediSep™ silica cartridge) eluting in a gradient of dichloromethane to 5% methanol in dichloromethane to afford the desired product.

LC/MS ($C_{45}H_{46}BrN_5O_6$) 832 [M+H]$^+$; RT 1.24 (Method B)
High-Resolution Mass (ESI+):
  Empirical formula: $C_{45}H_{46}N_6O_6Br$
  [M+2H]$^{2+}$ calculated: 416.6388
  [M+2H]$^{2+}$ measured: 416.6374

EXAMPLE 785: 4-Methylphenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate To a solution of product from Preparation 6cb (50 mg, 0.09 mmol) and N,N-diisopropylethylamine (38 µL, 0.19 mmol) in dichloromethane (5 mL), cooled to 0° C., was added 4-methylphenyl chloroformate (15 µL, 0.1 mmol) and the mixture was stirred at ambient temperature for 1 h. The reaction was diluted with dichloromethane, then washed successively with 1M aqueous sodium hydroxide, and brine. The organic extract was dried over magnesium sulfate, filtered and concentrated in vacuo. Purification by flash column chromatography (CombiFlash R$_f$, 12 g RediSep™ silica cartridge; dichloromethane to 5% methanol in dichloromethane) afforded the desired product.

LC/MS ($C_{42}H_{42}N_4O_4$) 667 [M+H]$^+$; RT 1.50 (Method B)
High-Resolution Mass (ESI+):
  Empirical formula: $C_{42}H_{42}N_4O_4$
  [M+H]$^+$ calculated: 667.3279
  [M+H]$^+$ measured: 667.3287

EXAMPLE 786: 4-Cyanophenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate Step A: 6-{1,5-Dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carbonyl chloride To a solution of the product from Preparation 6cb (300 mg, 0.56 mmol) and N,N-diisopropylethylamine (0.29 mL, 1.69 mmol) in dichloromethane (10 mL), cooled to 0° C., was added triphosgene (167 mg, 0.56 mmol) and the mixture was allowed to warm to ambient temperature over 1 h. The reaction was diluted with dichloromethane, washed with 1M aqueous HCl, and dried over magnesium sulphate. Concentration in vacuo afforded a yellow solid that was used directly in the next step without further purification, and assuming quantitative transformation.

LC/MS ($C_{35}H_{35}ClN_4O_3$) 595 [M+H]$^+$; RT 1.41 (Method B)

Step B: 4-Cyanophenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate To a solution of the carbamoyl chloride from Step A (50 mg, 0.072 mmol) in acetonitrile (5 mL) was added potassium carbonate (50 mg, 0.36 mmol) and 4-hydroxybenzonitrile (10 mg, 0.086 mmol). After heating at 60° C. for ca. 16 h the reaction was allowed to cool to ambient temperature, then diluted with ethyl acetate and washed successively with 1M aqueous sodium hydroxide, and brine. The organics extract was dried over magnesium sulphate, concentrated in vacuo, and purified by preparative HPLC to afford the desired product.

LC/MS ($C_{42}H_{39}N_5O_4$) 678 [M+H]$^+$; RT 1.41 (Method B)
High-Resolution Mass (ESI+):
Empirical formula: $C_{42}H_{39}N_5O_4$
[M+H]$^+$ calculated: 678.3075
[M+H]$^+$ measured: 678.3086

EXAMPLE 787: 3-[2-(Dimethylcarbamoyl)ethyl]phenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 786, replacing 4-hydroxybenzonitrile in Step B with 3-(3-hydroxyphenyl)-N,N-dimethylpropanamide.

LC/MS ($C_{46}H_{49}N_5O_5$) 752 [M+H]$^+$; RT 1.39 (Method B)
High-Resolution Mass (ESI+):
Empirical formula: $C_{46}H_{49}N_5O_5$
[M+2H]$^{2+}$ calculated: 376.6940
[M+2H]$^{2+}$ measured: 376.6930

EXAMPLE 788: 4-[2-(Dimethylcarbamoyl)ethyl]phenyl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 786, replacing 4-hydroxybenzonitrile in Step B with 3-(4-hydroxyphenyl)-N,N-dimethylpropanamide.

LC/MS ($C_{46}H_{49}N_5O_5$) 752 [M+H]$^+$; RT 1.38 (Method B)
High-Resolution Mass (ESI+):
Empirical formula: $C_{46}H_{49}N_5O_5$
[M+2H]$^{2+}$ calculated: 376.6940
[M+2H]$^{2+}$ measured: 376.6926

EXAMPLE 789: 1H-Indol-5-yl 6-{1,5-dimethyl-4-[methyl(phenyl)carbamoyl]-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 786, replacing 4-hydroxybenzonitrile in Step B with 1H-indol-5-ol.
LC/MS ($C_{43}H_{41}N_5O_4$) 692 [M+H]$^+$; RT 1.41 (Method B)
High-Resolution Mass (ESI+):
Empirical formula: $C_{43}H_{41}N_5O_4$
[M+H]$^+$ calculated: 692.3231
[M+H]$^+$ measured: 692.3210

EXAMPLE 790: Cyclohexyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 777, replacing the compound from Preparation 6be in Step A with the compound from Preparation 6bb, and replacing phenylacetyl chloride with cyclohexyl chloroformate.

LC/MS ($C_{41}H_{46}N_4O_5$) 675 [M+H]$^+$; RT 1.45 (Method B)
High-Resolution Mass (ESI+):
Empirical formula: $C_{41}H_{46}N_4O_5$
[M+H]$^+$ calculated: 675.3541
[M+H]$^+$ measured: 675.3548

EXAMPLE 791: Cyclohexyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 777, replacing the compound from Preparation 6be in Step A with the compound from Preparation 6ba, and replacing phenylacetyl chloride with cyclohexyl chloroformate.

LC/MS ($C_{45}H_{53}N_5O_6$) no ionisation; RT 1.28 (Method B)
High-Resolution Mass (ESI+):
Empirical formula: $C_{45}H_{53}N_5O_6$
[M+H]$^+$ calculated: 760.4069
[M+H]$^+$ measured: 760.4078

EXAMPLE 792: N-Cyclohexyl-6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxamide The procedure is as in Example 777, replacing the compound from Preparation 6be in Step A with the compound from Preparation 6bb, and replacing phenylacetyl chloride with cyclohexyl isocyanate.

LC/MS ($C_{41}H_{47}N_5O_4$) 674 [M+H]$^+$; RT 1.34 (Method B)
High-Resolution Mass (ESI+):
Empirical formula: $C_{41}H_{47}N_5O_4$
[M+H]$^+$ calculated: 674.3701
[M+H]$^+$ measured: 674.3696

EXAMPLE 793: N-Cyclohexyl-6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxamide The procedure is as in Example 777, replacing the compound from Preparation 6be in Step A with the compound from Preparation 6ba, and replacing phenylacetyl chloride with cyclohexyl isocyanate.

LC/MS ($C_{45}H_{54}N_6O_5$) no ionisation; RT 1.18 (Method B)

High-Resolution Mass (ESI+):
Empirical formula: $C_{45}H_{54}N_6O_5$
[M+H]$^+$ calculated: 759.4228
[M+H]$^+$ measured: 759.4192

EXAMPLE 794: 5-[2-(2-Cyclohexylacetyl)-7-[(3S)-3-(morpholin-4-ylmethyl)-1,2,3,4-tetrahydroisoquinoline-2-carbonyl]-1,2,3,4-tetrahydroisoquinolin-6-yl]-N-(4-hydroxyphenyl)-N,1,2-trimethyl-1H-pyrrole-3-carboxamide The procedure is as in Example 777, replacing the compound from Preparation 6be in Step A with the compound from Preparation 6ba, and replacing phenylacetyl chloride with 2-cyclohexylacetyl chloride.
LC/MS ($C_{46}H_{55}N_5O_5$) no ionisation; RT 1.24 (Method B)
High-Resolution Mass (ESI+):
Empirical formula: $C_{46}H_{55}N_5O_5$
[M+H]$^+$ calculated: 758.4276
[M+H]$^+$ measured: 758.4247

EXAMPLE 795: 5-[2-(2-Cyclohexylacetyl)-7-[(3R)-3-methyl-1,2,3,4-tetrahydroisoquinoline-2-carbonyl]-1,2,3,4-tetrahydroisoquinolin-6-yl]-N-(4-hydroxyphenyl)-N,1,2-trimethyl-1H-pyrrole-3-carboxamide The procedure is as in Example 777, replacing the compound from Preparation 6be in Step A with the compound from Preparation 6bb, and replacing phenylacetyl chloride with 2-cyclohexylacetyl chloride.
LC/MS ($C_{42}H_{48}N_4O_4$) 673 [M+H]$^+$; RT 1.24 (Method B)
High-Resolution Mass (ESI+):
Empirical formula: $C_{42}H_{48}N_4O_4$
[M+H]$^+$ calculated: 673.3748
[M+H]$^+$ measured: 673.3741

EXAMPLE 796: Cyclopentyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 777, replacing the compound from Preparation 6be in Step A with the compound from Preparation 6ba, and replacing phenylacetyl chloride with cyclopentyl chloroformate.
LC/MS ($C_{44}H_{51}N_5O_6$) 746 [M+H]$^+$; RT 1.24 (Method B)
High-Resolution Mass (ESI+):
Empirical formula: $C_{44}H_{51}N_5O_6$
[M+H]$^+$ calculated: 746.3912
[M+H]$^+$ measured: 746.3891

EXAMPLE 797: (1R,2S,5R)-5-Methyl-2-(propan-2-yl)cyclohexyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 777, replacing the compound from Preparation 6be in Step A with the compound from Preparation 6ba, and replacing phenylacetyl chloride with (1R,2S,5R)-5-methyl-2-(propan-2-yl)cyclohexyl chloroformate.
LC/MS ($C_{49}H_{61}N_5O_6$) 816 [M+H]$^+$; RT 1.47 (Method B)
High-Resolution Mass (ESI+):
Empirical formula: $C_{49}H_{61}N_5O_6$
[M+H]$^+$ calculated: 816.4695
[M+H]$^+$ measured: 816.4717

EXAMPLE 798: 5-{2-[2-(Adamantan-1-yl)acetyl]-7-[(3S)-3-(morpholin-4-ylmethyl)-1,2,3,4-tetrahydroisoquinoline-2-carbonyl]-1,2,3,4-tetrahydroisoquinolin-6-yl}-N-(4-hydroxyphenyl)-N,1,2-trimethyl-1H-pyrrole-3-carboxamide The procedure is as in Example 777, replacing the compound from Preparation 6be in Step A with the compound from Preparation 6ba, and replacing phenylacetyl chloride with 2-(adamantan-1-yl)acetyl chloride.
LC/MS ($C_{50}H_{59}N_5O_5$) 810 [M+H]$^+$; RT 1.32 (Method B)
High-Resolution Mass (ESI+):
Empirical formula: $C_{50}H_{59}N_5O_5$
[M+H]$^+$ calculated: 810.4589
[M+H]$^+$ measured: 810.4586

EXAMPLE 799: N-(4-Hydroxyphenyl)-N,1,2-trimethyl-5-{7-[(3R)-3-methyl-1,2,3,4-tetrahydroisoquinoline-2-carbonyl]-2-[2-(piperidin-1-yl)acetyl]-1,2,3,4-tetrahydroisoquinolin-6-yl}-1H-pyrrole-3-carboxamide Step A: N-[4-(Benzyloxy)phenyl]-N,1,2-trimethyl-5-{7-[(3R)-3-methyl-1,2,3,4-tetrahydroisoquinoline-2-carbonyl]-2-[2-(piperidin-1-yl)acetyl]-1,2,3,4-tetrahydroisoquinolin-6-yl}-1H-pyrrole-3-carboxamide To a solution of the compound from Preparation 6bb (50 mg, 0.08 mmol) in DMF (2 mL) was added 2-(1H-benzotriazole-1-yl)-1,1,3,3-tetramethyluronium hexafluorophosphate (30 mg, 0.08 mmol), N,N-diisopropylethylamine (41 µL, 0.23 mmol, 3 eq), and 2-(piperidin-1-yl)acetic acid (13 mg, 0.09 mmol), and the mixture was stirred at ambient temperature for ca. 16 h. The reaction was concentrated in vacuo and partitioned between ethyl acetate and water. The organic phase was washed with brine, dried over magnesium sulfate, filtered and concentrated in vacuo. Purification by flash column chromatography (CombiFlash R$_f$, 4 g RediSep™ silica cartridge; dichloromethane to 10% methanol in dichloromethane) afforded the desired product.
LC/MS ($C_{48}H_{53}N_5O_4$) no ionisation; RT 1.29 (Method B)

Step B: N-(4-Hydroxyphenyl)-N,1,2-trimethyl-5-{7-[(3R)-3-methyl-1,2,3,4-tetrahydroisoquinoline-2-carbonyl]-2-[2-(piperidin-1-yl)acetyl]-1,2,3,4-tetrahydroisoquinolin-6-yl}-1H-pyrrole-3-carboxamide To a solution of the product from Step A (30 mg, 0.04 mmol) in ethanol (5 mL) was added 10% Pd/C (catalytic amount) and the mixture was shaken under an atmosphere of hydrogen for ca 16 h. The mixture was filtered through celite, eluted with methanol, and the filtrate concentrated in vacuo. Purification by preparative HPLC (H$_2$O-TFA/acetonitrile; gradient elution) afforded the desired product.
LC/MS (C$_{41}$H$_{47}$N$_5$O$_4$) 674 [M+H]$^+$; RT 1.09 (Method B)
High-Resolution Mass (ESI+):
Empirical formula: C$_{41}$H$_{47}$N$_5$O$_4$
[M+2H]$^{2+}$ calculated: 337.6887
[M+2H]$^{2+}$ measured: 337.6887

EXAMPLE 800: (1r,4r)-4-{[(tert-Butoxy)carbonyl]amino}cyclohexyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate Step A: (1r,4r)-4-{[(tert-Butoxy)carbonyl]amino}cyclohexyl chloroformate Triphosgene (69 mg, 0.23 mmol) was dissolved in dichloromethane (3 mL) and cooled to 0° C. To this was added a solution of tert-butyl N-(4-hydroxycyclohexyl)carbamate (100 mg, 0.46 mmol) and triethylamine (0.06 mL, 0.46 mmol, 2 eq) in dichloromethane (1 mL) drop-wise. After stirring for 2 h at ambient temperature, the reaction was concentrated in vacuo then re-dissolved/suspended in dichloromethane and filtered. The filtrate (2 mL) was used directly in the next step, assuming a quantitative transformation.

Step B: (1r,4r)-4-{[(tert-Butoxy)carbonyl]amino}cyclohexyl 6-(4-{[4-(benzyloxy)phenyl](methyl)carbamoyl}-1,5-dimethyl-1H-pyrrol-2-yl)-7-[(3R)-3-methyl-1,2,3,4-tetrahydroisoquinoline-2-carbonyl]-1,2,3,4-tetrahydroisoquinoline-2-carboxylate A solution of product from Preparation 6bb (50 mg, 0.08 mmol) in dichloromethane (3 mL) was cooled to 0° C. To this was added triethylamine (54 µL, 0.39 mmol) and the solution of the product from Step A (0.49 mmol) and the mixture was stirred for 30 min at ambient temperature. The reaction was diluted with dichloromethane then washed sequentially with 1M aqueous sodium hydroxide, and brine. The organic phase was dried over magnesium sulfate, filtered and concentrated in vacuo. Purification by flash column chromatography (CombiFlash R$_f$, 4 g RediSep™ silica cartridge; dichloromethane to 3% methanol in dichloromethane) afforded the desired product.
LC/MS (C$_{53}$H$_{61}$N$_5$O$_7$) 780 [M-Boc+H]$^+$; RT 1.60 (Method B)

Step C: (1r,4r)-4-{[(tert-Butoxy)carbonyl]amino}cyclohexyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate To a solution of the product from Step B (96 mg, 0.11 mmol) in ethanol (5 mL) was added 10% Pd/C (catalytic amount) and the mixture was shaken under an atmosphere of hydrogen for ca. 16 h. The mixture was filtered through celite, eluted with methanol, and the filtrate concentrated in vacuo. Purification by flash column chromatography (CombiFlash R$_f$, 4 g RediSep™ silica cartridge; dichloromethane to 5% methanol in dichloromethane) afforded the desired product.
LC/MS (C$_{46}$H$_{55}$N$_5$O$_7$) 790 [M+H]$^+$; RT 1.43 (Method B)
High-Resolution Mass (ESI+):
Empirical formula: C$_{46}$H$_{55}$N$_5$O$_7$
[M+H]$^+$ calculated: 790.4174
[M+H]$^+$ measured: 790.4166

EXAMPLE 801: (1r,4r)-4-Aminocyclohexyl 6-{4-[(4-hydroxyphenyl)(methyl)carbamoyl]-1,5-dimethyl-1H-pyrrol-2-yl}-7-[(3R)-3-ethyl-1,2,3,4-tetrahydroisoquinoline-2-carbonyl]-1,2,3,4-tetrahydroisoquinoline-2-carboxylate hydrochloride The product from Example 800 (48 mg, 0.06 mmol) was dissolved in 4M HCl in 1,4-dioxane (5 mL) and stirred at ambient temperature for ca 15 min. The reaction was concentrated in vacuo to obtain a solid which was suspended in ether and stirred for 1 h at 0° C. The solid was filtered, washed with ether, and dried under vacuum to afford the desired product.
LC/MS (C$_{41}$H$_{47}$N$_5$O$_5$) 690 [M+H]$^+$; RT 1.10 (Method B)
High-Resolution Mass (ESI+):
Empirical formula: C$_{41}$H$_{47}$N$_5$O$_5$
[M+2H]$^{2+}$ calculated: 345.6861
[M+2H]$^{2+}$ measured: 345.6864

EXAMPLE 802: (1r,4r)-4-(Dimethylamino)cyclohexyl 6-{4-[(4-hydroxyphenyl)(methyl)carbamoyl]-1,5-dimethyl-1H-pyrrol-2-yl}-7-[(3R)-3-ethyl-1,2,3,4-tetrahydroisoquinoline-2-carbonyl]-1,2,3,4-tetrahydroisoquinoline-2-carboxylate To a solution of the product from Example 801 (20 mg, 0.03 mmol, 1 eq) in methanol (2 mL) was added paraformaldehyde (4 mg, 0.14 mmol), acetic acid (8 µL, 0.14 mmol, 5 eq) and sodium cyanoborohydride (9 mg, 0.14 mmol), and the mixture was stirred at ambient temperature for ca 16 h. The reaction was quenched by the addition of water (1 mL) and extracted with dichloromethane. The organic extract was washed sequentially with water, and brine, and then dried over magnesium sulfate, filtered and concentrated in vacuo. Purification by preparative HPLC (H$_2$O-TFA/acetonitrile; gradient elution) afforded the desired product
LC/MS (C$_{43}$H$_{51}$N$_5$O$_5$) 718 [M+H]$^+$; RT 1.10 (Method B)
High-Resolution Mass (ESI+):
Empirical formula: C$_{43}$H$_{51}$N$_5$O$_5$
[M+2H]$^{2+}$ calculated: 359.7018
[M+2H]$^{2+}$ measured: 359.7017

EXAMPLE 803: 4-(N-Methylacetamido)phenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate The procedure is as in Example 709, replacing benzyl 3-hydroxybenzoate from Step B with N-(4-hydroxyphenyl)-N-methylacetamide.
LC/MS (C$_{48}$H$_{52}$N$_6$O$_7$) 825 [M+H]$^+$; RT 1.07 (Method B)
High-Resolution Mass (ESI+):
Empirical formula: C$_{48}$H$_{52}$N$_6$O$_7$
[M+2H]$^{2+}$ calculated: 413.2022
[M+2H]$^{2+}$ measured: 413.2031

EXAMPLE 804: 4-[2-(Dimethylcarbamoyl)ethyl]phenyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate The procedure is as in Example 709, replacing the product from Preparation 6ba in Step A with the product from Preparation 6bb, and replacing benzyl 3-hydroxybenzoate from Step B with 3-(4-hydroxyphenyl)-N,N-dimethylpropanamide.

LC/MS ($C_{46}H_{49}N_5O_6$) 384 $[M+2H]^{2+}$; RT 2.49 (Method A)

High-Resolution Mass (ESI+):
Empirical formula: $C_{46}H_{49}N_5O_6$
$[M+2H]^{2+}$ calculated: 384.6914
$[M+2H]^{2+}$ measured: 384.6933

EXAMPLE 805: Tolyl 6-[4-[(5-cyano-1,2-dimethyl-1H-pyrrol-3-yl)-(4-hydroxyphenyl)carbamoyl]-1,5-dimethyl-1H-pyrrol-2-yl]-7-[(3S)-3-(morpholinomethyl)-3,4-dihydro-1H-isoquinoline-2-carbonyl]-3,4-dihydro-1H-isoquinoline-2-carboxylate hydrochloride Step A: Benzyl 7-formyl-6-(4-ethoxycarbonyl-1,5-dimethyl-1H-pyrrol-2-yl)-3,4-dihydro-1H-isoquinoline-2-carboxylate To a solution of 1.3 g of ethyl 1,2-dimethyl-1H-pyrrole-3-carboxylate (7.97 mmol) in 15 mL of N,N-dimethylacetamide there are successively added 2.5 g of benzyl 6-bromo-7-formyl-3,4-dihydro-1H-isoquinoline-2-carboxylate (6.64 mmol), 1.3 g of potassium acetate (13.3 mmol), and then the batch is stirred under argon for 20 minutes. 0.2 g of palladium catalyst $PdCl_2(PPh_3)_2$ (0.33 mmol) is then added. The reaction mixture is then heated at 85° C. for 4.5 hours. The mixture is allowed to return to ambient temperature and is then diluted with ethyl acetate. After filtration, the organic phase is washed with saturated aqueous sodium chloride solution, dried over magnesium sulphate, filtered and concentrated to dryness. The crude product thereby obtained is purified by chromatography over silica gel (petroleum ether/ethyl acetate gradient). The title product is obtained in the form of a yellow foam.

$^1$H NMR (400 MHz, dmso-d6) δ ppm: 9.78 (s, 1H), 7.78 (s, 1H), 7.45-7.3 (m, 5H), 7.32 (s, 1H), 6.39 (s, 1H), 5.14 (s, 2H), 4.72 (m, 2H), 4.18 (q, 2H), 3.68 (m, 2H), 3.31 (s, 3H), 2.93 (t, 2H), 2.55 (s, 3H), 1.25 (t, 3H)

Step B: 2-Benzyloxycarbonyl-6-(4-ethoxycarbonyl-1,5-dimethyl-1H-pyrrol-2-yl)-3,4-dihydro-1H-isoquinoline-7-carboxylic acid A solution containing 1.3 g of the compound obtained in Step A (2.82 mmol) and 2.4 mL (22.6 mmol) of 2-methyl-2-butene in a mixture composed of 2.5 mL of acetone and 2.5 mL of tetrahydrofuran is prepared. There are added, dropwise at 0° C., 20 mL of an aqueous solution containing a mixture of 0.64 g of $NaClO_2$ (7.05 mmol) and 1.4 g of $NaHPO_4$ (9.88 mmol). The batch is then stirred vigorously at ambient temperature for 16 hours. The reaction mixture is then concentrated to remove the acetone and the tetrahydrofuran. Ethyl acetate is added and the organic phase is washed with water and then with saturated aqueous sodium chloride solution, dried over magnesium sulphate, filtered and concentrated to dryness. The yellow foam then obtained is subsequently used without being otherwise purified.

$^1$H NMR (400 MHz, dmso-d6) δ ppm: 12.75 (m, 1H), 7.69 (s, 1H), 7.44-7.3 (m, 5H), 7.14 (s, 1H), 6.2 (s, 1H), 5.14 (s, 2H), 4.67 (m, 2H), 4.15 (q, 2H), 3.67 (m, 2H), 3.21 (s, 3H), 2.86 (m, 2H), 2.49 (s, 3H), 1.24 (t, 3H)

Step C: Benzyl 6-(4-ethoxycarbonyl-1,5-dimethyl-1H-pyrrol-2-yl)-7-[(3S)-3-(morpholinomethyl)-3,4-dihydro-1H-isoquinoline-2-carbonyl]-3,4-dihydro-1H-isoquinoline-2-carboxylate To a solution of 1.5 g of the compound obtained in Step B (2.49 mmol) in 13 mL of dichloromethane there are added 0.636 g of 4-[[(3S)-1,2,3,4-tetrahydroisoquinolin-3-yl]methyl]morpholine (2.74 mmol), 1.1 mL of N,N,N-triethylamine (7.47 mmol), 0.51 g of 1-ethyl-3-(3'-dimethylaminopropyl)-carbodiimide (EDC) (2.99 mmol) and then 0.4 g of hydroxybenzotriazole (HOBT) (2.99 mmol). The reaction mixture is stirred at ambient temperature for 16 hours and is then diluted with a mixture of dichloromethane and saturated sodium hydrogen carbonate solution. After separation of the phases, the organic phase is dried over magnesium sulphate, filtered and evaporated to dryness. The crude product thereby obtained is then purified by chromatography over silica gel (dichloromethane/ethyl acetate gradient). The product is obtained in the form of a white foam.

$^1$H NMR (500 MHz, dmso-d6) δ ppm: 7.4-7.3 (m, 5H), 7.25-7.15 (4*s, 2H), 7.2-6.9 (m, 4H), 6.32/6.28/6.1 (3*bs, 1H), 5.15 (3*s, 2H), 5.15/4.85/3.7 (3*m, 1H), 5-4 (m, 2H), 4.7 (m, 2H), 4.1 (m, 2H), 3.78/3.6 (2*m, 2H), 3.6-3.4 (m, 4H), 3.45/3.39/3.2 (3*s, 3H), 3-2.45 (m, 2H), 2.9 (m, 2H), 2.5-1.9 (4*m, 4H), 2.5/2.41/2.05 (4*bs, 3H), 2.35-1.7 (m, 2H), 1.2/1.1 (3*t, 3H)

$^{13}$C NMR (500 MHz, dmso-d6) δ ppm: 130/125, 129-126, 128, 110, 66.5, 66.5, 59, 57.5, 53.5, 49.5/44.5/43, 45.5, 44.5/41, 41.5, 31.5, 30/29, 28, 15, 11.5

Step D: 1,2-Dimethyl-5-[7-[(3S)-3-(morpholinomethyl)-3,4-dihydro-1H-isoquinoline-2-carbonyl]-1,2,3,4-tetrahydroisoquinolin-6-yl]-1H-pyrrole-3-carboxylic acid To a solution of 1.1 g of the compound obtained in Step C (1.59 mmol) in 8 ml of ethanol there is added 0.9 ml of aqueous 5N sodium hydroxide solution (4.77 mmol). The reaction mixture is stirred at ambient temperature for 24 hours at 80° C. and a second addition of 0.9 ml of aqueous 5N sodium hydroxide solution is made. After being in contact for a period of 24 hours at the same temperature, this operation is carried out a second time. The ethanol is then concentrated and the reaction mixture is diluted with water before adding aqueous 1N hydrochloric acid solution until the pH is 7. After extracting the aqueous phase with dichloromethane, the organic phases are combined and concentrated to dryness to obtain the title product in the form of a yellow foam.

$^1$H NMR (500 MHz, dmso-d6) δ ppm: 7.2-6.9 (m, 4H), 7.05/7 (2*s, 2H), 6.31/6.25/6.1 (3*s, 1H), 5.1/4.85/3.7 (3*m, 1H), 4.15/4.1 (m, 2H), 3.91/3.81 (bs+dd, 2H), 3.6-3.4 (m, 4H), 3.4/3.35/3.15 (3*s, 3H), 3-2.9 (m, 2H), 2.9-1.9 (m, 2H), 2.75 (m, 2H), 2.5/2.4/1.98 (3*s, 3H), 2.5-1.9 (m, 6H)

$^{13}$C NMR (500 MHz, dmso-d6) δ ppm: 130/125, 129-126, 110.5, 66.5, 57/54, 49.5/44.5/43, 47.5, 44, 43.5, 32, 30, 29, 11.5

Step E: 1,2-Dimethyl-5-[2-(4-methylphenoxy)carbonyl-7-[(3S)-3-(morpholinomethyl)-3,4-dihydro-1H-isoquinoline-2-carbonyl]-3,4-dihydro-1H-isoquinolin-6-yl]-1H-pyrrole-3-carboxylic acid To a solution of 0.35 g of the compound obtained in Step D (0.66 mmol) in 1 ml of dioxane there is added, at 0° C., 0.33 ml of aqueous 2N sodium hydroxide solution (0.66 mmol) and, each in several portions, 0.106 ml of p-tolyl chloroformate (0.73 mmol) and 0.36 ml of aqueous 2N sodium hydroxide solution (0.73 mmol). The reaction mixture is stirred for 2 hours at ambient temperature and is then diluted with water and extracted with dichloromethane. The aqueous phase is acidified and then extracted with dichloromethane. The organic phases are combined, dried over magnesium sulphate, filtered and concentrated.

The residue obtained is taken up in 12 ml of methanol and 3.2 ml of aqueous 1N potassium hydroxide solution (3.26 mmol) and then the reaction mixture is stirred at ambient temperature for 20 minutes. After adding aqueous 0.1N hydrochloric acid solution until the pH is 4, the mixture is extracted with dichloromethane. The organic phases are combined, washed with saturated aqueous sodium chloride solution, dried over magnesium sulphate, filtered and concentrated. The residue is then taken up in a mixture of dichloromethane and iso-propyl ether. The solid then obtained is filtered off and washed with ether. The title product is obtained in the form of a solid, which is subsequently used without being otherwise purified.

$^{1}$H NMR (500 MHz, dmso-d6) δ ppm: 11.5 (bs, 1H), 7.28 (bs, 1H), 7.2-6.9 (m, 4H), 7.2 (bd, 2H), 7.02 (bd, 2H), 6.88 (bs, 1H), 6.35/6.28/6.12 (3*s, 1H), 5.11/4.85/3.7 (3*m, 1H), 4.85-4.65 (m, 2H), 4.8-4.1 (m, 2H), 4.2-3.6 (m, 2H), 3.6-3.4 (m, 4H), 3.45/3.4/3.18 (3*s, 3H), 3-1.8 (m, 2H), 2.97 (ml, 2H), 2.5/2.41/1.99 (4*s, 3H), 2.5-1.9 (4*m, 4H), 2.35/2.18 (2*m, 2H), 2.25 (bs, 3H)

$^{13}$C NMR (500 MHz, dmso-d6) δ ppm: 130, 129, 129-126, 125, 122, 110.5, 66.5, 58, 54, 49.5/44/43, 45.5, 44.5/41.5, 41.5, 32, 30-29, 28, 20.5, 11

Step F: Tolyl 6-{4-[(5-cyano-1,2-dimethyl-1H-pyrrol-3-yl)-(4-hydroxyphenyl)carbamoyl]-1,5-dimethyl-1H-pyrrol-2-yl}-7-[(3S)-3-(morpholinomethyl)-3,4-dihydro-1H-isoquinoline-2-carbonyl]-3,4-dihydro-1H-isoquinoline-2-carboxylate hydrochloride To a solution of 0.232 g of the compound obtained in Step E (0.35 mmol) in 9 mL of dichloroethane there is added 0.05 mL of 1-chloro-N,N,2-trimethyl-prop-1-en-1-amine (0.385 mmol). The reaction mixture is stirred at ambient temperature for 2 hours and there is then added 0.131 g of 4-[4-[tert-butyl(dimethyl)silyl]oxyanilino]-1,5-dimethyl-1H-pyrrole-2-carbonitrile (0.385 mmol, product of Preparation 3f). The batch is stirred at 80° C. overnight. The reaction mixture is diluted with a mixture of dichloromethane and saturated aqueous sodium hydrogen carbonate solution. After separation of the phases, the organic phase is dried over magnesium sulphate, filtered and concentrated to dryness. The crude product thereby obtained is subsequently used without being otherwise purified.

To a solution of the compound thereby obtained in 1.8 ml of tetrahydrofuran there is added 0.53 ml of a 1N solution of tetrabutylammonium fluoride in tetrahydrofuran (13.5 mmol). The reaction mixture is stirred at ambient temperature for 1 hour and is then diluted with a mixture of dichloromethane and saturated aqueous sodium hydrogen carbonate solution. The aqueous phase is extracted with dichloromethane and then the organic phases are combined, dried over magnesium sulphate, filtered and concentrated. The crude product is then purified by chromatography over silica gel (dichloromethane/methanol gradient). The solid thereby obtained is converted to the hydrochloride form, dissolved in a mixture of acetonitrile and water, filtered and then lyophilised to isolate the title product.

High-Resolution Mass (ESI/FIA/HR and MS/MS):
  Empirical formula: $C_{52}H_{53}N_7O_6$
  [M+H]$^+$ calculated: 872.4130
  [M+H]$^+$ measured: 872.4130
  Elemental microanalysis: (%, theoretical:measured)
  % C=68.75:68.07; % H=5.99:5.90; % N=10.79:10.68; % Cl$^-$=3.90:3.84

EXAMPLE 806: N-(4-Hydroxyphenyl)-5-(2-[(2S)-2-hydroxy-2-phenylacetyl]-6-{[(3R)-3-methyl-3,4-dihydroisoquinolin-2(1H)-yl]carbonyl}-2,3-dihydro-1H-isoindol-5-yl)-N,1,2-trimethyl-1H-pyrrole-3-carboxamide

EXAMPLE 807: Cyclohexyl 6-{4-[(4-hydroxyphenyl)(methyl)carbamoyl]-1,5-dimethyl-1H-pyrrol-2-yl}-7-[(3S)-3-[2-(morpholin-4-yl)ethyl]-1,2,3,4-tetrahydroisoquinoline-2-carbonyl]-1,2,3,4-tetrahydroisoquinoline-2-carboxylate The procedure is as in Example 777, replacing the compound from Preparation 6be in Step A with the compound from Preparation 6bc, and replacing phenylacetyl chloride with cyclohexyl chloroformate.

LC/MS ($C_{46}H_{55}N_5O_6$) 774 [M+H]$^+$; RT 1.22 (Method B)

EXAMPLE 808: Phenyl 6-{4-[(4-hydroxyphenyl)(methyl)carbamoyl]-1,5-dimethyl-1H-pyrrol-2-yl}-7-[(3R)-3-[3-(morpholin-4-yl)propyl]-1,2,3,4-tetrahydroisoquinoline-2-carbonyl]-1,2,3,4-tetrahydroisoquinoline-2-carboxylate The procedure is as in Example 777, replacing the compound from Preparation 6be in Step A with product from Preparation 6bd; and replacing phenylacetyl chloride in Step A with phenyl chloroformate.

LC/MS ($C_{47}H_{51}N_5O_6$) 782 [M+H]$^+$; RT 1.15 (Method B)

EXAMPLE 809: Cyclohexyl 6-{4-[(4-hydroxyphenyl)(methyl)carbamoyl]-1,5-dimethyl-1H-pyrrol-2-yl}-7-[(3R)-3-[3-(morpholin-4-yl)propyl]-1,2,3,4-tetrahydroisoquinoline-2-carbonyl]-1,2,3,4-tetrahydroisoquinoline-2-carboxylate The procedure is as in Example 777, replacing the compound from Preparation 6be in Step A with the compound from Preparation 6bd, and replacing phenylacetyl chloride with cyclohexyl chloroformate.

LC/MS ($C_{47}H_{57}N_5O_6$) 788 [M+H]$^+$; RT 1.21 (Method B)

EXAMPLE 810: Phenyl 6-{1,5-dimethyl-4-[methyl(phenyl)carbamoyl]-1H-pyrrol-2-yl}-7-[(3R)-3-[3-(morpholin-4-yl)propyl]-1,2,3,4-tetrahydroisoquinoline-2-carbonyl]-1,2,3,4-tetrahydroisoquinoline-2-carboxylate EXAMPLE 811: Cyclohexyl 6-{1,5-dimethyl-4-[methyl(phenyl)carbamoyl]-1H-pyrrol-2-yl}-7-[(3R)-3-[3-(morpholin-4-yl)propyl]-1,2,3,4-tetrahydroisoquinoline-2-carbonyl]-1,2,3,4-tetrahydroisoquinoline-2-carboxylate The procedure is as in Example 114, replacing the product from Preparation 6cb with the product from Preparation 6cd, and replacing phenyl chloroformate with cyclohexyl chloroformate.

LC/MS ($C_{47}H_{57}N_5O_5$) 772 [M+H]$^+$; RT 1.33 (Method B)

Pharmacological Study

EXAMPLE A: INHIBITION OF BCL-2 BY THE FLUORESCENCE POLARISATION TECHNIQUE

The fluorescence polarisation tests were carried out on microplates (384 wells). The Bcl-2 protein, labelled (histag-Bcl-2 such that Bcl-2 corresponds to the UniProtKB® primary accession number: P10415), at a final concentration of 2.50×10$^{-8}$ M, is mixed with a fluorescent peptide (Fluorescein-REIGAQLRRMADDLNAQY), at a final concentration of 1.00×10$^{-8}$ M in a buffer solution (Hepes 10 mM, NaCl 150 mM, Tween20 0.05%, pH 7.4), in the presence or in the absence of increasing concentrations of test compounds. After incubation for 2 hours, the fluorescence polarisation is measured.

The results are expressed in IC$_{50}$ (the concentration of compound that inhibits fluorescence polarisation by 50%) and are presented in Table 1 below.

The results show that the compounds of the invention inhibit interaction between the Bcl-2 protein and the fluorescent peptide described hereinbefore.

EXAMPLE B: IN VITRO CYTOTOXICITY

The cytotoxicity studies were carried out on the RS4;11 leukaemia cell line and on H146 small Cell Lung Carcinoma cell line. The cells are distributed onto microplates and exposed to the test compounds for 48 hours. The cell viability is then quantified by a colorimetric assay, the Microculture Tetrazolium Assay (Cancer Res., 1987, 47, 939-942). The results are expressed in IC$_{50}$ (the concentration of compound that inhibits cell viability by 50%) and are presented in Table 1 below.

The results show that the compounds of the invention are cytotoxic.

TABLE 1

IC$_{50}$ of Bcl-2 inhibition (fluorescence polarisation test) and of cytotoxicity for RS4;11 cells

| | IC$_{50}$ (nM) Bcl-2 FP | IC$_{50}$ (nM) MTT RS4;11 |
|---|---|---|
| Example 1 | 13 | 140 |
| Example 2 | 397 | >1880 |
| Example 3 | 18 | 236 |
| Example 4 | 9.2 | 71 |
| Example 5 | 43 | 70 |
| Example 6 | 95 | >1880 |
| Example 7 | 72% @ 3.3 µM | 1080 |
| Example 8 | 7.3 | 98 |
| Example 9 | 9.0 | 125 |
| Example 10 | 127 | ND |
| Example 11 | 22 | 763 |
| Example 12 | 43 | 759 |
| Example 13 | 108 | 729 |
| Example 14 | 7.9 | 27 |
| Example 15 | 19 | 93 |
| Example 16 | 6.0 | 27 |
| Example 17 | 91 | 1760 |
| Example 18 | 38 | 1290 |
| Example 19 | 47 | 774 |
| Example 20 | 20 | >150 |
| Example 21 | 14 | 112 |
| Example 22 | 70 | >150 |
| Example 23 | 13 | 61 |
| Example 24 | 19 | >150 |
| Example 25 | 29 | 144 |
| Example 26 | 30 | 86 |
| Example 27 | 83 | ND |
| Example 28 | 23 | >150 |
| Example 29 | 28 | >150 |
| Example 30 | 16 | 119 |
| Example 31 | 7.4 | 113 |
| Example 32 | 47 | 141 |
| Example 33 | 33 | 460 |
| Example 34 | 4.9 | 19 |
| Example 35 | 4.7 | 8.5 |
| Example 36 | 4.8 | 6.2 |
| Example 37 | 4.9 | 18 |
| Example 38 | 23 | 532 |
| Example 39 | 14 | 106 |
| Example 40 | 3.6 | 34 |
| Example 41 | 26 | 78 |
| Example 42 | 38 | >150 |
| Example 43 | 77 | 502 |
| Example 44 | 13 | 443 |
| Example 45 | 15 | 20 |
| Example 46 | 3.7 | 2.8 |
| Example 47 | 12 | 45 |
| Example 48 | 8.7 | 40 |
| Example 49 | 23 | 58 |
| Example 50 | 18 | 26 |
| Example 51 | 5.5 | 23 |
| Example 52 | 3.8 | 56 |
| Example 53 | 2.4 | 5.0 |
| Example 54 | 4.0 | 2.4 |
| Example 55 | 16 | 372 |
| Example 56 | 3.8 | 59 |
| Example 57 | 65 | 1250 |
| Example 58 | 4.2 | 3.3 |
| Example 59 | 3.2 | 6.8 |
| Example 60 | 5.9 | 46 |
| Example 61 | 4.4 | 85 |
| Example 62 | 20 | 113 |
| Example 63 | 4.4 | 12 |
| Example 64 | 27 | 204 |
| Example 65 | 6.5 | 51 |
| Example 66 | 16 | 80 |
| Example 67 | 9.4 | 51 |
| Example 68 | 2.9 | 1.8 |
| Example 69 | 3.1 | 3.46 |
| Example 70 | 5.1 | 9.8 |
| Example 71 | 3.7 | 9.9 |
| Example 72 | 21 | 229 |
| Example 73 | 4.3 | 36 |
| Example 74 | 6.1 | 94 |
| Example 75 | 4.0 | 6.2 |

TABLE 1-continued

IC$_{50}$ of Bcl-2 inhibition (fluorescence polarisation test) and of cytotoxicity for RS4;11 cells

| | IC$_{50}$ (nM) Bcl-2 FP | IC$_{50}$ (nM) MTT RS4;11 |
|---|---|---|
| Example 76 | 24 | >150 |
| Example 77 | 4.0 | 84 |
| Example 78 | 4.4 | 142 |
| Example 79 | 5.6 | >150 |
| Example 80 | 5.5 | 71 |
| Example 81 | 21 | >150 |
| Example 82 | 17 | >150 |
| Example 83 | 15 | 122 |
| Example 84 | 4.9 | 33 |
| Example 85 | 6.1 | 58 |
| Example 86 | 5.5 | 60 |
| Example 87 | 5.1 | 43 |
| Example 88 | 3.5 | 3.9 |
| Example 89 | 3.5 | 24 |
| Example 90 | 6.2 | 39 |
| Example 91 | 7.0 | 73 |
| Example 92 | 20 | 105 |
| Example 93 | 5.1 | 11 |
| Example 94 | 5.6 | 19 |
| Example 95 | 14 | 115 |
| Example 96 | 3.9 | 9.1 |
| Example 97 | 4.9 | 15 |
| Example 98 | 3.8 | 1.8 |
| Example 99 | 5.5 | 13 |
| Example 100 | 3.9 | 6.5 |
| Example 101 | 2.6 | 31 |
| Example 102 | 5.0 | 75 |
| Example 103 | 3.6 | 46 |
| Example 104 | 6.7 | 65 |
| Example 105 | 7.3 | 31 |
| Example 106 | 5.3 | 38 |
| Example 107 | 3.5 | 6.9 |
| Example 108 | 2.7 | 15 |
| Example 109 | 8.6 | 89 |
| Example 110 | 19 | 329 |
| Example 111 | 8.4 | 64 |
| Example 112 | 42 | 394 |
| Example 113 | 3.6 | 25 |
| Example 114 | 3.8 | 28 |
| Example 115 | 3.4 | 24 |
| Example 116 | 21 | 181 |
| Example 117 | 2.5 | 39 |
| Example 118 | 3.4 | 43 |
| Example 119 | 622 | >150 |
| Example 120 | 2.5 | 8.2 |
| Example 121 | 2.9 | 2.8 |
| Example 122 | 2.6 | 5.4 |
| Example 123 | 5.3 | 8.3 |
| Example 124 | 12 | 50 |
| Example 125 | 8.7 | 49 |
| Example 126 | 5.9 | 5.2 |
| Example 127 | 3.3 | 6.4 |
| Example 128 | 3.5 | 8.2 |
| Example 129 | 3.3 | 39 |
| Example 130 | 3.1 | 36 |
| Example 131 | 4.0 | 11 |
| Example 132 | 4.6 | 32 |
| Example 133 | 7.0 | 8.2 |
| Example 134 | 4.3 | 2.0 |
| Example 135 | 8.4 | 99 |
| Example 136 | 6.7 | 24 |
| Example 137 | 9.4 | 47 |
| Example 138 | 12 | 114 |
| Example 139 | 5.1 | 0.84 |
| Example 140 | 6.6 | 4.0 |
| Example 141 | 5.9 | 82 |
| Example 142 | 5.5 | 53 |
| Example 143 | 5.5 | 9.3 |
| Example 144 | 4.8 | 82 |
| Example 145 | 4.2 | 5.5 |
| Example 146 | 2.8 | 6.0 |
| Example 147 | 3.2 | 2.3 |
| Example 148 | 3.0 | 10 |
| Example 149 | 11 | 124 |
| Example 150 | 4.3 | 16 |
| Example 151 | 5.3 | 19 |
| Example 152 | 6.5 | 29 |
| Example 153 | 4.2 | 3.6 |
| Example 154 | 3.9 | 5.9 |
| Example 155 | 3.2 | 2.9 |
| Example 156 | 6.8 | 121 |
| Example 157 | 21 | >600 |
| Example 158 | 4.6 | 3.5 |
| Example 159 | 8.5 | 163 |
| Example 160 | 6.9 | 86 |
| Example 161 | 68 | >150 |
| Example 162 | 33 | >150 |
| Example 163 | 27 | >150 |
| Example 164 | 14 | >150 |
| Example 165 | 18 | >150 |
| Example 166 | 6.4 | 58 |
| Example 167 | 6.5 | 20 |
| Example 168 | 5.7 | 6.6 |
| Example 169 | 3.3 | 3.0 |
| Example 170 | 12 | 491 |
| Example 171 | 5.1 | 63 |
| Example 172 | 3.4 | 28 |
| Example 173 | 55 | >600 |
| Example 174 | 5.9 | 407 |
| Example 175 | 4.2 | 90 |
| Example 176 | 78 | ND |
| Example 185 | 3.7 | 4.5 |
| Example 186 | 2.5 | 4.5 |
| Example 187 | 3.0 | 4.6 |
| Example 197 | 26 | >150 |
| Example 211 | 3.4 | 6.9 |
| Example 214 | 2.7 | 4.1 |
| Example 216 | 2.4 | 2.9 |
| Example 232 | 2.9 | 11 |
| Example 245 | 4.2 | 92 |
| Example 253 | 5.2 | 22 |
| Example 392 | 2.0 | 14 |
| Example 434 | 2.9 | 1.6 |
| Example 446 | 4.3 | 14 |
| Example 448 | 4.0 | 8.2 |
| Example 474 | 4.5 | 2.6 |
| Example 476 | 1.8 | ND |
| Example 488 | 5.3 | 13 |
| Example 489 | 3.2 | 68 |
| Example 560 | 8.8 | 70 |
| Example 564 | 4.5 | 3.3 |
| Example 573 | 18 | 43 |
| Example 574 | 8.8 | 11 |
| Example 575 | 6.3 | 12 |
| Example 577 | 5.9 | 4.7 |
| Example 579 | 4.4 | 17 |
| Example 591 | 2.5 | 7.0 |
| Example 629 | 7.2 | 9.0 |
| Example 631 | 5.2 | 8.2 |
| Example 633 | 6.1 | 22 |
| Example 634 | 6.9 | 21 |
| Example 636 | 11 | 34 |
| Example 709 | 4.8 | >150 |
| Example 715 | 2.2 | >150 |
| Example 721 | 4.9 | >150 |
| Example 733 | 1.5 | >150 |
| Example 735 | 12 | >150 |
| Example 775 | 2.4 | 6.3 |
| Example 776 | 2.2 | 1.1 |
| Example 777 | 4.1 | 30 |
| Example 778 | 3.1 | 52 |
| Example 779 | 2.9 | 24 |
| Example 780 | 3.5 | 17 |
| Example 781 | 2.6 | 9.7 |
| Example 782 | 51 | 112 |
| Example 783 | 23 | >150 |
| Example 784 | 5.1 | 2.9 |
| Example 785 | 3.3 | 7.8 |
| Example 786 | 8.4 | 24 |
| Example 787 | 5.0 | 6.2 |

TABLE 1-continued

IC$_{50}$ of Bcl-2 inhibition (fluorescence polarisation test) and of cytotoxicity for RS4;11 cells

| | IC$_{50}$ (nM) Bcl-2 FP | IC$_{50}$ (nM) MTT RS4;11 |
|---|---|---|
| Example 788 | 4.4 | 14 |
| Example 789 | 8.9 | 14 |
| Example 790 | 3.4 | 20 |
| Example 791 | 2.8 | 54 |
| Example 792 | 4.6 | 21 |
| Example 793 | 4.4 | 92 |
| Example 794 | 4.6 | 70 |
| Example 795 | 5.3 | 32 |
| Example 796 | 6.2 | 48 |
| Example 797 | 21 | 125 |
| Example 798 | 9.1 | 76 |
| Example 799 | 15 | >150 |
| Example 800 | 2.0 | 3.2 |
| Example 801 | 2.7 | >150 |
| Example 802 | 4.0 | 99 |
| Example 803 | 4.6 | 37 |
| Example 804 | 3.6 | 2.2 |
| Example 805 | 3.1 | 0.12 |
| Example 806 | 33 | >150 |
| Example 807 | 3.9 | 26 |
| Example 808 | 2.7 | 1.6 |
| Example 809 | 3.1 | 9.8 |
| Example 811 | 3.8 | 94 |

ND: not determined

For partial inhibitors, the percentage fluorescence polarisation inhibition for a given concentration of the test compound is indicated. Accordingly, 72% @3.3 µM means that 72% fluorescence polarisation inhibition is observed for a concentration of test compound equal to 3.3 µM.

EXAMPLE C: INDUCTION OF CASPASE ACTIVITY IN VIVO

The ability of the compounds of the invention to activate caspase 3 is evaluated in a xenograft model of RS4;11 leukaemia cells.

1×10$^7$ RS4;11 cells are grafted sub-cutaneously into immunosuppressed mice (SCID strain). 25 to 30 days after the graft, the animals are treated orally with the various compounds. Sixteen hours after treatment, the tumour masses are recovered and lysed, and the caspase 3 activity is measured in the tumour lysates.

This enzymatic measurement is carried out by assaying the appearance of a fluorigenic cleavage product (DEVDase activity, Promega). It is expressed in the form of an activation factor corresponding to the ratio between the two caspase activities: the activity for the treated mice divided by the activity for the control mice.

The results show that the compounds of the invention are capable of inducing apoptosis in RS4;11 tumour cells in vivo.

EXAMPLE D: QUANTIFICATION OF THE CLEAVED FORM OF CASPASE 3 IN VIVO

The ability of the compounds of the invention to activate caspase 3 is evaluated in a xenograft model of RS4;11 leukaemia cells.

1×10$^7$ RS4;11 cells are grafted sub-cutaneously into immunosuppressed mice (SCID strain). 25 to 30 days after the graft, the animals are treated orally with the various compounds. After treatment, the tumour masses are recovered and lysed, and the cleaved (activated) form of caspase 3 is quantified in the tumour lysates.

The quantification is carried out using the "Meso Scale Discovery (MSD) ELISA platform" test, which specifically assays the cleaved form of caspase 3. It is expressed in the form of an activation factor corresponding to the ratio between the quantity of cleaved caspase 3 in the treated mice divided by the quantity of cleaved caspase 3 in the control mice.

The results show that the compounds of the invention are capable of inducing apoptosis in RS4;11 tumour cells in vivo.

EXAMPLE E: ANTI-TUMOUR ACTIVITY IN VIVO

The anti-tumour activity of the compounds of the invention is evaluated in a xenograft model of RS4;11 leukaemia cells.

1×10$^7$ RS4;11 cells are grafted sub-cutaneously into immunosuppressed mice (SCID strain). 25 to 30 days after the graft, when the tumour mass has reached about 150 mm$^3$, the mice are treated orally with the various compounds in two different regimes (daily treatment for five days per week for two weeks, or two treatments weekly for two weeks). The tumour mass is measured twice weekly from the start of treatment.

The results obtained therefore show that the compounds of the invention are capable of inducing significant tumour regression during the treatment period.

EXAMPLE F: PHARMACEUTICAL COMPOSITION: TABLETS

| | |
|---|---|
| 1000 tablets containing a dose of 5 mg of a compound selected from Examples 1 to 811 | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:

1. A method of treating cancer in a subject in need thereof, wherein the cancer is selected from the group consisting of cancers of the bladder, brain, breast and uterus, cancer of the colon, oesophagus and liver, non-Hodgkin lymphomas, melanomas, malignant haemopathies, myelomas, ovarian cancer, non-small-cell lung cancer, prostate cancer, and small-cell lung cancer, comprising administration of a compound of formula (I):

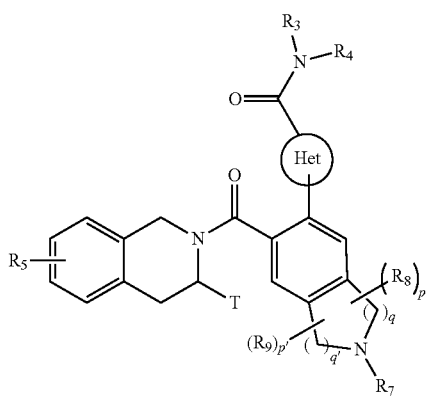

wherein:
Het represents a heteroaryl group;
T represents a hydrogen atom, a linear or branched $(C_1-C_6)$alkyl group, an alkyl$(C_1-C_4)$—$NR_1R_2$ group or an alkyl$(C_1-C_4)$—$OR_6$ group;
$R_1$ and $R_2$ independently of one another represent a hydrogen atom or a linear or branched $(C_1-C_6)$alkyl group,
or $R_1$ and $R_2$ form with the nitrogen atom carrying them a heterocycloalkyl group;
$R_3$ represents a linear or branched $(C_1-C_6)$alkyl group, a linear or branched $(C_2-C_6)$alkenyl group, a linear or branched $(C_2-C_6)$alkynyl group, a cycloalkyl group, a $(C_3-C_{10})$cycloalkyl-$(C_1-C_6)$alkyl group wherein the alkyl group may be linear or branched, a heterocycloalkyl group, an aryl group or a heteroaryl group, wherein one or more carbon atoms of the groups defined hereinbefore, or carbon atoms of their possible substituents, may be deuterated;
$R_4$ represents an aryl, heteroaryl, cycloalkyl or linear or branched $(C_1-C_6)$alkyl group, wherein one or more carbon atoms of the groups defined hereinbefore, or carbon atoms of their possible substituents, may be deuterated;
$R_5$ represents a hydrogen atom or a halogen atom, a linear or branched $(C_1-C_6)$alkyl group, or a linear or branched $(C_1-C_6)$alkoxy group;
$R_6$ represents a hydrogen atom or a linear or branched $(C_1-C_6)$alkyl group;
$R_7$ represents a group selected from $R'_7$, $R'_7$—CO—, $R'_7$—O—CO—, $NR'_7R''_7$—CO—, $R'_7$—$SO_2$—, and $R'_7$—$NR''_7$—$SO_2$— wherein $R'_7$ et $R''_7$ independently of one another represent a hydrogen atom, a linear or branched $(C_1-C_6)$alkyl group, a linear or branched $(C_2-C_6)$alkenyl group, a linear or branched $(C_2-C_5)$alkynyl group, a cycloalkyl, a heterocycloalkyl, an aryl group, or a heteroaryl;
$R_8$ and $R_9$ represent, independently of one another, an oxo group or a halogen atom;
p and p' are, independently of one another, integers equal to 0, 1, 2, 3 or 4;
q and q' are, independently of one another, integers equal to 1, 2 or 3;
wherein when the compound of formula (I) contains a hydroxy group, this latter group may be optionally substituted by one of the following groups: —PO(OM)(OM'), —PO(OM)($O^-M_1^+$), —PO($O^-M_1^+$)($O^-M_2^+$), —PO($O^-$)($O^-$)$M_3^{2+}$, —PO(OM)(O[$CH_2CH_2O$]$_n$$CH_3$), or —PO($O^-M_1^+$)(O[$CH_2CH_2O$]$_n$$CH_3$), wherein M and M' independently of one another represent a hydrogen atom, a linear or branched $(C_1-C_6)$alkyl group, a linear or branched $(C_2-C_6)$alkenyl group, a linear or branched $(C_2-C_6)$alkynyl group, a cycloalkyl or a heterocycloalkyl, both the cycloalkyl and heterocycloalkyl being composed of from 5 to 6 ring members, $M_1^+$ and $M_2^+$ independently of one another represent a pharmaceutically acceptable monovalent cation, $M_3^{2+}$ represents a pharmaceutically acceptable divalent cation and n is an integer comprised between 1 to 5,
wherein:
"aryl" means a phenyl, naphthyl, biphenyl or indenyl group,
"heteroaryl" means any mono- or bi-cyclic group composed of from 5 to 10 ring members, having at least one aromatic moiety and having from 1 to 4 hetero atoms selected from oxygen, sulphur and nitrogen,
"cycloalkyl" means any mono- or bi-cyclic non-aromatic carbocyclic group having from 3 to 10 ring members, which may include fused, bridged or spiro ring systems,
"heterocycloalkyl" means any mono- or bi-cyclic non-aromatic carbocyclic group, composed of from 3 to 10 ring members, and having from one to 3 hetero atoms selected from oxygen, sulphur, SO, $SO_2$ and nitrogen, wherein the bicyclic group may be fused or spiro type,
wherein the aryl, heteroaryl, cycloalkyl and heterocycloalkyl groups so defined and the alkyl, alkenyl, alkynyl, alkoxy, may be optionally substituted by from 1 to 3 groups selected from the group consisting of: linear or branched $(C_1-C_6)$alkyl group; linear or branched $(C_2-C_6)$alkenyl group; linear or branched $(C_2-C_6)$alkynyl group; $(C_3-C_6)$spiro; linear or branched $(C_1-C_6)$alkoxy; $(C_1-C_6)$alkyl-S—; hydroxyl; oxo; N-oxide; nitro; cyano; —COOR'; —OCOR'; —NR'R''; R'CONR''—; NR'R''CO—; linear or branched $(C_1-C_6)$polyhaloalkyl; trifluoromethoxy; $(C_1-C_6)$alkylsulphonyl; halogen; aryl; heteroaryl; aryloxy; arylthio; cycloalkyl and heterocycloalkyl, wherein R' and R" independently of one another represent a hydrogen atom, a linear or branched $(C_1-C_6)$alkyl group or an unsubstituted aryl group,
wherein said linear or branched $(C_1-C_6)$alkyl groups, said linear or branched $(C_2-C_6)$alkenyl group, said linear or branched $(C_2-C_6)$alkynyl group, said linear or branched $(C_1-C_6)$alkoxy, said aryl, said heteroaryl, said aryloxy, said arylthio, said cycloalkyl, and said heterocycloalkyl are optionally substituted by from 1 to 3 groups selected from the group consisting of: linear or branched $(C_1-C_6)$alkyl; linear or branched $(C_2-C_6)$alkenyl group; linear or branched $(C_2-C_6)$alkynyl group; $(C_3-C_6)$spiro; linear or branched $(C_1-C_6)$alkoxy; $(C_1-C_6)$alkyl-S—; hydroxyl; oxo; N-oxide; nitro; cyano; —COOR'; —OCOR'; —NR'R''; R'CONR''—; NR'R''CO—; linear or branched $(C_1-C_6)$polyhaloalkyl; trifluoromethoxy; $(C_1-C_6)$alkylsulphonyl; halogen; aryl; heteroaryl; aryloxy; arylthio; cycloalkyl and heterocycloalkyl, wherein R' and R" independently of one another represent a hydrogen atom, a linear or branched $(C_1-C_5)$alkyl group or an unsubstituted aryl group,
its enantiomers and diastereoisomers, and addition salts thereof with a pharmaceutically acceptable acid or base, wherein the compound of formula (I) is administered alone or in combination with one or more pharmaceutically acceptable excipients.

2. The method according to claim 1, wherein the compound of formula (I) is a compound of formula (IA):

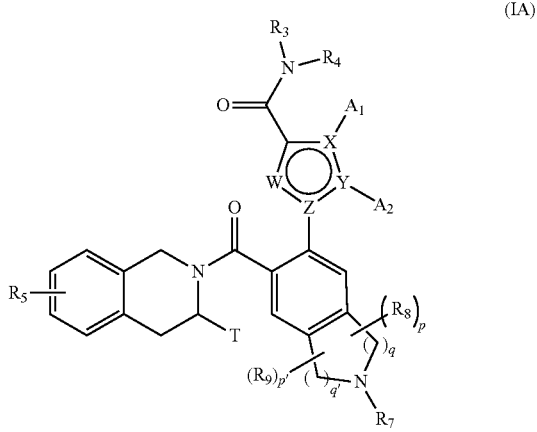

(IA)

wherein:
W represents a C-A₃ group or a nitrogen atom;
X, Y and Z represent a carbon atom or a nitrogen atom, wherein only one of them represent a nitrogen atom, while the two others represent carbon atoms;
$A_1$, $A_2$ and $A_3$ independently of one another represent a hydrogen atom or a halogen atom, a linear or branched ($C_1$-$C_6$)polyhaloalkyl group, a linear or branched ($C_1$-$C_6$)alkyl group or a cycloalkyl group,
or $A_3$ represents a hydrogen atom (when W represents a C-$A_3$ group) and $A_1$ and $A_2$, together with the atoms carrying them, form an optionally substituted aromatic or non-aromatic ring Cy, composed of 5, 6 or 7 ring members, which may have from one to 4 hetero atoms selected independently from oxygen, sulphur and nitrogen, wherein the nitrogen in question may be substituted by a group representing a hydrogen atom, a linear or branched ($C_1$-$C_6$)alkyl group or a —C(O)—O-Alk group wherein Alk is a linear or branched ($C_1$-$C_6$)alkyl group,
or W represents a nitrogen atom and $A_1$ and $A_2$, together with the atoms carrying them, form an optionally substituted aromatic or non-aromatic ring Cy, composed of 5, 6 or 7 ring members, which may have from one to 4 hetero atoms selected independently from oxygen, sulphur and nitrogen, wherein the nitrogen in question may be substituted by a group representing a hydrogen atom, a linear or branched ($C_1$-$C_6$)alkyl group or a —C(O)—O-Alk group wherein Alk is a linear or branched ($C_1$-$C_6$)alkyl group;
T represents a hydrogen atom, a linear or branched ($C_1$-$C_6$)alkyl group, an alkyl($C_1$-$C_4$)—$NR_1R_2$, group or an alkyl($C_1$-$C_4$)—$OR_6$ group;
$R_1$ and $R_2$ independently of one another represent a hydrogen atom or a linear or branched ($C_1$-$C_6$)alkyl group,
or $R_1$ and $R_2$ form with the nitrogen atom carrying them a heterocycloalkyl;
$R_3$ represents a linear or branched ($C_1$-$C_6$)alkyl group, a linear or branched ($C_2$-$C_6$)alkenyl group, a linear or branched ($C_2$-$C_6$)alkynyl group, a cycloalkyl group, a ($C_3$-$C_{10}$)cycloalkyl-($C_1$-$C_6$)alkyl group wherein the alkyl group may be linear or branched, a heterocycloalkyl group, an aryl group or a heteroaryl group, wherein one or more carbon atoms of the groups defined hereinbefore, or carbon atoms of their possible substituents, may be deuterated;
$R_4$ represents an aryl, heteroaryl, cycloalkyl or linear or branched ($C_1$-$C_6$)alkyl group, wherein one or more carbon atoms of the groups defined hereinbefore, or carbon atoms of their possible substituents, may be deuterated;
$R_5$ represents a hydrogen atom or a halogen atom, a linear or branched ($C_1$-$C_6$)alkyl group, or a linear or branched ($C_1$-$C_6$)alkoxy group;
$R_6$ represents a hydrogen atom or a linear or branched ($C_1$-$C_6$)alkyl group;
$R_7$ represents a group selected from $R'_7$, $R'_7$—CO—, $R'_7$—O—CO—, $NR'_7R''_7$—CO—, $R'_7$—$SO_2$—, and $R'_7$—$NR''_7$—$SO_2$— wherein $R'_7$ et $R''_7$ independently of one another represent a hydrogen atom, a linear or branched ($C_1$-$C_6$)alkyl group, a linear or branched ($C_2$-$C_6$)alkenyl group, a linear or branched ($C_2$-$C_6$) alkynyl group, a cycloalkyl, a heterocycloalkyl, an aryl group, or a heteroaryl;
$R_8$ and $R_9$ represent, independently of one another, an oxo group or a halogen atom;
p and p' are, independently of one another, integers equal to 0, 1, 2, 3 or 4;
q and q' are, independently of one another, integers equal to 1, 2 or 3:
wherein when the compound of formula (IA) contains a hydroxy group, this latter group may be optionally substituted by one of the following groups: —PO(OM)(OM'), —PO(OM)($O^-M_1^+$), —PO($O^-M_1^+$)($O^-M_2^+$), —PO($O^-$)($O^-$)$M_3^{2+}$, —PO(OM)(O[$CH_2CH_2O$]$_n$$CH_3$), or —PO($O^-$$M_1^+$)(O[$CH_2CH_2O$]$_n$$CH_3$), wherein M and M' independently of one another represent a hydrogen atom, a linear or branched ($C_1$-$C_6$)alkyl group, a linear or branched ($C_2$-$C_6$) alkenyl group, a linear or branched ($C_2$-$C_6$)alkynyl group, a cycloalkyl or a heterocycloalkyl, both the cycloalkyl and heterocycloalkyl being composed of from 5 to 6 ring members, $M_1^+$ and $M_2^+$ independently of one another represent a pharmaceutically acceptable monovalent cation, $M_3^{2+}$ represents a pharmaceutically acceptable divalent cation and n is an integer comprised between 1 to 5,
wherein:
"aryl" means a phenyl, naphthyl, biphenyl or indenyl group,
"heteroaryl" means any mono- or bi-cyclic group composed of from 5 to 10 ring members, having at least one aromatic moiety and having from 1 to 4 hetero atoms selected from oxygen, sulphur and nitrogen,
"cycloalkyl" means any mono- or bi-cyclic non-aromatic carbocyclic group having from 3 to 10 ring members, which may include fused, bridged or spiro ring systems,
"heterocycloalkyl" means any mono- or bi-cyclic non-aromatic carbocyclic group, composed of from 3 to 10 ring members, and having from one to 3 hetero atoms selected from oxygen, sulphur, SO, $SO_2$ and nitrogen, wherein the bicyclic group may be fused or spiro type,
wherein the aryl, heteroaryl, cycloalkyl and heterocycloalkyl groups so defined and the alkyl, alkenyl, alkynyl, alkoxy, may be optionally substituted by from 1 to 3 groups selected from the group consisting of: linear or branched ($C_1$-$C_6$)alkyl group; linear or branched ($C_2$-$C_6$)alkenyl group; linear or branched ($C_2$-$C_6$)alkynyl group; ($C_3$-$C_6$) spiro; linear or branched ($C_1$-$C_6$)alkoxy; ($C_1$-$C_6$)alkyl-S—; hydroxyl; oxo; N-oxide; nitro; cyano; —COOR'; —OCOR'; —NR'R''; R'CONR''—; NR'R''CO—; linear or branched ($C_1$-$C_6$)polyhaloalkyl; trifluoromethoxy; ($C_1$-$C_6$)alkylsulphonyl; halogen; aryl; heteroaryl; aryloxy; arylthio; cycloalkyl or heterocycloalkyl, wherein R' and R'' independently of one another represent a hydrogen atom, a linear or branched ($C_1$-$C_6$)alkyl group or an unsubstituted aryl group, wherein the Cy moiety may be optionally substituted by from 1 to 3 groups selected from the group consisting of linear or branched ($C_1$-$C_6$)alkyl, linear or branched ($C_1$-$C_6$) polyhaloalkyl, hydroxy, linear or branched ($C_1$-$C_6$)alkoxy, COOH, $NR_1'R_1''$ and halogen, wherein $R_1'$ and $R_1''$ independently of one another represent a hydrogen atom, a linear or branched ($C_1$-$C_6$)alkyl group or an unsubstituted aryl group, wherein said linear or branched ($C_1$-$C_6$)alkyl groups, said linear or branched ($C_2$-$C_6$)alkenyl group, said linear or branched ($C_2$-$C_6$)alkynyl group, said linear or branched ($C_1$-$C_6$)alkoxy, said aryl, said heteroaryl, said aryloxy, said arylthio, said cycloalkyl, and said heterocycloalkyl are optionally substituted by from 1 to 3 groups selected from the group consisting of: linear or branched ($C_1$-$C_6$)alkyl; linear or branched ($C_2$-$C_6$)alkenyl group; linear or branched ($C_2$-$C_6$)alkynyl group; ($C_3$-$C_6$)spiro; linear or branched ($C_1$-$C_6$)alkoxy; ($C_1$-$C_6$)alkyl-S—; hydroxyl; oxo; N-oxide; nitro; cyano; —COOR'; —OCOR'; —NR'R''; R'CONR''—; NR'R''CO—; linear or branched ($C_1$-$C_6$)polyhaloalkyl; trifluoromethoxy; ($C_1$-$C_6$)alkylsulphonyl; halogen; aryl; heteroaryl; aryloxy; arylthio; cycloalkyl and heterocycloalkyl, wherein that R' and R'' independently of one another represent a hydrogen atom, a linear or branched ($C_1$-$C_5$)alkyl group or an unsubstituted aryl group, its enantiomers and diastereoisomers, and addition salts thereof with a pharmaceutically acceptable acid or base.

3. The method according to claim 1, wherein the compound of formula (I) is a compound of formula (IA-1):

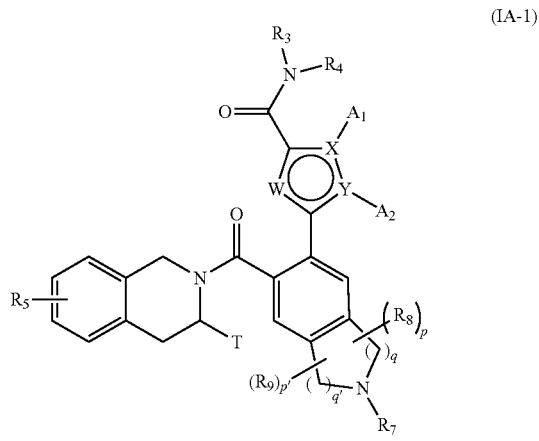

(IA-1)

wherein
W represents a C-$A_3$ group or a nitrogen atom;
X and Y represent a carbon atom or a nitrogen atom, wherein only one of them represents a nitrogen atom;
$A_1$, $A_2$ and $A_3$ independently of one another represent a hydrogen atom or a halogen atom, a linear or branched ($C_1$-$C_6$)polyhaloalkyl group, a linear or branched ($C_1$-$C_6$)alkyl group or a cycloalkyl group,
or $A_3$ represents a hydrogen atom (when W represents a C-$A_3$ group) and $A_1$ and $A_2$, together with the atoms carrying them, form an optionally substituted aromatic or non-aromatic ring Cy, composed of 5, 6 or 7 ring members, which may have from one to 4 hetero atoms selected independently from oxygen, sulphur and nitrogen, wherein the nitrogen in question may be substituted by a group representing a hydrogen atom, a linear or branched ($C_1$-$C_6$)alkyl group or a —C(O)—O-Alk group wherein Alk is a linear or branched ($C_1$-$C_6$)alkyl group,
or W represents a nitrogen atom and A, and $A_2$, together with the atoms carrying them, form an optionally substituted aromatic or non-aromatic ring Cy, composed of 5, 6 or 7 ring members, which may have from one to 4 hetero atoms selected independently from oxygen, sulphur and nitrogen, wherein the nitrogen in question may be substituted by a group representing a hydrogen atom, a linear or branched ($C_1$-$C_6$)alkyl group or a —C(O)—O-Alk group wherein Alk is a linear or branched ($C_1$-$C_6$)alkyl group;
T represents a hydrogen atom, a linear or branched ($C_1$-$C_6$)alkyl group, an alkyl($C_1$-$C_4$)—$NR_1R_2$, group or an alkyl($C_1$-$C_4$)—$OR_6$ group;
$R_1$ and $R_2$ independently of one another represent a hydrogen atom or a linear or branched ($C_1$-$C_6$)alkyl group,
or $R_1$ and $R_2$ form with the nitrogen atom carrying them a heterocycloalkyl;
$R_3$ represents a linear or branched ($C_1$-$C_6$)alkyl group, a linear or branched ($C_2$-$C_6$)alkenyl group, a linear or branched ($C_2$-$C_6$)alkynyl group, a cycloalkyl group, a ($C_3$-$C_{10}$)cycloalkyl-($C_1$-$C_6$)alkyl group wherein the alkyl group may be linear or branched, a heterocycloalkyl group, an aryl group or a heteroaryl group, wherein one or more carbon atoms of the groups defined hereinbefore, or carbon atoms of their possible substituents, may be deuterated;
$R_4$ represents an aryl, heteroaryl, cycloalkyl or linear or branched ($C_1$-$C_6$)alkyl group, wherein one or more carbon atoms of the groups defined hereinbefore, or carbon atoms of their possible substituents, may be deuterated;
$R_5$ represents a hydrogen atom or a halogen atom, a linear or branched ($C_1$-$C_5$)alkyl group, or a linear or branched ($C_1$-$C_6$)alkoxy group;
$R_6$ represents a hydrogen atom or a linear or branched ($C_1$-$C_6$)alkyl group;
$R_7$ represents a group selected from $R'_7$, $R'_7$—CO—, $R'_7$—O—CO—, $NR'_7R''_7$—CO—, $R'_7$—$SO_2$—, and $R'_7$—$NR''_7$—$SO_2$— wherein $R'_7$ et $R''_7$ independently of one another represent a hydrogen atom, a linear or branched ($C_1$-$C_6$)alkyl group, a linear or branched ($C_2$-$C_6$)alkenyl group, a linear or branched ($C_2$-$C_6$) alkynyl group, a cycloalkyl, a heterocycloalkyl, an aryl group, or a heteroaryl;
$R_8$ and $R_9$ represent, independently of one another, an oxo group or a halogen atom;
p and p' are, independently of one another, integers equal to 0, 1, 2, 3 or 4;
q and q' are, independently of one another, integers equal to 1, 2 or 3;

wherein when the compound of formula (IA-1) contains a hydroxy group, this latter group may be optionally substituted by one of the following groups: —PO(OM)(OM'), —PO(OM)($O^-M_1^+$), —PO($O^-M_1^+$)($O^-M_2^+$), —PO($O^-$)($O^-$)$M_3^{2+}$, —PO(OM)(O[$CH_2CH_2O$]$_n CH_3$), or —PO($O^- M_1^+$)(O[$CH_2CH_2O$]$_n CH_3$), wherein M and M' independently of one another represent a hydrogen atom, a linear or branched ($C_1$-$C_6$)alkyl group, a linear or branched ($C_2$-$C_6$) alkenyl group, a linear or branched ($C_2$-$C_6$)alkynyl group, a cycloalkyl or a heterocycloalkyl, both the cycloalkyl and heterocycloalkyl being composed of from 5 to 6 ring members, $M_1^+$ and $M_2^+$ independently of one another represent a pharmaceutically acceptable monovalent cation, $M_3^{2+}$ represents a pharmaceutically acceptable divalent cation and n is an integer comprised between 1 to 5, wherein:

"aryl" means a phenyl, naphthyl, biphenyl or indenyl group,

"heteroaryl" means any mono- or bi-cyclic group composed of from 5 to 10 ring members, having at least one aromatic moiety and having from 1 to 4 hetero atoms selected from oxygen, sulphur and nitrogen, "cycloalkyl" means any mono- or bi-cyclic non-aromatic carbocyclic group having from 3 to 10 ring members, which may include fused, bridged or spiro ring systems, "heterocycloalkyl" means any mono- or bi-cyclic non-aromatic carbocyclic group, composed of from 3 to 10 ring members, and having from one to 3 hetero atoms selected from oxygen, sulphur, SO, $SO_2$ and nitrogen, wherein the bicyclic group may be fused or spiro type, wherein the aryl, heteroaryl, cycloalkyl and heterocycloalkyl groups so defined and the alkyl, alkenyl, alkynyl, alkoxy, may be optionally substituted by from 1 to 3 groups selected from the group consisting of: linear or branched ($C_1$-$C_6$)alkyl group; linear or branched ($C_2$-$C_6$)alkenyl group; linear or branched ($C_2$-$C_6$)alkynyl group; ($C_3$-$C_6$) spiro; linear or branched ($C_2$-$C_6$)alkoxy; ($C_1$-$C_6$)alkyl-S—; hydroxyl; oxo; N-oxide; nitro; cyano; —COOR'; —OCOR'; —NR'R"; R'CONR"—; NR'R"CO—; linear or branched ($C_1$-$C_6$)polyhaloalkyl; trifluoromethoxy; ($C_1$-$C_6$)alkylsulphonyl; halogen; aryl; heteroaryl; aryloxy; arylthio; cycloalkyl and heterocycloalkyl, wherein R' and R" independently of one another represent a hydrogen atom, a linear or branched ($C_1$-$C_6$)alkyl group or an unsubstituted aryl group, wherein the Cy moiety may be optionally substituted by from 1 to 3 groups selected from the group consisting of linear or branched ($C_1$-$C_6$)alkyl, linear or branched ($C_1$-$C_6$) polyhaloalkyl, hydroxy, linear or branched ($C_1$-$C_6$)alkoxy, COOH, $NR_1'R''$ and halogen, wherein $R_1'$ and $R_1''$ independently of one another represent a hydrogen atom, a linear or branched ($C_1$-$C_6$)alkyl group or an unsubstituted aryl group, wherein said linear or branched ($C_1$-$C_6$)alkyl groups, said linear or branched ($C_2$-$C_6$)alkenyl group, said linear or branched ($C_2$-$C_6$)alkynyl group, said linear or branched ($C_1$-$C_6$)alkoxy, said aryl, said heteroaryl, said aryloxy, said arylthio, said cycloalkyl, and said heterocycloalkyl are optionally substituted by from 1 to 3 groups selected from the group consisting of: linear or branched ($C_1$-$C_6$)alkyl; linear or branched ($C_2$-$C_6$)alkenyl group; linear or branched ($C_2$-$C_6$)alkynyl group; ($C_3$-$C_6$)spiro; linear or branched ($C_1$-$C_5$)alkoxy; ($C_1$-$C_6$)alkyl-S—; hydroxyl; oxo; N-oxide; nitro; cyano; —COOR'; —OCOR'; —NR'R"; R'CONR"—; NR'R"CO—; linear or branched ($C_1$-$C_6$)polyhaloalkyl; trifluoromethoxy; ($C_1$-$C_6$)alkylsulphonyl; halogen; aryl; heteroaryl; aryloxy; arylthio; cycloalkyl and heterocycloalkyl, wherein R' and R" independently of one another represent a hydrogen atom, a linear or branched ($C_1$-$C_6$)alkyl group or an unsubstituted aryl group, its enantiomers and diastereoisomers, and addition salts thereof with a pharmaceutically acceptable acid or base.

4. The method according to claim 1, wherein the compound of formula (I) is a compound of formula (IA-2):

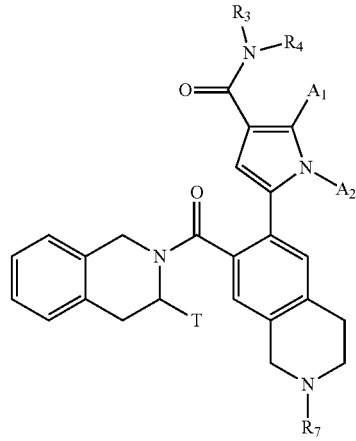

(IA-2)

wherein $A_1$, and $A_2$ independently of one another represent a hydrogen atom or a halogen atom, a linear or branched ($C_1$-$C_6$)polyhaloalkyl group, a linear or branched ($C_1$-$C_6$)alkyl group or a cycloalkyl group, or $A_1$ and $A_2$, together with the atoms carrying them, form an optionally substituted aromatic or non-aromatic ring Cy, composed of 5, 6 or 7 ring members, which may have from one to 4 hetero atoms selected independently from oxygen, sulphur and nitrogen, wherein the nitrogen in question may be substituted by a group representing a hydrogen atom, a linear or branched ($C_1$-$C_6$) alkyl group or a —C(O)—O-Alk group wherein Alk is a linear or branched ($C_1$-$C_6$)alkyl group;

T represents a hydrogen atom, a linear or branched ($C_1$-$C_6$)alkyl group, an alkyl($C_1$-$C_4$)—$NR_1R_2$, group or an alkyl($C_1$-$C_4$)—$OR_6$ group;

$R_1$ and $R_2$ independently of one another represent a hydrogen atom or a linear or branched ($C_1$-$C_6$)alkyl group, or $R_1$ and $R_2$ form with the nitrogen atom carrying them a heterocycloalkyl;

$R_3$ represents a linear or branched ($C_1$-$C_6$)alkyl group, a linear or branched ($C_2$-$C_6$)alkenyl group, a linear or branched ($C_2$-$C_6$)alkynyl group, a cycloalkyl group, a ($C_3$-$C_{10}$)cycloalkyl-($C_1$-$C_6$)alkyl group wherein the alkyl group may be linear or branched, a heterocycloalkyl group, an aryl group or a heteroaryl group, wherein one or more carbon atoms of the groups defined hereinbefore, or carbon atoms of their possible substituents, may be deuterated;

$R_4$ represents an aryl, heteroaryl, cycloalkyl or linear or branched ($C_1$-$C_6$)alkyl group, wherein one or more carbon atoms of the groups defined hereinbefore, or carbon atoms of their possible substituents, may be deuterated;

$R_6$ represents a hydrogen atom or a linear or branched ($C_1$-$C_6$)alkyl group;

$R_7$ represents a group selected from $R'_7$, $R'_7$—CO—, $R'_7$—O—CO—, $NR'_7R''_7$—CO—, $R'_7$—$SO_2$—, and $R'_7$—$NR''_7$—$SO_2$— wherein $R'_7$ et R" independently of one another represent a hydrogen atom, a linear or branched ($C_1$-$C_6$)alkyl group, a linear or branched ($C_2$-$C_6$)alkenyl group, a linear or branched ($C_2$-$C_6$) alkynyl group, a cycloalkyl, a heterocycloalkyl, an aryl group, or a heteroaryl;

$R_8$ and $R_9$ represent, independently of one another, an oxo group or a halogen atom;

p and p' are, independently of one another, integers equal to 0, 1, 2, 3 or 4;

q and q' are, independently of one another, integers equal to 1, 2 or 3;

wherein when the compound of formula (IA-2) contains a hydroxy group, this latter group may be optionally substituted by one of the following groups: —PO(OM)(OM'), —PO(OM)(O$^-$M$_1{}^+$), —PO(O$^-$M$_1{}^+$)(O$^-$M$_2{}^+$), —PO(O$^-$)(O$^-$)M$_3{}^{2+}$, —PO(OM)(O[CH$_2$CH$_2$O]$_n$CH$_3$), or —PO(O$^-$M$_1{}^+$)O[CH$_2$CH$_2$O]$_n$CH$_3$), wherein M and M' independently of one another represent a hydrogen atom, a linear or branched (C$_1$-C$_6$)alkyl group, a linear or branched (C$_2$-C$_6$)alkenyl group, a linear or branched (C$_2$-C$_6$)alkynyl group, a cycloalkyl or a heterocycloalkyl, both the cycloalkyl and heterocycloalkyl being composed of from 5 to 6 ring members, M$_1{}^+$ and M$_2{}^+$ independently of one another represent a pharmaceutically acceptable monovalent cation, M$_3{}^{2+}$ represents a pharmaceutically acceptable divalent cation and n is an integer comprised between 1 to 5, wherein:
- "aryl" means a phenyl, naphthyl, biphenyl or indenyl group,
- "heteroaryl" means any mono- or bi-cyclic group composed of from 5 to 10 ring members, having at least one aromatic moiety and having from 1 to 4 hetero atoms selected from oxygen, sulphur and nitrogen,
- "cycloalkyl" means any mono- or bi-cyclic non-aromatic carbocyclic group having from 3 to 10 ring members, which may include fused, bridged or spiro ring systems,
- "heterocycloalkyl" means any mono- or bi-cyclic non-aromatic carbocyclic group, composed of from 3 to 10 ring members, and having from one to 3 hetero atoms selected from oxygen, sulphur, SO, SO$_2$ and nitrogen, wherein the bicyclic group may be fused or spiro type, wherein the aryl, heteroaryl, cycloalkyl and heterocycloalkyl groups so defined and the alkyl, alkenyl, alkynyl, alkoxy, may be optionally substituted by from 1 to 3 groups selected from the group consisting of: linear or branched (C$_1$-C$_6$)alkyl group; linear or branched (C$_2$-C$_6$)alkenyl group; linear or branched (C$_2$-C$_6$)alkynyl group; (C$_3$-C$_6$) spiro; linear or branched (C$_1$-C$_6$)alkoxy; (C$_1$-C$_6$)alkyl-S—; hydroxyl; oxo; N-oxide; nitro; cyano; —COOR'; —OCOR'; —NR'R"; R'CONR"—; NR'R"CO—; linear or branched (C$_1$-C$_6$)polyhaloalkyl; trifluoromethoxy; (C$_1$-C$_6$)alkylsulphonyl; halogen; aryl; heteroaryl; aryloxy; arylthio; cycloalkyl and heterocycloalkyl, wherein R' and R" independently of one another represent a hydrogen atom, a linear or branched (C$_1$-C$_6$)alkyl group or an aryl group, wherein the Cy moiety may be optionally substituted by from 1 to 3 groups selected from the group consisting of linear or branched (C$_1$-C$_6$)alkyl, linear or branched (C$_1$-C$_6$) polyhaloalkyl, hydroxy, linear or branched (C$_1$-C$_6$)alkoxy, COOH, NR$_1$'R$_1$" and halogen, wherein R$_1$' and R$_1$" independently of one another represent a hydrogen atom, a linear or branched (C$_1$-C$_6$)alkyl group or an unsubstituted aryl group, wherein said linear or branched (C$_1$-C$_6$)alkyl groups, said linear or branched (C$_2$-C$_6$)alkenyl group, said linear or branched (C$_2$-C$_6$)alkynyl group, said linear or branched (C$_1$-C$_6$)alkoxy, said aryl, said heteroaryl, said aryloxy, said arylthio, said cycloalkyl, and said heterocycloalkyl are optionally substituted by from 1 to 3 groups selected from the group consisting of: linear or branched (C$_1$-C$_6$)alkyl; linear or branched (C$_2$-C$_6$)alkenyl group; linear or branched (C$_2$-C$_6$)alkynyl group; (C$_3$-C$_6$)spiro; linear or branched (C$_1$-C$_6$)alkoxy; (C$_1$-C$_6$)alkyl-S—; hydroxyl; oxo; N-oxide; nitro; cyano; —COOR'; —OCOR'; —NR'R"; R'CONR"—; NR'R"CO—; linear or branched (C$_1$-C$_6$)polyhaloalkyl; trifluoromethoxy; (C$_1$-C$_6$) alkylsulphonyl; halogen; aryl; heteroaryl; aryloxy; arylthio; cycloalkyl and heterocycloalkyl, wherein R' and R" independently of one another represent a hydrogen atom, a linear or branched (C$_1$-C$_6$)alkyl group or an unsubstituted aryl group, its enantiomers and diastereoisomers, and addition salts thereof with a pharmaceutically acceptable acid or base.

5. The method according to claim 1, wherein R$_4$ represents a phenyl substituted at the para position by a group of formula —OPO(OM)(OM'), —OPO(OM)(O$^-$M$^+$), —OPO(O$^-$M$_1{}^+$)(O$^-$M$_2{}^+$), —OPO(O$^-$)(O$^-$)M$_3{}^{2+}$, —OPO(OM)(O[CH$_2$CH$_2$O]$_n$CH$_3$), or —OPO(O$^-$M$_1{}^+$)(O[CH$_2$CH$_2$O]$_n$CH$_3$), wherein M and M' independently of one another represent a hydrogen atom, a linear or branched (C$_1$-C$_6$) alkyl group, a linear or branched (C$_2$-C$_6$)alkenyl group, a linear or branched (C$_2$-C$_6$)alkynyl group, a cycloalkyl or a heterocycloalkyl, both the cycloalkyl and heterocycloalkyl being composed of from 5 to 6 ring members, M$_1{}^+$ and M$_3{}^{2+}$ independently of one another represent a pharmaceutically acceptable monovalent cation, M$_3{}^{2+}$ represents a pharmaceutically acceptable divalent cation and n is an integer comprised between 1 to 5, wherein the phenyl group may be optionally substituted by one or more halogen atoms.

6. The method according to claim 1, wherein Het represents one of the following groups: 5,6,7,8-tetrahydroindolizine, indolizine or 1,2-dimethyl-1H-pyrrole.

7. The method according to claim 1, wherein q=1 and q'=1.

8. The method according to claim 1, wherein q=2 and q'=1.

9. The method according to claim 1, wherein T represents a hydrogen atom, a methyl group, a (morpholin-4-yl)methyl group, a 3-(morpholin-4-yl)propyl group, a dimethylaminomethyl group, or a (4-methylpiperazin-1-yl)methyl group.

10. The method according to claim 1, wherein R$_3$ represents a linear or branched (C$_1$-C$_6$)alkyl group, an aryl group or a heteroaryl group.

11. The method according to claim 1, wherein R$_3$ represents phenyl, methyl, ethyl, propyl, butyl, 1-methyl-1H-pyrrolo[2,3-b]pyridine or 5-cyano-1,2-dimethyl-1H-pyrrole.

12. The method according to claim 1, wherein R$_4$ represents a linear or branched (C$_1$-C$_6$)alkyl group or an aryl group.

13. The method according to claim 1, wherein R$_4$ represents a phenyl or 4-hydroxyphenyl group.

14. The method according to claim 1, wherein R$_7$ represents a group R'$_7$—CO— or R'$_7$—O—CO—.

15. The method according to claim 1, wherein R'$_7$ represents aryl, cycloalkyl or alkyl.

16. The method according to claim 1, wherein R'$_7$ represents a naphthalene, phenyl or indole group.

17. The method according to claim 16, wherein the phenyl group is substituted by a group selected from the group consisting of alkyl, cyano, alkynyl, halogen, alkoxy, and —NR'R".

18. The method according to claim 17, wherein the phenyl group is substituted by a group selected from the group consisting of methyl, ethyl, methoxy, chloro, bromo, cyano, 2-dimethylaminoethylamino, ethynyl, 2-dimethylaminoethoxy, 2-(dimethylamino)ethyl(methyl)amino, and dimethylcarbamoylethyl.

19. The method according to claim 1, wherein p=p'=O.

20. The method according to claim 1, wherein the compound of formula (I) is selected from the group consisting of:

N-(4-Hydroxyphenyl)-N-methyl-3-{7-[(3R)-3-methyl-1,2,3,4-tetrahydro isoquinoline-2-carbonyl]-2-(2-phenylacetyl)-1,2,3,4-tetrahydroisoquinolin-6-yl}-5,6,7,8-tetrahydroindolizine-1-carboxamide;

Phenyl 6-{1-[(4-hydroxyphenyl)(methyl)carbamoyl]-5,6,7,8-tetrahydroindolizin-3-yl}-7-[(3R)-3-methyl-1,2,3,4-tetrahydro isoquinoline-2-carbonyl]-1,2,3,4-tetrahydro isoquinoline-2-carboxylate;

Phenyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydro isoquinoline-2-carboxylate;

Phenyl 6-{-[(4-hydroxyphenyl)(methyl)carbamoyl]-5,6,7,8-tetrahydroindolizin-3-yl}-7-[(3S)-3-(morpholin-4-ylmetbyl)-1,2,3,4-tetrahydroisoquinoline-2-carbonyl]-1,2,3,4-tetrahydroisoquinoline-2-carboxylate hydrochloride;

Phenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate hydrochloride;

4-Methylphenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate hydrochloride;

2-Methylphenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Methoxyphenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Chiorophenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Ethylphenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Cyanophenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

2-Methoxyphenyl 6-{1-[(4-hydroxyphenyl)(methyl)carbamoyl]-5,6,7,8-tetrahydro indolizin-3-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Methylphenyl 6-{4-[(4-hydroxyphenyl)(methyl)carbamoyl]-1,5-dimethyl-11H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Chlorophenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Cyanophenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

4-Cyanophenyl 6-({4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate;

4-{[2-(Dimethylamino)ethyl]amino}phenyl 6-{1-[(4-hydroxyphenyl)(methyl) carbamoyl]-5,6,7,8-tetrahydroindolizin-3-yl}-7-[(3R)-3-methyl-1,2,3,4-tetrahydroisoquinoline-2-carbonyl]-1,2,3,4-tetrahydroisoquinoline-2-carboxylate;

Phenyl 6-{4-[(4-hydroxyphenyl)(propyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

Phenyl 6-{4-[butyl(4-hydroxyphenyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

Phenyl 6-{4-[(4-hydroxyphenyl)(methyl)carbamoyl]-1,5-dimethyl-1H-pyrrol-2-yl}-7-[(3S)-3-[(4-methylpiperazin-I-yl)methyl]-1,2,3,4-tetrahydroisoquinoline-2-carbonyl]-1,2,3,4-tetrahydroisoquinoline-2-carboxylate;

N-Butyl-N-(4-hydroxypbenyl)-1,2-dimethyl-5-{7-[(3S)-3-(morpholin-4-ylmethyl)-1,2,3,4-tetrahydroisoquinoline-2-carbonyl]-2-(2-phenyl acetyl)-1,2,3,4-tetrahydroisoquinolin-6-yl}-1H-pyrrole-3-carboxamide;

3-[2-(Dimethylamino)ethoxy]phenyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate;

4-{[2-(Dimethylamino)ethyl](methyl)amino}phenyl 6-{4-[(4-hydroxyphenyl) (methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate;

4-Ethynylphenyl 6-{4-[(4-hydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

Naphthalen-2-yl 6-{4-[(4-bydroxyphenyl)(methyl)carbamoyl]-1,5-dimethyl-1H-pyrrol-2-yl}-7-[(3S)-3-(morpholin-4-ylmethyl)-1,2,3,4-tetrahydroisoquinoline-2-carbonyl]-1,2,3,4-tetrahydroisoquinoline-2-carboxylate;

1H-Indol-5-yl 6-{4-[(4-hydroxyphenyl)(methyl)carbamoyl]-1,5-dimethyl-1H-pyrrol-2-yl}-7-[(3S)-3-(morpholin-4-ylmethyl)-1,2,34-tetrahydroisoquinoline-2-carbonyl]-1,2,3,4-tetrahydroisoquinoline-2-carboxylate;

3-[2-(Dimethylcarbamoyl)ethyl]phenyl 6-{4-[(4-hydroxyphenyl)(methyl) carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate;

4-Bromophenyl 6-{4-[(4-hydroxyphenyl)(methyl)carbamoyl]-1,5-dimethyl-1H-pyrrol-2-yl}-7-[(3S)-3-

(morpholin-4-ylmethyl)-1,2,3,4-tetrahydroisoquinoline-2-carbonyl]-1,2,3,4-tetrahydroisoquinoline-2-carboxylate;

(1r,4r)-4-{[(tert-Butoxy)carbonyl]amino}cyclohexyl 6-{4-[(4-hydroxyphenyl) (methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate;

4-[2-(Dimethylcarbamoyl)ethyl]phenyl 6-{4-[(4-hydroxyphenyl)(methyl) carbamoyl]-1,5-dimethyl-1H-pyrrol-2-yl}-7-[(3R)-3-methyl-1,2,3,4-tetrahydro isoquinoline-2-carbonyl]-1,2,3,4-tetrahydroisoquinoline-2-carboxylate; and Cyclohexyl 6-{4-[(4-hydroxyphenyl)(methyl)carbamoyl]-1,5-dimethyl-1H-pyrrol-2-yl}-7-[(3R)-3-[3-(morpholin-4-yl)propyl]-1,2,3,4-tetrahydroisoquinoline-2-carbonyl]-1,2,3,4-tetrahydroisoquinoline-2-carboxylate.

21. The method according to claim 1, wherein the compound of formula (I) is selected from the group consisting of:

N-(4-Hydroxyphenyl)-N-methyl-3-{7-[(3R)-3-methyl-1,2,3,4-tetrahydroisoquinoline-2-carbonyl]-2-{2-[4-(4-methylpiperazin-1-yl)phenyl]acetyl}-1,2,3,4-tetrahydroisoquinolin-6-yl}-5,6,7,8-tetrahydroindolizine-1-carboxamide, N-(4-Hydroxyphenyl)-N-methyl-3-{7-[(3R)-3-methyl-1,2,3,4-tetrahydroisoquinoline-2-carbonyl]-2-(2-{4-[(4-methylpiperazin-1-yl)methyl]phenyl}acetyl)-1,2,3,4-tetrahydroisoquinolin-6-yl}-5,6,7,8-tetrahydroindolizine-1-carboxamide, N-(4-Hydroxyphenyl)-N-methyl-3-{7-[(3R)-3-methyl-1,2,3,4-tetrahydroisoquinoline-2-carbonyl]-2-{2-[4-(morpholin-4-ylmethyl)phenyl]acetyl}-1,2,3,4-tetrahydroisoquinolin-6-yl}-5,6,7,8-tetrahydroindolizine-1-carboxamide, 3-[2-(2-{4-[(Dimethylamino)methyl]phenyl}acetyl)-7-[(3R)-3-methyl-1,2,3,4-tetrahydroisoquinoline-2-carbonyl]-1,2,3,4-tetrahydroisoquinolin-6-yl]-N-(4-hydroxyphenyl)-N-methyl-5,6,7,8-tetrahydroindolizine-1-carboxamide, 3-[2-(2-{4-[2-(Dimethylamino)ethoxy]phenyl}acetyl)-7-[(3R)-3-methyl-1,2,3,4-tetrahydroisoquinoline-2-carbonyl]-1,2,3,4-tetrahydroisoquinolin-6-yl]-N-(4-hydroxyphenyl)-N-methyl-5,6,7,8-tetrahydroindolizine-1-carboxamide, N-(4-Hydroxyphenyl)-N-methyl-3-{7-[(3R)-3-methyl-1,2,3,4-tetrahydroisoquinoline-2-carbonyl]-2-{2-[3-(4-methylpiperazin-1-yl)phenyl]acetyl}-1,2,3,4-tetrahydroisoquinolin-6-yl}-5,6,7,8-tetrahydroindolizine-1-carboxamide, (1r,4r)-4-{[(tert-Butoxy)carbonyl]amino}cyclohexyl 6-{4-[(4-hydroxyphenyl)(methyl)carbamoyl]-1,5-dimethyl-1H-pyrrol-2-yl}-7-[(3R)-3-methyl-1,2,3,4-tetrahydroisoquinoline-2-carbonyl]-1,2,3,4-tetrahydroisoquinoline-2-carboxylate.

22. The method according to claim 1, wherein the compound of formula (I) is administered as a pharmaceutical composition comprising the compound of formula (I) in combination with one or more pharmaceutically acceptable excipients.

* * * * *

UNITED STATES PATENT AND TRADEMARK OFFICE
CERTIFICATE OF CORRECTION

PATENT NO. : 10,689,364 B2
APPLICATION NO. : 15/704330
DATED : June 23, 2020
INVENTOR(S) : James Edward Paul Davidson et al.

It is certified that error appears in the above-identified patent and that said Letters Patent is hereby corrected as shown below:

In the Claims

Column 199, Line 53: ($C_2$-$C_5$) should read ($C_2$-$C_6$).

Column 200, Line 59: ($C_1$-$C_5$) should read ($C_1$-$C_6$).

Column 203, Line 26: ($C_1$-$C_5$) should read ($C_1$-$C_6$).

Column 204, Line 37: ($C_1$-$C_5$) should read ($C_1$-$C_6$).

Column 205, Line 28: ($C_2$-$C_6$) should read ($C_1$-$C_6$).

Column 206, Line 62: R" should read R"$_7$.

Column 209, Line 20: ylmetbyl should read ylmethyl.
        Line 43: Chiorophenyl should read Chlorophenyl.
        Line 64: 11H should read 1H.

Column 210, Line 30: -l-yl should read -1-yl.

Signed and Sealed this
Twenty-fifth Day of August, 2020

Andrei Iancu
*Director of the United States Patent and Trademark Office*